US007294759B2

(12) United States Patent
Allen et al.

(10) Patent No.: US 7,294,759 B2
(45) Date of Patent: Nov. 13, 2007

(54) ALTERATION OF OIL TRAITS IN PLANTS

(75) Inventors: William B. Allen, Urbandale, IA (US); Rebecca E. Cahoon, Webster Groves, MO (US); Omolayo O. Famodu, Newark, DE (US); Leslie T. Harvell, Newark, DE (US); Timothy G. Helentjaris, Ankeny, IA (US); Changjiang Li, Urbandale, IA (US); Keith S. Lowe, Johnston, IA (US); Igor Cunha Oliveira, Urbandale, IA (US); Bo Shen, Johnston, IA (US); Mitchell C. Tarczynski, West Des Moines, IA (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 729 days.

(21) Appl. No.: 10/180,375

(22) Filed: Jun. 26, 2002

(65) Prior Publication Data

US 2003/0126638 A1   Jul. 3, 2003

Related U.S. Application Data

(60) Provisional application No. 60/301,913, filed on Jun. 29, 2001.

(51) Int. Cl.
*C12N 15/82* (2006.01)
*A01H 1/00* (2006.01)

(52) U.S. Cl. ..................... 800/281; 800/298

(58) Field of Classification Search .............. 536/23.6; 800/281, 298
See application file for complete search history.

(56) References Cited

U.S. PATENT DOCUMENTS

| 5,004,863 A | 4/1991 | Umbeck |
| 5,159,135 A | 10/1992 | Umbeck |
| 5,416,011 A | 5/1995 | Hinchee et al. |
| 5,463,174 A | 10/1995 | Moloney et al. |
| 5,518,908 A | 5/1996 | Corbin et al. |
| 5,569,834 A | 10/1996 | Hinchee et al. |
| 5,631,152 A | 5/1997 | Fry et al. |

FOREIGN PATENT DOCUMENTS

| EP | 0 301 749 A2 | 2/1989 |
| WO | WO 99/67405 | 12/1999 |
| WO | WO 00/04761 | 2/2000 |
| WO | WO 00/28058 | 5/2000 |

OTHER PUBLICATIONS

Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
Paula P. Chee et al., Transformation of Soybean (Glycine max) by Infecting Germinating Seeds with Agrobacterium tumefaciens, Plant Phys., vol. 91:1212-1218, Jun. 12, 1989.
Maud A. W. Hinchee et al., Production of Transgenic Soybean Plants using Agrobacterium-Mediated DNA Transfer, Bio/Technology, vol. 6:915-922, Aug. 1988.
Marc De Block et al., Transformation of Brassica napus and Brassica oleracea Using Agrobacterium tumefaciens and the Expression of the bar and neo Genes in the Transgenic Plants, Plant Phys., vol. 91:694-701, Apr. 3, 1989.
N. P. Everett et al., Genetic Engineering of Sunflower (Helianthus Annuus L.), Bio/Technology, vol. 5:1201-1204, 1987.
S. D. Tanksley et al., RFLP Mapping in Plant Breeding: New Tools for an Old Science, Bio/Technology, vol. 7:257-264, Mar. 1989.
David Edwards et al., Multiple Genes Encoding the Conserved CCAAT-Box Transcription Factor Complex Are Expressed in Arabidopsis, Plant Phys., vol. 117:1015-1022, 1998.
Dennis E. McCabe et al., Stable Transformation of Soybean (Glycine Max) by Particle Acceleration, Bio/Technology, vol. 6:923-926, Aug. 1988.
Paul Christou et al., Stable Transformation of Soybean Callus by DNA-Coated Gold Particles, Plant Phys., vol. 87:671-674,1988.
Ming Cheng et al., Production of fertile transgenic peanut (Arachis hypogaea L.) plants using Agrobacterium tumefaciens, Plant Cell Reports, vol. 15;653-657, 1996.
A. H. McKently et al., Agrobacterium-mediated transformation of peanut (Arachis hypogaea L.) embryo axes and the development of transgenic plants, Plant Cell Reports, vol. 14:699-703, 1995.
Jan E. Grant et al., Transformation of peas (Pisum sativum L.) using immature cotyledons, Plant Cell Reports, vol. 15:254-258, 1995.
Benny Bytebier et al., T-DNA organization in tumor cultures and transgenic plants of the monocotyledon Asparagus officinalis, PNAS, vol. 84:5345-5349, Aug. 1987.
Yuechun Wan et al., Generation of Large Numbers of Independently Transformed Fertile Barley Plants, Plant Phys., vol. 104:37-48, 1994.
Carol A. Rhodes et al., Genetically Transformed Maize Plants from Protoplasts, Science, vol. 240:204-207, Apr. 8, 1988.
William J. Gordon-Kamm et al., Transformation of Maize Cells and Regeneration of Fertile Transgenic Plants, The Plant Cell, vol. 2:603-618, Jul. 1990.
Michael E. Fromm et al., Inheritance and Expression of Chimeric Genes in the Progeny of Transgenic Maize Plants, Bio/Technology, vol. 8:833-839, Sep. 1990.

(Continued)

*Primary Examiner*—Elizabeth F. McElwain

(57) ABSTRACT

The preparation and use of nucleic acid fragments useful in altering the oil phenotype in plants are disclosed. Recombinant DNA construct incorporating such nucleic acid fragments and suitable regulatory sequences can be used to create transgenic plants having altered lipid profiles. Methods for altering the oil phenotype in plants using such nucleic acid fragments also are disclosed.

3 Claims, 2 Drawing Sheets

OTHER PUBLICATIONS

Figure 1:
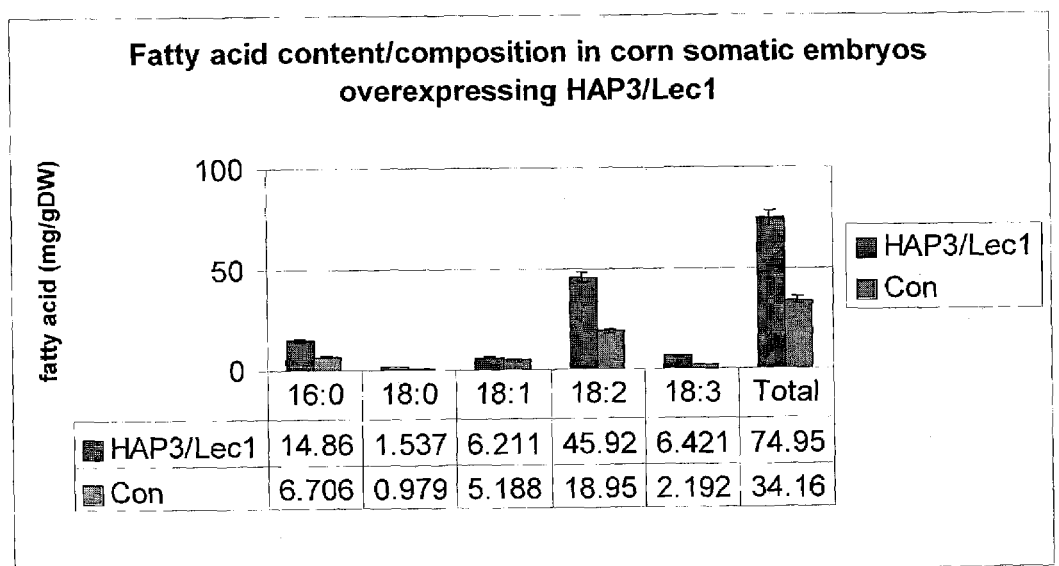

Michael G. Koziel et al., Field Performance of Elite Transgenic Maize Plants Expressing an Insecticidal Protein Derived from *Bacillus thuringiensis*, Bio/Technology, vol. 11:194-199, Feb. 11, 1993.

Charles L. Armstrong et al., Field Evaluation of European Corn Borer Control in Progeny of 173 Transgenic Corn Events Expressing an Insecticidal Protein from *Bacillus thuringiensis*, Crop Science, vol. 35:550-557, 1995.

David A. Somers et al., Fertile, Transgenic Oat Plants, Bio/Technology, vol. 10:1589-1594, Dec. 1992.

M. E. Horn et al., Transgenic plants of Orchardgrass (Dactylis glomerata L.) from protoplasts, Plant Cell Reports, vol. 7:469-472, 1988.

Kinya Toriyama et al., Haploid and diploid plant regeneration from protoplasts of anther callus in rice, Theor. Appl. Genet., vol. 73:16-19, 1986.

Sung Hun Park et al., T-DNA integration into genomic DNA of rice following Agrobacterium inoculation of isolated shoot apices. Plant Molecular Biology, vol. 32:1135-1148, 1996.

M. Abedinia et al., An Efficient Transformation System for the Australian Rice Cultivar, Jarrah, Aus. J. Plant Phys., vol. 24:133-141, 1997.

W. Zhang et al., Efficient regeneration of transgenic plants from rice protoplasts and correctly regulated expression of the foreign gene in the plants, Theor. Appl. Genet., vol. 76:835-840, 1988.

H. M. Zhang et al., Transgenic rice plants produced by electroporation-mediated plasmid uptake into protoplasts, Plant Cell Reports, vol. 7:379-384, 1988.

M. Battraw et al., Expression of a chimeric neomycin phosphotransferase II gene in first and second generation transgenic rice plants, Plant Science, vol. 86:191-202, 1992.

Paul Christou et al., Production of Transgenic Rice (Orzya Sativa L.) Plants from Agronomically Important Indica and Japonica Varieties Via Electric Discharge Particle Acceleration of Exogenous DNA into Immature Zygotic Embryos, Bio/Technology, vol. 9:957-962, Oct. 1991.

A. De La Pena et al., Transgenic rye plants obtained by injecting DNA into young floral tillers, Nature, vol. 325:274-276, Jan. 15, 1987.

Robert Bower et al., Transgenic sugarcane plants via microprojectile bombardment, The Plant Journal, vol. 2(3):409-416, 1992.

Zeng-Yu Wang et al., Transgenic Plants of Tall Fescue (Festuca Arundinacea Schreb.) Obtained by direct Gene Transfer to Protoplasts, Bio/Technology, vol. 10:691-696, Jun. 1992.

Vimla Vasil et al., Herbicide Resistant Fertile Transgenic Wheat Plants Obtained by Microprojectile Bombardment of Regenerable Embryogenic Callus, Bio/Technology, vol. 10:667-674, Jun. 1992.

William R. Marcotte, Jr. et al., Regulation of a Wheat Promoter by Abscisic Acid in Rice Protoplasts, Nature, vol. 335:454-457, Sep. 29, 1988.

Donald R. McCarty et al., Molecular Analysis of viviparous-1: An Abscisic Acid-Insensitive Mutant of Maize, The Plant Cell, vol. 1:523-532, May 1989.

Donald R. McCarty et al., The Viviparous-1 Developmental Gene of Maize Encodes a Novel Transcriptional Activator, Cell, vol. 66:895-905, Sep. 6, 1991.

Tsukaho Hattori et al., The Viviparous-1 gene and abscisic acid activate the C1 regulatory gene for anthocyanin biosynthesis during seed maturation in maize, Genes & Development, vol. 6:609-618, 1992.

Stephen A. Goff et al., Transactivation of anthocyanin biosynthetic genes following transfer of B regulatory genes into maize tissues, The EMBO Journa, vol. 9(8):2517-2522, 1990.

Paul Christou et al., Inheritance and expression of foreign genes in transgenic soybean plants, Proc. Natl. Acad. Scie USA, vol. 86:7500-7504, 1989.

* cited by examiner

ALTERATION OF OIL TRAITS IN PLANTS

This application claims the priority benefit of U.S. Provisional Application 60/301,913 filed Jun. 29, 2001, the disclosure of which is hereby incorporated by reference in its entirety.

FIELD OF THE INVENTION

The present invention is in the field of plant breeding and genetics and, in particular, relates to the alteration of oil phenotype in plants through the controlled expression of selective genes.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to produce economically large amounts of the desired lipid.

There are serious limitations to using mutagenesis to alter fatty acid composition. Screens will rarely uncover mutations that a) result in a dominant ("gain-of-function") phenotype, b) are in genes that are essential for plant growth, and c) are in an enzyme that is not rate-limiting and that is encoded by more than one gene. In cases where desired phenotypes are available in mutant corn lines, their introgression into elite lines by traditional breeding techniques is slow and expensive, since the desired oil compositions are likely the result of several recessive genes.

Recent molecular and cellular biology techniques offer the potential for overcoming some of the limitations of the mutagenesis approach, including the need for extensive breeding. Some of the particularly useful technologies are seed-specific expression of foreign genes in transgenic plants [see Goldberg et al (1989) *Cell* 56:149-160], and the use of antisense RNA to inhibit plant target genes in a dominant and tissue-specific manner [see van der Krol et al (1988) *Gene* 72:45-50]. Other advances include the transfer of foreign genes into elite commercial varieties of commercial oilcrops, such as soybean [Chee et al (1989) *Plant Physiol.* 91:1212-1218; Christou et al (1989) *Proc. Natl. Acad. Sci. U.S.A.* 86:7500-7504; Hinchee et al (1988) *Bio/Technology* 6:915-922; EPO publication 0 301 749 A2], rapeseed [De Block et al (1989) *Plant Physiol.* 91:694-701], and sunflower [Everett et al(1987) *Bio/Technology* 5:1201-1204], and the use of genes as restriction fragment length polymorphism (RFLP) markers in a breeding program, which makes introgression of recessive traits into elite lines rapid and less expensive [Tanksley et al (1989) *Bio/Technology* 7:257-264]. However, application of each of these technologies requires identification and isolation of commercially-important genes.

The regulation of transcription of most eukaryotic genes is coordinated through sequence-specific binding of proteins to the promoter region located upstream of the gene. Many of these protein-binding sequences have been conserved during evolution and are found in a wide variety of organisms. One such feature is the "CCAAT" sequence element.

(Edwards et al, 1998, *Plant Physiol.* 117:1015-1022). CCAAT boxes are a feature of gene promoters in many eukaryotes including several plant gene promoters.

HAP proteins constitute a large family of transcription factors first identified in yeast. They combine to from a heteromeric protein complex that activates transcription by binding to CCAAT boxes in eukaryotic promoters. The orthologous Hap proteins display a high degree of evolutionary conservation in their functional domains in all species studied to date (Li et al, 1991).

WO 00/28058 published on May 18, 2000 describes Hap3-type CCAAT-box binding transcriptional activator polynucleotides and polypeptides, especially, the leafy cotyledon 1 transcriptional activator (LEC1) polynucleotides and polypeptides.

WO 99/67405 describes leafy cotyledon1 genes and their uses.

The human, murine and plant homologues of CCAAT-binding proteins have been isolated and characterized based on their sequence similarity with their yeast counterparts (Li et al, 1991). This high degree of sequence homology translates remarkably into functional interchangeability among orthologue proteins of different species (Sinha et al, 1995). Unlike yeast, multiple forms of each HAP homolog have been identified in plants (Edwards et al, 1998).

Molecular and genetic analysis revealed HAP members to be involved in the control of diverse and critical biological processes ranging from development and cell cycle regulation to metabolic control and homeostasis (Lotan et al, 1998; Lopez et al, 1996). In yeast, HAPs are involved in the transcriptional control of metabolic relevant processes such as the regulation of catabolic derepression of cyc1 and other genes involved in respiration (Becker et al., 1991).

In mammalian systems, several reports describe HAPs as direct or indirect regulators of several important genes involved in lipid biosynthesis such as fatty acid synthase (Roder et al, 1997), farnesyl diphosphate (FPP) synthase (Jackson et al, 1995; Ericsson et al, 1996), glycerol-3-phosphate acyltransferase (GPA, Jackson et al, 1997), acetyl-CoA carboxylase (ACC, Lopez et al, 1996) and 3-hydroxy-3-methylglutaryl-coenzyme A (HMG-CoA) synthase (Jackson et al, 1995), among others.

In addition, other CCAAT-binding transcription factors have also been reported to be involved in different aspects of the control of lipid biosynthesis and adipocyte growth and differentiation in mammalian systems (see McKnight et al, 1989).

It appears that the currently available evidence to date points to a family of proteins of the CCAAT-binding transcription factors as important modulators of metabolism and lipid biosynthesis in mammalian systems. Such a determination has not been made for plant systems.

SUMMARY OF THE INVENTION

This invention concerns an isolated nucleotide fragment comprising a nucleic acid sequence selected from the group consisting of:

(a) a nucleic acid sequence encoding a fifth polypeptide having Hap2-like transcription factor activity, the fifth polypeptide having at least 70% identity based on the Clustal method of alignment when compared to a sixth polypeptide selected from the group consisting of SEQ ID NOs:2, 4, 5, 6,10, 12, 14, 16, 18, 20, 22, 24, 26, 28, 30, 32, 34, 36, 38,40, 42, 46, 48, 50, 52, 54, 56, 58, 60, 62, 64, 66, 68, 70, 72, 74, 76, 78, 80, 82, or 208, 210, 212, 214, or 216;

(b) a nucleic acid sequence encoding a seventh polypeptide having Hap5-like transcription factor activity, the seventh polypeptide having at least 80% identity based on the Clustal method of alignment when compared to an eighth polypeptide selected from the group consisting of SEQ ID NOs:84, 86, 88, 90, 92, 94, 96, 98, 100, 102, 104, 106, 108, 110, 112, 114, 116, 118, 120, 122, 124, 126, 128, or 221;

(c) a nucleic acid sequence encoding a seventeenth polypeptide having Hap3/Lec1-like activity, the seventeenth polypeptide having at least 70% identity based on the Clustal method of alignment when compared to a eighteenth polypeptide selected from the group consisting of SEQ ID NOs:130, 132, 134, or 136.

Also of interest are the complements of such nucleotide fragment as well as the use of such fragments or a part thereof in antisense inhibition or co-suppression in a transformed plant.

In a second embodiment, this invention concerns recombinant DNA constructs comprising such fragments, plants comprising such recombinant DNA constructs in their genome, seeds obtained from such plants and oil obtained from these seeds.

In a third embodiment, this invention concerns a method for altering oil phenotype in a plant which comprises: (a) transforming a plant with a recombinant DNA construct the invention, (b) growing the transformed plant under conditions suitable for expression of the recombinant DNA construct; and (c) selecting those transformed plants whose oil phenotype has been altered compared to the oil phenotype of an untransformed plant.

In a fourth embodiment, this invention concerns a method for altering oil phenotype in a plant which comprises:

(a) transforming a plant with a recombinant DNA construct comprising isolated nucleotide fragment comprising a nucleic acid sequence selected from the group consisting of:
(i) a nucleic acid sequence encoding a plant Hap3/Lec1 transcription factor having at least 60% identity based on the Clustal method of alignment when compared to a second polypeptide selected from the group consisting of even SEQ ID NOs: from 130 to 148, and SEQ ID NOs:195 and 196;
(ii) the complement of the nucleic acid sequence of (i);
(iii) the sequence of (i) or (ii) or a part thereof which is useful in antisense inhibition or co-suppression in a transformed plant;
(iv) a nucleic acid sequence encoding a plant Lec1-related CCAAT binding transcription factor having at least 60% identity based on the Clustal method of alignment when compared to a second polypeptide selected from the group consisting of even SEQ ID NOs: from 150 to 178, and SEQ ID NOs:197 to 202;
(v) the complement of the nucleic acid sequence of (iv);
(vi) the sequence of (iv) or (v) or a part thereof which is useful in antisense inhibition or co-suppression in a transformed plant;
wherein said nucleic acid sequence is operably linked to at least one regulatory sequence;
(b) growing the transformed plant under conditions suitable for expression of the recombinant DNA construct; and
(c) selecting those transformed plants whose oil phenotype has been altered compared to the oil phenotype of an untransformed plant.

In a fifth embodiment, this invention concerns a method for altering oil phenotype in a plant which comprises:
(a) transforming a plant with a recombinant DNA construct comprising an isolated nucleic acid fragment operably linked to at least one regulatory sequence wherein said fragment has a nucleic acid sequence encoding a polypeptide having a sequence identity of at least 60% based on the Clustal method of alignment when compared to a polypeptide selected from the group consisting of even SEQ ID NOs: from 2 to 178, and 206 to 214, and SEQ ID NOs:179 to 202, 216 to 219, 221, and 222;
(b) growing the transformed plant under conditions suitable for expression of the recombinant DNA construct; and
(c) selecting those transformed plants whose oil phenotype has been altered compared to the oil phenotype of an untransformed plant.

In a sixth embodiment, this invention concerns method of mapping genetic variations related to altered oil phenotypes in a plant comprising:
(a) crossing two plant varieties; and
(b) evaluating genetic variations with respect to nucleic acid sequences set forth in any one of the odd SEQ ID NOs: from 1 to 177, or 207 to 215, or SEQ ID NO:220 in progeny plants resulting from the cross of step (a) wherein the evaluation is made using a method selected from the group consisting of: RFLP analysis, SNP analysis, and PCR-based analysis.

In a seventh embodiment, this invention concerns a method of molecular breeding to obtain altered oil phenotypes in a plant comprising:
(a) crossing two plant varieties; and
(b) evaluating genetic variations with respect to nucleic acid sequences set forth in any one of the odd SEQ ID NOs: from 1 to 177, or 207 to 215, or SEQ ID NO:220 in progeny plants resulting from the cross of step (a) wherein the evaluation is made using a method selected from the group consisting of: RFLP analysis, SNP analysis, and PCR-based analysis.

In an eighth embodiment, this invention concerns a method for altering oil phenotype in a plant which comprises:
(a) transforming a plant with a recombinant DNA construct comprising isolated nucleotide fragment comprising a nucleic acid sequence selected from the group consisting of:
(i) a nucleic acid sequence encoding a plant Hap3/Lec1 transcription factor having at least 70% identity based on the Clustal method of alignment when compared to a second polypeptide selected from the group consisting of SEQ ID NOs:130 to 148, and SEQ ID NOs:195, 196, and 206;
(ii) the complement of the nucleic acid sequence of (iv);
(iii) the sequence of (iv) or (v) or a part thereof which is useful in antisense inhibition or co-suppression in a transformed plant;
(b) growing the transformed plant under conditions suitable for expression of the recombinant DNA construct; and
(c) selecting those transformed plants whose oil phenotype has been altered compared to the oil phenotype of an untransformed plant.

In a ninth embodiment, this invention concerns a method to isolate nucleic acid fragments associated with altering oil phenotype in a plant which comprises:
(a) comparing even SEQ ID NOs: from 2 to 178, and 206 to 214, and SEQ ID NOs:179 to 202, 216 to 219, 221, and 222 with other polypeptide sequences for the purpose of identifying polypeptides associated with altering oil phenotype in a plant;
(b) identifying the conserved sequences(s) or 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with altering oil phenotype by sequence dependent protocols.

BRIEF DESCRIPTION OF THE FIGURES AND SEQUENCE LISTINGS

The invention can be more fully understood from the following detailed description and the accompanying drawings and Sequence Listing which form a part of this application.

FIG. 1 shows the fatty acid composition of maize somatic embryos over-expressing Hap3/Lec1 (solid bars, "Hap3/Lec1") compared to control embryos (striped bars, "con"). A ubiquitin promoter was used to drive Hap3/Lec1 expression in maize embryogenic callus. More than ten different events were analyzed by GC for fatty acid content/composition and compared to controls transformed with the selectable marker (BAR gene) plasmid alone. The somatic embryos over-expressing Lec1 contain elevated fatty acid contents averaging 119% over control oil levels.

Figure 2:
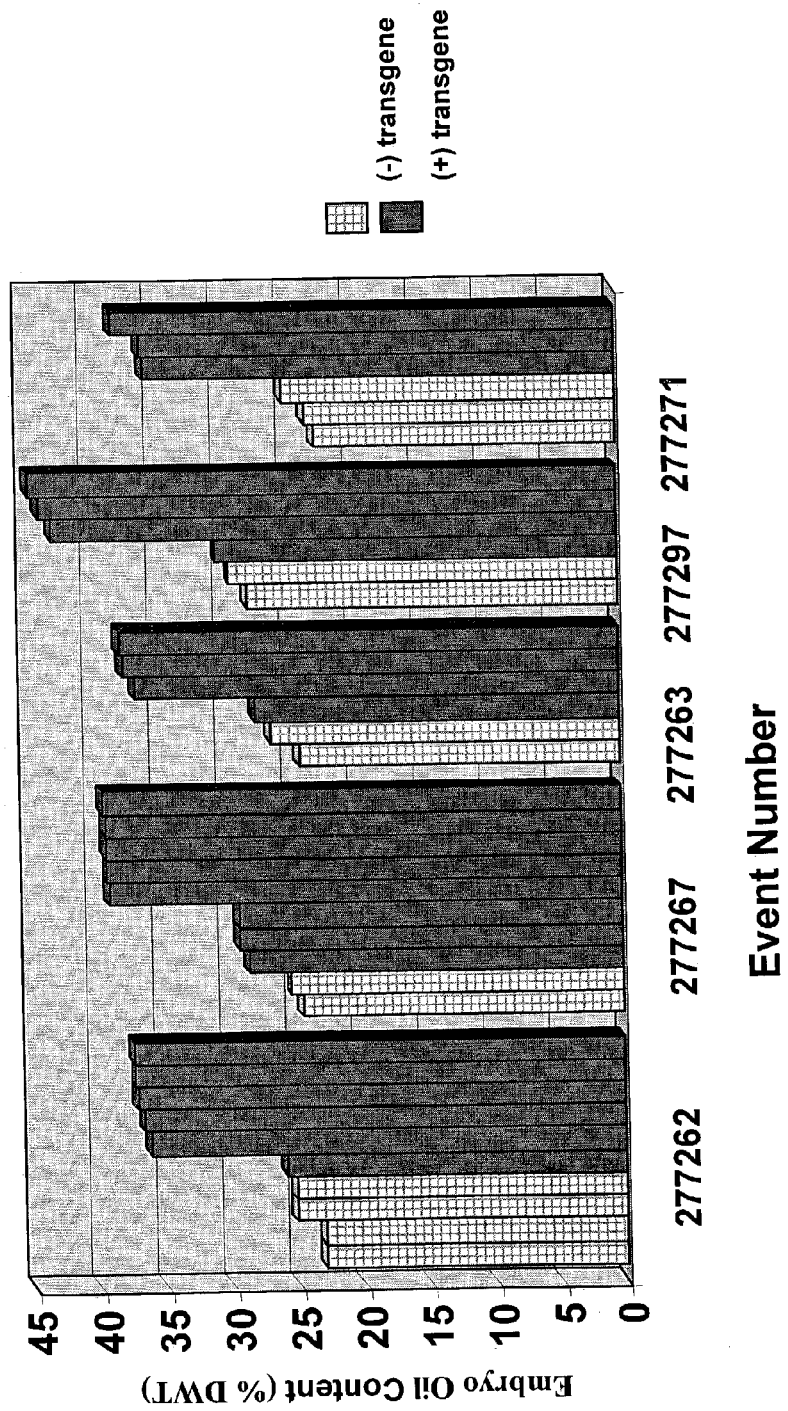

FIG. 2 shows the fatty acid composition of maize embryos transformed with additional copies of Hap3/Lec1 (solid bars, "+transgene") compared to control embryos (cross-hatched bars, "−transgene"). An oleosin promoter was used to direct the expression of a transgenic copy of Hap3/Lec 1. More than twenty events producing segregating T1 seed were analyzed by NMR for embryo oil content. Six to twelve embryos were analyzed for each of five different events. Some embryos within each event contained elevated oil content. The same embryos from these five events were analyzed by PCR to determine the presence or absence of the Lec1 construct. Embryos with high oil were always found to contain the Lec1 construct (darkly shaded bars), whereas embryos with normal levels of oil were typically found not to contain the Lec1 construct (cross-hatched bars). These data demonstrate the presence of the Lec1 gene does lead to increased oil in the embryo. It is believed that embryos containing sharply higher levels of oil were homozygous for the Lec1 construct, as these events were segregating 1:2:1. The oil concentration in the embryos containing the Lec1 construct greatly surpassed any increase previously achieved through enzymatic modification of the fatty acid biosynthetic pathway, with some embryos containing an average increase of 56% in embryo oil content.

Table 1 lists the polypeptides that are described herein, the designation of the cDNA clones that comprise the nucleic acid fragments encoding polypeptides representing all or a substantial portion of these polypeptides (for the corresponding SEQ ID NO: identifier as used in the attached Sequence Listing see Table 3). The sequence descriptions and Sequence Listing attached hereto comply with the rules governing nucleotide and/or amino acid sequence disclosures in patent applications as set forth in 37 C.F.R. §1.821-1.825.

TABLE 1

Genes Involved in Alteration of Oil Traits in Plants

| Gene Name | Clone | Plant |
|---|---|---|
| Hap2a transcription factor | ncs.pk0013.c4 | Catalpa [*Catalpa speciosa*] |
| Hap2c-like transcription factor | etr1c.pk006.f9 | cattail [*Typha latifolia*] |
| Hap2a transcription factor | vmb1na.pk015.d18:fis | grape [*Vitis* sp.] |
| Hap2a transcription factor | vpl1c.pk008.o5:fis | grape [*Vitis* sp.] |
| Hap2c-like transcription factor | vdb1c.pk001.m5:fis | grape [*Vitis* sp.] |
| Hap2 transcription factor | cho1c.pk004.b19:fis | maize [*Zea mays*] |
| Hap2 transcription factor | p0015.cdpgu90r:fis | maize [*Zea mays*] |
| Hap2a transcription factor | cta1n.pk0010.f3:fis | maize [*Zea mays*] |
| Hap2a-like transcription factor | cco1n.pk0014.d4:fis | maize [*Zea mays*] |
| Hap2a-like transcription factor | cco1n.pk086.d20:fis | maize [*Zea mays*] |
| Hap2b transcription factor | p0126.cnlau71r:fis | maize [*Zea mays*] |
| Hap2b-like transcription factor | p0104.cabav52r | maize [*Zea mays*] |
| Hap2c transcription factor | cho1c.pk007.l21:fis | maize [*Zea mays*] |
| Hap2c-like transcription factor | contig of: cca.pk0026.d6 cen3n.pk0061.e10:fis cen3n.pk0135.c2 cho1c.pk001.n24 p0092.chwae40r | maize [*Zea mays*] |
| Hap2c-like transcription factor | cpf1c.pk006.e3:fis | maize [*Zea mays*] |
| Hap2c-like transcription factor | contig of: cr1n.pk0080.g6 p0003.cgpge51r | maize [*Zea mays*] |
| Hap2c-like transcription factor | p0015.cpdfm55r:fis | maize [*Zea mays*] |
| Hap2c-like transcription factor | p0083.cldct11r:fis | maize [*Zea mays*] |

TABLE 1-continued

Genes Involved in Alteration of Oil Traits in Plants

| Gene Name | Clone | Plant |
|---|---|---|
| Hap2c-like transcription factor | p0083.cldeu68r:fis | maize [*Zea mays*] |
| Hap2a transcription factor | pps1c.pk001.h3:fis | prickly poppy [*Argemone mexicana*] |
| Hap2c-like transcription factor | pps1c.pk007.j21:fis | prickly poppy [*Argemone mexicana*] |
| Hap2 transcription factor | rr1.pk0030.f7:fis | rice [*Oryza sativa*] |
| Hap2a transcription factor | r1s72.pk0023.c8:fis | rice [*Oryza sativa*] |
| Hap2a-like transcription factor | rca1n.pk002.c15 | rice [*Oryza sativa*] |
| Hap2a-like transcription factor | rds3c.pk001.g9 | rice [*Oryza sativa*] |
| Hap2b transcription factor | rca1n.pk002.j3:fis | rice [*Oryza sativa*] |
| Hap2c-like transcription factor | rca1n.pk029.n22:fis | rice [*Oryza sativa*] |
| Hap2c-like transcription factor | rl0n.pk131.j17 | rice [*Oryza sativa*] |
| Hap2a transcription factor | sdp3c.pk018.b9:fis | soybean [*Glycine max*] |
| Hap2a transcription factor | sfl1.pk0102.h8 | soybean [*Glycine max*] |
| Hap2a transcription factor | srr3c.pk001.l10:fis | soybean [*Glycine max*] |
| Hap2a-like transcription factor | sdp2c.pk003.o5:fis | soybean [*Glycine max*] |
| Hap2b transcription factor | sif1c.pk001.m16:fis | soybean [*Glycine max*] |
| Hap2c-like transcription factor | src1c.pk003.o16:fis | soybean [*Glycine max*] |
| Hap2c-like transcription factor | src3c.pk012.m6:fis | soybean [*Glycine max*] |
| Hap2c-like transcription factor | hss1c.pk011.h10:fis | sunflower [*Helianthus* sp.] |
| Hap2 transcription factor | wr1.pk0094.f2:fis | wheat-common [*Triticum aestivum*] |
| Hap2a-like transcription factor | wre1n.pk0143.h2:fis | wheat-common [*Triticum aestivum*] |
| Hap2b transcription factor | wds1f.pk002.p21:fis | wheat-common [*Triticum aestivum*] |
| Hap2c transcription factor | contig of: wdi1c.pk002.b10 wr1.pk0153.c7:fis | wheat-common [*Triticum aestivum*] |
| Hap2c-like transcription factor | wre1n.pk0066.e4:fis | wheat-common [*Triticum aestivum*] |
| Hap2c-like transcription factor | ncs.pk0013.c4:fis | catalpa [*Catalpa speciosa*] |
| Hap2c-like transcription factor | p0117.chc1n94r:fis | maize [*Zea mays*] |
| Hap2c-like transcription factor | rdi2c.pk011.f19:fis | rice [*Oryza sativa*] |
| Hap2c-like transcription factor | sfl1.pk0101.g7:fis | soybean [*Glycine max*] |
| Hap2c-like transcription factor | wdi1c.pk002.b10:fis | wheat-common [*Triticum aestivum*] |
| Hap5c-like transcription factor | ect1c.pk001.k17:fis | Canna [*Canna edulis*] |
| Hap5a-like transcription factor | vrr1c.pk004.o20:fis | grape [*Vitis* sp.] |
| Hap5a-like transcription factor | clm1f.pk001.k17:fis | maize [*Zea mays*] |
| Hap5b-like transcription factor | cde1n.pk003.a5:fis | maize [*Zea mays*] |
| Hap5b-like transcription factor | cen3n.pk0164.a10:fis | maize [*Zea mays*] |
| Hap5b-like transcription factor | p0118.chsbc77r | maize [*Zea mays*] |
| Hap5c-like transcription factor | cco1n.pk055.o18:fis | maize [*Zea mays*] |
| Hap5c-like transcription factor | cho1c.pk001.l23:fis | maize [*Zea mays*] |
| Hap5c-like transcription factor | cse1c.pk001.h6:fis | maize [*Zea mays*] |
| Hap5a-like transcription factor | rlm3n.pk005.d20:fis | rice [*Oryza sativa*] |

TABLE 1-continued

Genes Involved in Alteration of Oil Traits in Plants

| Gene Name | Clone | Plant |
|---|---|---|
| Hap5b-like transcription factor | rr1.pk0003.a3:fis | rice [*Oryza sativa*] |
| Hap5b-like transcription factor | rr1.pk0039.d4:fis | rice [*Oryza sativa*] |
| Hap5c-like transcription factor | rca1n.pk021.b20:fis | rice [*Oryza sativa*] |
| Hap5a-like transcription factor | sdp2c.pk029k17:fis | soybean [*Glycine max*] |
| Hap5a-like transcription factor | sdp2c.pk044.e5:fis | soybean [*Glycine max*] |
| Hap5b-like transcription factor | sgs4c.pk004.j2 | soybean [*Glycine max*] |
| Hap5b-like transcription factor | src3c.pk002.h4:fis | soybean [*Glycine max*] |
| Hap5b-like transcription factor | src3c.pk009.b15:fis | soybean [*Glycine max*] |
| Hap5b-like transcription factor | src3c.pk019.d4:fis | soybean [*Glycine max*] |
| Hap5c-like transcription factor | sls1c.pk032.j4:fis | soybean [*Glycine max*] |
| Hap5 transcription factor | wdk2c.pk009.e4:fis | wheat-common [*Triticum aestivum*] |
| Hap5a-like transcription factor | contig of: w1m96.pk036.j11 w1m96.pk060.d5:fis | wheat-common [*Triticum aestivum*] |
| Hap5c-like transcription factor | wle1n.pk0076.h7:fis | wheat-common [*Triticum aestivum*] |
| Hap5c-like transcription factor | sgs4c.pk004.j2:fis | soybean [*Glycine max*] |
| Lec1-embryonic type | eas1c.pk003.e16 | amaranth [*Amaranthus retroflexus*] |
| Lec1-embryonic type | fds1n.pk008.m14 | balsam pear [*Momordica charantia*] |
| Lec1-embryonic type | p0015.cdpgp75rb:fis | maize [*Zea mays*] |
| Lec1-embryonic type | p0083.clder12r:fis | maize [*Zea mays*] |
| Lec1-embryonic type | pps1c.pk002.l19 | prickly poppy [*Argemone mexicana*] |
| Lec1-embryonic type | Contig of: scb1c.pk004.j10 se1.pk0042.d8:fis | soybean [*Glycine max*] |
| Lec1-embryonic type | se2.11d12:fis | soybean [*Glycine max*] |
| Lec1-embryonic type | ses2w.pk0015.a4:fis | soybean [*Glycine max*] |
| Lec1-embryonic type | vs1n.pk013.m13:fis | vernonia [*Vernonia mespilifolia*] |
| Lec1-embryonic type | wdk3c.pk023.h15:fis | wheat-common [*Triticum aestivum*] |
| Lec1-related CCAAT binding protein | ect1c.pk007.p18:fis | Canna [*Canna edulis*] |
| Lec1-related CCAAT binding protein | fds.pk0003.h5:fis | balsam pear [*Momordica charantia*] |
| Lec1-related CCAAT binding protein | eef1c.pk004.c8:fis | eucalyptus [*Eucalyptus grandis*] |
| Lec1-related CCAAT binding protein | cbn10.pk0005.e6:fis | maize [*Zea mays*] |
| Lec1-related CCAAT binding protein | p0006.cbysa51r:fis | maize [*Zea mays*] |
| Lec1-related CCAAT binding protein | rl0n.pk0061.c8:fis | rice [*Oryza sativa*] |
| Lec1-related CCAAT binding protein | rsl1n.pk002.g10:fis | rice [*Oryza sativa*] |
| Lec1-related CCAAT binding protein | ses4d.pk0037.e3:fis | soybean [*Glycine max*] |
| Lec1-related CCAAT binding protein | src2c.pk003.i13:fis | soybean [*Glycine max*] |
| Lec1-related CCAAT binding protein | src2c.pk011.m12:fis | soybean [*Glycine max*] |
| Lec1-related CCAAT binding protein | src2c.pk025.b3:fis | soybean [*Glycine max*] |
| Lec1-related CCAAT binding protein | src3c.pk028.j21:fis | soybean [*Glycine max*] |
| Lec1-related CCAAT binding protein | wkm1c.pk0002.d7:fis | wheat-common [*Triticum aestivum*] |

TABLE 1-continued

Genes Involved in Alteration of Oil Traits in Plants

| Gene Name | Clone | Plant |
|---|---|---|
| Lec1-related CCAAT binding protein | wlk8.pk0001.e10:fis | wheat-common [*Triticum aestivum*] |
| Lec1-related CCAAT binding protein | w1m96.pk037.k9:fis | wheat-common [*Triticum aestivum*] |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

All patents, patent applications and publications which are referred to herein are incorporated by reference in their entirety.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for g or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool: Altschul et al (1993) *J. Mol Biol.* 215:403-410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell "Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. The term "recombinant DNA construct" and "recombinant DNA construct" are used interchangeably herein. A recombinant DNA construct comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or recombinant DNA constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al, (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al, (1987) *Nature* (London) 327:70-73; U.S. Pat. No. 4,945,050), or an Agrobacterium-mediated method using an appropriate Ti plasmid containing the transgene (Ishida Y. et al, 1996, *Nature Biotech*. 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises an isolated polynucleotide operably linked to at least one regulatory sequence. The term also embraces an isolated polynucleotide comprising a region encoding all or part of a functional RNA and at least one of the naturally occurring regulatory sequences directing expression in the source (e.g., organism) from which the polynucleotide was isolated, such as, but not limited to, an isolated polynucleotide comprising a nucleotide sequence encoding a herbicide resistant target gene and the corresponding promoter and 3' end sequences directing expression in the source from which sequences were isolated.

A "transgene" is a recombinant DNA construct that has been introduced into the genome by a transformation procedure.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

The terms "recombinant construct", "expression construct", "recombinant expression construct", "recombinant DNA construct" and "recombinant DNA construct" are used interchangeably herein. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al, (1985) *EMBO J.* 4:2411-2418; De Almeida et al, (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al (1998) *Plant Cell* 10:1747-1757).

Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al (1995) *Proc. Natl. Acad. Sci USA* 92:8149-8153; Bensen et al (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

The terms Hap3, Lec1, and Hap3/Lec1 are used interchangeably herein and refer to a class of transcription factors. The Hap3/Lec1 class is part of a broader family that includes other transcription factors such as Hap5, Hap2, and Lec1-CCAAT. The terms Hap3-like, Lec1-like, Hap3/Lec1-like, Hap5-like, Hap2-like, Lec1-CCAAT-like, etc. refer to any transcription factors that share sequence identity as disclosed herein and/or functionality with the nucleotide sequences and the corresponding amino acid sequences encoded by such nucleotide sequences disclosed in the present invention.

Surprisingly and unexpectedly, it has been found that there are a variety of regulatory/structural nucleic acid fragments, which heretofore have not been associated with altering oil phenotype in plants, that appear to be useful in altering oil phenotype in plants. In addition to the CCAAT-binding transcription factors, other proteins which heretofore have not been associated with altering oil phenotype in plants, have been identified. The nucleic acids identified encode a diverse class of regulatory and structural polypeptides whose expression correlates with altered oil phenotypes in plants. Altering the expression of these polypeptides would be expected to have an effect in altering oil accumulation in plants.

Other protein classes identified herein include:
 a Hap2 transcription factor;
 a Hap5 transcription factor;
 a Hap3/Lec1 or Lec1-CCAAT binding transcription factor.

They can be characterized as an isolated nucleotide fragment comprising a nucleic acid sequence selected from the group consisting of:

(a) a nucleic acid sequence encoding a fifth polypeptide having Hap2-like transcription factor activity, the fifth polypeptide having at least 70% identity based on the Clustal method of alignment when compared to a sixth polypeptide selected from the group consisting of SEQ ID NOs:2, 4, 5, 6, 10, 12, 14, 16, 18, 20, 22, 24, 26, 28, 30, 32, 34, 36, 38, 40, 42, 46, 48, 50, 52, 54, 56, 58, 60, 62, 64, 66, 68, 70, 72, 74, 76, 78, 80, 82, or 208, 210, 212, 214, or 216; or (b) a nucleic acid sequence encoding a seventh polypeptide having Hap5-like transcription factor activity, the seventh polypeptide having at least 80% identity based on the Clustal method of alignment when compared to an eighth polypeptide selected from the group consisting of SEQ ID NOs:84, 86, 88, 90, 92, 94, 96, 98, 100, 102, 104, 106, 108, 110, 112, 114, 116, 118, 120, 122, 124, 126, 128, or 221; or (c) a nucleic acid sequence encoding a seventeenth polypeptide having Hap3/Lec1-like activity, the seventeenth polypeptide having at least 70% identity based on the Clustal method of alignment when compared to a eighteenth polypeptide selected from the group consisting of SEQ ID NOs:130, 132, 134, or 136.

It is understood by one skilled in the art that other percent identity ranges may be useful in the above mentioned characterization. Useful percent identities would include, but not be limited to, 45%, 55%, 60%, 65%, 70%, 75%, 80%, 85%, 90%, 95% and all integer percentages from 45 to 100%.

The complement of the nucleotide fragments of this inventions are encompassed within the scope of this invention.

Those skilled in the art with also appreciate that the nucleotide fragment of this invention and/or the complement thereof can be used in whole or in part in antisense inhibition or co-suppression of a transformed plant.

In a more preferred embodiment, the first polypeptide mentioned above is as follows with respect to each part, the first polypeptide in
 part (a) is a Hap2 transcription factor;
 part (b) is a Hap5 transcription factor;
 part (c) is a Hap3/Lec1 or Lec1-CCAAT binding transcription factor Lec1 homologs may be further identified by using conserved sequence motifs. The following amino acid sequence (given in single letter code, with "x" representing any amino acid). Under lined amino acids are those that are conserved in Lec1 but not found in Lec1-related proteins. REQDxxMPxANVxRIMRxxLPxxAKISD-DAKExIQECVSExISFxTxEANxRCxx xxRKTxxxE (SEQ ID NO:223).

In a further embodiment, this invention encompasses recombinant DNA construct comprising any of the isolated nucleic acid fragments of the invention or complement thereof operably linked to at least one regulatory sequence. It is also understood that recombinant DNA constructs comprising such fragments or complements thereof or parts of either can be used in antisense inhibition or suppression of a transformed plant.

Also within the scope of this invention is a plant comprising in its genome a recombinant DNA construct as described herein. Recombinant DNA constructs designed for plant expression such as those described herein can be introduced into a plant cell in a number of art-recognized ways. Those skilled in the art will appreciate that the choice of method might depend on the type of plant (i.e, monocot or dicot) and/or organelle (i.e., nucleus, chloroplast, mitochondria) targeted for transformation. Suitable methods for transforming plant cells include microinjection, electroporation, Agrobacterium mediated transformation, direct gene transfer and particle-accelerated or "gene gun" transformation technology as is discussed above.

Examples of plants which can be transformed include, but are not limited to, corn, soybean, wheat, rice, canola, Brassica, sorghum, sunflower, and coconut.

The regeneration, development and cultivation of plants from single plant protoplast transformants or from various transformed explants is well known in the art (Weissbach and Weissbach, In, Methods for Plant Molecular Biology, (Eds.), Academic Press, Inc., San Diego, Calif. (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated. Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834 5,416,011, McCabe et. al., *BiolTechnology* 6:923 (1988), Christou et al., *Plant Physiol*. 87:671-674 (1988)); Brassica (U.S. Pat. No. 5,463,174);

peanut (Cheng et al., *Plant Cell Rep.* 15:653-657 (1996), McKently et al., *Plant Cell Rep.* 14:699-703 (1995)); papaya; and pea (Grant et al., Plant *Cell Rep.* 15:254-258, (1995)).

Transformation of monocotyledons using electroporation, particle bombardment, and Agrobacterium have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603-618 (1990), Fromm et al., *BiolTechnology* 8:833 (1990), Koziel et al., *BiolTechnology* 11: 194, (1993), Armstrong et al., *Crop Science* 35:550-557 (1995)); oat (Somers et al., *BiolTechnology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., *Bio/Technology*9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

Seeds obtained from such plants and oil obtained from these seeds constitute another aspect of the present invention.

In an even further aspect, the invention concerns a method for altering oil phenotype in a plant which comprises:

(a) transforming a plant with a recombinant DNA construct of the invention;

(b) growing the transformed plant under conditions suitable for expression of the recombinant DNA construct; and (c) selecting those transformed plants whose oil phenotype has been altered compared to the oil phenotype of an untransformed plant.

In a more specific embodiment, the invention concerns a method for altering oil phenotype in a plant which comprises:

(a) transforming a plant with a recombinant DNA construct comprising isolated nucleotide fragment comprising a nucleic acid sequence selected from the group consisting of:

(i) a nucleic acid sequence encoding a plant Hap3/Lec1 transcription factor having at least 60% identity based on the Clustal method of alignment when compared to a second polypeptide selected from the group consisting of even SEQ ID NOs: from 130 to 148, and SEQ ID NOs:195 and 196;

(ii) the complement of the nucleic acid sequence of (i);

(iii) the sequence of (i) or (ii) or a part thereof which is useful in antisense inhibition or co-suppression in a transformed plant;

(iv) a nucleic acid sequence encoding a plant Lec 1-related CCAAT binding transcription factor having at least 60% identity based on the Clustal method of alignment when compared to a second polypeptide selected from the group consisting of even SEQ ID NOs: from 150 to 178, and SEQ ID NOs:197 to 202;

(v) the complement of the nucleic acid sequence of (vii);

(vi) the sequence of (iv) or (v) or a part thereof which is useful in antisense inhibition or co-suppression in a transformed plant;

wherein said nucleic acid sequence is operably linked to at least one regulatory sequence;

(b) growing the transformed plant under conditions suitable for expression of the recombinant DNA construct; and (c) selecting those transformed plants whose oil phenotype has been altered compared to the oil phenotype of an untransformed plant.

It is understood by one skilled in the art that other percent identity ranges may be useful in the above mentioned method. Useful percent identities would include, but not be limited to, 45%, 55%, 60%, 65%, 70%, 75%, 80%, 85%, 90%, 95% and all integer percentages from 45 to 100%.

In an even further aspect, this invention concerns a method to isolate nucleic acid fragments associated with altering oil phenotype in a plant which comprises:

(a) comparing even SEQ ID NOs: from 2 to 178, and 206 to 214, and SEQ ID NOs:179 to 202, 216 to 219, 221, and 222 with other polypeptide sequences for the purpose of identifying polypeptides associated with altering oil phenotype in a plant;

(b) identifying the conserved sequences(s) or 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with altering oil phenotype by sequence dependent protocols.

In a most preferred aspect, this invention concerns a method for altering oil phenotype in a plant which comprises:

(a) transforming a plant with a recombinant DNA construct comprising an isolated nucleic acid fragment operably linked to at least one regulatory sequence wherein said fragment has a nucleic acid sequence encoding a polypeptide having a sequence identity of at least 60% based on the Clustal method of alignment when compared to a polypeptide selected from the group consisting of even;

(b) growing the transformed plant under conditions suitable for expression of the recombinant DNA construct; and (c) selecting those transformed plants whose oil phenotype has been altered compared to the oil phenotype of an untransformed plant.

It is understood by one skilled in the art that other percent identity ranges may be useful in the above mentioned method. Useful percent identities would include, but not be limited to, 45%, 55%, 60%, 65%, 70%, 75%, 80%, 85%, 90%, 95% and all integer percentages from 45 to 100%.

In another aspect, this invention also concerns a method of mapping genetic variations related to altered oil phenotypes in a plant comprising:

(a) crossing two plant varieties; and (b) evaluating genetic variations with respect to nucleic acid sequences set forth in any one of the odd SEQ ID NOs: from 1 to 177, or 207 to 215, or SEQ ID NO:220 in progeny plants resulting from the cross of step (a) wherein the evaluation is made using a method selected from the group consisting of: RFLP analysis, SNP analysis, and PCR-based analysis.

In another embodiment, this invention concerns a method of molecular breeding to obtain altered oil phenotypes in a plant comprising:

(a) crossing two plant varieties; and (b) evaluating genetic variations with respect to nucleic acid sequences set forth in any one of the odd SEQ ID NOs: from 1 to 177, or 207 to 215, or SEQ ID NO:220 in progeny plants resulting from the cross of step (a) wherein the evaluation is made using a method selected from the group consisting of: RFLP analysis, SNP analysis, and PCR-based analysis.

The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. RFLP analysis takes advantage of this and utilizes Southern blotting with a probe corresponding to the gene of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms: ("RFLPs"). RFLPs have been widely used in human and plant genetic analyses (Glassberg, UK Patent Application 2135774; Skolnick et al, Cytogen. Cell Genet. 32:58-67 (1982); Botstein et al, Ann. J. Hum. Genet. 32:314-331 (1980); Fischer et al (PCT Application WO 90/13668; Uhlen, PCT Appliction WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W. H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, new polymorphisms can be identified by sequencing random genomic or cDNA molecules. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism or by other biochemical interpretation. SNPs can be sequenced by a number of methods. Two basic methods may be sued for DNA sequencing, the chain termination method of Sanger et al, Proc. Natl. Acad. Sci. (U.S.A.) 74:5463-5467 (1977), and the chemical degradation method of Maxam and Gilbert, Proc. Natl., Acad. Sci. (U.S.A.) 74: 560-564 (1977).

Polymerase chain reaction ("PCR") is a powerful technique used to amplify DNA millions of fold, by repeated replication of a template, in a short period of time. (Mullis et al, Cold Spring Harbor Symp. Quant. Biol. 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

Furthermore, single point mutations can be detected by modified PCR techniques such as the ligase chain reaction ("LCR") and PCR-single strand conformational polymorphisms ("PCR-SSCP") analysis. The PCR technique can also be sued to identify the level of expression of genes in extremely small samples of material, e.g., tissues or cells from a body. The technique is termed reverse transcription-PCR ("RT-PCR").

In another embodiment, this invention concerns a method for altering oil phenotype in a plant which comprises:

(a) transforming a plant with a recombinant DNA construct comprising isolated nucleotide fragment comprising a nucleic acid sequence selected from the group consisting of:

(i) a nucleic acid sequence encoding a plant Hap3/Lec1 transcription factor having at least 70% identity based on the Clustal method of alignment when compared to a second polypeptide selected from the group consisting of SEQ ID NOs:130 to 148, and SEQ ID NOs:195 and 196;

(ii) the complement of the nucleic acid sequence of (iv);

(iii) the sequence of (iv) or (v) or a part thereof which is useful in antisense inhibition or co-suppression in a transformed plant;

(b) growing the transformed plant under conditions suitable for expression of the recombinant DNA construct; and (c) selecting those transformed plants whose oil phenotype has been altered compared to the oil phenotype of an untransformed plant.

It is understood by one skilled in the art that other percent identity ranges may be useful in the above mentioned method. Useful percent identities would include, but not be limited to, 45%, 50%, 55%, 60%, 65%, 75%, 80%, 85%, 90%, 95% and all integer percentages from 45 to 100%.

In another aspect this invention concerns a method to isolate nucleic acid fragments associated with altering oil phenotype in a plant which comprises:

(a) comparing SEQ ID NOs:130 to 148, and SEQ ID NOs:195, 196, and 206 with other polypeptide sequences for the purpose of identifying polypeptides associated with altering oil phenotype in a plant;

(b) identifying the conserved sequences(s) or 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with altering oil phenotype by sequence dependent protocols.

EXAMPLES

The present invention is further defined in the following Examples, in which parts and percentages are by weight and degrees are Celsius, unless otherwise stated. The disclosure of each reference set forth herein is incorporated herein by reference in its entirety.

Example 1

Composition of cDNA Libraries; Isolation and Sequencing of cDNA Clones cDNA libraries representing mRNAs from various plant tissues were prepared. The characteristics of the libraries are described below.

TABLE 2 cDNA Libraries from Various Plants

| Library | Tissue | Clone |
|---|---|---|
| cbn10 | Corn Developing Kernel (Embryo and Endosperm); 10 Days After Pollination | cbn10.pk0005.e6:fis cbn10.pk0064.e6 |
| cc71se-a | Corn Callus Type II Tissue, Somatic Embryo Formed | cc71se-a.pk0002.e11:fis |
| cc71se-b | Corn Callus Type II Tissue, Somatic Embryo Formed | cc71se-b.pk0018.e4:fis |
| cca | Corn Callus Type II Tissue, Undifferentiated, Highly Transformable | cca.pk0026.d6 |
| ccase-b | Corn Callus Type II Tissue, Somatic Embryo Formed, Highly Transformable | ccase-b.pk0003.b9:fis |
| cco1n | Corn Cob of 67 Day Old Plants Grown in Green House* | cco1n.pk062.j7 cco1n.pk086.d20:fis cco1n.pk0014.d4:fis cco1n.pk055.o18 cco1n.pk089.g17 cco1n.pk068.f18:fis |
| cde1c | Corn (*Zea Mays*, B73) developing embryo 20 DAP | cde1c.pk003.o22:fis |
| cde1n | Corn (*Zea mays*, B73) developing embryo 20 DAP normalized | cde1n.pk003.a5 cde1n.pk001.n24:fis |
| cdo1c | Corn (*Zea mays* L.) ovary, 5 days after silking (includes pedicel and glumes) | cdo1c.pk001.c1:fis |
| ceb3 | Corn Embryo 20 Days After Pollination | ceb3.pk0012.a7 |
| ceb5 | Corn Embryo 30 Days After Pollination | ceb5.pk0081.b4 |
| cen3n | Corn Endosperm 20 Days After Pollination* | cen3n.pk0164.a10 cen3n.pk0044.b8:fis cen3n.pk0112.e10:fis |
| cho1c | Corn (*Zea mays* L., Alexho Synthetic High Oil) embryo 20 DAP | cho1c.pk003.p17:fis cho1c.pk003.n23 cho1c.pk004.b19:f15 cho1c.pk007.l21:fis cho1c.pk001.l23:fis cho1c.pk009.g10 |
| clm1f | Corn (*Zea mays*, B73) leaf at V6-VT (full length) | clm1f.pk001.k17 clm1f.pk002.o13:fis |
| cpd1c | Corn (*Zea mays* L.) pooled BMS treated with chemicals related to protein kinases | cpd1c.pk011.15:fis cpd1c.pk008.e21 |
| cpf1c | Corn (*Zea mays* L.) pooled BMS treated with chemicals related to protein synthesis | cpf1c.pk006.e3:fis |

TABLE 2-continued cDNA Libraries from Various Plants

| Library | Tissue | Clone |
|---|---|---|
| cpj1c | Corn (*Zea mays* L.) pooled BMS treated with chemicals related to membrane ionic force | cpj1c.pk005.m20:fis |
| cr1n | Corn Root From 7 Day Old Seedlings* | cr1n.pk0080.g6 |
| cse1c | Corn (*Zea mays* L.) seedling at V2 stage treated with Ethylene collected at 6 hr, 23 hr, 72 hr | cse1c.pk001.h6 |
| cta1n | Corn Tassel* | cta1n.pk0070.f3:fis<br>cta1n.pk0074.h11 |
| ctn1c | Corn (*Zea mays* L., B73) night harvested tassel (v12 stage). | ctn1c.pk002.o4 |
| ect1c | *Canna edulis* Tubers | ect1c.pk001.k17:fis<br>ect1c.pk007.p18:fis |
| eef1c | *Eucalyptus tereticornis* flower buds from adult tree | eef1c.pk004.c8:fis |
| etr1c | Cattail (*Typha latifolia*) root | etr1c.pk006.f9 |
| fds | *Momordica charantia* Developing Seed | fds.pk0003.h5:fis |
| hss1c | *Sclerotinia* infected sunflower plants | hss1c.pk011.h10:fis |
| ncs | *Catalpa speciosa* Developing Seed | ncs.pk0013.c4 |
| p0006 | Young shoot | p0006.cbysa51r:fis |
| p0015 | 13 DAP embryo | p0015.cdpgu90r:fis<br>p0015.cdpfm55r:fis |
| p0016 | Tassel shoTassel shoots, pooled, 0.1-1.4 cm | p0016.ctsbf56rb |
| p0026 | Regenerating callus 5 days after auxin removal Hi-II callus 223a, 1129e | p0026.ccrab39r |
| p0027 | GS3 shoot cultures that were transformed with PHP5869 and were maintained on 273T shoot multiplication medium since 3/17/94 (sample received on 5/29/96 for RNA prep). The original transformation was done on 11/6/93 | p0027.cgsag51r |
| p0031 | CM45 shoot culture. It was initiated on 2/28/96 from seed derived meristems. The culture was maintained on 273N medium. | p0031.ccmau15r:fis<br>p0031.ccmbc81r |
| p0032 | Regenerating callus, 10 and 14 days after auxin removal. Hi-II callus 223a, 1129e 10 days. Hi-II callus 223a, 1129e 14 days | p0032.crcav77r:fis |
| p0037 | corn Root Worm infested V5 roots | p0037.crwbs90r:fis |
| p0083 | 7 DAP whole kernels | p0083.cldct11r:fis<br>p0083.cldeu68r:fis<br>p0083.clder12r |
| p0086 | P0067 screened 1; 11 DAP pericarp | p0086.cbsaa24r |
| p0118 | Night harvested, pooled stem tissue from the 4-5 internodes subtending the tassel; V8-V12 stages, Screened 1 | p0118.chsbc77r<br>p0118.chsbh89r |
| p0125 | Anther: Prophase I sceened 1 | p0125.czaab60rb:fis |
| p0126 | Night harvested leaf tissue; V8-V10 | p0126.cnlau71r:fis |
| p0134 | Hi-II callus 223a, 1129e, 10 days hi-II callus 233a, 1129e, 14 days | p0134.carah47r |
| pps1c | Prickly poppy developing seeds | pps1c.pk001.h3:fis<br>pps1c.pk007.j21:fis |
| rbm5c | Rice (*Oryza sativa*, Cypress) bran 10 days after milling | rbm5c.pk001.a19 |
| rca1c | Rice Nipponbare Callus. | rca1c.pk007.b22:fis |
| rca1n | Rice (*Oryza sativa* L., Nipponbare) callus normalized. | rca1n.pk029.n22<br>rca1n.pk002.j3<br>rca1n.pk021.b20:fis<br>rca1n.pk004.j14:fis<br>rca1n.pk026.m9<br>rca1n.pk008.o5:fis |
| rl0n | Rice 15 Day Old Leaf* | rl0n.pk096.h23<br>rl0n.pk0061.c8:fis<br>rl0n.pk131.j17<br>rl0n.pk0015.a4:fis |
| rlm3n | Rice (*Oryza Sativa*, YM) leaf mixture (rsr9) normalized at 45 C. for 24 hrs using 20 fold excess of driver | rlm3n.pk005.d20:fis |
| rlr2 | Rice (*Oryza sativa* L.) leaf (15 DAG) 2 hrs after infection of strain 4360-R-62 (AVR2-YAMO); Resistant | rlr2.pk0012.d2 |
| rlr24 | Rice Leaf 15 Days After Germination, 24 Hours After Infection of Strain *Magnaporthe grisea* 4360-R-62 (AVR2-YAMO); Resistant | rlr24.pk0032.e10 |
| rls6 | Rice Leaf 15 Days After Germination, 6 Hours After Infection of Strain *Magnaporthe grisea* 4360-R-67 (AVR2-YAMO); Susceptible | rls6.pk0033.a9:fis |

TABLE 2-continued cDNA Libraries from Various Plants

| Library | Tissue | Clone |
|---|---|---|
| rls72 | Rice Leaf 15 Days After Germination, 72 Hours After Infection of Strain *Magnaporthe grisea* 4360-R-67 (AVR2-YAMO); Susceptible | rls72.pk0023.c8:fis |
| rr1 | Rice Root of Two Week Old Developing Seedling | rr1.pk0039.d4:fis<br>rr1.pk0003.a3:fis<br>rr1.pk097.f22:fis<br>rr1.pk0047.g12:fis |
| rsl1n | Rice (*Oryza sativa*, YM) 15 day old seedling normalized | rsl1n.pk002.g10:fis<br>rsl1n.pk002.j2:fis<br>rsl1n.pk006.n24:fis<br>rsl1n.pk013.g2 |
| scb1c | Soybean (*Glycine max* L., 2872) Embryogenic suspension culture subjected to 4 bombardments and collected 12 hrs later. | scb1c.pk004.n19:fis |
| sde4c | Soybean Developing Embryo (9-11 mm) | sde4c.pk0001.a2:fis |
| sdp2c | Soybean (*Glycine max* L.) developing pods 6-7 mm | sdp2c.pk003.o5:fis<br>sdp2c.pk023.n6:fis<br>sdp2c.pk029.k17:fis<br>sdp2c.pk044.e5:fis |
| sdp3c | Soybean Developing Pods (8-9 mm) | sdp3c.pk018.b9:fis<br>sdp3c.pk019.n1:fis |
| spd4c | Soybean (*Glycine max* L.) developing pods 10-12 mm | sdp4c.pk009.e3s<br>dp4c.pk016.e10 |
| sdr1f | Soybean (*Glycine max*, Wye) 10 day old root | sdr1f.pk001.p7 |
| sds1f | Soybean (*Glycine max*, Wye) 11 day old seedling full length library using trehalose | sds1f.pk001.f7:fis |
| se1 | Soybean Embryo, 6 to 10 Days After Flowering | se1.pk0042.d8:fis |
| se2 | Soybean Embryo, 13 Days After Flowering | se2.11d12:fis |
| ses2w | Soybean Embryogenic Suspension 2 Weeks After Subculture | ses2w.pk0015.a4:fis<br>ses2w.pk0035.a9:fis<br>ses2w.pk0012.d10:fis |
| ses4d | Soybean Embryogenic Suspension 4 Days After Subculture | ses4d.pk0037.e3:fis<br>ses4d.pk0044.c12<br>ses4d.pk0006.a12<br>ses4d.pk0006.a12:fis<br>ses4d.pk0043.d10:fis |
| sfl1 | Soybean Immature Flower | sfl1.pk0102.h8<br>sfl1.pk131.j19<br>sfl1.pk135.g3<br>sfl1.pk0029.h10:fis |
| sgc5c | Soybean (*Glycine max* L., Wye) germanating cotyledon (¾ yellow; 15-24 DAG) | sgc5c.pk001.h16 |
| sgs1c | Soybean Seeds 4 Hours After Germination | sgs1c.pk004.f19:fis |
| sgs4c | Soybean (*Glycine max* L.) seeds 2 days after germination. | sgs4c.pk004.j2<br>sgs4c.pk006.g6<br>sgs4c.pk006.n21 |
| sic1c | Soybean (*Glycine max*) pooled tissue of root, stem, and leaf with iron chlorosis conditions | sic1c.pk003.o13:fis<br>sic1c.pk003.o18:fis |
| sifl c | Soybean (*Glycine max*) pooled tissue of basal stem and root infected with fusarium | sifl c.pk001.m16:fis |
| sls1c | Soybean (*Glycine max* L., S1990) infected with *Sclerotinia sclerotiorum mycelium*. | sls1c.pk010.l1:fis<br>sls1c.pk032.j4 |
| sls1c | Soybean (*Glycine max* L., S1990) infected with *Sclerotinia sclerotiorum mycelium*. | sls1c.pk010.l1:fis<br>sls1c.pk020.h24 |
| sls2c | Soybean (*Glycine max* L., Manta) infected with *Sclerotinia sclerotiorum mycelium*. | sls2c.pk007.c23:fis |
| sr1 | Soybean Root | sr1.pk0041.a11:fis<br>sr1.pk0049.c2 |
| srb | Scarlett runner bean (R. Goldberg) | srb.08g04 |
| src1c | Soybean 8 Day Old Root Infected With Cyst Nematode | src1c.pk003.o16:fis |
| src2c | Soybean (*Glycine max* L., 437654) 8 day old root inoculated with eggs of cyst Nematode (Race 1) for 4 days. | src2c.pk025.b3:fis<br>src2c.pk011.m12:fis<br>src2c.pk009.g9:fis<br>src2c.pk003.i13:fis |
| src3c | Soybean 8 Day Old Root Infected With Cyst Nematode | src3c.pk018.d10:fis<br>sr3c.pk011.g22<br>src3c.pk012.n16:fis<br>src3c.pk019.d4:fis<br>src3c.pk009.b15<br>src3c.pk028.j21:fis |
| srr1c | Soybean 8-Day-Old Root | srr1c.pk001.i24:fis |
| srr3c | Soybean 8-Day-Old Root | srr3c.pk001.l10:fis |
| tlw1c | Tobacco (*Nicotiana benthamiana*) Leaves Wounded by Abrasion and Harvested After 1.5 Hour. | tlw1c.pk006.o16 |

TABLE 2-continued cDNA Libraries from Various Plants

| Library | Tissue | Clone |
|---------|--------|-------|
| vdb1c | Grape (*Vitis* sp.) developing bud | vdb1c.pk001.m5:fis |
| vmb1na | Grape (*Vitis* sp.) midstage berries normalized | vmb1na.pk015.d18:fis |
| vpl1c | Grape (*Vitis* sp.) In vitro plantlets | vpl1c.pk008.o5:fis |
| vrr1c | Grape (*Vitis* sp.) resistant roots | vrr1c.pk004.o20:fis |
| vs1n | Vernonia Seed* | vs1n.pk013.m13:fis |
| wdelf | Wheat (*Triticum aestivum*, Hi Line) developing endosperm 2-7 DPA | wde1f.pk003.h2:fis |
| wdk2c | Wheat Developing Kernel, 7 Days After Anthesis. | wdk2c.pk009.e4 |
| wdk2c | Wheat Developing Kernel, 7 Days After Anthesis. | wdk2c.pk018.c16:fis |
| wdk3c | Wheat Developing Kernel, 14 Days After Anthesis. | wdk3c.pk023.h15:fis |
| wdk5c | Wheat Developing Kernel, 30 Days After Anthesis | wdk5c.pk006.m13 |
| wdk9n | Wheat (*Triticum aestivu*, Spring Wheat) kernels 3, 7, 14 and 21 days after anthesis | wdk9n.pk001.k5 |
| wdr1f | Wheat (*Triticum aestivum*) developing root (full length) | wdr1f.pk003.b21:fis |
| wds1f | Wheat developing seedling full length | wds1f.pk002.p21:fis |
| wia1c | Wheat (*Triticum aestivum*, Hi Line) immature anthers | wia1c.pk001.d20:fis |
| wkm1c | Wheat Kernel malted 55 Hours at 22 Degrees Celsius | wkm1c.pk0002.d7:fis |
| wl1n | Wheat Leaf From 7 Day Old Seedling* | wl1n.pk0114.f9 |
| wle1n | Wheat Leaf From 7 Day Old Etiolated Seedling* | wle1n.pk0076.h7:fis |
| wlk8 | Wheat Seedlings 8 Hours After Treatment With Fungicide** | wlk8.pk0001.e10:fis |
| wlm96 | Wheat Seedlings 96 Hours After Inoculation With *Erysiphe graminis f. sp tritici* | wlm96.pk060.d5<br>wlm96.pk037.k9:fis<br>wlm96.pk035.j11:fis<br>wlm96.pk0007.e4:fis |
| wr1 | Wheat Root From 7 Day Old Seedling | wr1.pk0094.f2:fis<br>wr1.pk0153.c7:fis<br>wr1.pk148.f7:fis |
| wre1n | Wheat Root From 7 Day Old Etiolated Seedling* | wre1n.pk0066.e4:fis<br>wre1n.pk0143.h2:fis |

*These libraries were normalized essentially as described in U.S. Pat. No. 5,482,845, incorporated herein by reference.
**Application of 6-iodo-3-propyl-2-propyloxy-4(3H)-quinazolinone; synthesis and methods of using this compound are described in U.S. Pat. No. 5,747,497.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al, (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res*. 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding proteins involved in altering plant oil traits were identified by gene profiling (see Example 7) and by conducting BLAST (Basic Local Alignment Search Tool; Altschul et al (1993) *J. Mol. Biol.* 215:403-410; searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Proteins Involved in Altering Oil

Phenotypes

The BLASTX search using the EST sequences from clones listed in Table 3 revealed similarity of the polypeptides encoded by the cDNAs to Hap2 homologs, Hap5 homologs, and Lec1 transcription factors from various species including Arabidopsis thaliana, rice (*Oryza sativa*), corn (*Zea mays*), soybean (*Glycine max*), cucmber (*Cucumis sativus*), Sordaria (*Sordaria macrospora*), sesame (*Sesamum indicum*), grape (*Vitis* sp.), Brassica (*Brassica napus*), and tobacco (*Nicotiana tabacum*). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to Proteins Involved in Altering Oil Phenotypes

| SEQ ID NO. | Gene Name | Clone | Homolog | Genbank # | pLOG |
|---|---|---|---|---|---|
| 2 | Hap2a | ncs.pk0013.c4 | No hits | | — |
| 4 | Hap2c | etr1c.pk006.f9 | No hits | | — |
| 6 | Hap2a | vmb1na.pk015.d18 | *Arabidopsis* | 11282597 | 8.1 |
| 8 | Hap2a | vpl1c.pk008.o5:fis | Grape | 7141243 | 91.2 |
| 10 | Hap2c | vdb1c.pk001.m5:fis | Rice | 7489565 | 38.0 |
| 12 | Hap2c | cho1c.pk004.b19:fis | Rice | 7489565 | 94.3 |
| 14 | Hap2c | p0015.cdpgu90r:fis | Rice | 7489565 | 96.2 |
| 16 | Hap2a | cta1n.pk0070.f3:fis | Rice | 7489565 | 38.1 |
| 18 | Hap2a | cco1n.pk0014.d4:fis | *Arabidopsis* | 6634774 | 37.2 |
| 20 | Hap2a | cco1n.pk086.d20:fis | *Arabidopsis* | 6634774 | 36.3 |
| 22 | Hap2b | p0126.cnlau71r:fis | Rice | 7489565 | 23.7 |
| 24 | Hap2b | p0104.cabav52r | Rice | 7489565 | 16.7 |
| 26 | Hap2b | cho1c.pk007.l21:fis | Rice | 7489565 | 35.0 |
| 28 | Hap2c | contig of: cca.pk0026.d6 cen3n.pk0061.e10:fis cen3n.pk0135.c2 cho1c.pk001.n24 p0092.chwae40r | Rice | 7489565 | 43.5 |
| 30 | Hap2c | cpf1c.pk006.e3:fis | Rice | 7489565 | 44.0 |
| 32 | Hap2c | contig of: cr1n.pk0080.g6 p0003.cgpge51r | Rice | 7489565 | 35.0 |
| 34 | Hap2c | p0015.cdpfm55r:fis | *Arabidopsis* | 4587559 | 26.4 |
| 36 | Hap2 | p0083.cldct11r:fis | Rice | 7489565 | 91.4 |
| 38 | Hap2 | p0083.cldeu68r:fis | Rice | 7489565 | 14.2 |
| 40 | Hap2a | pps1c.pk001.h3:fis | *Arabidopsis* | 9293997 | 45.5 |
| 42 | Hap2c | pps1c.pk007.j21:fis | *Arabidopsis* | 5903072 | 53.7 |
| 44 | Hap2 | rr1.pk0030.f7:fis | Rice | 7489565 | identical |
| 46 | Hap2a | r1s72.pk0023.c8:fis | *Arabidopsis* | 9293997 | 36.5 |
| 48 | Hap2a | rca1n.pk002.c15 | Grape | 7141243 | 7.7 |
| 50 | Hap2a | rds3c.pk001.g9 | Rice | 7489565 | 18.2 |
| 52 | Hap2b | rca1n.pk002.j3:fis | Rice | 7489565 | 26.0 |
| 54 | Hap2c | rca1n.pk029.n22:fis | *Arabidopsis* | 8778470 | 29.2 |
| 56 | Hap2b | r10n.pk131.j17 | Rice | 7489565 | 10.5 |
| 58 | Hap2a | sdp3c.pk018.b9:fiS | *Arabidopsis* | 2398521 | 74.5 |
| 60 | Hap2a | sfl1.pk0102.h8 | Grape | 7141243 | 36.7 |
| 62 | Hap2a | srr3c.pk001.l10:fis | *Brassica* | 1586551 | 48.7 |
| 64 | Hap2a | sdp2c.pk003.o5:fiS | *Arabidopsis* | 6634774 | 53.0 |
| 66 | Hap2b | sif1c.pk001.m16:fis | *Arabidopsis* | 6714441 | 180.0 |
| 68 | Hap2c | src1c.pk003.o16:fis | Rice | 7489565 | 33.5 |
| 70 | Hap2c | src3c.pk012.m6:fis | Rice | 7489565 | 31.5 |
| 72 | Hap2a | hss1c.pk011.h10:fis | *Arabidopsis* | 9293997 | 48.7 |
| 74 | Hap2c | wr1.pk0094.f2:fis | Rice | 7489565 | 92.7 |
| 76 | Hap2a | wre1n.pk0143.h2:fis | *Arabidopsis* | 6634774 | 35.0 |
| 78 | Hap2b | wds1f.pk002.p21:fis | *Arabidopsis* | 6714441 | 26.5 |
| 80 | Hap2b | contig of: wdi1c.pk002.b10 wr1.pk0153.c7:fis | Rice | 7489565 | 38.5 |
| 82 | Hap2c | wre1n.pk0066.e4:fis | Rice | 7489565 | 42.7 |
| 84 | Hap5c | ect1c.pk001.k17:fis | Rice | 5257260 | 57.0 |
| 86 | Hap5a | vrr1c.pk004.o20:fis | *Arabidopsis* | 6523090 | 93.0 |
| 88 | Hap5a | clm1f.pk001.k17:fis | *Arabidopsis* | 6523090 | 66.7 |
| 90 | Hap5b | cde1n.pk003.a5:fis | *Arabidopsis* | 3776575 | 57.0 |
| 92 | Hap5b | cen3n.pk0164.a10:fis | *Arabidopsis* | 3776575 | 57.0 |
| 94 | Hap5b | p0118.chsbc77r | *Arabidopsis* | 3776575 | 58.5 |
| 96 | Hap5c | cco1n.pk055.o18 | Rice | 5257260 | 41.0 |
| 98 | Hap5c | cho1c.pk001.l23:fis | Rice | 5257260 | 82.0 |
| 100 | Hap5c | cse1c.pk001.h6:fis | Rice | 5257260 | 86.4 |
| 102 | Hap5a | rlm3n.pk005.d20:fis | *Arabidopsis* | 6523090 | 66.7 |
| 104 | Hap5b | rr1.pk0003.a3:fis | *Arabidopsis* | 6289057 | 58.5 |
| 106 | Hap5b | rr1.pk0039.d4:fis | *Arabidopsis* | 3776575 | 57.2 |
| 108 | Hap5c | rca1n.pk021.b20:fis | Rice | 5257260 | 74.0 |
| 110 | Hap5a | sdp2c.pk029.k17:fis | *Arabidopsis* | 6523090 | 90.5 |
| 112 | Hap5a | sdp2c.pk044.e5:fis | *Arabidopsis* | 6523090 | 92.4 |
| 114 | Hap5b | sgs4c.pk004.j2 | *Arabidopsis* | 3776575 | 18.5 |
| 116 | Hap5b | src3c.pk002.h4:fis | *Arabidopsis* | 6289057 | 61.1 |
| 118 | Hap5b | src3c.pk009.b15:fis | *Arabidopsis* | 6289057 | 61.5 |
| 120 | Hap5b | src3c.pk019.d4:fis | *Arabidopsis* | 6056368 | 51.5 |
| 122 | Hap5c | sls1c.pk032.j4:fis | *Arabidopsis* | 6289057 | 74.5 |
| 124 | Hap5 | wdk2c.pk009.e4:fis Contig of: | Rice | 5257260 | 20.0 |

TABLE 3-continued

BLAST Results for Sequences Encoding Polypeptides Homologous to Proteins Involved in Altering Oil Phenotypes

| SEQ ID NO. | Gene Name | Clone | Homolog | Genbank # | pLOG |
|---|---|---|---|---|---|
| 126 | Hap5a | w1m96.pk036.j11 | Arabidopsis | 9758288 | 19.7 |
|  |  | w1m96.pk060.d5:fis |  |  |  |
| 128 | Hap5c | wle1n.pk0076.h7:fis | Rice | 5257260 | 82.0 |
| 130 | Lec1 | eas1c.pk003.e16 | Arabidopsis | 9758795 | 49.2 |
| 132 | Lec1 | fds1n.pk008.m14 | Arabidopsis | 9758795 | 46.1 |
| 134 | Lec1 | p0015.cdpg75rb:fis | Arabidopsis | 9758795 | 45.4 |
| 136 | Lec1 | p0083.clder12r:fis | Arabidopsis | 6552738 | 35.2 |
| 138 | Lec1 | pps1c.pk002.l19 | Arabidopsis | 9758795 | 45.2 |
|  |  | Contig of: |  |  |  |
| 140 | Lec1 | scb1c.pk004.j10 | Arabidopsis | 9758795 | 47.4 |
|  |  | se1.pk0042.d8:fis |  |  |  |
| 142 | Lec1 | se2.11d12:fis | Arabidopsis | 9758795 | 52.2 |
| 144 | Lec1 | ses2w.pk0015.a4:fis | Arabidopsis | 9758795 | 43.7 |
| 146 | Lec1 | vs1n.pk013.m13:fis | Arabidopsis | 9758795 | 53.1 |
| 148 | Lec1 | wdk3c.pk023.h15:fis | Arabidopsis | 9758795 | 36.7 |
| 150 | Lec1-CCAAT | ect1c.pk007.p18:fis | Zea mays | 22380 | 44.7 |
| 152 | Lec1-CCAAT | fds.pk0003.h5:fis | Arabidopsis | 6729485 | 57.7 |
| 154 | Lec1-CCAAT | eef1c.pk004.c8:fis | Zea mays | 22380 | 61.7 |
| 156 | Lec1-CCAAT | cbn10.pk0005.e6:fis | Zea mays | 22380 | 72.2 |
| 158 | Lec1-CCAAT | p0006.cbysa51r:fis | Arabidopsis | 2244810 | 55.5 |
| 160 | Lec1-CCAAT | rl0n.pk0061.c8:fis | Zea mays | 22380 | 46.5 |
| 162 | Lec1-CCAAT | rsl1n.pk002.g10:fis | Zea mays | 22380 | 68.7 |
| 164 | Lec1-CCAAT | ses4d.pk0037.e3:fis | Arabidopsis | 2398529 | 49.0 |
| 166 | Lec1-CCAAT | src2c.pk003.i13:fis | Arabidopsis | 3738293 | 41.1 |
| 168 | Lec1-CCAAT | src2c.pk011.m12:fis | Arabidopsis | 6729485 | 62.0 |
| 170 | Lec1-CCAAT | src2c.pk025.b3:fis | Zea mays | 22380 | 45.5 |
| 172 | Lec1-CCAAT | src3c.pk028.j21:fis | Zea mays | 22380 | 54.3 |
| 174 | Lec1-CCAAT | wkm1c.pk0002.d7:fis | Zea mays | 22380 | 79.5 |
| 176 | Lec1-CCAAT | wlk8.pk0001.e10:fis | Arabidopsis | 2398529 | 52.7 |
| 178 | Lec1-CCAAT | wlm96.pk037.k9:fis | Zea mays | 22380 | 73.5 |
| 206 | Lec1 | rice genome seq | Oryza sativa | 7378310 | 180 |
| 208 | Hap2 | ncs.pk0013.c4:fis | Arabidopsis | 9293997 | 46.7 |
| 210 | Hap2 | p0117.chcln94r:fis | Oryza sativa | 1489565 | 26.0 |
| 212 | Hap2 | rdi2c.pk011.f19:fis | Oryza sativa | 1489565 | 45.0 |
| 214 | Hap2 | sfl1.pk0101.g7:fis | Vitis sp. | 7141243 | 38.4 |
| 216 | Hap2 | wdi1c.pk002.b10:fis | Oryza sativa | 1489565 | 40.3 |
| 221 | Hap5 | sgs4c.pk004.j2:fis | Arabidopsis | 15223482 | 69.0 |

The sequence of the entire cDNA insert in the clones listed in Table 3 was determined. Further sequencing and searching of the DuPont proprietary database allowed the identification of other corn, rice, soybean and/or wheat clones encoding polypetides involved in altering oil phenotypes. The BLASTX search using the sequences from clones listed in Table 4 revealed similarity of the polypeptides encoded by the various cDNAs from plant and fungal species (noted by their NCBI General Identifier No. in Tables 3 and 4). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 4

Percent Identity of Amino Acid Sequences Deduced From the Nucleotide Sequences of cDNA Clones Encoding Polypeptides Homologous to Polypeptides Involved in Altering Plant Oil Phenotypes

| SEQ ID NO. | Accession No. (SEQ ID NO) | Percent Identity |
|---|---|---|
| 2 | 1586551 (187) | 23.4% |
| 4 | 7489565 (181) | 27.4% |
| 6 | 11282597 (179) | 22.1% |

TABLE 4-continued

Percent Identity of Amino Acid Sequences Deduced From the Nucleotide Sequences of cDNA Clones Encoding Polypeptides Homologous to Polypeptides Involved in Altering Plant Oil Phenotypes

| SEQ ID NO. | Accession No. (SEQ ID NO) | Percent Identity |
|---|---|---|
| 10 | 7489565 (181) | 36.1% |
| 12 | 7489565 (181) | 67.2% |
| 14 | 7489565 (181) | 70.6% |
| 16 | 7489565 (181) | 33.2% |
| 18 | 6634774 (182) | 40.1% |
| 20 | 6634774 (182) | 39.1% |
| 22 | 7489565 (181) | 28.2% |
| 24 | 7489565 (181) | 53.2% |
| 26 | 7489565 (181) | 34.0% |
| 28 | 7489565 (181) | 39.5% |
| 30 | 7489565 (181) | 39.5% |
| 32 | 7489565 (181) | 35.5% |
| 34 | 4587559 (202) | 54.1% |
| 36 | 7489565 (181) | 67.2% |
| 38 | 7489565 (181) | 29.0% |
| 40 | 9293997 (217) | 31.5% |
| 42 | 5903072 (184) | 35.3% |
| 46 | 5903072 (184) | 33.7% |
| 48 | 7141243 (180) | 34.5% |
| 50 | 7489565 (181) | 35.7% |
| 52 | 7489565 (181) | 27.2% |
| 54 | 8778470 (185) | 40.5% |

TABLE 4-continued

Percent Identity of Amino Acid Sequences Deduced From the Nucleotide Sequences of cDNA Clones Encoding Polypeptides Homologous to Polypeptides Involved in Altering Plant Oil Phenotypes

| SEQ ID NO. | Accession No. (SEQ ID NO) | Percent Identity |
|---|---|---|
| 56 | 7489565 (181) | 22.1% |
| 58 | 2398521 (186) | 49.1% |
| 60 | 7141243 (180) | 40.9% |
| 62 | 1586551 (187) | 37.8% |
| 64 | 6634774 (182) | 49.2% |
| 66 | 6714441 (188) | 32.5% |
| 68 | 7489565 (181) | 32.4% |
| 70 | 7489565 (181) | 31.1% |
| 72 | 9293997 (217) | 40.6% |
| 74 | 7489565 (181) | 68.5% |
| 76 | 6634774 (182) | 36.5% |
| 78 | 6714441 (188) | 23.7% |
| 80 | 7489565 (181) | 34.5% |
| 82 | 7489565 (181) | 37.4% |
| 84 | 5257260 (189) | 62.9% |
| 86 | 6523090 (190) | 77.7% |
| 88 | 6523090 (190) | 53.8% |
| 90 | 3776575 (191) | 50.7% |
| 92 | 3776575 (191) | 51.6% |
| 94 | 3776575 (191) | 60.0% |
| 96 | 5257260 (189) | 62.7% |
| 98 | 5257260 (189) | 75.0% |
| 100 | 5257260 (189) | 77.5% |
| 102 | 6523090 (190) | 53.8% |
| 104 | 6289057 (192) | 60.6% |
| 106 | 3776575 (191) | 52.1% |
| 108 | 5257260 (189) | 77.9% |
| 110 | 6523090 (190) | 70.3% |
| 112 | 6523090 (190) | 70.7% |
| 114 | 3776575 (191) | 35.7% |
| 116 | 6289057 (192) | 53.2% |
| 118 | 6289057 (192) | 52.8% |
| 120 | 6056368 (193) | 73.0% |
| 122 | 6289057 (192) | 57.1% |
| 124 | 5257260 (189) | 27.3% |
| 126 | 9758288 (194) | 46.3% |
| 128 | 5257260 (189) | 74.9% |
| 130 | 9758795 (196) | 49.0% |
| 132 | 9758795 (196) | 49.7% |
| 134 | 9758795 (196) | 49.8% |
| 136 | 6552738 (195) | 38.9% |
| 208 | 9293997 (217) | 34.9% |
| 210 | 7489565 (218) | 28.6% |
| 212 | 7489565 (218) | 35.7% |
| 214 | 7141243 (219) | 42.3% |
| 216 | 7489565 (218) | 34.9% |
| 221 | 15223482 (222) | 64.8% |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of cDNAs to receptor protein kinases, MEK3 homologs, Hap2 homologs, LIP 15 homologs, calcium EF-hand proteins, ATP citrate lyase, glucose metabolism proteins such as SNF1 homologs, Lec1 transcription factors, and seed developmentally regulated transcription factors such as CKC (Aintegumenta-like) homologs.

Example 4

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al (1975) Sci. Sin. Peking 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al (1985) Nature 313:810-812) and the 3' region of the nopaline synthase gene from the T-DNA of the Ti plasmid of *Agrobacterium tumefaciens*.

The particle bombardment method (Klein et al (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per ml). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al (1990) *Bio/Technology* 8:833-839).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al (1987) *Nature (London)* 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al (1985) *Nature* 313:810-812), the hygromycin phosphotransferase gene from plasmid pJR225 (from *E. coli*; Gritz et al(1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression Vector for Plant Transformation by Particle Gun Bombardment.

A seed specific gene expression cassette was used for making recombinant DNA constructs for expression of candidate genes in corn. The expression cassette is composed of the 0.9 kb oleosin promoter, the intron 1 of the maize shrunken 1 gene and adjacent exon (Vasil et al, 1989, *Plant Physiol* 91: 1575-1579; Mascarenhas et al, 1990, *Plant Mol Biol* 15:913-920) and 3' transcription termination region from the nopaline synthase (Nos) gene. In between the exon adjacent to the shrunken 1 gene and the nopaline synthase (Nos) gene are unique restriction endonuclease sites MfeI and XmaI. This vector has been designated pBN256 (REF. Jennie Shen's patent). pMUT256 refers to a pBN256 plasmid in which a EcoRI site has been removed by site directed mutagenesis. A modified version of pMUT256, designated pMUT256e was modified by additon of a synthetic multiple cloning site. The synthetic polylinker was generated by annealing of oligos (5'-acagtacagtacagtacagtacagt-3') and (5'-actgtactgtactgtacgtgactgt-3') [SEQ ID NOs: 430 and 431, respectively] and subsequent subcloning into the pMut256 open with MfeI and XmaI. Additional expression cassettes/vectors will be described in reference to specific examples where they have been used (see below).

Example 7

Isolation and Cloning of Candidate Genes into Embryo-specific Plant Expression Vectors.

HAP3/LEC1 (Heme-Activated Protein 3/Leafy Cotyledon 1):
A full length clone (p0015.cdpgp75rb, SEQ ID NO:133 for the corn homolog of the HAP3/Lec1 gene was obtained from DuPont/Pioneer EST Database. The ORF of maize HAP3/Lec1 (a 1 kb SalI/HpaI fragment, PCT Application No. WO 00/28058, published on May 18, 2000) was moved into an expression cassette containing a maize oleosin promoter (a 0.9 kb BamHI/XhoI fragment, PCT Application No. WO 99/164579, published on Dec. 16, 1999) and a polyadenylation sequence from the Agrobacterium nopaline synthase gene. This expression cassette was then subcloned adjacent to a 35S::Bar expression cassette (Sidorenko et al. (2000) *Plant J* 22:471-482). The resulting expression cassettes flanked by T-DNA border sequences were then mobilized into the Agrobacterium "super-binary" vector (Komari, 1990) using electroporation. Additional constructs were made to confer expression patterns different from those obtained with the oleosin promoter. A ubiquitin promoter (UBI, Christensen et al. (1992) *Plant Mol Biol* 18:675-680), a lipid transfer protein (LTP) promoter (U.S. Pat. No. 5,525,716), and a gamma zein promoter (GZP) (Boronat et al. (1986) *Plant Science* 47:95-102) were each fused to Lec1as described above for the oleosin promoter. The two transcription units, LTP-Lec1 and GZP-Lec1, were combined into one expression construct next to the 35S:Bar expression construct and flanked by T-DNA border sequences (as described above).

HAP2 (Heme-Activated Protein 2):
A full length clone (cho1c.pk006.b14, a 30 nucleotide shorter cDNA than cho1c.pk004. b19: fis, shown in SEQ ID NO:11) for the corn homolog of the HAP2 gene was obtained from DuPont/Pioneer EST Database. The ApoI/ApaI 1.1 kb fragment of cho1c.pk006. b14 was isolated and subcloned into pMUT256e opened by digestion with EcoRI/ApaI. One clone was selected for corn transformation by restriction digestion analysis for correct insert size. Subcloning artifacts were excluded by 5' and 3' sequence of the vector-insert boundaries.

HAP2 (Heme-Activated Protein 5)
A full length clone (cho1c.pk001.123, shown in SEQ ID NO:97) for the corn homolog of HAP5 gene was obtained from DuPont/Pioneer EST Database. The EcoRI/ApaI 1.1 kb fragment of cho1c.pk001.123 was isolated and subcloned into pMUT256e opened by digestion with EcoRI/ApaI. One clone was selected for corn transformation after restriction digestion analysis for correct insert size. Subcloning artifacts were excluded by 5' and 3' sequence of the vector-insert boundaries.

Example 8

Transformation of Immature Embryos BY Particle Bombardment and Regeneration of Corn Plants Immature maize embryos from greenhouse donor plants are bombarded with a plasmid containing the gene of the invention operably linked to a weak promoter, such as the nos promoter, or an inducible promoter, such as ln2, plus a plasmid containing the selectable marker gene PAT (Wohileben et al (1988) *Gene* 70:25-37) that confers resistance to the herbicide Bialaphos. Transformation is performed as follows. The ears are surface sterilized in 30% Chloral bleach plus 0.5% Micro detergent for 20 minutes, and rinsed two times with sterile water. The immature embryos are excised and placed embryo axis side down (scutellum side up), 25 embryos per plate. These are cultured on 560 L medium 4 days prior to bombardment in the dark. Medium 560 L is an N6-based medium containing Eriksson's vitamins, thiamine, sucrose, 2,4-D, and silver nitrate. The day of bombardment, the embryos are transferred to 560 Y medium for 4 hours and are arranged within the 2.5-cm target zone. Medium 560Y is a high osmoticum medium (560 L with high sucrose concentration). A plasmid vector comprising the gene of the invention operably linked to the selected promoter is constructed. This plasmid DNA plus plasmid DNA containing a PAT selectable marker is precipitated onto 1.1 μm (average diameter) tungsten pellets using a CaCl$_2$ precipitation procedure as follows: 100 μl prepared tungsten particles in water, 10 μl (1 μg) DNA in TrisEDTA buffer (1 μg total), 100 μl 2.5 M CaCl$_2$, 10 μl 0.1 M spermidine. Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment. The sample plates are bombarded at level #4 in particle gun #HE34-1 or #HE34-2. All samples receive a single shot at 650 PSI, with a total of ten aliquots taken from each tube of prepared particles/DNA. Following bombardment, the embryos are kept on 560Y medium, an N6 based medium, for 2 days, then transferred to 560R selection medium, an N6 based medium containing 3 mg/liter Bialaphos, and subcultured every 2 weeks. After approximately 10 weeks of selection, selection-resistant callus clones are sampled for PCR and activity of the gene of interest. Positive lines are transferred to 288J medium, an N6 based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored for expression of the gene of interest.

Example 9

Transformation of Callus and Regeneration of Corn Plants—Particle Gun.

Type II Callus Isolation and Maintenance.

After 10-21 days, type II callus is initiated from the scutellum and appears as a friable, embryogenic outgrowth of rapidly dividing cells. Callus is subcultured every 5-10 days and maintained on N6 medium supplemented with 1 mg/L 2,4-D (CM). These cultures are used in transformation experiments from 5 to 12 weeks after initiation.

Preparation of Callus for Transformation.

Proembryogenic type II callus is transferred to #4 Whatman filter paper on CM media. The CM plates with callus is wrapped with parafilm and incubated in the dark Conviron growth chamber (45% humidity, 27-28° C.) for two days before bombardment. Prior to bombardment, the osmotic plates are left partially ajar for thirty minutes in the laminar flow hood to allow moisture on the tissue to dissipate.

Gold Particle Preparation

Sixty mg of 0.6 micron gold is weighed out in a siliconized eppendorf tube (Axgen Microtubes—1.7 ml clear tube). The tube is left stationary for 15 minutes and spun down. The pellet is rinsed with sterile water three more times. Subsequently, one ml of sterile water is added to the gold pellet and vortexed for 10 minutes. The gold particles are divided into 50 ul aliquots.

DNA/Gold Preparation

Fifty µL of 0.6 micron gold in sterile dd H2O. A 2:1 molar ratio of trait gene:bar gene (usually ~5-10 ug in total DNA) is added and vortexed. Subsequently, fifty µL of 2.5 M $CaCl_2$ is added quickly into the suspension and vortexed followed by the addition of 20 µL of 0.1 M spermidine and vortexed and spun down. The pellet is rinsed 3× in 100% ethanol. The pellet is gently resuspended by tapping the side of the eppendorf tube several times. The DNA prep is stored in the 20° C. freezer.

Loading of the Macrocarrier

The DNA/gold prep is thawed and sonicated (2 strokes) in the Branson 200 Ultrasonic cleaner prior to the addition to macrocarriers. The suspension is mixed well by pipetting in and out. Immediately, 6 µl of DNA/gold suspension is dispensed quickly to the center of each macrocarrier. Once the DNA prep is dried onto the macrocarrier, the PDS-100/He Gun is used to bombard the maize callus cells with the DNA-coated gold particles.

Particle Gun Parameters.

Plates containing callus are the bombarded with the PDS-1000/He Gun using the following parameters: 1) DNA precipitated onto 0.6 µM Gold particles; 2) 8 cm distance from stopping screen; 3) 27-29 inches Hg vacuum; 4) 1050-1100 PSI He pressure.

Selection of Transgenic Callus Lines.

After 3-4 days of incubation in the dark chamber the callus is transferred (3-4 mm clumps) onto media containing 3-5 ppm bialaphos (SM3 or SM5). The SM plates are incubated in the dark at 27° C. for ~7-14 days. Thereafter, all callus is transferred onto SM (5 ppm bialaphos) keeping track of unique lines as above. Each clump may be split into several pieces at this transfer.

Regeneration of Transgenic Maize Plants.

Callus events are isolated onto fresh SM medium, sampled for PCR (polymerase chain reaction) and placed on first-stage regeneration media (RM31). After 10-14 days, the proembryogenic callus are transferred onto fresh RM3 plates and placed in the light chamber at 26° C. Plantlets approximately 2-3 cm are removed and transfer to RM4 media tubs. After 1-2 weeks plants from RM4 are potted to a maximum of two plantlets per pot. The pots are then placed in the Conviron growth chamber (photolight=20 hours, humidity=65%, temperature=24° C.) and watered with Roots2 solution. Plants (~20 cm tall) are tested for expression of the bar gene by performing a 2% basta swipe test.

Example 10

Analysis of Fatty Acid Content and Composition by Gas Chromatography (GC)

Fatty acid (FA) determination was done from a total of 300-400 mg of tissue lyophilized for 24 hours. The tissue was then ground using a FastPrep mill (Biol101) at 4.5 speed and 20 seconds in the presence of 0.5 ml of 2.5% Sulfuric Acid+97.5% Methanol and Heptadecanoic acid (17:0, stock 10 mg/ml in Tuloene) as an external standard. Thereafter, another 0.5 ml 2.5% Sulfuric Acid +97.5% Methanol was used to wash each tube and incubate in 95° C. for 1 hour for transesterification. The tubes were removed from the water bath and allowed to cool down to RT. FAs were extracted in one volume of heptane:$H_2O$ (1:1) and cleared by centrifugation. The supernatant (50 ul) containing the fatty acid methyl esters were loaded into a Hewlett Packard 6890 gas chromatograph fitted with a 30 m×0.32 mm Omegawax column and the separated peaks were analyzed and characterized.

Example 11

Lec 1 Over-Expression Leads to Altered Fatty Acid Accumulation in Maize Somatic Embryos The ubiquitin promoter (Christensen et al (1992) *Plant Mol Biol* 18:675-89) was used to drive Hap3/Lec1 expression (outlined in Example 7) in maize embryogenic callus to test what phenotype would arise from over-expression of Lec1 in somatic embryos. Transformation of the construct into maize embryogenic callus and generation of somatic embryos is outlined in Example 9.

More than ten different events were analysed by GC for fatty acid content/composition and compared to controls transformed with the selectable marker (BAR gene) plasmid alone. A pool of three embryos each from XX different events showed that the somatic embryos overexpressing Lec1 contain elevated fatty acid content (average 119% increase over control) with no significant alteration in fatty acid composition when compared to the control somatic embryos (FIG. 1).

Example 12

Nuclear Magnetic Resonance (NMR) ANALYSIS

Seed are imbibed in distilled water for 12-24 hours at 4° C. The embryo is dissected away and stored in a 48 well plate. The samples are lyophilized over-night in a Virtis 24×48 lyophilizer. The NMR (Process Control Technologies—PCT (Ft. Collins, Colo.) is set up as per the manufacturer's instructions. The NMR is calibrated using a series of 5 mm NMR tubes containing precisely measured amounts of corn oil (Mazola). The calibration standards are 3, 6, 9, 12, 15, 18, 21, 27, 33, and 40 mg of oil.

Example 13

Lec 1 Over-Expression Leads to Altered Oil Accumulation in Maize Kernels

The Hap3/Lec1 expression construct with the oleosin promoter (outlined in Example 7) was introduced into maize to test what phenotype would arise from seed specific over-expression. Transformation of the construct into maize was accomplished using *Agrobacterium tumefaciens* as follows.

Freshly isolated immature embryos of maize, about 10 days after pollination (DAP), are incubated with the Agrobacterium. The preferred genotype for transformation is the highly transformable genotype Hi-II (Armstrong, C. L., 1991, Development and Availability of Germplasm with High Type II Culture Formation Response, *Maize Genetics Cooperation Newsletter*, 65:92-93). An $F_1$ hybrid created by crossing with an Hi-II with an elite inbred may also be used. After Agrobacterium treatment of immature embryos, the embryos are cultured on medium containing toxic levels of herbicide. Only those cells which receive the herbicide-resistance gene, and the linked gene(s), grow on selective medium. Transgenic events so selected are propagated and regenerated to whole plants, produce seed, and transmit transgenes to progeny.

The engineered *Agrobacterium tumefaciens* LBA4404 is constructed as per U.S. Pat. No. 5,591,616 to contain the linked gene(s) and the selectable marker gene. Typically either BAR (D'Halluin et al (1992) *Methods Enzymol.* 216:415-426) or PAT (Wohileben et al (1988) *Gene* 70:25-37) may be used.

To use the engineered vector in plant transformation, a master plate of single bacterial colonies is first prepared by inoculating the bacteria on minimal AB medium and then incubating the bacteria plate inverted at 28° C. in darkness for about 3 days. A working plate is then prepared by selecting a single colony from the plate of minimal A medium and streaking it across a plate of YP medium. The YP-medium bacterial plate is then incubated inverted at 28° C. in darkness for 1-2 days.

Agrobacterium for plant transfection and co-cultivation is prepared 1 day prior to transformation. Into 30 ml of minimal A medium in a flask is placed 50 μg/ml spectinomycin (or appropriate bacterial antibiotic depending on marker in co-integrate), 100 μM acetosyringone, and about a ⅛ loopful of Agrobacterium from a 1 to 2-day-old working plate. The Agrobacterium is then grown at 28° C. at 200 rpm in darkness overnight (about 14 hours). In mid-log phase, the Agrobacterium is harvested and resuspended at 3 to $5 \times 10^8$ CFU/ml in 561 Q medium+100 μM acetosyringone using standard microbial techniques and standard curves.

Immature Embryo Preparation

Nine to ten days after controlled pollination of a corn plant, developing immature embryos are opaque and 1-1.5 mm long and are the appropriate size for Agro-infection. The husked ears are sterilized in 50% commercial bleach and 1 drop Tween for 30 minutes, and then rinsed twice with sterile water. The immature embryos are aseptically removed from the caryopsis and placed into 2 ml of sterile holding solution comprising of 561Q+100 μM acetosyringone.

Agrobacterium Infection and Co-cultivation of Embryos

Holding solution is decanted from excised immature embryos and replaced with prepared Agrobacterium. Following gentle mixing and incubation for about 5 minutes, the Agrobacterium is decanted from the immature embryos. Immature embryos are then moved to a plate of 562P medium, scutellum surface upwards, and incubated at 20° C. for 3 days in darkness followed by incubation at 28° C. for 3 days in darkness on medium 562P+100 mg/ml carbenecillin (see U.S. Pat. No. 5,981,840).

Selection of Transgenic Events

Following incubation, the immature embryos are transferred to 563O medium for selection of events. The transforming DNA possesses a herbicide-resistance gene, in this example the PAT gene, which confers resistance to bialaphos. At 10- to 14-day intervals, embryos are transferred to 563O medium. Actively growing putative transgenic embryogenic tissue is visible in 6-8 weeks.

Regeneration of $T_0$ Plants

Transgenic embryogenic tissue is transferred to 288W medium and incubated at 28° C. in darkness until somatic embryos matured, or about 10 to 18 days. Individual matured somatic embryos with well-defined scutellum and coleoptile are transferred to 272 embryo germination medium and incubated at 28° C. in the light. After shoots and roots emerge, individual plants are potted in soil and hardened-off using typical horticultural methods.

Confirmation of Transformation

Putative transgenic events are subjected to analysis to confirm their transgenic nature. Events are tested for the presence of Lec1 by PCR amplification. Additionally, $T_0$ plants are painted with bialaphos herbicide. The subsequent lack of a herbicide-injury lesion indicates the presence and action of the herbicide resistance gene. The plants are monitored and scored for altered Lec1 expression and/or phenotype such as increased organic sulfur compounds.

Media Recipes

Medium 561 Q contains the following ingredients: 950.000 ml of D-I Water, Filtered; 4.000 g of Chu (N6) Basal Salts (Sigma C-1416); 1.000 ml of Eriksson's Vitamin Mix (1000+Sigma-1511); 1.250 ml of Thiamine.HCL.4 mg/ml; 3.000 ml of 2, 4-D 0.5 mg/ml (No. 2A); 0.690 g of L-proline; 68.500 g of Sucrose; and 36.000 g of Glucose.

Directions are: dissolve ingredients in polished deionized water in sequence; adjust pH to 5.2 w/KOH; Q.S. to volume with polished deionized water after adjusting pH; and filter sterilize (do not autoclave).

Medium 562 P contains the following ingredients: 950.000 ml of D-I Water, Filtered; 4.000 g of Chu (N6) Basal Salts (Sigma C-1416); 1.000 ml of Eriksson's Vitamin Mix (1000×Sigma-1511); 1.250 ml of Thiamine.HCL.4 mg/ml; 4.000 ml of 2, 4-D 0.5 mg/ml; 0.690 g of L-proline; 30.000 g of Sucrose; 3.000 g of Gelrite, which is added after Q.S. to volume; 0.425 ml of Silver Nitrate 2 mg/ml #; and 1.000 ml of Aceto Syringone 100 mM #. Directions are: dissolve ingredients in polished deionized water in sequence; adjust pH to 5.8 w/KOH; Q.S. to volume with polished deionized water after adjusting pH; and sterilize and cool to 60° C. Ingredients designated with a # are added after sterilizing and cooling to temperature.

Medium 563 O contains the following ingredients: 950.000 ml of D-I Water, Filtered; 4.000 g of Chu (N6) Basal Salts (Sigma C-1416); 1.000 ml of Eriksson's Vitamin Mix (1000×Sigma-1511); 1.250 ml of Thiamine.HCL.4 mg/ml; 30.000 g of Sucrose; 3.000 ml of 2, 4-D 0.5 mg/ml (No. 2A); 0.690 g of L-proline; 0.500 g of Mes Buffer; 8.000 g of Agar (Sigma A-7049, Purified), which is added after Q.S. to volume; 0.425 ml of Silver Nitrate 2 mg/ml #; 3.000 ml of Bialaphos 1 mg/ml #; and 2.000 ml of Agribio Carbenicillin 50 mg/ml #. Directions are: dissolve ingredients in polished deionized water in sequence; adjust to pH 5.8 w/koh; Q.S. to volume with polished deionized water after adjusting pH; sterilize and cool to 60° C. Ingredients designated with a # are added after sterilizing and cooling to temperature.

Medium 288 W contains the following ingredients: 950.000 ml of D-I $H_2O$; 4.300 g of MS Salts; 0.100 g of Myo-Inositol; 5.000 ml of MS Vitamins Stock Solution (No. 36J); 1.000 ml of Zeatin.5 mg/ml; 60.000 g of Sucrose; 8.000 g of Agar (Sigma A-7049, Purified), which is added after Q.S. to volume; 2.000 ml of IAA 0.5 mg/ml #; 1.000 ml of 0.1 Mm ABA #; 3.000 ml of Bialaphos 1 mg/ml #; and 2.000 ml of Agribio Carbenicillin 50 mg/ml #. Directions are: dissolve ingredients in polished deionized water in sequence; adjust to pH 5.6; Q.S. to volume with polished deionized water after adjusting pH; sterilize and cool to 60° C. Add 3.5 g/L of Gelrite for cell biology. Ingredients designated with a # are added after sterilizing and cooling to temperature.

Medium 272 contains the following ingredients: 950.000 ml of deionized water; 4.300 g of MS Salts; 0.100 g of Myo-Inositol; 5.000 of MS Vitamins Stock Solution; 40.000 g of Sucrose; and 1.500 g of Gelrite, which is added after Q.S. to volume. Directions are: dissolve ingredients in polished deionized water in sequence; adjust to pH 5.6; Q.S. to volume with polished deionized water after adjusting pH; and sterilize and cool to 60° C.

Medium minimal A contains the following ingredients: 950.000 ml of deionized water; 10.500 g of potassium phosphate dibasic K2HPO4; 4.500 g of potassium phosphate monobasic KH2PO4; 1.000 g of ammonium sulfate; 0.500 g of sodium citrate dihydrate; 10.000 ml of sucrose 20% solution #; and 1.000 ml of 1 M magnesium sulfate #. Directions are: dissolve ingredients in polished deionized water in sequence; Q.S. to volume with deionized water; sterilize and cool to 60° C. Ingredients designated with a # are added after sterilizing and cooling to temperature.

Medium minimal AB contains the following ingredients: 850.000 ml of deionized water; 50.000 ml of stock solution 800A; 9 g of Phytagar which is added after Q.S. to volume; 50.000 ml of stock solution 800B #; 5.000 g of glucose #; and 2.000 ml of spectinomycin 50/mg/ml stock #. Directions are: dissolve ingredients in polished deionized water in sequence; Q.S. to volume with polished deionized water less 100 ml per liter; sterilize and cool to 60° C. Ingredients designated with a # are added after sterilizing and cooling to temperature. Stock solution 800A contains the following ingredients: 950.000 ml of deionized water; 60.000 g of potassium phosphate dibasic K2HPO4; and 20.000 g of sodium phos. monobasic, hydrous. Directions are: dissolve ingredients in polished deionized water in sequence; adjust pH to 7.0 with potassium hydroxide; Q.S. to volume with polished deionized water after adjusting pH; and sterilize and cool to 60° C. Stock solution 800B contains the following ingredients: 950.000 ml of deionized water; 20.000 g of ammonium chloride; 6.000 g of magnesium sulfate 7-$H_2O$, $MgSO_4$, 7 $H_2O$; 3.000 g of potassium chloride; 0.200 g of calcium chloride (anhydrate); and 0.050 g of ferrous sulfate 7-hydrate. Directions are: dissolve ingredients in polished deionized water in sequence; Q.S. to volume with polished deionized water; and sterilize and cool to 60° C.

Medium minimal YP contains the following ingredients: 950.000 ml of deionized water; 5.000 g of yeast extract (Difco); 10.000 g of peptone (Difco); 5.000 g of sodium chloride; 15.000 g of bacto-agar, which is added after Q.S. to volume; and 1.000 ml of spectinomycin 50 mg/ml stock #. Directions are: dissolve ingredients in polished deionized water in sequence; adjust pH to 6.8 with potassium hydroxide; Q.S. to volume with polished deionized water after adjusting pH; sterilize and cool to 60° C. Ingredients designated with a # are added after sterilizing and cooling to temperature.

More than twenty events producing segregating T1 seed were analyzed by NMR for embryo oil content (see Example 12). Six to twelve embryos analyzed for each of five different events showed that some embryos within each event contained elevated oil content. These results are shown in FIG. 2. The same embryos from these five events were analyzed by PCR to determine the presence or absence of the Lec1 construct. Embryos with high oil are always found to contain the Lec1 construct (darkly shaded bars), whereas embryos with normal levels of oil were typically found not to contain the Lec1 construct (cross-hatched bars). These data demonstrate the presence of the Lec1 gene does lead to increased oil in the embryo. It is believed that embryos containing sharply higher levels of oil were homozygous for the Lec1 construct, as these events were segregating 1:2:1. For these events, the oil concentration in the embryos containing the Lec1 construct greatly surpassed any increase previously achieved through enzymatic modification of the fatty acid biosynthetic pathway, with some embryos containing an average increase of 56% in embryo oil content (FIG. 2, Event 277267). Plants derived from seed that contained high oil exhibit some phenotypic changes in growth and development. There is an accumulation of additional leaves during early growth and development phase, and strong leaf curling throughout plant growth and development.

Example 14

Additional Promoters Coupled to Lec1 Also Result in Altered Maize Kernel Oil Accumulation Other types of seed-specific promoters, the lipid transfer protein promoter and the gamma zein promoter, were also tested for their ability to alter oil accumulation in maize kernels when expressing Lec1. Transformation and analysis of these constructs was essentially the same as protocols outlined in Example 13. More than twenty events producing segregating T1 seed are analyzed by NMR for embryo oil content (see Example 12). Six to twelve embryos were analyzed for each event. Events containing embryos with high oil content were analyzed further. The same embryos from these events are analyzed by PCR to determine the presence or absence of the Lec1 construct. As with the oleosin promoter containing construct, all embryos with high oil contents are found to contain the Lec1 construct, whereas embryos with lower or normal oil contents are typically found not to contain the Lec1 construct. Like the events containing Lec1 and the oleosin promoter, the oil concentration in the embryo for these events also greatly surpass any increase previously achieved through enzymatic modification, with some embryos containing an average increase of more than 50% in embryo oil content.

Surprisingly, plants derived from seed containing high oil using this construct do not show the abnormal phenotype found for plants expressing Lec1 under the control of the oleosin promoter. It is believed that these data demonstrate that high oil can be achieved in the embryo without negative agronomic effects when the appropriate expression is employed.

What is claimed is:

1. A method for altering oil phenotype in a plant which comprises:

(a) transforming a plant with a recombinant DNA construct comprising an isolated nucleotide sequence encoding a plant Hap3/Lec1 transcription factor comprising SEQ ID 134, wherein said isolated nucleic acid sequence is operably linked to at least one regulatory sequence;

(b) growing the transformed plant under conditions suitable for expression of the recombinant DNA construct; and (c) selecting transformed plants having an altered oil phenotype as compared to the oil phenotype of an untransformed plant.

2. A method for altering oil phenotype in a plant which comprises:

(a) transforming a plant with a recombinant DNA construct comprising an isolated nucleotide fragment encoding a plant Hap3/lec1 transcription factor having at least 80% sequence identity based on the Clustal method of alignment when compared to the amino acid sequence set forth in SEQ ID NO:134; wherein said nucleic acid sequence is operably linked to at least one regulatory sequence, (b) growing the transformed plant under conditions suitable for expression of the recombinant DNA construct; and (c) selecting transformed plants having an altered oil phenotype as compared to the oil phenotype of an untransformed plant.

3. The method of claim 1 or 2 wherein the plant is selected from the group consisting of corn, soybean, wheat, rice, canola, *Brassica*, sorghum, sunflower, and coconut.

* * * * *

SEQUENCE LISTING

```
<160> NUMBER OF SEQ ID NOS: 222

<210> SEQ ID NO 1
<211> LENGTH: 638
<212> TYPE: DNA
<213> ORGANISM: Catalpa speciosa
<220> FEATURE:
<221> NAME/KEY: unsure
<222> LOCATION: (402)
<223> OTHER INFORMATION: n = A, C, G, or T
<220> FEATURE:
<221> NAME/KEY: unsure
<222> LOCATION: (520)
<223> OTHER INFORMATION: n = A, C, G, or T
<220> FEATURE:
<221> NAME/KEY: unsure
<222> LOCATION: (526)
<223> OTHER INFORMATION: n = A, C, G, or T
<220> FEATURE:
<221> NAME/KEY: unsure
<222> LOCATION: (539)
<223> OTHER INFORMATION: n = A, C, G, or T
<220> FEATURE:
<221> NAME/KEY: unsure
<222> LOCATION: (542)
<223> OTHER INFORMATION: n = A, C, G, or T
<220> FEATURE:
<221> NAME/KEY: unsure
<222> LOCATION: (558)
<223> OTHER INFORMATION: n = A, C, G, or T
<220> FEATURE:
<221> NAME/KEY: unsure
<222> LOCATION: (563)
<223> OTHER INFORMATION: n = A, C, G, or T
<220> FEATURE:
<221> NAME/KEY: unsure
<222> LOCATION: (581)
<223> OTHER INFORMATION: n = A, C, G, or T
<220> FEATURE:
<221> NAME/KEY: unsure
<222> LOCATION: (609)
<223> OTHER INFORMATION: n = A, C, G, or T
<220> FEATURE:
<221> NAME/KEY: unsure
<222> LOCATION: (619)
<223> OTHER INFORMATION: n = A, C, G, or T
<220> FEATURE:
<221> NAME/KEY: unsure
<222> LOCATION: (622)
<223> OTHER INFORMATION: n = A, C, G, or T
<220> FEATURE:
<221> NAME/KEY: unsure
<222> LOCATION: (629)..(630)
<223> OTHER INFORMATION: n = A, C, G, or T
<220> FEATURE:
<221> NAME/KEY: unsure
<222> LOCATION: (632)
<223> OTHER INFORMATION: n = A, C, G, or T
```

```
<400> SEQUENCE: 1
gtgctcttta aaattcacaa gtacatctga cctctacatc aacacacatt gactctaaat      60
tctctctcta aattctgtca acccccaaat tctagggttt tgttttaatt gtcatcagat     120
ttcgccttaa caggacacat tggttgattt ctttgggaga aattagggga gcatgcaatc     180
caagtcccag agcggcaacc aaggagaatc aaccctttat aatgttccta actccaaagt     240
aaatccggat tcttggtgga ataatactgg gatataatcc ttttcctcaa caatgatggg     300
gtgggaaatg catcaagatt catcatccct agaacaatct gtgggatgga caagtcgcag     360
tctaaaggtg gtataaatga ggaagatgat gatactacca aacgatcac aaagttagta      420 cacctccggc tgccaagata gaaactatag gcaggagggc cgagctccag caagctccac     480
ctaccaatac atccaaagaa acaatgggat cgttaatcan ggccanagtt gagctggghg     540
gnatcagtag ctgggggnca aancctaaga tcatatacgg nggaagatgg aactaaggca     600
gcatggtcnc ccaattaang anagcacann anggtgga                            638
```

<210> SEQ ID NO 2
<211> LENGTH: 77
<212> TYPE: PRT
<213> ORGANISM: Catalpa speciosa
<220> FEATURE:
<221> NAME/KEY: UNSURE
<222> LOCATION: (35)
<223> OTHER INFORMATION: Xaa = any amino acid
<220> FEATURE:
<221> NAME/KEY: UNSURE
<222> LOCATION: (76)
<223> OTHER INFORMATION: Xaa = any amino acid

```
<400> SEQUENCE: 2

Met Gln Ser Lys Ser Gln Ser Gly Asn Gln Gly Glu Ser Asn Leu Tyr
  1               5                  10                  15

Asn Val Pro Asn Ser Lys Val Asn Pro Asp Ser Trp Trp Asn Asn Thr
             20                  25                  30

Gly Ile Xaa Ser Phe Ser Ser Thr Met Met Gly Gly Asn Ala Ser Arg
         35                  40                  45

Phe Ile Ile Pro Arg Thr Ile Cys Gly Met Asp Lys Ser Gln Ser Lys
     50                  55                  60

Gly Gly Ile Asn Glu Glu Asp Asp Asp Thr Thr Xaa Thr
 65                  70                  75
```

<210> SEQ ID NO 3
<211> LENGTH: 441
<212> TYPE: DNA
<213> ORGANISM: Typha latifolia
<220> FEATURE:
<221> NAME/KEY: unsure
<222> LOCATION: (378)
<223> OTHER INFORMATION: n = A, C, G, or T
<220> FEATURE:
<221> NAME/KEY: unsure
<222> LOCATION: (415)
<223> OTHER INFORMATION: n = A, C, G, or T

```
<400> SEQUENCE: 3
atttaggaga gagcttgagg tcgagaggag cagcagagga ggaaggaggc aggagaagca      60
aagggtttcg agaaggggga catgctcccc ttataaggac atggaaacca gaaagcaact     120
aggtcatcca ttgctgaagc aagactcatt ttcaaatgtc aactaatctg ttccaccaag     180
aagcatcggt aatgggtgaa gaccacctta gtgagaagca tacttcaaca caatctggga     240
```

-continued

| | |
|---|---|
| atgctggtag ttatggaaat ataagggatg gttatccaaa atcagtatta tccttggcaa | 300 |
| atccagaagc tgcctttgta cctccgaaac ttgattgtag ccagtctttt acttgcatgc | 360 |
| catacccttt tgctgatnca tgctttggtg gtgtcatggc tgcatatggt tcgcnatgcc | 420 |
| tttattcaac aacaaatggt g | 441 |

<210> SEQ ID NO 4
<211> LENGTH: 95
<212> TYPE: PRT
<213> ORGANISM: Typha latifolia
<220> FEATURE:
<221> NAME/KEY: UNSURE
<222> LOCATION: (75)
<223> OTHER INFORMATION: Xaa = any amino acid
<220> FEATURE:
<221> NAME/KEY: UNSURE
<222> LOCATION: (87)
<223> OTHER INFORMATION: Xaa = any amino acid

<400> SEQUENCE: 4

```
Met Ser Thr Asn Leu Phe His Gln Glu Ala Ser Val Met Gly Glu Asp
 1               5                  10                  15

His Leu Ser Glu Lys His Thr Ser Thr Gln Ser Gly Asn Ala Gly Ser
            20                  25                  30

Tyr Gly Asn Ile Arg Asp Gly Tyr Pro Lys Ser Val Leu Ser Leu Ala
        35                  40                  45

Asn Pro Glu Ala Ala Phe Val Pro Pro Lys Leu Asp Cys Ser Gln Ser
    50                  55                  60

Phe Thr Cys Met Pro Tyr Pro Phe Ala Asp Xaa Cys Phe Gly Gly Val
65                  70                  75                  80

Met Ala Ala Tyr Gly Ser Xaa Cys Leu Tyr Ser Thr Thr Asn Gly
                85                  90                  95
```

<210> SEQ ID NO 5
<211> LENGTH: 849
<212> TYPE: DNA
<213> ORGANISM: Vitis sp.

<400> SEQUENCE: 5

| | |
|---|---|
| ctgaggttgc agagacacca tggattccca ccaacggcca tgatttcctt ccaaactcct | 60 |
| acctttagg gtttattcct ctgctctcat cccacattag atttggggct aggggatttt | 120 |
| tgttttctt ggtggaaaag aataatgccg actaaaccca aaattgagga tcggcggata | 180 |
| gaacctggtg gtaagagcaa tccgtcatca acagtctact cccaaccttg gtggcatggt | 240 |
| gttgggaaca atgccatctc cccagctgcc ttgggtggaa gcccatcaaa atcaacttca | 300 |
| gttgaacacc ttaacagtca tatcacgagc aatggtttcc aattacaagc taatggcagg | 360 |
| ctggatgatg gaactacctt taataaagga acacaaccta cggtagccct gcaatctgat | 420 |
| ggaaggaatg gacaggaaca ccagcacctc aatcctactg cttcctcaac actgccaatt | 480 |
| atgagtgaac atcttgaacc aaattcccaa atggaacttg ttggtcactc aattgtgttg | 540 |
| acatcatatc cgtatcaaga tccacataat gtggggatta tgacttctta tgggccacag | 600 |
| gctatggtat gcaagaagt tggttgcatt tctgtgtgtt gtggtaacat tactgttggt | 660 |
| ggcactacca cttctgaaag tgatgcctca accttgaaaa ctagattctc ctgtactagg | 720 |
| gcctgcccct cttataggg aggtcagcca ctgtagtgaa taatctgttt cataagaaaa | 780 |
| tcatcagttt ttatgtgaag gttccttctt ctagatttgg tctcgcccaa gaaaaaaaaa | 840 |
| aaaaaaaaa | 849 |

<210> SEQ ID NO 6
<211> LENGTH: 154
<212> TYPE: PRT
<213> ORGANISM: Vitis sp.

<400> SEQUENCE: 6

```
Met Pro Thr Lys Pro Lys Ile Glu Asp Arg Arg Ile Glu Pro Gly Gly
  1               5                  10                  15

Lys Ser Asn Pro Ser Ser Thr Val Tyr Ser Gln Pro Trp Trp His Gly
             20                  25                  30

Val Gly Asn Asn Ala Ile Ser Pro Ala Ala Leu Gly Gly Ser Pro Ser
         35                  40                  45

Lys Ser Thr Ser Val Glu His Leu Asn Ser His Ile Thr Ser Asn Gly
     50                  55                  60

Phe Gln Leu Gln Ala Asn Gly Arg Leu Asp Asp Gly Thr Thr Phe Asn
 65                  70                  75                  80

Lys Gly Thr Gln Pro Thr Val Ala Leu Gln Ser Asp Gly Arg Asn Gly
                 85                  90                  95

Gln Glu His Gln His Leu Asn Pro Thr Ala Ser Ser Thr Leu Pro Ile
            100                 105                 110

Met Ser Glu His Leu Glu Pro Asn Ser Gln Met Glu Leu Val Gly His
        115                 120                 125

Ser Ile Val Leu Thr Ser Tyr Pro Tyr Gln Asp Pro His Asn Val Gly
    130                 135                 140

Ile Met Thr Ser Tyr Gly Pro Gln Ala Met
145                 150
```

<210> SEQ ID NO 7
<211> LENGTH: 1334
<212> TYPE: DNA
<213> ORGANISM: Vitis sp.

<400> SEQUENCE: 7

```
ctcatttgaa aatccgtaga ccgaaccatg gacttcgtat ccatcattct tctctctcca      60
tagctcctca attctagggt ttctctcact cttcttcctc tctgaatgga agctgtggac     120
aagaacaaaa gcatcctcag caagctgtat caatgatgcc tatgactatg ctgaatacc     180
accttgcacc accttcccag ctggaacttg ttggccactc aattgcgtgt gcatcatatc     240
catattctga accttattac acgggagtca ttcctgctta tggacctcag ggtttggtac     300
aatctcaatt tcttggtgtg aatgtggcta gaatggcttt gcctattgaa atggcagagg     360
aacctgttta tgtgaatgca aaacagtatc atgggattct gaggcgaaga caatcacggg     420
cgaaggccga gctggaaaaa aaactgataa agttaggaa gccatatctt catgaatcaa      480
ggcaccagca tgctatgaga agggcaagag gatgtggagg ccgttttctc aacacaaaga     540
agcttgattc taatgcatcg tatgacatgc ctgacaaggg ctctgatcca gatgtaaacc     600
tttcaacacg acccatcagc tcatcagtct ctgaatctct gccctccaat tcttcccgaa     660
atgaggattc ccccaccagt catctagatg caagaggtcc ctctgtgcag gaattgcaca     720
ataggcaaac agcctcccat ggaaatggca acagctgtta tccacacaac cagggatttc     780
agttgtcgac ataccattcc cttaaagatg atcgcgtgga agaggagac acgcagggc      840
ggcagcatga gagaattctg gtgaataggg ccccccacag ggccctaacc atcaaatgaa     900
accttcgttg ctaagggatg aagggtcttt ccagcattgc tctgatctat tgcagatggc     960
```

```
atcagcttcc atgtgggctt gagggtgtca cagaagtggg ctagttcaaa tacaaaaata    1020
agtgaggagc atccttctgt gacttctact caagtatctg gtaacggatc cggatggcag    1080
cattgcaggg caaagctgga agcattaccc caaccaatca gagggggggg ggacccctgg    1140
cctatgtgtt gtattttcag gcaaatcatt cttggcttgt attttcata ttcctgtgtt     1200 tgttggaccg ggggggaaag acagagagat tgggaatcgt ctaatttcac tcattacctt    1260
tttggaaaaa aaaaaaaaaa aaaaaaaaaa aaaaaaaaaa aaaaaaaaaa aaaaaaaaaa    1320
aaaaaaaaaa aaaa                                                      1334
```

<210> SEQ ID NO 8
<211> LENGTH: 261
<212> TYPE: PRT
<213> ORGANISM: Vitis sp.

<400> SEQUENCE: 8

```
Cys Gly Gln Glu Gln Lys His Pro Gln Ala Val Ser Met Met Pro
  1               5                  10                  15

Met Thr Met Ala Glu Tyr His Leu Ala Pro Pro Ser Gln Leu Glu Leu
                 20                  25                  30

Val Gly His Ser Ile Ala Cys Ala Ser Tyr Pro Tyr Ser Glu Pro Tyr
             35                  40                  45

Tyr Thr Gly Val Ile Pro Ala Tyr Gly Pro Gln Gly Leu Val Gln Ser
         50                  55                  60

Gln Phe Leu Gly Val Asn Val Ala Arg Met Ala Leu Pro Ile Glu Met
 65                  70                  75                  80

Ala Glu Glu Pro Val Tyr Val Asn Ala Lys Gln Tyr His Gly Ile Leu
                 85                  90                  95

Arg Arg Arg Gln Ser Arg Ala Lys Ala Glu Leu Glu Lys Lys Leu Ile
            100                 105                 110

Lys Val Arg Lys Pro Tyr Leu His Glu Ser Arg His Gln His Ala Met
        115                 120                 125

Arg Arg Ala Arg Gly Cys Gly Gly Arg Phe Leu Asn Thr Lys Lys Leu
    130                 135                 140

Asp Ser Asn Ala Ser Tyr Asp Met Pro Asp Lys Gly Ser Asp Pro Asp
145                 150                 155                 160

Val Asn Leu Ser Thr Arg Pro Ile Ser Ser Val Ser Glu Ser Leu
                165                 170                 175

Pro Ser Asn Ser Ser Arg Asn Glu Asp Ser Pro Thr Ser His Leu Asp
            180                 185                 190

Ala Arg Gly Pro Ser Val Gln Glu Leu His Asn Arg Gln Thr Ala Ser
        195                 200                 205

His Gly Asn Gly Asn Ser Cys Tyr Pro His Asn Gln Gly Phe Gln Leu
    210                 215                 220

Ser Thr Tyr His Ser Leu Lys Asp Asp Arg Val Glu Glu Gly Asp His
225                 230                 235                 240

Ala Gly Arg Gln His Glu Arg Ile Leu Val Asn Arg Ala Pro His Arg
                245                 250                 255

Ala Leu Thr Ile Lys
            260
```

<210> SEQ ID NO 9
<211> LENGTH: 987
<212> TYPE: DNA
<213> ORGANISM: Vitis sp.

-continued

```
<400> SEQUENCE: 9
gcacgaggga aggtcaaagt caaatgaagc cagttttctt tatggctaat ccagatgttg      60
tcttcaatcc ttcacaagtt gactatggcc attctgtgac tcatgttgca tatccttatg    120
ctgatcctta ccatgggggg ttagtggctg catatggtcc acatgctgtt attcagcccc    180
agctggtggg gatagcacct accagagtcc cactgccctt tgatattgca gaggatggac    240 ctattttgt caatgcaaaa cagtatcatg gaattctcag gaggaggcag tcacgagcaa     300
agatggaggc ccagaacaaa cttgtcaaag cccgaaagcc atatctgcac gagtctcggc    360
atcttcatgc cctaaatagg gttagaggat ctggtgacg cttcctcagc acgaaaaagc     420
tccaagaacc ggactcaact tccaatgctg gctgtcatag tgtatctggc tctggtcatt    480
ttcaccagaa gggagacaca actgagcagc cggagcacag gttctcaggc atgtctcccc    540
acatgggtgg agccatgcaa ggtggtggcg gtgggactta tggcaatgg agtcctgctc     600 ctggttgtcc ggtgagaagt cgataggaac aagatcgatg gagtcactgg tctgggcaat    660
tcatccttgg ctttgttact ttcgtttcat gcgtgttaag aagataaaca catcaaactt    720
catggtgtag tagaaatact ctgcctttcc catttccaaa tgcatacatt ttggctctgt    780
aaacatggtt gagaagaggc tatgcttgaa actctctgtt tgtgaaccat gttttgttt     840 tttcaagaca atgtgagata ttggttcacc ggtattttgt ttgttgctta cagaaagcaa    900
accctgcctt ttgtgcttaa aaaaaaaaaa aaaaaaaaa aaaaaaaaa aaaaaaaaa       960 aaaaaaaaaa aaaaaaaaaa aaaaaaa                                         987

<210> SEQ ID NO 10
<211> LENGTH: 205
<212> TYPE: PRT
<213> ORGANISM: Vitis sp.

<400> SEQUENCE: 10

Glu Gly Gln Ser Gln Met Lys Pro Val Phe Met Ala Asn Pro Asp
  1               5                  10                  15

Val Val Phe Asn Pro Ser Gln Val Asp Tyr Gly His Ser Val Thr His
                 20                  25                  30

Val Ala Tyr Pro Tyr Ala Asp Pro Tyr His Gly Gly Leu Val Ala Ala
             35                  40                  45

Tyr Gly Pro His Ala Val Ile Gln Pro Gln Leu Val Gly Ile Ala Pro
         50                  55                  60

Thr Arg Val Pro Leu Pro Phe Asp Ile Ala Glu Asp Gly Pro Ile Phe
 65                  70                  75                  80

Val Asn Ala Lys Gln Tyr His Gly Ile Leu Arg Arg Arg Gln Ser Arg
                 85                  90                  95

Ala Lys Met Glu Ala Gln Asn Lys Leu Val Lys Ala Arg Lys Pro Tyr
            100                 105                 110

Leu His Glu Ser Arg His Leu His Ala Leu Asn Arg Val Arg Gly Ser
        115                 120                 125

Gly Gly Arg Phe Leu Ser Thr Lys Lys Leu Gln Glu Pro Asp Ser Thr
    130                 135                 140

Ser Asn Ala Gly Cys His Ser Val Ser Gly Gly His Phe His Gln
145                 150                 155                 160

Lys Gly Asp Thr Thr Glu Gln Pro Glu His Arg Phe Ser Gly Met Ser
                165                 170                 175

Pro His Met Gly Gly Ala Met Gln Gly Gly Gly Gly Thr Tyr Gly
            180                 185                 190
```

```
Gln Trp Ser Pro Ala Pro Gly Cys Pro Val Arg Ser Arg
    195                 200                 205
```

<210> SEQ ID NO 11
<211> LENGTH: 1256
<212> TYPE: DNA
<213> ORGANISM: Zea mays

<400> SEQUENCE: 11

```
gcacgagctc tgtctgtgtg cgagcgcaag agaaagggag tcagagagag agggaggaga     60
ccttgcagag gagcgaagca agcaaggtgg gaaagaggca gcaagggcgg cgggctgccg    120
gaagggaac atgctccctc ctcatctcac agtacgaact gaaaaacaag agtaaagaat     180
ttccgtgaga tgagacagaa tggcgcggtg atgattcagt ttggccatca gatgcctgat    240
tacgactccc cggctaccca gtcaaccagt gagacgagcc atcaagaagc gtctggaatg    300
agcgaaggga gcctcaacga gcataataat gaccattcag gcaaccttga tgggtactcg    360
aagagtgacg aaaacaagat gatgtcagcg ttatccctgg gcaatccgga aacagcttac    420
gcacataatc cgaagcctga ccgtactcag tccttcgcca tatcataccc atatgccgat    480
ccatactacg gtggcgcggt ggcagcagct tatgggcccg catgctatcat gcaccctcag    540
ctggttggca tggttccgtc ctctcgagtg ccactgccga tcgagccagc cgctgaagag    600
cccatctatg tcaacgcgaa gcagtaccac gctattctcc ggaggagaca gctccgtgca    660
aagctagagg cggaaaacaa gctcgtgaaa agccgcaagc cgtacctcca cgagtctcgg    720
cacctgcacg cgatgaagag agctcgggga caggcgggc ggttcctgaa cacgaagcag    780
cagccggagt cccccggcag cggcggctcc tcggacgcgc aacgcgtgcc cgcgaccgcg    840
agcggcggcc tgttcacgaa gcatgagcac agcctgccgc ccggcggtcg ccaccactat    900
cacgcgagag gggcggtga gtagggagcc ccgacactgg caactcatcc ttggcttatc    960
agcgattcga ctcggctctc gctcgtctga aactgaactc tctgcaacta ctgtaactgt   1020
aactaaactg ggtgtgcccg gattggcggt cgttctgttc tactactact agtacccttag  1080
tacctgctac gcgtcgttgg gtctggacta gagagccgtg ctggttcttt gatgaacttg   1140
gctggacttg aggtgttgac tagcgcgaaa ctgagttcca tgtaaacttt tgcttcaaga   1200
ccgatgactg gcggcataat aagtagcagt aataaccaaa aaaaaaaaa aaaaaa       1256
```

<210> SEQ ID NO 12
<211> LENGTH: 244
<212> TYPE: PRT
<213> ORGANISM: Zea mays

<400> SEQUENCE: 12

```
Met Arg Gln Asn Gly Ala Val Met Ile Gln Phe Gly His Gln Met Pro
  1               5                  10                  15

Asp Tyr Asp Ser Pro Ala Thr Gln Ser Thr Ser Glu Thr Ser His Gln
             20                  25                  30

Glu Ala Ser Gly Met Ser Glu Gly Ser Leu Asn Glu His Asn Asn Asp
         35                  40                  45

His Ser Gly Asn Leu Asp Gly Tyr Ser Lys Ser Asp Glu Asn Lys Met
     50                  55                  60

Met Ser Ala Leu Ser Leu Gly Asn Pro Glu Thr Ala Tyr Ala His Asn
 65                  70                  75                  80

Pro Lys Pro Asp Arg Thr Gln Ser Phe Ala Ile Ser Tyr Pro Tyr Ala
                 85                  90                  95
```

```
Asp Pro Tyr Tyr Gly Gly Ala Val Ala Ala Tyr Gly Pro His Ala
            100                 105                 110

Ile Met His Pro Gln Leu Val Gly Met Val Pro Ser Ser Arg Val Pro
        115                 120                 125

Leu Pro Ile Glu Pro Ala Ala Glu Glu Pro Ile Tyr Val Asn Ala Lys
    130                 135                 140

Gln Tyr His Ala Ile Leu Arg Arg Gln Leu Arg Ala Lys Leu Glu
145                 150                 155                 160

Ala Glu Asn Lys Leu Val Lys Ser Arg Lys Pro Tyr Leu His Glu Ser
                165                 170                 175

Arg His Leu His Ala Met Lys Arg Ala Arg Gly Thr Gly Gly Arg Phe
            180                 185                 190

Leu Asn Thr Lys Gln Gln Pro Glu Ser Pro Gly Ser Gly Gly Ser Ser
        195                 200                 205

Asp Ala Gln Arg Val Pro Ala Thr Ala Ser Gly Gly Leu Phe Thr Lys
    210                 215                 220

His Glu His Ser Leu Pro Pro Gly Gly Arg His His Tyr His Ala Arg
225                 230                 235                 240

Gly Gly Gly Glu

<210> SEQ ID NO 13
<211> LENGTH: 1203
<212> TYPE: DNA
<213> ORGANISM: Zea mays

<400> SEQUENCE: 13
ccacgcgtcc ggcaagagaa agggagtcag agagagagag agagggagga gaccttgcag    60
aggagcgaag caagcaaggt gggaaagagg cagcagcaag ggcggcgggc tgccggaagg   120
ggaacatgct ccctcctcat ctcacagaga atggcgcggt gatgattcag tttggccatc   180
agatgcctga ttacgactcc ccggctaccc agtcaaccag tgagacgagc catcaagaag   240
cgtctggaat gagcgaaggg agcctcaacg agcataataa tgaccattca ggcaaccttg   300
atgggtactc gaagagtgac gaaaacaaga tgatgtcagc gttatccctg gcaatccgg   360 aaacagctta cgcacataat ccgaagcctg accgtactca gtccttcgcc atatcatacc   420
catatgccga tccatactac ggtggcgcgg tggcagcagc ttatgcccg catgctatca   480 tgcaccctca gctggttggc atggttccgt cctctcgagt gccactgccg atcgagccag   540
ccgctgaaga gcccatctat gtcaacgcga agcagtacca cgctattctc cggaggagac   600
agctccgtgc aaagctagag gcggaaaaca agctcgtgaa agccgcaag ccgtacctcc   660 acgagtctcg gcacctgcac gcgatgaaga gagctcgggg aacaggcggg cggttcctga   720
acacgaagca gcagccggag tcccccggca gcggcggctc ctcggacgcg caacgcgtgc   780
ccgcgaccgc gagcggcggc ctgttcacga agcatgagca cagcctgccg cccggcggtc   840
gccaccacta tcacgcgaga ggggcggtg agtaggagc ccgacactg caactcatc   900 cttggcttat cagcgattcg actcggctct ccctcgtctg aaactgaact ctctgcaact   960
actgtaactg taactaaact gggtgtgccc ggattggcgg tcgttctgtt ctactactag  1020
tacctgctac gcgtcgttgg gttgggtctg actagagag cgtgctggtt ctttgatgaa   1080
cttggctgga cttgagggtg ttgactagcg cgaagctgag ttccatgtaa aacttttgct  1140
tcaagaccga tgactggcgg cataataagt agcagtaata accaaaaaaa aaaaaaaaa   1200 aag                                                                1203
```

<210> SEQ ID NO 14
<211> LENGTH: 288
<212> TYPE: PRT
<213> ORGANISM: Zea mays

<400> SEQUENCE: 14

```
Pro Ala Arg Glu Arg Glu Ser Glu Arg Glu Arg Glu Gly Gly Asp Leu
 1               5                  10                  15

Ala Glu Glu Arg Ser Lys Gln Gly Gly Lys Glu Ala Ala Ala Arg Ala
            20                  25                  30

Ala Gly Cys Arg Lys Gly Asn Met Leu Pro His Leu Thr Glu Asn
        35                  40                  45

Gly Ala Val Met Ile Gln Phe Gly His Gln Met Pro Asp Tyr Asp Ser
    50                  55                  60

Pro Ala Thr Gln Ser Thr Ser Glu Thr Ser His Gln Glu Ala Ser Gly
65                  70                  75                  80

Met Ser Glu Gly Ser Leu Asn Glu His Asn Asn Asp His Ser Gly Asn
                85                  90                  95

Leu Asp Gly Tyr Ser Lys Ser Asp Glu Asn Lys Met Met Ser Ala Leu
            100                 105                 110

Ser Leu Gly Asn Pro Glu Thr Ala Tyr Ala His Asn Pro Lys Pro Asp
        115                 120                 125

Arg Thr Gln Ser Phe Ala Ile Ser Tyr Pro Tyr Ala Asp Pro Tyr Tyr
    130                 135                 140

Gly Gly Ala Val Ala Ala Ala Tyr Gly Pro His Ala Ile Met His Pro
145                 150                 155                 160

Gln Leu Val Gly Met Val Pro Ser Ser Arg Val Pro Leu Pro Ile Glu
                165                 170                 175

Pro Ala Ala Glu Glu Pro Ile Tyr Val Asn Ala Lys Gln Tyr His Ala
            180                 185                 190

Ile Leu Arg Arg Arg Gln Leu Arg Ala Lys Leu Glu Ala Glu Asn Lys
        195                 200                 205

Leu Val Lys Ser Arg Lys Pro Tyr Leu His Glu Ser Arg His Leu His
    210                 215                 220

Ala Met Lys Arg Ala Arg Gly Thr Gly Gly Arg Phe Leu Asn Thr Lys
225                 230                 235                 240

Gln Gln Pro Glu Ser Pro Gly Ser Gly Gly Ser Ser Asp Ala Gln Arg
                245                 250                 255

Val Pro Ala Thr Ala Ser Gly Gly Leu Phe Thr Lys His Glu His Ser
            260                 265                 270

Leu Pro Pro Gly Gly Arg His His Tyr His Ala Arg Gly Gly Gly Glu
        275                 280                 285
```

<210> SEQ ID NO 15
<211> LENGTH: 1301
<212> TYPE: DNA
<213> ORGANISM: Zea mays

<400> SEQUENCE: 15

```
gcacgagcca gtgcgacggc cacggcctga gcggcgctgc cagcaaggcg gctagtatga      60
gcagcatgga gtcgcggccg ggccgaacga acctggtgga gcccataggg cacggcgccg     120
cgctgccgtc cggcggccag gcagtgcagc cgtggtggac gagctccggg gctgtgctcg     180
gtgcagtctc gccagccgtc gtggcggtgg cgcccgggag cgggacgggg attagcctgt     240
```

-continued

```
cgagcagccc ggcaggtggt agtggtggtg gcggcgcggc taaaggagcc gcgagtgacg      300
agagcagcga ggattcacgg agatctgggg aaccaaaaga tggaagcgct agtcaagaaa      360
agaaccatgc cacatcgcag atacccgctc tggcgccaga gtatttggca ccatactcgc      420
agctggaact gaaccaatca attgcttctg cagcatatca gtacccagat ccttactatg      480
caggcatggt tgctccctat ggaagtcatg ctgtggctca ttttcagcta cctggactaa      540
ctcaatctcg aatgccatta cctcttgaag tatccgagga gcctgtttat gtaaatgcca      600
agcagtacca tggtatctta agacgacggc agtcccgtgc taaggctgaa cttgagaaaa      660
aggtggtcaa agccagaaag ccataccttc acgagtctcg tcatcagcac gcgatgagga      720
gggcaagagg aaacggggga cgcttcctga cacaaagaa agtgacagt ggtgctccca       780 atggaggcga aaacgccgag catctccatg tccctcccga cttactacag ctacgacaga      840
acgaggcttg aagtagcggt atggctctgg catccttgaa cagcagttcc tgtccacggg      900
cgtaggcatt cgagaccgga ttcatatagc tctccacagc atacgcgcag ccatctctgc      960
ggtaacgcac gttctcctga acgagctttg tagcgagata ggtatgcaag tgcaatctgg     1020
gcgcaggaat ccatcatcaa gtgcccaatg cccatgggt aggtacgctg tttcaggcaa      1080
ttcattcttg gctttcacgt tccacccttg tgtaactggt gtgttgtaaa tgtgtggaaa     1140
actaagcttt tgctctgtat cgggccgttc agcggaactg caaaacgcct gtataattaa     1200
gatcgaactt tggattaact cggtaatgct ttgtctggtt ttcttttaaa aaaaaaaaa      1260 aaaaaaaaaa aaaaaaaaaa aacaaaaaaa aaaaaaaaa a                         1301
```

<210> SEQ ID NO 16
<211> LENGTH: 264
<212> TYPE: PRT
<213> ORGANISM: Zea mays

<400> SEQUENCE: 16

```
Met Ser Ser Met Glu Ser Arg Pro Gly Arg Thr Asn Leu Val Glu Pro
 1               5                  10                  15

Ile Gly His Gly Ala Ala Leu Pro Ser Gly Gly Gln Ala Val Gln Pro
            20                  25                  30

Trp Trp Thr Ser Ser Gly Ala Val Leu Gly Ala Val Ser Pro Ala Val
        35                  40                  45

Val Ala Val Ala Pro Gly Ser Gly Thr Gly Ile Ser Leu Ser Ser Ser
    50                  55                  60

Pro Ala Gly Gly Ser Gly Gly Gly Ala Ala Lys Gly Ala Ala Ser
 65                  70                  75                  80

Asp Glu Ser Ser Glu Asp Ser Arg Arg Ser Gly Glu Pro Lys Asp Gly
                 85                  90                  95

Ser Ala Ser Gln Glu Lys Asn His Ala Thr Ser Gln Ile Pro Ala Leu
            100                 105                 110

Ala Pro Glu Tyr Leu Ala Pro Tyr Ser Gln Leu Glu Leu Asn Gln Ser
        115                 120                 125

Ile Ala Ser Ala Ala Tyr Gln Tyr Pro Asp Pro Tyr Tyr Ala Gly Met
    130                 135                 140

Val Ala Pro Tyr Gly Ser His Ala Val Ala His Phe Gln Leu Pro Gly
145                 150                 155                 160

Leu Thr Gln Ser Arg Met Pro Leu Pro Leu Glu Val Ser Glu Glu Pro
                165                 170                 175

Val Tyr Val Asn Ala Lys Gln Tyr His Gly Ile Leu Arg Arg Arg Gln
            180                 185                 190
```

Ser Arg Ala Lys Ala Glu Leu Glu Lys Lys Val Lys Ala Arg Lys
        195                 200                 205

Pro Tyr Leu His Glu Ser Arg His Gln His Ala Met Arg Arg Ala Arg
    210                 215                 220

Gly Asn Gly Gly Arg Phe Leu Asn Thr Lys Lys Ser Asp Ser Gly Ala
225                 230                 235                 240

Pro Asn Gly Gly Glu Asn Ala Glu His Leu His Val Pro Pro Asp Leu
                245                 250                 255

Leu Gln Leu Arg Gln Asn Glu Ala
            260

<210> SEQ ID NO 17
<211> LENGTH: 1258
<212> TYPE: DNA
<213> ORGANISM: Zea mays

<400> SEQUENCE: 17
gcacgaggcc acgccgccgg ccacgcccca gacgaccccg cccgccgccg ccgcctcccg       60
ctccctccgc gcgcagccct cgtccggccg cccgggtccg agcgcgctcg ctcctcctcc      120
ccacgtcgga cagtttaagt gtggcttcat gcatgagta gttgcagtta gcgtggcttt      180
tctccgtgct tgctcctggt cgtgctttgc cttgcaaagg aaggaatcat gacatctgtt      240
gttcacagtg tttcaggtga ccacagggct gaggatcaaa atcaacagaa gaagcaagct      300
gaacctgggg accagcaaga agccccagtt actagttcag atagccaacc aacagtaggc      360
acaccatcaa cagattatgt ggcaccctat gcccctcatg acatgagcca tgcaatgggt      420
caatacgctt atccaaatat tgacccatac tatggaagcc tttatgcagc agcttacggt      480
ggacagccat tgatgcatcc accgttagtt ggaatgcatc cggctggctt accttttgcct     540
accgatgcaa ttgaagagcc tgtgtatgta aatgcaaagc aatacaatgc catattaaga      600
cggcgtcaat ctcgggctaa agctgaatca gaacgaaagc ttatcaaggg gcgtaagccc      660
tatctccatg agtcacgtca tcagcatgcc ttgaaaaggg ccaggggagc tggaggtcgg      720
tttctcaact caaagtcaga tgacaaggaa gagaactccg actcgagtca caaagagaat      780
cagaacggag ttgcgcccca caggagcggc caaccgtcaa cccctccgtc tcccaacggt      840
gcatcgtcag ctaatcaggg caggcagtcg tgaatgatgg atgattcaaa actcacagct      900
gaagagattt cagcccctga gctagatatg gcagcagttt tgtacagaaa acgctagcaa      960
catggtgtcg gtcggtcggt cggttgttgt aggacatgtt ccatagaaaa agcatagacg     1020
agtctacagg ttttggagcc ttggtttggt cctctgtgta ttcacctttc tgtacaatct     1080
tagtagcgtt gtgtaccttc ccctggaagg aaggatagct tcagttagcg cttcagaaag     1140
tcaagtgtgt agcatattgg cttattgttt gctttgcttg acaatggag atttgggagt     1200
ggagttcata accctgctga ataaatactc ttagctggct aaaaaaaaaa aaaaaaa       1258

<210> SEQ ID NO 18
<211> LENGTH: 214
<212> TYPE: PRT
<213> ORGANISM: Zea mays

<400> SEQUENCE: 18

Met Thr Ser Val Val His Ser Val Ser Gly Asp His Arg Ala Glu Asp
1               5                   10                  15

Gln Asn Gln Gln Lys Lys Gln Ala Glu Pro Gly Asp Gln Gln Glu Ala
            20                  25                  30

```
Pro Val Thr Ser Ser Asp Ser Gln Pro Thr Val Gly Thr Pro Ser Thr
        35                  40                  45

Asp Tyr Val Ala Pro Tyr Ala Pro His Asp Met Ser His Ala Met Gly
    50                  55                  60

Gln Tyr Ala Tyr Pro Asn Ile Asp Pro Tyr Tyr Gly Ser Leu Tyr Ala
65                  70                  75                  80

Ala Ala Tyr Gly Gly Gln Pro Leu Met His Pro Pro Leu Val Gly Met
                85                  90                  95

His Pro Ala Gly Leu Pro Leu Pro Thr Asp Ala Ile Glu Glu Pro Val
            100                 105                 110

Tyr Val Asn Ala Lys Gln Tyr Asn Ala Ile Leu Arg Arg Arg Gln Ser
        115                 120                 125

Arg Ala Lys Ala Glu Ser Glu Arg Lys Leu Ile Lys Gly Arg Lys Pro
    130                 135                 140

Tyr Leu His Glu Ser Arg His Gln His Ala Leu Lys Arg Ala Arg Gly
145                 150                 155                 160

Ala Gly Gly Arg Phe Leu Asn Ser Lys Ser Asp Asp Lys Glu Glu Asn
                165                 170                 175

Ser Asp Ser Ser His Lys Glu Asn Gln Asn Gly Val Ala Pro His Arg
            180                 185                 190

Ser Gly Gln Pro Ser Thr Pro Pro Ser Pro Asn Gly Ala Ser Ser Ala
        195                 200                 205

Asn Gln Gly Arg Gln Ser
    210

<210> SEQ ID NO 19
<211> LENGTH: 1170
<212> TYPE: DNA
<213> ORGANISM: Zea mays

<400> SEQUENCE: 19
gcacgagcca cgccgtcggc cacgccccga cgaccaacac ctgctccctc cgccgccgcc      60
cgtgtcctcc cgctccgtcc gcgcgccgcc ctcatacctc caagcgcggt tggatctgct     120
ctgggtccaa gtccgctcga tcctcctctc gtcggaaact ttatgtgtgc cttcatccac     180
gaagagctga agatatcaca tgactagttg cagttagtgt ggcttttctc cctgcttggt     240
cctgattgtg tgctttgcct tgcaaaggaa ggaatcatga cctctgttgt tcagagcgtt     300
tcaggtgacc acagggctga ggatcaaagt catcagaaga agcaaactga acctggggac     360
cagcaagaag ccccagttac tagttcagat agccaaccaa cagtgggcac accatcaaca     420
gattatgtgg cacccatatgc ccctcatgac atgagccatg caatgggtca atatgcttat     480
ccaaatattg atccatacta tggaagtctt tatgcggcgg cttatggtgg acatccattg     540
atgcatccaa cattagtcgg aatgcatccg gctggcttac ctttgcctac cgatgcaatt     600
gaagagccag tgtatgtaaa tgcaaagcaa tacaatgcca tattaagacg gcgtcaatct     660
cgggctaaag ctgaatcaga acggaagctt gtcaagggcc gcaagcccta tctccatgag     720
tcacggcatc agcatgcctt gaaaagggcc aggggagctg gaggtcggtt tctcaattcg     780
aagtcagatg acaaggaaga gaactccgac tcaagtcaaa aagagattca gaacggagtt     840
gcgccccaaa agggtggcca accgtcaacc cctccgtctc ccaacggtgc gtcgtcagct     900
tatcaggcgc ctagtcgtga atgatgattc ggaactcaca actgaagaga ttttagtccc     960
tgacgctagt tgtggcagca gctttgtaca gtaagtgcta gcgggcagca gcgaaatggt    1020
```

| | |
|---|---|
| gtcatagaaa aacgttgacg agtcagacag gttttggagt cttggttttt tttcctctgt | 1080 |
| ttattttacc tgtctgcaat tttagtagct ttgtgtccct tccctggat agttttttgg | 1140 |
| tcagcgctta agaaaaaaaa aaaaaaaaaa | 1170 |

<210> SEQ ID NO 20
<211> LENGTH: 215
<212> TYPE: PRT
<213> ORGANISM: Zea mays

<400> SEQUENCE: 20

```
Met Thr Ser Val Val Gln Ser Val Ser Gly Asp His Arg Ala Glu Asp
 1               5                  10                  15

Gln Ser His Gln Lys Lys Gln Thr Glu Pro Gly Asp Gln Gln Glu Ala
             20                  25                  30

Pro Val Thr Ser Ser Asp Ser Gln Pro Thr Val Gly Thr Pro Ser Thr
         35                  40                  45

Asp Tyr Val Ala Pro Tyr Ala Pro His Asp Met Ser His Ala Met Gly
     50                  55                  60

Gln Tyr Ala Tyr Pro Asn Ile Asp Pro Tyr Tyr Gly Ser Leu Tyr Ala
 65                  70                  75                  80

Ala Ala Tyr Gly Gly His Pro Leu Met His Pro Thr Leu Val Gly Met
                 85                  90                  95

His Pro Ala Gly Leu Pro Leu Pro Thr Asp Ala Ile Glu Glu Pro Val
            100                 105                 110

Tyr Val Asn Ala Lys Gln Tyr Asn Ala Ile Leu Arg Arg Arg Gln Ser
        115                 120                 125

Arg Ala Lys Ala Glu Ser Glu Arg Lys Leu Val Lys Gly Arg Lys Pro
    130                 135                 140

Tyr Leu His Glu Ser Arg His Gln His Ala Leu Lys Arg Ala Arg Gly
145                 150                 155                 160

Ala Gly Gly Arg Phe Leu Asn Ser Lys Ser Asp Asp Lys Glu Glu Asn
                165                 170                 175

Ser Asp Ser Ser Gln Lys Glu Ile Gln Asn Gly Val Ala Pro Gln Lys
            180                 185                 190

Gly Gly Gln Pro Ser Thr Pro Pro Ser Pro Asn Gly Ala Ser Ser Ala
        195                 200                 205

Tyr Gln Ala Pro Ser Arg Glu
    210                 215
```

<210> SEQ ID NO 21
<211> LENGTH: 1892
<212> TYPE: DNA
<213> ORGANISM: Zea mays

<400> SEQUENCE: 21

| | |
|---|---|
| ccacgcgtcc gcccgctggg gctgggctac ctcgttcgct tcgctgcctc tgcctactcc | 60 |
| tctctcccct ctttctccgc tcatgtgctg gtccatcgtc tgcctcctcg gtttgtcctg | 120 |
| aatccttgga cagacgcaca caggctcagc tcaggcggtt gctggatcct ttggcgttcc | 180 |
| ccatccggcc aagaatcctg caagagcctg cttggagttg agccggcca aacctgctgc | 240 |
| cgtcgacgtc tcgggcgagg cagccttgag catcagtctc cttgacgagg caagcaggcc | 300 |
| atgatgagct tcaagggaca cgaggggttc ggtcaggtgt ccggagccgg gatgagccag | 360 |
| gcctcccatg gcgccgcgcc tgccggagcc ccgctgccgt ggtgggctgg ggcccagctg | 420 |
| ctgtccggcg agccggcgcc cctgtccccg gaggaggcgc ccgggacac ccagttccag | 480 |

-continued

```
gtcgtgccgg gggcctctca gggcacgccg gatccagcgc cgcccaaggg agggacacct       540
aaggtcctca agttctctgt gttccaaggg aatttggagt cgggtggtaa aggagagaaa       600
accccaaaga actctaccgc tgtcgttctg cagtcgccat cgcggaata caatggtcgt        660 ttcgagatcg gtctcggtca atctatgctg gtcccttcca gttattcttg tgctgaccag       720
tgctatggca tgcttacgac ttatggaatg agatccatgt ctggtgggag aatgctgttg       780
ccactaattg cgccagccga tgcacccgtt tatgtgaacc cgaaacagta cgaaggcatc       840
ctccgtcgtc gccgtgctcg cgctaaggcg gagagcgaga acaggctcac caaaggcaga       900
aagccttatc tccatgagtc gcgccacctc cacgcgatgc gccgggtgag aggctccggc       960
gggcgcttcc tcaacacgaa taaaggaggg cacggcacgg acgttgctgc aaacgggggc      1020
agcaagatgg cggcggcggc ggcaccatcc cgtctcgcca tgcccctag cgctgagcct      1080 ccatggctgt cagggctcag cgacggcagc aacccgtgct gccactcccg gagtagtgtc      1140
tccagcttgt ccgggtccta cgtggcgagc atctacggtg gcttggagca gcacctccgg      1200
gcgccgccct tcttcacccc gctgccgccc gtcatggacg gcgaccacgg cggccccacg      1260
gccgccacca tctcctcctt caagtgggcg gccagcgacg gctgctgcga gctcctcagg      1320
gcgtgaaccg aggagggagg ggatggctac tcagacgaac ggccttctcc ccgatggctg      1380
gttgtctgta ggcaaatcat tcttggctgt tctgcattgg ggtgcgacct acacatcatc      1440
cgcctaccgt acctacccca cccgtgtccc tgaaattcca gggtgcttgg gttacttaca      1500
ggggtcttgt gtggtgatgt ggctcccccca tatgcatttg ctgtaacata gcgtaccca      1560 accactgttg cttggtactt ctcgctatca ctgcctcatc agtatggatt ctgcatttct      1620
gcgttgtcac agtgtatgaa taattgaggc gtcagacttc agggttgctc cagttcttgg      1680
agataggtct gggtttgttt gaagcttgcc tggaggtctg aaactttgtg tttggtgaag      1740
atgctacgtt attgcagttt gaatctgtaa gtttgggatc agcattcagt tgttgcatcg      1800
tctgtgctct ggtgccgagg tgttcgttct gaatatttga ttcaattcaa aatcttcagc      1860
taagttacta ctgggacaaa aaaaaaaaa aa                                    1892
```

<210> SEQ ID NO 22
<211> LENGTH: 341
<212> TYPE: PRT
<213> ORGANISM: Zea mays

<400> SEQUENCE: 22

```
Met Met Ser Phe Lys Gly His Glu Gly Phe Gly Gln Val Ser Gly Ala
  1               5                  10                  15

Gly Met Ser Gln Ala Ser His Gly Ala Ala Pro Ala Gly Ala Pro Leu
             20                  25                  30

Pro Trp Trp Ala Gly Ala Gln Leu Leu Ser Gly Glu Pro Ala Pro Leu
         35                  40                  45

Ser Pro Glu Glu Ala Pro Arg Asp Thr Gln Phe Gln Val Val Pro Gly
     50                  55                  60

Ala Ser Gln Gly Thr Pro Asp Pro Ala Pro Lys Gly Gly Thr Pro
 65                  70                  75                  80

Lys Val Leu Lys Phe Ser Val Phe Gln Gly Asn Leu Glu Ser Gly Gly
                 85                  90                  95

Lys Gly Glu Lys Thr Pro Lys Asn Ser Thr Ala Val Val Leu Gln Ser
            100                 105                 110

Pro Phe Ala Glu Tyr Asn Gly Arg Phe Glu Ile Gly Leu Gly Gln Ser
```

```
              115                 120                 125
Met Leu Val Pro Ser Ser Tyr Ser Cys Ala Asp Gln Cys Tyr Gly Met
    130                 135                 140

Leu Thr Thr Tyr Gly Met Arg Ser Met Ser Gly Gly Arg Met Leu Leu
145                 150                 155                 160

Pro Leu Ile Ala Pro Ala Asp Ala Pro Val Tyr Val Asn Pro Lys Gln
                165                 170                 175

Tyr Glu Gly Ile Leu Arg Arg Arg Ala Arg Ala Lys Ala Glu Ser
            180                 185                 190

Glu Asn Arg Leu Thr Lys Gly Arg Lys Pro Tyr Leu His Glu Ser Arg
        195                 200                 205

His Leu His Ala Met Arg Arg Val Arg Gly Ser Gly Arg Phe Leu
    210                 215                 220

Asn Thr Asn Lys Gly Gly His Gly Thr Asp Val Ala Ala Asn Gly Gly
225                 230                 235                 240

Ser Lys Met Ala Ala Ala Ala Pro Ser Arg Leu Ala Met Pro Pro
                245                 250                 255

Ser Ala Glu Pro Pro Trp Leu Ser Gly Leu Ser Asp Gly Ser Asn Pro
            260                 265                 270

Cys Cys His Ser Arg Ser Ser Val Ser Ser Leu Ser Gly Ser Tyr Val
                275                 280                 285

Ala Ser Ile Tyr Gly Gly Leu Glu Gln His Leu Arg Ala Pro Pro Phe
    290                 295                 300

Phe Thr Pro Leu Pro Pro Val Met Asp Gly Asp His Gly Gly Pro Thr
305                 310                 315                 320

Ala Ala Thr Ile Ser Ser Phe Lys Trp Ala Ala Ser Asp Gly Cys Cys
                325                 330                 335

Glu Leu Leu Arg Ala
            340

<210> SEQ ID NO 23
<211> LENGTH: 323
<212> TYPE: DNA
<213> ORGANISM: Zea mays
<220> FEATURE:
<221> NAME/KEY: unsure
<222> LOCATION: (201)
<223> OTHER INFORMATION: n = A, C, G, or T
<220> FEATURE:
<221> NAME/KEY: unsure
<222> LOCATION: (244)
<223> OTHER INFORMATION: n = A, C, G, or T
<220> FEATURE:
<221> NAME/KEY: unsure
<222> LOCATION: (276)
<223> OTHER INFORMATION: n = A, C, G, or T
<220> FEATURE:
<221> NAME/KEY: unsure
<222> LOCATION: (279)
<223> OTHER INFORMATION: n = A, C, G, or T
<220> FEATURE:
<221> NAME/KEY: unsure
<222> LOCATION: (296)
<223> OTHER INFORMATION: n = A, C, G, or T
<220> FEATURE:
<221> NAME/KEY: unsure
<222> LOCATION: (320)
<223> OTHER INFORMATION: n = A, C, G, or T

<400> SEQUENCE: 23
acgccatcat gcgtcggcgc tgtgcccgtg ccaaagcaga gagggaaaat aggctggtca    60
aaggcaggaa gccatatctc catgagtcac gccatcagca tgcactgcgt cgcccgcgag   120
```

```
gctctggcgg acgcttcctg aacacaaaga aagaatccag cgggaaggat gctggtggtg      180
gcagcaaggc aatgtttcaa ncaaccccct catgcgccag gtggcgttct cccaagctcc      240
aaanatccac cagtccagac ctgggccaac cccgancanc gttttccacc tgttcnggtt      300
tccaaagttt tttcaaccct ttt                                             323
```

```
<210> SEQ ID NO 24
<211> LENGTH: 77
<212> TYPE: PRT
<213> ORGANISM: Zea mays
<220> FEATURE:
<221> NAME/KEY: UNSURE
<222> LOCATION: (67)
<223> OTHER INFORMATION: Xaa = any amino acid

<400> SEQUENCE: 24
```

```
Ala Ile Met Arg Arg Arg Cys Ala Arg Ala Lys Ala Glu Arg Glu Asn
 1               5                  10                  15

Arg Leu Val Lys Gly Arg Lys Pro Tyr Leu His Glu Ser Arg His Gln
            20                  25                  30

His Ala Leu Arg Arg Pro Arg Gly Ser Gly Gly Arg Phe Leu Asn Thr
        35                  40                  45

Lys Lys Glu Ser Ser Gly Lys Asp Ala Gly Gly Ser Lys Ala Met
    50                  55                  60

Phe Gln Xaa Thr Pro Ser Cys Ala Arg Trp Arg Ser Pro
65                  70                  75
```

```
<210> SEQ ID NO 25
<211> LENGTH: 1195
<212> TYPE: DNA
<213> ORGANISM: Zea mays

<400> SEQUENCE: 25
gcaccagacc agaggaaggg acggcgggga ggtggcaagg cgcagagagc aggttcgctt       60
ggcggacgca ccgagggagg cgtgtgggag ccatgcttct ccgtcttcg tcttcgtctt      120 ccgcttccgc ttccgcttcc aaaggtaact cctttgggaa aaccgttaac gatcatctga      180
ggtcaacttt gagttttgat aacaagcaac ctccatttgc aagtcaaaac tttgactacg      240
gtcaaacaat agcttgcatt tcatacccgt acaatcattc tggctcagga gatgtctggg      300
cagcctatga gtcacgcacc agcgctgcca ctgtgttccg ttcccaaatt gctggtgggg      360
gtacatccac aagaattccc ttgcctttgg aattagcaga gaatgaaccc atatatgtga      420
atcccaaaca atatcacggg atacttcgca agacagtt acgtgccaag ttagaggctc       480
agaacaagct agtcagagcc cgaaagcctt accttcatga gtctaggcat cttcatgcaa      540
tgaagagggc acgaggttcc ggtggacgat cctcaacac taagcagctc cagcagtctc      600
acactgccct caccaggtcc accaccacaa gtggcacaag ctcctcaggc tcaactcatc      660
tgcggcttgg tggtggcgca gccgcagctg gagatcgatc tgtgctggca cccaaaacaa      720
tggcctcaca agacagtagc aagaaggccg tttcttcagc cctcgccttc actgcgactc      780
caatgctgcg cagagatgac ggcttcttgc agcacccaag ccatcttttc agttttctg       840 gtcattttgg gcaggcaagc gcgcaagctg cgtccataa tggaagtcag catagggttc       900
cagttatgag atgaccggtt tgcgaaccat agctggtgat ccaggcgtct agggtcaact      960
tcgctgtggt gtcttagtct ctcaggcaat tcatccttgg cttaatttct ggcttttat     1020 tagaaggtac caaaatgtgt tccataccgt tgtggccaca gagcccataa accaggggt     1080
```

```
ttgatggttg gcactcctac ccaaactatt gtcttgttgc agtggtgttt gttagaataa    1140
accttgacta ttattctgta caaaaaaaaa aaaaaaaaaa aaaaaaaaaa aaaaa          1195
```

<210> SEQ ID NO 26
<211> LENGTH: 273
<212> TYPE: PRT
<213> ORGANISM: Zea mays

<400> SEQUENCE: 26

```
Met Leu Leu Pro Ser Ser Ser Ser Ser Ala Ser Ala Ser Ala Ser
 1               5                  10                  15

Lys Gly Asn Ser Phe Gly Lys Thr Val Asn Asp His Leu Arg Ser Thr
                20                  25                  30

Leu Ser Phe Asp Asn Lys Gln Pro Pro Phe Ala Ser Gln Asn Phe Asp
            35                  40                  45

Tyr Gly Gln Thr Ile Ala Cys Ile Ser Tyr Pro Tyr Asn His Ser Gly
        50                  55                  60

Ser Gly Asp Val Trp Ala Ala Tyr Glu Ser Arg Thr Ser Ala Ala Thr
 65                 70                  75                  80

Val Phe Arg Ser Gln Ile Ala Gly Gly Thr Ser Thr Arg Ile Pro
                85                  90                  95

Leu Pro Leu Glu Leu Ala Glu Asn Glu Pro Ile Tyr Val Asn Pro Lys
            100                 105                 110

Gln Tyr His Gly Ile Leu Arg Arg Arg Gln Leu Arg Ala Lys Leu Glu
        115                 120                 125

Ala Gln Asn Lys Leu Val Arg Ala Arg Lys Pro Tyr Leu His Glu Ser
    130                 135                 140

Arg His Leu His Ala Met Lys Arg Ala Arg Gly Ser Gly Gly Arg Phe
145                 150                 155                 160

Leu Asn Thr Lys Gln Leu Gln Gln Ser His Thr Ala Leu Thr Arg Ser
                165                 170                 175

Thr Thr Thr Ser Gly Thr Ser Ser Gly Ser Thr His Leu Arg Leu
            180                 185                 190

Gly Gly Gly Ala Ala Ala Ala Gly Asp Arg Ser Val Leu Ala Pro Lys
        195                 200                 205

Thr Met Ala Ser Gln Asp Ser Ser Lys Lys Ala Val Ser Ser Ala Leu
    210                 215                 220

Ala Phe Thr Ala Thr Pro Met Leu Arg Arg Asp Asp Gly Phe Leu Gln
225                 230                 235                 240

His Pro Ser His Leu Phe Ser Phe Ser Gly His Phe Gly Gln Ala Ser
                245                 250                 255

Ala Gln Ala Gly Val His Asn Gly Ser Gln His Arg Val Pro Val Met
            260                 265                 270

Arg
```

<210> SEQ ID NO 27
<211> LENGTH: 1376
<212> TYPE: DNA
<213> ORGANISM: Zea mays

<400> SEQUENCE: 27

```
tctctatcta tctatacggt tcaagggact gaagaaggta gagagagaaa ctcgaagggg    60
agaggacaga agaggggagat acaggttaat ttttaggtac cagatcatct gatttctcag   120
aagcaaaatg ttgtttggag ctcagtgaca ccatcttgta atgcctgtga ttttacggga   180
```

-continued

```
aatggaggat cattctgtcc atcccatgtc taagtctaac catggctcct tgtcaggaaa        240
tggttatgag atgaaacatt caggccataa agtttgcgat agggattcat catcggagtc        300
tgatcggtct caccaagaag catcagcagc aagtgaaagc agtccaaatg aacacacatc        360
aactcaatca gacaatgatg aagatcatgg gaaagataat caggacacaa tgaagccagt        420
attgtccttg gggaaggaag ctctgccttt tttggcccca aaattacatt acagcccatc        480
ttttgcttgt attccttata ctgctgatgc ttattatagt gcggttgggg tcttgacagg        540
atatcctcca catgccattg tccatcccca gcaaaatgat acaacgaaca ctccgggtat        600
gttacctgtg aacctgcag aagaaccaat atatgttaat gcaaacaat accatgcaat         660
ccttaggagg aggcaaacac gtgctaaatt ggaggcccag aacaagatgg tgaaaaatcg        720
gaagccatat cttcatgagt cccgacatcg tcatgccatg aaacgggctc gtggatcagg        780
aggacggttc ctcaacacaa agcagctcca ggagcagaac cagcagtatc aggcatcgag        840
tggttcattg tgctcaaaga tcattgccaa cagcataatc tcccaaagtg gccccacctg        900
cacgccctct tctggcactg caggtgcttc aacagccggc caggaccgca gctgcttgcc        960
ctcagttggc ttccgcccca cgacaaactt cagtgaccaa ggtcgaggag gcttgaagct       1020
ggccgtgatc ggcatgcagc agcgtgtttc caccataagg tgaagagaag tgggcacaac       1080
accattccca ggcacactgc ctgtggcaac tcatccttgg ctcttggaac tttgaatatg       1140
caatcgacat gtagcttgag atcctcagaa taaaccaaac cttcagttat atgcaagcct       1200
tttttgaggt tgctgttgct gtacctgaga actgtggtta ggttatgagt ttgttcctca       1260
aaactgaccc atacatgaca tgctaccttg tgctgagttt ctgagacaaa gccatcgaaa       1320
catgatcttg tggttcagta aaaaaaaaaa aaaaaaaaa aaaaaaaaa aaaaaa            1376
```

<210> SEQ ID NO 28
<211> LENGTH: 300
<212> TYPE: PRT
<213> ORGANISM: Zea mays

<400> SEQUENCE: 28

```
Met Pro Val Ile Leu Arg Glu Met Glu Asp His Ser Val His Pro Met
 1               5                  10                  15

Ser Lys Ser Asn His Gly Ser Leu Ser Gly Asn Gly Tyr Glu Met Lys
            20                  25                  30

His Ser Gly His Lys Val Cys Asp Arg Asp Ser Ser Glu Ser Asp
        35                  40                  45

Arg Ser His Gln Glu Ala Ser Ala Ser Glu Ser Pro Asn Glu
    50                  55                  60

His Thr Ser Thr Gln Ser Asp Asn Asp Glu Asp His Gly Lys Asp Asn
 65                  70                  75                  80

Gln Asp Thr Met Lys Pro Val Leu Ser Leu Gly Lys Glu Gly Ser Ala
                85                  90                  95

Phe Leu Ala Pro Lys Leu His Tyr Ser Pro Ser Phe Ala Cys Ile Pro
            100                 105                 110

Tyr Thr Ala Asp Ala Tyr Tyr Ser Ala Val Gly Val Leu Thr Gly Tyr
        115                 120                 125

Pro Pro His Ala Ile Val His Pro Gln Gln Asn Asp Thr Thr Asn Thr
    130                 135                 140

Pro Gly Met Leu Pro Val Glu Pro Ala Glu Glu Pro Ile Tyr Val Asn
145                 150                 155                 160
```

```
Ala Lys Gln Tyr His Ala Ile Leu Arg Arg Arg Gln Thr Arg Ala Lys
            165                 170                 175

Leu Glu Ala Gln Asn Lys Met Val Lys Asn Arg Lys Pro Tyr Leu His
            180                 185                 190

Glu Ser Arg His Arg His Ala Met Lys Arg Ala Arg Gly Ser Gly Gly
            195                 200                 205

Arg Phe Leu Asn Thr Lys Gln Leu Gln Glu Gln Asn Gln Gln Tyr Gln
            210                 215                 220

Ala Ser Ser Gly Ser Leu Cys Ser Lys Ile Ile Ala Asn Ser Ile Ile
225                 230                 235                 240

Ser Gln Ser Gly Pro Thr Cys Thr Pro Ser Ser Gly Thr Ala Gly Ala
            245                 250                 255

Ser Thr Ala Gly Gln Asp Arg Ser Cys Leu Pro Ser Val Gly Phe Arg
            260                 265                 270

Pro Thr Thr Asn Phe Ser Asp Gln Gly Arg Gly Gly Leu Lys Leu Ala
            275                 280                 285

Val Ile Gly Met Gln Gln Arg Val Ser Thr Ile Arg
            290                 295                 300
```

<210> SEQ ID NO 29
<211> LENGTH: 1492
<212> TYPE: DNA
<213> ORGANISM: Zea mays

<400> SEQUENCE: 29

```
gcacgagctc acttgcttcg acgtatttct caatctatct atacggttca agggaccgaa      60
gaaggtagag agagaaactt gaaggggaga ggaaggagat acaggttcat gttcatttag     120
gtgtcagttc atctgatttc tcagaagcaa aatgttgttt ggagctcagt gacaccatct     180
tgtaatgcat gtgccttttta cgggaaatgg aggatcattc tgtccatcca agtctaagt     240
ctaaccatgg ttccttgtca ggaaatggtt atgagatgaa aaatccaggc catgaagttt     300
gtgataggga ttcatcatca gagtctgatc gatctcaccc agaagcatca gcagtgagtg     360
aaagcagtct agatgaacac acatcaactc aatcagacaa tgatgaagat catgggaagg     420
ataatcagga cacattgaag ccagtattgt ccttgggaa ggaagggtct gccttttttgg     480
ccccaaaaat agattacaac ccgtcttttc cttatattcc ttatactgct gacgcttact     540
atggtggcgt tggggtcttg acaggatatg ctccgcatgc cattgtccat ccccagcaaa     600
atgatacaac aaatagtccg gttatgttgc ctgcggaacc tgcagaagaa gaaccaatat     660
atgtcaatgc aaaacaatac catgcaatcc ttaggaggag gcagacacgt gctaaactgg     720
aggcgcagaa caagatggtg aaaggtcgga agccatacct tcatgagtct cgacaccgtc     780
atgccatgaa gcgggcccgt ggctcaggag gcgggttcct caacacaaag cagcagctcc     840
aggagcagaa ccagcggtac caggcgtcga gtggttcaat gtgctcaaag accattggca     900
acagcgtaat ctcccaaagt ggccccattt gcacgccctc ttctgacgct gcaggtgctt     960
cagcagccag ccaggaccgc ggctgcttgc cctcggttgg cttccgcccc acagccaact    1020
tcagtgagca aggtggaggc ggctcgaagc tggtcatgaa cggcatgcag cagcgtgttt    1080
ccaccataag gtgaagagaa gtgggcacga caccattccc aggcgcgcac tgcctgtggc    1140
aactcatcct ggcttttga aactatggat atgcaatgga catgtagctt cgagttcctc    1200
agaataacca aacgtgaaga aatatgcaaag tccttttgag atttgctgta gctgaaagaa    1260
ctgtggttag gttgagtttc ttcctggaga ctgatccata catgacatgc tacctcgtgc    1320
```

```
tgagtttctg aggtgaagcc atcgaaacat gaccgtgtgg ttcagtaaaa aaaaaaaaa      1380 aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aa            1492
```

<210> SEQ ID NO 30
<211> LENGTH: 301
<212> TYPE: PRT
<213> ORGANISM: Zea mays

<400> SEQUENCE: 30

```
Met Cys Leu Leu Arg Glu Met Glu Asp His Ser Val His Pro Lys Ser
 1               5                  10                  15

Lys Ser Asn His Gly Ser Leu Ser Gly Asn Gly Tyr Glu Met Lys Asn
            20                  25                  30

Pro Gly His Glu Val Cys Asp Arg Asp Ser Ser Glu Ser Asp Arg
        35                  40                  45

Ser His Pro Glu Ala Ser Ala Val Ser Glu Ser Ser Leu Asp Glu His
    50                  55                  60

Thr Ser Thr Gln Ser Asp Asn Asp Glu Asp His Gly Lys Asp Asn Gln
65                  70                  75                  80

Asp Thr Leu Lys Pro Val Leu Ser Leu Gly Lys Glu Gly Ser Ala Phe
                85                  90                  95

Leu Ala Pro Lys Ile Asp Tyr Asn Pro Ser Phe Pro Tyr Ile Pro Tyr
            100                 105                 110

Thr Ala Asp Ala Tyr Tyr Gly Gly Val Gly Val Leu Thr Gly Tyr Ala
        115                 120                 125

Pro His Ala Ile Val His Pro Gln Gln Asn Asp Thr Thr Asn Ser Pro
    130                 135                 140

Val Met Leu Pro Ala Glu Pro Ala Glu Glu Pro Ile Tyr Val Asn
145                 150                 155                 160

Ala Lys Gln Tyr His Ala Ile Leu Arg Arg Arg Gln Thr Arg Ala Lys
                165                 170                 175

Leu Glu Ala Gln Asn Lys Met Val Lys Gly Arg Lys Pro Tyr Leu His
            180                 185                 190

Glu Ser Arg His Arg His Ala Met Lys Arg Ala Arg Gly Ser Gly Gly
        195                 200                 205

Arg Phe Leu Asn Thr Lys Gln Gln Leu Gln Glu Gln Asn Gln Arg Tyr
    210                 215                 220

Gln Ala Ser Ser Gly Ser Met Cys Ser Lys Thr Ile Gly Asn Ser Val
225                 230                 235                 240

Ile Ser Gln Ser Gly Pro Ile Cys Thr Pro Ser Ser Asp Ala Ala Gly
                245                 250                 255

Ala Ser Ala Ala Ser Gln Asp Arg Gly Cys Leu Pro Ser Val Gly Phe
            260                 265                 270

Arg Pro Thr Ala Asn Phe Ser Glu Gln Gly Gly Gly Ser Lys Leu
        275                 280                 285

Val Met Asn Gly Met Gln Gln Arg Val Ser Thr Ile Arg
    290                 295                 300
```

<210> SEQ ID NO 31
<211> LENGTH: 725
<212> TYPE: DNA
<213> ORGANISM: Zea mays
<220> FEATURE:
<221> NAME/KEY: unsure
<222> LOCATION: (546)

<223> OTHER INFORMATION: n = A, C, G, or T
<220> FEATURE:
<221> NAME/KEY: unsure
<222> LOCATION: (554)
<223> OTHER INFORMATION: n = A, C, G, or T
<220> FEATURE:
<221> NAME/KEY: unsure
<222> LOCATION: (636)
<223> OTHER INFORMATION: n = A, C, G, or T
<220> FEATURE:
<221> NAME/KEY: unsure
<222> LOCATION: (671)
<223> OTHER INFORMATION: n = A, C, G, or T
<220> FEATURE:
<221> NAME/KEY: unsure
<222> LOCATION: (697)
<223> OTHER INFORMATION: n = A, C, G, or T

<400> SEQUENCE: 31

```
gcagcaaaca ctagggtacc attgccagtt gggcctgcag cagaggaacc catatttgtc      60
aatgcaaagc aatacaatgc tatcctccgg aggaggcaaa acgcgcaaa actggaggcc      120
caaaataaac tggtgaaagg tcggaagcca tatctccatg aatctcggca tcgtcatgca      180
atgaagcgag tccgtggacc agggcgtttc ctcaacaaaa aggagctcca ggagcagcag      240
ctgaaggcac tgccttcact tcagactcca acaggtgggg tcagcaaaat ggcctttggc      300
aggaacctat gccctgaaag cagcacatct cactcgcctt cgacgagctc tacaatctcg      360
agtgcttcaa actggagtgg cacgctagct catcaagagc acgttagctt cgcatctgct      420
aataaattcc tccccagcat gaacttccac gcggagaatg gagtgaaaag atggccatca      480
atggcgtccg ccaccacacc cctgtcctga gtgaacaacc ttcaactgtg ggggtgctgt      540
gctggnacca tcantgggcg cgctccgtgt gcccgtggca attcatcttg cttatgatg      600
tatcttatag ttaatttgct ttcactttca tatggnactt gtctcagatt aaactcgtga      660
tatttattgc nactgggatg actggaaata atctcangtt tcttaccaaa aaaaaaaaaa      720
aaaaa                                                                  725
```

<210> SEQ ID NO 32
<211> LENGTH: 169
<212> TYPE: PRT
<213> ORGANISM: Zea mays

<400> SEQUENCE: 32

```
Ala Ala Asn Thr Arg Val Pro Leu Pro Val Gly Pro Ala Ala Glu Glu
 1               5                  10                  15

Pro Ile Phe Val Asn Ala Lys Gln Tyr Asn Ala Ile Leu Arg Arg Arg
                20                  25                  30

Gln Lys Arg Ala Lys Leu Glu Ala Gln Asn Lys Leu Val Lys Gly Arg
            35                  40                  45

Lys Pro Tyr Leu His Glu Ser Arg His Arg His Ala Met Lys Arg Val
        50                  55                  60

Arg Gly Pro Gly Arg Phe Leu Asn Lys Lys Glu Leu Gln Glu Gln Gln
    65                  70                  75                  80

Leu Lys Ala Leu Pro Ser Leu Gln Thr Pro Thr Gly Gly Val Ser Lys
                85                  90                  95

Met Ala Phe Gly Arg Asn Leu Cys Pro Glu Ser Ser Thr Ser His Ser
            100                 105                 110

Pro Ser Thr Ser Ser Thr Ile Ser Ser Ala Ser Asn Trp Ser Gly Thr
        115                 120                 125

Leu Ala His Gln Glu His Val Ser Phe Ala Ser Ala Asn Lys Phe Leu
```

```
                130                 135                 140
Pro Ser Met Asn Phe His Ala Glu Asn Gly Val Lys Arg Trp Pro Ser
145                 150                 155                 160

Met Ala Ser Ala Thr Thr Pro Leu Ser
                165
```

<210> SEQ ID NO 33
<211> LENGTH: 831
<212> TYPE: DNA
<213> ORGANISM: Zea mays

<400> SEQUENCE: 33

```
ccacgcgtcc gcatatatgt gaatcccaaa caatatcacg ggatacttcg cagaagacag    60
ttacgtgcca agctagaggc tcagaacaag ctagtcagag cccgaaagtc ttaccttcat   120
gagtctaggc atcttcatgc aatgaagagg gcacgaggtt ccggtggacg attcctcaac   180
actaagcagc tccagcagtc tcacacagcc ctcaccaggt ccaccaccac aagtggcaca   240
agctcctcag gctcaactca tctgcggctt ggtggtggcg cagccgcagc tggagatcga   300
tctgtgctgg cacccaaaac aatggcctca caagacagta gcaagaaggc cgtttcttca   360
gccctcgcct tcactgcgac tccaatgctg cgcagagatg acggcttctt gcagcaccca   420
agccatcttt tcagttttc tggtcatttt gggcaggcaa gcgcgcaagc tggcgtccat   480
aatggaagtc agcatagggt tccagttatg agatgaccgg tttgcgaacc atagctggtg   540
atccaggcgt ctagggtcaa cttcgctgtg gtgtcttagt ctctcaggca attcatcctt   600
ggcttaattt ctggcttttt attagaaggt accaaaatgt gttccatacc gttgtggcca   660
cagagcccat aaaccagggg gtttgatggt tggcactcct acccaaacta ttgttgcagt   720
ggtgtttgtt agaataaacc ttgactatta ttctgtacaa tttgccttta tcttgtactg   780
ccaattattg tgtagtggtc aaaaaaaaaa aaaaaaaaa aaaaaaaaa g               831
```

<210> SEQ ID NO 34
<211> LENGTH: 98
<212> TYPE: PRT
<213> ORGANISM: Zea mays

<400> SEQUENCE: 34

```
Ile Tyr Val Asn Pro Lys Gln Tyr His Gly Ile Leu Arg Arg Arg Gln
  1               5                  10                  15

Leu Arg Ala Lys Leu Glu Ala Gln Asn Lys Leu Val Arg Ala Arg Lys
             20                  25                  30

Ser Tyr Leu His Glu Ser Arg His Leu His Ala Met Lys Arg Ala Arg
         35                  40                  45

Gly Ser Gly Gly Arg Phe Leu Asn Thr Lys Gln Leu Gln Gln Ser His
     50                  55                  60

Thr Ala Leu Thr Arg Ser Thr Thr Ser Gly Thr Ser Ser Ser Gly
 65                  70                  75                  80

Ser Thr His Leu Arg Leu Gly Gly Gly Ala Ala Ala Gly Asp Arg
                 85                  90                  95

Ser Val
```

<210> SEQ ID NO 35
<211> LENGTH: 1307
<212> TYPE: DNA
<213> ORGANISM: Zea mays

<400> SEQUENCE: 35

-continued

```
ccacgcgtcc gctgtctgtg tgcgagcgca agagaaaggg agtcagagag agagagagag      60
ggaggagacc ttgcagagga gcgaagcaag caaggtggga agaggcagc agcaagggcg       120 gcgggctgcc ggaagggaa catgctccct cctcatctca cagtacgaac tgaaaaacaa       180
gagtaaagaa tttccgtgag atgagacaga atggcgcggt gatgattcag tttggccatc      240
agatgcctga ttacgactcc ccggctaccc agtcaaccag tgagacgagc atcaagaag       300 cgtctggaat gagcgaaggg agcctcaacg agcataataa tgaccattca ggcaaccttg      360
atgggtactc gaagagtgac gaaaacaaga tgatgtcagc gttatccctg gcaatccgg      420 aaacagctta cgcacataat ccgaagcctg accgtactca gtccttcgcc atatcatacc     480
catatgccga tccatactac ggtggcgcgg tggcagcagc ttatggcccg catgctatca     540
tgcaccctca gctggttggc atggttccgt cctctcgagt gccactgccg atcgagccag    600
ccgctgaaga gcccatctat gtcaacgcga agcagtacca cgctattctc cggaggagac     660
agctccgtgc aaagctagag gcggaaaaca agctcgtgaa aagccgcaag ccgtacctcc     720
acgagtctcg gcacctgcac gcgatgaaga gagctcgggg aacaggcggg cggttcctga    780
acacgaagca gcagccggag tcccccggca gcggcggctc ctcggacgcg caacgcgtgc    840
ccgcgaccgc gagcggcggc ctgttcacga agcatgagca cagcctgccg cccggcggtc    900
gccaccacta tcacgcgaga gggggcggtg agtagggagc cccgacactg gcaactcatc   960
cttggcttat cagcgattcg actcggctct ccctcgtctg aaactgaact ctctgcaact  1020
actgtaactg taactaaact gggtgtgccc ggattggcgg tcgttctgtt ctactactag  1080
tacctgctac gcgtcgttgg gttgggtctg gactagagag cgtgctggtt ctttgatgaa  1140
cttggctgga cttgagggtg ttgactagcg cgaagctgag ttccatgtaa aacttttgct   1200
tcaagaccga tgactggcgg cataataagt agcagtaata cccaaaaaaa aaaaaaaaa   1260 aaaaaaaaaa aaaaaaaaaa aaaaaaaaaa aaaaaaaaa aaaaag                  1307
```

<210> SEQ ID NO 36
<211> LENGTH: 244
<212> TYPE: PRT
<213> ORGANISM: Zea mays

<400> SEQUENCE: 36

```
Met Arg Gln Asn Gly Ala Val Met Ile Gln Phe Gly His Gln Met Pro
 1               5                  10                  15

Asp Tyr Asp Ser Pro Ala Thr Gln Ser Thr Ser Glu Thr Ser His Gln
            20                  25                  30

Glu Ala Ser Gly Met Ser Glu Gly Ser Leu Asn Glu His Asn Asn Asp
        35                  40                  45

His Ser Gly Asn Leu Asp Gly Tyr Ser Lys Ser Asp Glu Asn Lys Met
    50                  55                  60

Met Ser Ala Leu Ser Leu Gly Asn Pro Glu Thr Ala Tyr Ala His Asn
65                  70                  75                  80

Pro Lys Pro Asp Arg Thr Gln Ser Phe Ala Ile Ser Tyr Pro Tyr Ala
                85                  90                  95

Asp Pro Tyr Tyr Gly Gly Ala Val Ala Ala Tyr Gly Pro His Ala
            100                 105                 110

Ile Met His Pro Gln Leu Val Gly Met Val Pro Ser Ser Arg Val Pro
        115                 120                 125

Leu Pro Ile Glu Pro Ala Ala Glu Glu Pro Ile Tyr Val Asn Ala Lys
    130                 135                 140
```

Gln Tyr His Ala Ile Leu Arg Arg Gln Leu Arg Ala Lys Leu Glu
145                 150                 155                 160

Ala Glu Asn Lys Leu Val Lys Ser Arg Lys Pro Tyr Leu His Glu Ser
            165                 170                 175

Arg His Leu His Ala Met Lys Arg Ala Arg Gly Thr Gly Arg Phe
        180                 185                 190

Leu Asn Thr Lys Gln Gln Pro Glu Ser Pro Gly Ser Gly Ser Ser
        195                 200                 205

Asp Ala Gln Arg Val Pro Ala Thr Ala Ser Gly Leu Phe Thr Lys
        210                 215                 220

His Glu His Ser Leu Pro Pro Gly Gly Arg His His Tyr His Ala Arg
225                 230                 235                 240

Gly Gly Gly Glu

<210> SEQ ID NO 37
<211> LENGTH: 816
<212> TYPE: DNA
<213> ORGANISM: Zea mays

<400> SEQUENCE: 37
ccacgcgtcc gcgcagaaca agatggtgaa aggccggaag ccataccttc atgagtctcg     60
acaccgtcat gccatgaagc gggcccgtgg ctcaggaggg cggttcctca acacaaagca    120
gcagccccag gagcagaacc agcagtacca ggcgtcgagt ggttcaatgt gctcaaagac    180
cattggcaac agcgtaatct cccaaagtgg ccccatttgc acgccctctt ctgacgctgc    240
aggtgcttca gcagccagcc aggaccgcgg ctgcttgccc tcggtgggct tccgccccac    300
agccaacttc agtgagcaag gtggaggcgg ctcgaagctg gtcgtgaacg gcatgcagca    360 gcgtgttttcc accataaggt gaagagaagt gggcacgaca ccattcccag gcgcgcactg    420
cctgtggcaa ctcatccttg gcttttgaaa ctatggatat gcaatggaca tgtagcttcg    480
agttcctcag aataaccaaa cgtgaagaat atgcaaagtc cttttgagat tgctgtagc    540 tgaaagaact gtggttaggt tatgagtttc ttcctggaga ctgatccata catgacatgc    600
tacctcgtgc tgagtttctg aggtgaagcc atcgaaacat gaccgtgtgg ttcagtaccc    660
ttgctgcctt cagtgtctga taagctagct ctccagtttg cagtttctct gaattccagc    720
atgtctagtc tctgcttatc ttttgcatgt aacgtgatgg tgacttagca tacacatcta    780
ttcatccatc tatgttctca aaaaaaaaaa aaaaag                              816

<210> SEQ ID NO 38
<211> LENGTH: 78
<212> TYPE: PRT
<213> ORGANISM: Zea mays

<400> SEQUENCE: 38

His Ala Ser Ala Gln Asn Lys Met Val Lys Gly Arg Lys Pro Tyr Leu
1               5                   10                  15

His Glu Ser Arg His Arg His Ala Met Lys Arg Ala Arg Gly Ser Gly
            20                  25                  30

Gly Arg Phe Leu Asn Thr Lys Gln Gln Pro Gln Glu Gln Asn Gln Gln
        35                  40                  45

Tyr Gln Ala Ser Ser Gly Ser Met Cys Ser Lys Thr Ile Gly Asn Ser
    50                  55                  60

Val Ile Ser Gln Ser Gly Pro Ile Cys Thr Pro Ser Ser Asp
65                  70                  75

<210> SEQ ID NO 39
<211> LENGTH: 1630
<212> TYPE: DNA
<213> ORGANISM: Argemone mexicana

<400> SEQUENCE: 39

| | | | | | |
|---|---|---|---|---|---|
| gcacgagtgc | agacaagagt | agattttatg | aaatcgatgg | ctctaaaatc | tctaaaaagt | 60 |
| gagtgttcta | gggtttattc | ttttactgtt | ctcaataaca | attggatagg | agattgattg | 120 |
| tttttgaagt | aatttgaacc | atgcactcga | ttcctgggaa | tgtgaatgca | acagaatcgg | 180 |
| acgtgcaacg | tactccgcaa | tcaactattt | gttctcaacc | ttggtggtgt | ggtactgtgt | 240 |
| ataacactgg | ttcgtcagct | gagttgggag | aaagcacaat | aaaatcgtct | tcaatggaac | 300 |
| agccagacgg | tggaatgggt | attgatacca | gagaatcaca | tggtgatggt | ggtcctaatg | 360 |
| aggggggatgg | tattacgaga | aagatgcaca | ccaccatggc | ctcccaatct | gggccagatg | 420 |
| gaaactatgg | acatgaacat | ggaatctgc | agcatgctgc | atctgcaatg | ccccaaacta | 480 |
| gtggtgaata | cgtcataccg | cgtccacagt | ttgagcttgt | tggtcactca | gttgcatgtg | 540 |
| caacgtaccc | gtattctgat | atgtattata | ctggaatgat | ggctgctttg | ggaactcagg | 600 |
| ctcaggtaca | tcctcattta | tttggtgtac | aacacaccag | aatgcctttta | cctcttgaaa | 660 |
| tggctgaaga | gcctgtctat | gtaaatgcga | agcaatatca | tggaattctg | agacgaaggc | 720 |
| agtcgcgtgc | aaaggctgag | ctagaaagga | aactgattaa | atctagaaag | ccgtaccttc | 780 |
| atgaatctcg | gcaccaacat | gctatgagaa | gggcaagggg | ttgtggaggc | cgttttctca | 840 |
| acacaaaaaa | actcgaaaac | gggtcatcta | agcatacaac | tgagaacagc | atggcttctg | 900 |
| attgtaatgg | taaccggaac | tccccaagtg | gtcaacaaga | aatagaaggt | tccaacgtgc | 960 |
| aggaatcaca | ttcctacttt | aacagcaatg | ataaaagctg | ctaccaacat | aatcagggtc | 1020 |
| tgcagttatc | aagtttccat | ccattatctg | gtgagagagg | agaggaagga | gactgttcag | 1080 |
| gcctgcagcg | aggaagcatc | tcggtgaacc | aggcccagaa | cagggccctc | accatccagt | 1140 |
| gaacctctga | gtaggggaat | agggtttctc | catcgtcagt | atcccgtttg | ctgttactgc | 1200 |
| tctgggactt | caaataccat | gtaagcaacg | gaaagcagca | atggcgctga | agggatggac | 1260 |
| gcaaaccaga | aacggattcc | ccccaaggta | attggtgttt | ctcaggcaat | tcattcttgg | 1320 |
| cttggttctt | gtgtttgatg | gggaaagagg | agtgtaggtt | ctatttggtt | ctgtggtgtc | 1380 |
| cttacaactt | ctctactctt | tccctcttgt | ttttttttta | tcccttgttg | tacaaaggaa | 1440 |
| atgatagtgg | ctgttttaga | atctaagtag | tgagaagaaa | ccaaaccaaa | cccttttttc | 1500 |
| ttcaaaattt | cgtgaaacat | tgttttaact | ctgtagacat | caaaattttc | taggcatgta | 1560 |
| aaatattcgt | cttttttttt | ttccatgaaa | aaaaaaaaa | aaaaaaaaa | aaaaaaaaa | 1620 |
| aaaaaaaaaa | | | | | | 1630 |

<210> SEQ ID NO 40
<211> LENGTH: 333
<212> TYPE: PRT
<213> ORGANISM: Argemone mexicana

<400> SEQUENCE: 40

Met His Ser Ile Pro Gly Asn Val Asn Ala Thr Glu Ser Asp Val Gln
 1               5                  10                  15

Arg Thr Pro Gln Ser Thr Ile Cys Ser Gln Pro Trp Trp Cys Gly Thr
            20                  25                  30

Val Tyr Asn Thr Gly Ser Ser Ala Glu Leu Gly Glu Ser Thr Ile Lys
            35                  40                  45

Ser Ser Ser Met Glu Gln Pro Asp Gly Gly Met Gly Ile Asp Thr Arg
    50                  55                  60

Glu Ser His Gly Asp Gly Pro Asn Glu Gly Asp Gly Ile Thr Arg
65                  70                  75                  80

Lys Met His Thr Met Ala Ser Gln Ser Gly Pro Asp Gly Asn Tyr
                85                  90                  95

Gly His Glu His Gly Asn Leu Gln His Ala Ala Ser Ala Met Pro Gln
                100                 105                 110

Thr Ser Gly Glu Tyr Val Ile Pro Arg Pro Gln Phe Glu Leu Val Gly
            115                 120                 125

His Ser Val Ala Cys Ala Thr Tyr Pro Tyr Ser Asp Met Tyr Tyr Thr
    130                 135                 140

Gly Met Met Ala Ala Leu Gly Thr Gln Ala Gln Val His Pro His Leu
145                 150                 155                 160

Phe Gly Val Gln His Thr Arg Met Pro Leu Pro Leu Glu Met Ala Glu
                165                 170                 175

Glu Pro Val Tyr Val Asn Ala Lys Gln Tyr His Gly Ile Leu Arg Arg
            180                 185                 190

Arg Gln Ser Arg Ala Lys Ala Glu Leu Glu Arg Lys Leu Ile Lys Ser
        195                 200                 205

Arg Lys Pro Tyr Leu His Glu Ser Arg His Gln His Ala Met Arg Arg
    210                 215                 220

Ala Arg Gly Cys Gly Gly Arg Phe Leu Asn Thr Lys Lys Leu Glu Asn
225                 230                 235                 240

Gly Ser Ser Lys His Thr Thr Glu Asn Ser Met Ala Ser Asp Cys Asn
                245                 250                 255

Gly Asn Arg Asn Ser Pro Ser Gly Gln Gln Glu Ile Glu Gly Ser Asn
            260                 265                 270

Val Gln Glu Ser His Ser Tyr Phe Asn Ser Asn Asp Lys Ser Cys Tyr
        275                 280                 285

Gln His Asn Gln Gly Leu Gln Leu Ser Ser Phe His Pro Leu Ser Gly
    290                 295                 300

Glu Arg Gly Glu Glu Gly Asp Cys Ser Gly Leu Gln Arg Gly Ser Ile
305                 310                 315                 320

Ser Val Asn Gln Ala Gln Asn Arg Ala Leu Thr Ile Gln
                325                 330

<210> SEQ ID NO 41
<211> LENGTH: 1565
<212> TYPE: DNA
<213> ORGANISM: Argemone mexicana

<400> SEQUENCE: 41
caagaaagaa aagagagaag aaagaaaatt ttttgaaggt gggtttgaac agaggagaca      60
tgaccagatc tatcccaaca tctcttctcc ttatttctct cactttacca aatcccaaag     120
taaattcact ccagaagcgc gtaatatagg ttttcaaaaa cagttctgag gattttagat     180
tgttttcatc ttggtttgga atttacatag tgaagtaag tgaacaagaa tgcaagacaa      240
gtcaatttca catagtgttg ttagttgtcc aatttggtgg acttctactg gatcccaagt     300
tccacagagt tgtttatcaa agagtttaag cgtaaccttc gactcttctc gtcaagattg     360
cggtagtttg aagcagctag gttttcaact tcaagatcag gattcatcct cgactcaatc     420

-continued

```
aactggtcag tcgcatcatg aagtgggaaa tatgtctgga agcaacccta ctgggcaatg    480
catttcagct cagtgcgaaa aagttactta cgggaaacaa ggagatgttc aaacgaaatc    540
aattctatca cttggagctc cagaagttgt tctccctcaa caagttgatt ataaccacca    600
ctcagtggct cgtataccct atcattacgt tgatccgtat tacggtggca taatggcgtc    660
ttatggacca caggctatta ttcacccaca aatgatgggt ataacacctg cacgagtccc    720
attgcctctt gatcttgcag aaaatgagcc catgtatgtt aatgcaaaac agtaccgagc    780
aattcttaga cggaggcagt cccgtgctaa gcttgaggct caaaataaac ttatcaaaga    840
tcgcaagcct tatctacatg aatctcggca tcttcatgca ttgaagaggg ctaggggatc    900
tggtggacgt tttctcaaca cgaagcagct gcaagagttg aaacaaaaca actctaatgg    960
ccaaaatacc tccgagtcag cttatctaca gttgggagga aatctatctg aatcagaatt   1020
tggcaacggt ggcggtgctt ccaccacatc ctgctctgac atcactacag cctcaaacag   1080
cgaccacatt ttccgtcaac agaatctcag gtttgcgggt tacactcaca tgggtgggac   1140
catgcaagat ggaggtggag ggggcattat gagtaacggg tctcaccacc gtgttcccgt   1200
tacacagtaa aaaacatggg gagaaaaaca actttgtcag cctttccgat tttggtgtga   1260
agaatggtgt gtactctcag ggtggaactg gagaactggc tggcttgtgt tgtttaccca   1320
tgggcaaatc atccttggct tgttaccttt tatttatca ctatacttt tatatgatgt    1380 ttcttgctat atatgttttg ttgattttaa cttccataga tggacaatga tgaatttctg   1440
atactggatt gtccttgaaa ctcttcgctt ttattatata ttttgcgaaa aaaaaaaaa    1500 aaaaaaaaa aaaaaaaaa aaaaaaaaa aaaaaaaaa aaaaaaaaa aaaaaaaaa         1560 aaaaa                                                               1565
```

<210> SEQ ID NO 42
<211> LENGTH: 326
<212> TYPE: PRT
<213> ORGANISM: Argemone mexicana

<400> SEQUENCE: 42

```
Met Gln Asp Lys Ser Ile Ser His Ser Val Val Ser Cys Pro Ile Trp
  1               5                  10                  15

Trp Thr Ser Thr Gly Ser Gln Val Pro Gln Ser Cys Leu Ser Lys Ser
             20                  25                  30

Leu Ser Val Thr Phe Asp Ser Arg Gln Asp Cys Gly Ser Leu Lys
         35                  40                  45

Gln Leu Gly Phe Gln Leu Gln Asp Gln Asp Ser Ser Ser Thr Gln Ser
     50                  55                  60

Thr Gly Gln Ser His His Glu Val Gly Asn Met Ser Gly Ser Asn Pro
 65                  70                  75                  80

Thr Gly Gln Cys Ile Ser Ala Gln Cys Glu Lys Val Thr Tyr Gly Lys
                 85                  90                  95

Gln Gly Asp Val Gln Thr Lys Ser Ile Leu Ser Leu Gly Ala Pro Glu
            100                 105                 110

Val Val Leu Pro Gln Gln Val Asp Tyr Asn His His Ser Val Ala Arg
        115                 120                 125

Ile Pro Tyr His Tyr Val Asp Pro Tyr Gly Gly Ile Met Ala Ser
    130                 135                 140

Tyr Gly Pro Gln Ala Ile Ile His Pro Gln Met Met Gly Ile Thr Pro
145                 150                 155                 160

Ala Arg Val Pro Leu Pro Leu Asp Leu Ala Glu Asn Glu Pro Met Tyr
```

```
                  165                 170                 175
Val Asn Ala Lys Gln Tyr Arg Ala Ile Leu Arg Arg Gln Ser Arg
            180                 185                 190

Ala Lys Leu Glu Ala Gln Asn Lys Leu Ile Lys Asp Arg Lys Pro Tyr
            195                 200                 205

Leu His Glu Ser Arg His Leu His Ala Leu Lys Arg Ala Arg Gly Ser
            210                 215                 220

Gly Gly Arg Phe Leu Asn Thr Lys Gln Leu Gln Glu Leu Lys Gln Asn
225                 230                 235                 240

Asn Ser Asn Gly Gln Asn Thr Ser Glu Ser Ala Tyr Leu Gln Leu Gly
                245                 250                 255

Gly Asn Leu Ser Glu Ser Glu Phe Gly Asn Gly Gly Ala Ser Thr
            260                 265                 270

Thr Ser Cys Ser Asp Ile Thr Thr Ala Ser Asn Ser Asp His Ile Phe
            275                 280                 285

Arg Gln Gln Asn Leu Arg Phe Ala Gly Tyr Thr His Met Gly Gly Thr
290                 295                 300

Met Gln Asp Gly Gly Gly Gly Ile Met Ser Asn Gly Ser His His
305                 310                 315                 320

Arg Val Pro Val Thr Gln
                325

<210> SEQ ID NO 43
<211> LENGTH: 1187
<212> TYPE: DNA
<213> ORGANISM: Oryza sativa

<400> SEQUENCE: 43
gcacgaggca gaggagagaa gcaaggtgag aagtgaggag gcagcaaggg aggaggtttg      60
ccggagaggg gacatgctcc ctcctcatct cacagaaaat ggcacagtaa tgattcagtt     120
tggtcataaa atgcctgact acgagtcatc agctacccaa tcaactagtg gatctcctcg     180
tgaagtgtct ggaatgagcg aaggaagcct caatgagcag aatgatcaat ctggtaatct     240
tgatggttac acgaagagtg atgaaggtaa gatgatgtca gctttatctc tgggcaaatc     300
agaaactgtg tatgcacatt cggaacctga ccgtagccaa cccttggca tatcatatcc     360 atatgctgat tcgttctatg gtggtgctgt agcgacttat ggcacacatg ctattatgca     420
tccccagatt gtgggcgtga tgtcatcctc ccgagtcccg ctaccaatag aaccagccac     480
cgaagagcct atttatgtaa atgcaaagca ataccatgcg attctccgaa ggagacagct     540
ccgtgcaaag ttagaggctg aaaacaagct ggtgaaaaac cgcaagccgt acctccatga     600
atcccggcat caacacgcga tgaagagagc tcggggaaca gggggagat tcctcaacac     660 aaagcagcag cctgaagctt cagatggtgg cacccaagg ctcgtctctg caaacggcgt     720
tgtgttctca agcacgagc acagcttgtc gtccagtgat ctccatcatc gtcgtgtgaa     780
agagggcgct tgagatcctc gccgtttctg tcatggcaaa tcatccttgg cttatgtgtg     840
gtgcccagca aaaaaaaatc tgactgaacc tgtgtgtaaa ctgatgggta tgggtgggtt     900
ttgtgcaact gtaactaggg tgcttgacat ctgtgtctgt tgttcctctg cctccttagt     960
ttggagacgg tgcagctgca gctggtacca gtaatctgat catgctagac ttgtgacaag    1020
gacaaaacta gcaccccgtt atgtttcctg gcttctgaat ttggtggtca ttcagtaagc    1080
aagcactcga cgtcagcggg aggggttgc ttcgattgat ctagttcttt cgcgataaac    1140
ttatttaatt ttgaacaaag gttggtttca aaaaaaaaaa aaaaaaa                  1187
```

<210> SEQ ID NO 44
<211> LENGTH: 239
<212> TYPE: PRT
<213> ORGANISM: Oryza sativa

<400> SEQUENCE: 44

```
Met Leu Pro Pro His Leu Thr Glu Asn Gly Thr Val Met Ile Gln Phe
 1               5                  10                  15

Gly His Lys Met Pro Asp Tyr Glu Ser Ser Ala Thr Gln Ser Thr Ser
            20                  25                  30

Gly Ser Pro Arg Glu Val Ser Gly Met Ser Glu Gly Ser Leu Asn Glu
        35                  40                  45

Gln Asn Asp Gln Ser Gly Asn Leu Asp Gly Tyr Thr Lys Ser Asp Glu
    50                  55                  60

Gly Lys Met Met Ser Ala Leu Ser Leu Gly Lys Ser Glu Thr Val Tyr
65                  70                  75                  80

Ala His Ser Glu Pro Asp Arg Ser Gln Pro Phe Gly Ile Ser Tyr Pro
                85                  90                  95

Tyr Ala Asp Ser Phe Tyr Gly Gly Ala Val Ala Thr Tyr Gly Thr His
            100                 105                 110

Ala Ile Met His Pro Gln Ile Val Gly Val Met Ser Ser Ser Arg Val
        115                 120                 125

Pro Leu Pro Ile Glu Pro Ala Thr Glu Glu Pro Ile Tyr Val Asn Ala
    130                 135                 140

Lys Gln Tyr His Ala Ile Leu Arg Arg Arg Gln Leu Arg Ala Lys Leu
145                 150                 155                 160

Glu Ala Glu Asn Lys Leu Val Lys Asn Arg Lys Pro Tyr Leu His Glu
                165                 170                 175

Ser Arg His Gln His Ala Met Lys Arg Ala Arg Gly Thr Gly Gly Arg
            180                 185                 190

Phe Leu Asn Thr Lys Gln Gln Pro Glu Ala Ser Asp Gly Gly Thr Pro
        195                 200                 205

Arg Leu Val Ser Ala Asn Gly Val Val Phe Ser Lys His Glu His Ser
    210                 215                 220

Leu Ser Ser Ser Asp Leu His His Arg Val Lys Glu Gly Ala
225                 230                 235
```

<210> SEQ ID NO 45
<211> LENGTH: 1442
<212> TYPE: DNA
<213> ORGANISM: Oryza sativa

<400> SEQUENCE: 45

| gcacgagtac | agcgctccgc | attagggctc | gcctctcgtt | ggctagagcg | cgagagccag | 60 |
| tagccgcagc | tgcagcaagc | agcagcagca | gcgaagagcc | tgagcccag | aggaggcgtg | 120 |
| caccgcctcc | gattggccgg | cctctcggag | agagagagag | agagagagat | cgatcgagtc | 180 |
| ctattggccg | ccgcctccgc | gccctggctg | ctcactggtg | agcgagcatg | gagtcgaggc | 240 |
| cggggggaac | caacctcgtg | gagccgaggg | ggcagggcgc | gctgccgtcc | ggcataccga | 300 |
| tccagcagcc | gtggtggacg | acctccgccg | gggtcgggc | ggtgtcgccc | gccgtcgtgg | 360 |
| cgccggggag | cggtgcgggg | atcagcctgt | cgggcaggga | tggcggcggc | gacgacgcgg | 420 |
| cagaggagag | cagcgatgac | tcacgaagat | caggggagac | caaagatgga | agcactgatc | 480 |
| aagaaaagca | tcatgcaaca | tcgcagatga | ctgctttggc | atcagactat | ttaacaccat | 540 |

-continued

```
tttcacagct ggaactaaac caaccaattg cttcggcagc ataccagtac cctgactctt    600
actatatggg catggttggt ccctatggac ctcaagctat gtccgcacag actcatttcc    660
agctacctgg attaactcac tctcgtatgc cgttgcctct tgaaatatct gaggagcctg    720
tttatgtaaa tgctaagcaa tatcatggaa ttttaagacg gaggcagtca cgtgcgaagg    780
ctgaacttga gaaaaagtt gttaaatcaa gaaagcccta tcttcatgag tctcgtcatc     840
aacatgctat gcgaagggca agaggaacgg gtggacgctt cctgaacaca agaaaaatg     900 aagatggtgc tcccagtgag aaagccgaac caaacaaagg agagcagaac tccgggtatc    960
gccggatccc tcctgactta cagctcctac agaaggaaac atgaagtagc ggctcgaaac   1020
ctagaacagt ggcttctgtc caccggcatt cactcttgag gtgattcttg ctccagaatt   1080
gtgctccatc tttcaaatga tcttcatcga gcaaagtaat tatatgtaca ttcctctgaa   1140
tgatctatgc accaattgtt gatcctggca gggtaataat ctggatgtat tgagtccatc   1200
acagtgcgaa tgtcacgggt agatctgctg ttttcaggca attcattctt ggctttctat   1260
cccacccgtt gttgttgcaa gttaagctag cagtacttgt ctcagtgtcc gtgagacgtt   1320
tgtgtaagat taggttaaac tagaagttgt aatgctgtat taagtgtttg tatttctaat   1380
atgaaccgta acaaggccag agcagaactc gttatacata caaaaaaaaa aaaaaaaaa   1440 aa                                                                   1442
```

<210> SEQ ID NO 46
<211> LENGTH: 258
<212> TYPE: PRT
<213> ORGANISM: Oryza sativa

<400> SEQUENCE: 46

```
Met Glu Ser Arg Pro Gly Gly Thr Asn Leu Val Glu Pro Arg Gly Gln
 1               5                  10                  15

Gly Ala Leu Pro Ser Gly Ile Pro Ile Gln Gln Pro Trp Trp Thr Thr
            20                  25                  30

Ser Ala Gly Val Gly Ala Val Ser Pro Ala Val Val Ala Pro Gly Ser
        35                  40                  45

Gly Ala Gly Ile Ser Leu Ser Gly Arg Asp Gly Gly Asp Asp Ala
    50                  55                  60

Ala Glu Glu Ser Ser Asp Asp Ser Arg Arg Ser Gly Glu Thr Lys Asp
65                  70                  75                  80

Gly Ser Thr Asp Gln Glu Lys His His Ala Thr Ser Gln Met Thr Ala
                85                  90                  95

Leu Ala Ser Asp Tyr Leu Thr Pro Phe Ser Gln Leu Glu Leu Asn Gln
            100                 105                 110

Pro Ile Ala Ser Ala Ala Tyr Gln Tyr Pro Asp Ser Tyr Tyr Met Gly
        115                 120                 125

Met Val Gly Pro Tyr Gly Pro Gln Ala Met Ser Ala Gln Thr His Phe
    130                 135                 140

Gln Leu Pro Gly Leu Thr His Ser Arg Met Pro Leu Pro Leu Glu Ile
145                 150                 155                 160

Ser Glu Glu Pro Val Tyr Val Asn Ala Lys Gln Tyr His Gly Ile Leu
                165                 170                 175

Arg Arg Arg Gln Ser Arg Ala Lys Ala Glu Leu Glu Lys Lys Val Val
            180                 185                 190

Lys Ser Arg Lys Pro Tyr Leu His Glu Ser Arg His Gln His Ala Met
        195                 200                 205
```

```
Arg Arg Ala Arg Gly Thr Gly Gly Arg Phe Leu Asn Thr Lys Lys Asn
    210                 215                 220

Glu Asp Gly Ala Pro Ser Glu Lys Ala Glu Pro Asn Lys Gly Glu Gln
225                 230                 235                 240

Asn Ser Gly Tyr Arg Arg Ile Pro Pro Asp Leu Gln Leu Leu Gln Lys
                245                 250                 255

Glu Thr
```

```
<210> SEQ ID NO 47
<211> LENGTH: 423
<212> TYPE: DNA
<213> ORGANISM: Oryza sativa
<220> FEATURE:
<221> NAME/KEY: unsure
<222> LOCATION: (223)
<223> OTHER INFORMATION: n = A, C, G, or T
<220> FEATURE:
<221> NAME/KEY: unsure
<222> LOCATION: (330)
<223> OTHER INFORMATION: n = A, C, G, or T
<220> FEATURE:
<221> NAME/KEY: unsure
<222> LOCATION: (369)
<223> OTHER INFORMATION: n = A, C, G, or T
<220> FEATURE:
<221> NAME/KEY: unsure
<222> LOCATION: (389)
<223> OTHER INFORMATION: n = A, C, G, or T
<220> FEATURE:
<221> NAME/KEY: unsure
<222> LOCATION: (402)
<223> OTHER INFORMATION: n = A, C, G, or T

<400> SEQUENCE: 47
```

```
cattggttct aatcttgaca gagtttaagg ttggcacttt ctgtcagaag ttaagttagg    60
acttccacaa aattatacca tctctgggtg ttcttatagg tgtttctcac tatcaggaat   120
gtacagttct tgcagctgtc aagttctttg tacctatgtt tctgtatctt ctaaagattt   180
tgattcgtct gcactgtgca gccatatctc catgagtcac ggnatcaaca tgccctgaaa   240
agggctaggg gagctggagg ccgatttctt aattcaaaat cggatgacaa ggaaagagca   300
ttctgattcc aagttccaag agataaacan gatggagttg cacccccgtg ataatgggca   360
aacgtctanc tctccgtctt caaggggng gatcatcagc tnaacaaaat aaagaagtca   420
aaa                                                                423
```

```
<210> SEQ ID NO 48
<211> LENGTH: 34
<212> TYPE: PRT
<213> ORGANISM: Oryza sativa
<220> FEATURE:
<221> NAME/KEY: UNSURE
<222> LOCATION: (9)
<223> OTHER INFORMATION: Xaa = any amino acid

<400> SEQUENCE: 48
```

```
Gln Pro Tyr Leu His Glu Ser Arg Xaa Gln His Ala Leu Lys Arg Ala
  1               5                  10                  15

Arg Gly Ala Gly Gly Arg Phe Leu Asn Ser Lys Ser Asp Asp Lys Glu
                20                  25                  30

Arg Ala
```

```
<210> SEQ ID NO 49
<211> LENGTH: 479
```

```
<212> TYPE: DNA
<213> ORGANISM: Oryza sativa

<400> SEQUENCE: 49
ctcttctcat ctcatctccc tctcctctcc tctcgccgtc gccgtcgccg tcgccgccgc    60
tcgccgccgg cggggataga gttcgccggg atcgcctcgc cgggagagtt ccctcaccat   120
cccgcacctc cgctcgcctg gcctcttcct cccggaagtg tggtgtgctg caagctcctg   180
tctctcctac aaggtttcaa accaaaata tgcctgaagc acacggaaag ctgggtgat    240 taacgtctgt ttcttttgac tacaatcatc ctgattctgc ttctgtctgc aaaaacaacc   300
aagccatgac gtctgtagtt catgatgttt caggcaacca tggagctgat gagcggcaaa   360
aacagcaaag gcaaggtgaa cctgaggacc aagcaagaag cctcagttac tagtacagat   420
agccatacaa tggtaagcaa caccttcaac agattatgcg acaacctatg cccatcacg    479

<210> SEQ ID NO 50
<211> LENGTH: 35
<212> TYPE: PRT
<213> ORGANISM: Oryza sativa

<400> SEQUENCE: 50

Met Thr Ser Val Val His Asp Val Ser Gly Asn His Gly Ala Asp Glu
 1               5                  10                  15

Arg Gln Lys Gln Gln Arg Gln Gly Glu Pro Glu Asp Gln Ala Arg Ser
            20                  25                  30

Leu Ser Tyr
        35

<210> SEQ ID NO 51
<211> LENGTH: 1107
<212> TYPE: DNA
<213> ORGANISM: Oryza sativa

<400> SEQUENCE: 51
gcacgagcaa ttatccttgt attgaccaat gctatggtct tatgaccacc tacgcgatga    60
aatcaatgag tggcgggcga atgctactgc cgctgaacgc gccagccgat gcgccgatct   120
atgtcaacgc gaagcagtac gaaggcatcc tccgccgtcg ccgtgcccgc gccaaggccc   180
agagggagaa caggctggtc aaaggcagga agccctacct ccacgagtcg cgccaccgcc   240
acgccatgcg ccgggccaga ggctccggcg gccgcttcct caacaccaag aaagaagcca   300
ccgccgccgg atgcggcggc agcagcaaga cgcccctcgc gtccctcgtc agccccgccg   360
acgtagccca tcgtccaggc tccggcggcc gcgtccag cctctccggc tccgacgtgt    420
cgtcgccggg aggcgtcatg tacgaccacc accgccacga cgacgccgac gcggcggacc   480
actacaacag catcgaccac cacctccgca cgccgttctt caccccgctc ccgatcatca   540
tggacagcgg cggcggcggc ggcgaccacg cctcacactc cgccgccgcc gtcgccgccc   600
ccttcaggtg ggcgacggcg gccggcgacg gctgctgcga gctcctcaag gcgtgacagc   660
cttgaggcgg ggatctccag gcgtgcccag agctgctgct gatcgatcac catcagcttt   720
ggctgcctgt aggcaaatca ttcttggctc tttacttgca ttggggttct gcaagcaac    780 tctcctcgtc acctaccaaa actgtccctg aaacttctct agtgctgggg tctcgatcag   840
ggatgatgat gtgatggagg agaggcttac ccatatgcct gtaaattatg gttagtgttc   900
tgattaagca actagtagta cttggtaatt actggctatg aattagtagt atggactctg   960
gtgtcaggtt gctctttgtc tgaataaact ggagtcgttt gaagctttgc aaaaaaaaaa  1020
```

```
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaa                                       1107
```

<210> SEQ ID NO 52
<211> LENGTH: 217
<212> TYPE: PRT
<213> ORGANISM: Oryza sativa

<400> SEQUENCE: 52

```
Thr Ser Asn Tyr Pro Cys Ile Asp Gln Cys Tyr Gly Leu Met Thr Thr
 1               5                  10                  15

Tyr Ala Met Lys Ser Met Ser Gly Gly Arg Met Leu Leu Pro Leu Asn
             20                  25                  30

Ala Pro Ala Asp Ala Pro Ile Tyr Val Asn Ala Lys Gln Tyr Glu Gly
         35                  40                  45

Ile Leu Arg Arg Arg Arg Ala Arg Ala Lys Ala Gln Arg Glu Asn Arg
     50                  55                  60

Leu Val Lys Gly Arg Lys Pro Tyr Leu His Glu Ser Arg His Arg His
 65                  70                  75                  80

Ala Met Arg Arg Ala Arg Gly Ser Gly Gly Arg Phe Leu Asn Thr Lys
                 85                  90                  95

Lys Glu Ala Thr Ala Ala Gly Cys Gly Gly Ser Ser Lys Thr Pro Leu
            100                 105                 110

Ala Ser Leu Val Ser Pro Ala Asp Val Ala His Arg Pro Gly Ser Gly
        115                 120                 125

Gly Arg Ala Ser Ser Leu Ser Gly Ser Asp Val Ser Ser Pro Gly Gly
    130                 135                 140

Val Met Tyr Asp His His Arg His Asp Asp Ala Asp Ala Ala Asp His
145                 150                 155                 160

Tyr Asn Ser Ile Asp His His Leu Arg Thr Pro Phe Phe Thr Pro Leu
                165                 170                 175

Pro Ile Ile Met Asp Ser Gly Gly Gly Gly Asp His Ala Ser His
            180                 185                 190

Ser Ala Ala Val Ala Ala Pro Phe Arg Trp Ala Thr Ala Ala Gly
        195                 200                 205

Asp Gly Cys Cys Glu Leu Leu Lys Ala
    210                 215
```

<210> SEQ ID NO 53
<211> LENGTH: 977
<212> TYPE: DNA
<213> ORGANISM: Oryza sativa

<400> SEQUENCE: 53

```
gcacgaggca aactctagga tgccattgcc tgttgatcct tctgtagaag agcccatatt    60
tgtcaatgca aagcaataca atgcgatcct tagaagaagg caaacgcgtg caaaattgga   120
ggcccaaaat aaggcggtga aggtcggaa gccttacctc catgaatctc gacatcatca    180
tgctatgaag cgagcccgtg gatcaggtgg tcggttcctt accaaaaagg agctgctgga   240
acagcagcag cagcagcagc agcagaagcc accaccggca tcagctcagt ctccaacagg   300
tagagccaga acgagcggcg gtgccgttgt ccttggcaag aacctgtgcc agagaacag    360 cacatcctgc tcgccatcga caccgacagg ctccgagatc tccagcatct catttggggg   420
cggcatgctg gctcaccaag agcacatcag cttcgcatcc gctgatcgcc accccacaat   480
```

-continued

```
gaaccagaac caccgtgtcc ccgtcatgag gtgaaaacct cgggatcgcg ggacacgggc    540
ggttctggtt taccctcact ggcgcactcc ggtgtgcccg tggcaattca tccttggctt    600
atgaagtatc tacctgataa tagtctgctg tcagtttata tgcaatgcaa cctctgtcag    660
ataaactctt atagtttgtt ttattgtaag ctatgactga acgaactgtc gagcagatgg    720
ctaatttgta tgttgtgggt acagaaatcc tgaagctttt gatgtaccta attgcctttt    780
gcttatactc ttggtgtata cccattacca agttgcctta aaaaccctcc aattatgtaa    840
tcagtcatgg ttttatagaa ccttgccaca tgtaatcaat cacctgttttt tgtaaattga    900 tctataaacg ctataggctg ctgtgttatc tgcatttaaa aaaaaaaaa aaaaaaaaaa    960 aaaaaaaaaa aaaaaaa                                                   977
```

```
<210> SEQ ID NO 54
<211> LENGTH: 168
<212> TYPE: PRT
<213> ORGANISM: Oryza sativa

<400> SEQUENCE: 54
```

| Ala | Asn | Ser | Arg | Met | Pro | Leu | Pro | Val | Asp | Pro | Ser | Val | Glu | Glu | Pro |
|---|---|---|---|---|---|---|---|---|---|---|---|---|---|---|---|
| 1 | | | | 5 | | | | | 10 | | | | | 15 | |

Ile Phe Val Asn Ala Lys Gln Tyr Asn Ala Ile Leu Arg Arg Arg Gln
            20                  25                  30

Thr Arg Ala Lys Leu Glu Ala Gln Asn Lys Ala Val Lys Gly Arg Lys
        35                  40                  45

Pro Tyr Leu His Glu Ser Arg His His His Ala Met Lys Arg Ala Arg
    50                  55                  60

Gly Ser Gly Gly Arg Phe Leu Thr Lys Lys Glu Leu Leu Glu Gln Gln
65                  70                  75                  80

Gln Gln Gln Gln Gln Gln Lys Pro Pro Ala Ser Ala Gln Ser Pro
                85                  90                  95

Thr Gly Arg Ala Arg Thr Ser Gly Gly Ala Val Val Leu Gly Lys Asn
            100                 105                 110

Leu Cys Pro Glu Asn Ser Thr Ser Cys Ser Pro Ser Thr Pro Thr Gly
        115                 120                 125

Ser Glu Ile Ser Ser Ile Ser Phe Gly Gly Gly Met Leu Ala His Gln
    130                 135                 140

Glu His Ile Ser Phe Ala Ser Ala Asp Arg His Pro Thr Met Asn Gln
145                 150                 155                 160

Asn His Arg Val Pro Val Met Arg
                165

```
<210> SEQ ID NO 55
<211> LENGTH: 465
<212> TYPE: DNA
<213> ORGANISM: Oryza sativa
<220> FEATURE:
<221> NAME/KEY: unsure
<222> LOCATION: (280)
<223> OTHER INFORMATION: n = A, C, G, or T
<220> FEATURE:
<221> NAME/KEY: unsure
<222> LOCATION: (325)
<223> OTHER INFORMATION: n = A, C, G, or T
<220> FEATURE:
<221> NAME/KEY: unsure
<222> LOCATION: (349)
<223> OTHER INFORMATION: n = A, C, G, or T
<220> FEATURE:
<221> NAME/KEY: unsure
<222> LOCATION: (358)
```

```
<223> OTHER INFORMATION: n = A, C, G, or T
<220> FEATURE:
<221> NAME/KEY: unsure
<222> LOCATION: (368)
<223> OTHER INFORMATION: n = A, C, G, or T
<220> FEATURE:
<221> NAME/KEY: unsure
<222> LOCATION: (379)
<223> OTHER INFORMATION: n = A, C, G, or T
<220> FEATURE:
<221> NAME/KEY: unsure
<222> LOCATION: (385)
<223> OTHER INFORMATION: n = A, C, G, or T
<220> FEATURE:
<221> NAME/KEY: unsure
<222> LOCATION: (425)
<223> OTHER INFORMATION: n = A, C, G, or T
<220> FEATURE:
<221> NAME/KEY: unsure
<222> LOCATION: (429)..(430)
<223> OTHER INFORMATION: n = A, C, G, or T
<220> FEATURE:
<221> NAME/KEY: unsure
<222> LOCATION: (436)
<223> OTHER INFORMATION: n = A, C, G, or T
<220> FEATURE:
<221> NAME/KEY: unsure
<222> LOCATION: (459)
<223> OTHER INFORMATION: n = A, C, G, or T
<220> FEATURE:
<221> NAME/KEY: unsure
<222> LOCATION: (464)
<223> OTHER INFORMATION: n = A, C, G, or T

<400> SEQUENCE: 55
cttacagcag ccttaccttc acgaatctcg gcatcgccat gcaatgaaga gggctagggg      60
cactggtggg cgattcctga ataccaagca gctccagctg cagcaacagt ctcacactac     120
ctccaccaag accaccacag acagccaaaa tcttcaggt tcaagtcatc tacggctagg      180
tggtggcgca atcggagatc aaactccatt tccgttcaaa gcaatggatt cacaagctaa     240
catcaagaga gctgcagctt ctgcttccac cttcactgtn acttctgcgg acaaaaaga     300 cgacgccttc ttcgaccgcc atggncaaca tctcaataac ttctccggnc attttggnca     360
agcaagcnca caaggggng tcggnaagca tgcataaccg gtcaaaagca agagggttcc     420
tgctnatgnn gatganatga aagagcagct tggaaatcna acant                    465

<210> SEQ ID NO 56
<211> LENGTH: 131
<212> TYPE: PRT
<213> ORGANISM: Oryza sativa
<220> FEATURE:
<221> NAME/KEY: UNSURE
<222> LOCATION: (123)
<223> OTHER INFORMATION: Xaa = any amino acid

<400> SEQUENCE: 56

Leu Gln Gln Pro Tyr Leu His Glu Ser Arg His Arg His Ala Met Lys
 1               5                  10                  15

Arg Ala Arg Gly Thr Gly Gly Arg Phe Leu Asn Thr Lys Gln Leu Gln
                20                  25                  30

Leu Gln Gln Gln Ser His Thr Thr Ser Thr Lys Thr Thr Thr Asp Ser
            35                  40                  45

Gln Asn Ser Ser Gly Ser Ser His Leu Arg Leu Gly Gly Gly Ala Ile
        50                  55                  60

Gly Asp Gln Thr Pro Phe Pro Phe Lys Ala Met Asp Ser Gln Ala Asn
65                  70                  75                  80
```

```
Ile Lys Arg Ala Ala Ala Ser Ala Ser Thr Phe Thr Val Thr Ser Ala
                85                  90                  95

Gly Gln Lys Asp Asp Ala Phe Phe Asp Arg His Gly Gln His Leu Asn
            100                 105                 110

Asn Phe Ser Gly His Phe Gly Gln Ala Ser Xaa Gln Arg Gly Val Gly
        115                 120                 125

Lys His Ala
    130

<210> SEQ ID NO 57
<211> LENGTH: 1482
<212> TYPE: DNA
<213> ORGANISM: Glycine max

<400> SEQUENCE: 57
tttctgttct tctctgggga tctgaagaca tgcagtccaa gtctgaaact gcaaatcgac      60
tgagatcaga tcctcattcc tttcaacctg cagtgtttta ttctgagcct tggtggcgtg     120
gtattgggta caatcctgtg cccaaacaa tggctgggc aaatgcatcc aattcatcgt      180
ctcttgaatg ccctaatggt gattctgaat ccaatgaaga aggtcaatct ttgtccaata     240
gcgggatgaa tgaggaagat gatgatgcca ctaaggattc acagcctgct gttcctaatg     300
gaacaggaaa ttatgggcaa gaacagcaag ggatgcagca tactgcatca tctgcaccct     360
ccatgcgtga agaatgcctt actcagacac acagctggaa cttgtcggt cattcaattg      420
catgtgctac aaatccttat caggatccgt attatggggg catgatgcca gcttatggtc     480
accaacagtt gggatatgct ccttttatag gaatgcctca tgccagaatg ccttttgcccc    540
ttgagatggc tcaagaacct gtgtatgtga atgccaaaca gtaccaagga attctgaggc     600
gaagacaggc tcgtgctaaa gcagagcttg aaaggaagct cataaaatct agaaagccat     660
atcttcatga atctaggcat cagcatgcta tgagaagggc aagggtact ggaggacgat       720
ttgcaaagaa aactgacggt gagggctcaa accactcagg caaggaaaag gataatggta     780
ctgattctgt cctatcatca caatcaatta gttcatctgg ttctgaacct ttacattctg     840
actctgccga aacctggaat tctcctaaca tgcaacaaga tgcaagagca tcaaaagtgc     900
acaacaggtt caaagcaccc tgttaccaaa atggcagtgg ctcctaccat aatcataatg     960
gattgcaatc ttcagtgtac cattcatcct caggtgaaag actggaggaa agggattgtt    1020
cgggtcagca actgaaccac aattgatggg gggttagagg ccgaggttgg tttgtatcca    1080
agtgacatat ttggtgaata ccttggttat ctgtaaacac tcttggcaat atatatgcca    1140
agcggcaaat cattcttggc tttgttcttg tgtttgtggt gttaatgata ctatgggggg    1200
ggtgggggg gggggaatga ttggtatttg agatttctgt tgaagtcagt caatcaatcc    1260
ttcgttcttt tctcattttt gcattttgta aagttttata gtggttagga tggtcacttc    1320
agaagattat ggagtatggt gagaaacaaa ctcttgatgt gccaacactc gtttgactgg    1380
tttatctttg tgtagttcaa ccggttgtta atgttaacat aagacatcat aggataatga    1440
acatgctgtt agttacatta catcaaaaaa aaaaaaaaaa aa                       1482

<210> SEQ ID NO 58
<211> LENGTH: 338
<212> TYPE: PRT
<213> ORGANISM: Glycine max

<400> SEQUENCE: 58

Met Gln Ser Lys Ser Glu Thr Ala Asn Arg Leu Arg Ser Asp Pro His
```

```
                1               5              10              15
          Ser Phe Gln Pro Gly Ser Val Tyr Ser Glu Pro Trp Trp Arg Gly Ile
                         20                  25                  30

Gly Tyr Asn Pro Val Ala Gln Thr Met Ala Gly Ala Asn Ala Ser Asn
                         35                  40                  45

Ser Ser Ser Leu Glu Cys Pro Asn Gly Asp Ser Glu Ser Asn Glu Glu
                         50                  55                  60

Gly Gln Ser Leu Ser Asn Ser Gly Met Asn Glu Glu Asp Asp Asp Ala
           65                  70                  75                  80

Thr Lys Asp Ser Gln Pro Ala Val Pro Asn Gly Thr Gly Asn Tyr Gly
                             85                  90                  95

Gln Glu Gln Gln Gly Met Gln His Thr Ala Ser Ser Ala Pro Ser Met
                        100                 105                 110

Arg Glu Glu Cys Leu Thr Gln Thr Pro Gln Leu Glu Leu Val Gly His
                        115                 120                 125

Ser Ile Ala Cys Ala Thr Asn Pro Tyr Gln Asp Pro Tyr Tyr Gly Gly
                        130                 135                 140

Met Met Ala Ala Tyr Gly His Gln Gln Leu Gly Tyr Ala Pro Phe Ile
          145                 150                 155                 160

Gly Met Pro His Ala Arg Met Pro Leu Pro Leu Glu Met Ala Gln Glu
                            165                 170                 175

Pro Val Tyr Val Asn Ala Lys Gln Tyr Gln Gly Ile Leu Arg Arg Arg
                        180                 185                 190

Gln Ala Arg Ala Lys Ala Glu Leu Glu Arg Lys Leu Ile Lys Ser Arg
                        195                 200                 205

Lys Pro Tyr Leu His Glu Ser Arg His Gln His Ala Met Arg Arg Ala
                        210                 215                 220

Arg Gly Thr Gly Gly Arg Phe Ala Lys Lys Thr Asp Gly Glu Gly Ser
          225                 230                 235                 240

Asn His Ser Gly Lys Glu Lys Asp Asn Gly Thr Asp Ser Val Leu Ser
                            245                 250                 255

Ser Gln Ser Ile Ser Ser Ser Gly Ser Glu Pro Leu His Ser Asp Ser
                        260                 265                 270

Ala Glu Thr Trp Asn Ser Pro Asn Met Gln Gln Asp Ala Arg Ala Ser
                        275                 280                 285

Lys Val His Asn Arg Phe Lys Ala Pro Cys Tyr Gln Asn Gly Ser Gly
                        290                 295                 300

Ser Tyr His Asn His Asn Gly Leu Gln Ser Ser Val Tyr His Ser Ser
          305                 310                 315                 320

Ser Gly Glu Arg Leu Glu Glu Arg Asp Cys Ser Gly Gln Gln Leu Asn
                            325                 330                 335

His Asn

<210> SEQ ID NO 59
          <211> LENGTH: 1385
          <212> TYPE: DNA
          <213> ORGANISM: Glycine max

<400> SEQUENCE: 59
gcacgagggg attttgagtg gaggggaaaa gttgtgctaa gatgccgggg aaagctgaca      60
ctgatgattg gcgagtagag cggggtgagc agattcagtt tcagtcttcc atttactctc     120
atcatcagcc ttggtggtgt ggagtggggg aaaatgcctc taaatcatct tcagctgatc     180
agttaaatgg ttcaatcgtg aatggtatca cgcggtctga gaccaatgat aagtcaggtg     240
```

```
aaggtgttgc caaagaatac caaaacatca acatgccgt gttgtcaacc ccatttacca      300
tggacaaaca tcttgctcca atccccaga tggaacttgt tggtcattca gttgttttaa      360
catctcctta ttcagatgca cagcatggtc aaatcttgac tacttacggg caacaagtta      420
tgataaaccc tcaattgtac ggaatgtatc atgctagaat gcctttgcca cctgaaatgg      480
aagaggagcc tgtttatgtc aatgcaaagc agtatcatgg tattttgagg cgaagacagt      540
cacgtgctaa ggctgagctt gaaaagaaag taatcaaaaa caggaagcca tacctccatg      600
aatcccgtca ccttcatgcc atgagaaggg ctagaggcaa tggtggtcgc tttctcaaca      660
aaaagaagct cgaaaattac aattctgatg ccacttcaga cattgggcaa atactggtg      720 caaaccctc aacaaactca cctaacactc aacatttgtt caccaacaat gagaatctag      780
gctcatcaaa tgcgtcacaa gccacggttc aggacatgca cagagtggag agtttcaata      840
ttggttacca taatggaaat ggtcttgcag aactgtacca ttcacaagca aatggaaaaa      900
aggagggaaa ctgctttggt aaagagaggg accctaataa tggggctttc aaatgacact      960
tcgcccagcc atacagcaac agttaggtga agatgaaggg ttttatctc atccaacttg     1020 tgatgctgta ttgaaggcaa ttcattcttg gcttagttaa gtggtgagac cagtgacatg     1080
gagtacactc tgccttgttt ggtctctccc cttgcatttg tttctcttta caagtccata     1140
tgtaaaaatg gataacggaa agaaaaagaa aaatcacttt tgtttgagaa cttttttaag     1200
tttgttttta actgtgtgaa ggtttcataa aattgtggac tgacttgtgt gacatatgct     1260
ccacaaaacc ttaaaacttt cgtctatttt gtccaaaaaa aaaaaaaaa aaaaaaaaa       1320 aaaaaaaaaa aaagggaaaa aaaaaaaaaa aaaaaaaaa aaaaaaaaaa aaaaaaaaa       1380 aaaaa                                                                 1385

<210> SEQ ID NO 60
<211> LENGTH: 304
<212> TYPE: PRT
<213> ORGANISM: Glycine max

<400> SEQUENCE: 60

Met Pro Gly Lys Ala Asp Thr Asp Asp Trp Arg Val Glu Arg Gly Glu
 1               5                   10                  15

Gln Ile Gln Phe Gln Ser Ser Ile Tyr Ser His His Gln Pro Trp Trp
             20                  25                  30

Cys Gly Val Gly Glu Asn Ala Ser Lys Ser Ser Ser Ala Asp Gln Leu
         35                  40                  45

Asn Gly Ser Ile Val Asn Gly Ile Thr Arg Ser Glu Thr Asn Asp Lys
     50                  55                  60

Ser Gly Glu Gly Val Ala Lys Glu Tyr Gln Asn Ile Lys His Ala Val
 65                  70                  75                  80

Leu Ser Thr Pro Phe Thr Met Asp Lys His Leu Ala Pro Asn Pro Gln
                 85                  90                  95

Met Glu Leu Val Gly His Ser Val Val Leu Thr Ser Pro Tyr Ser Asp
            100                 105                 110

Ala Gln His Gly Gln Ile Leu Thr Thr Tyr Gly Gln Gln Val Met Ile
        115                 120                 125

Asn Pro Gln Leu Tyr Gly Met Tyr His Ala Arg Met Pro Leu Pro Pro
    130                 135                 140

Glu Met Glu Glu Glu Pro Val Tyr Val Asn Ala Lys Gln Tyr His Gly
145                 150                 155                 160
```

```
Ile Leu Arg Arg Arg Gln Ser Arg Ala Lys Ala Glu Leu Glu Lys Lys
                165                 170                 175

Val Ile Lys Asn Arg Lys Pro Tyr Leu His Glu Ser Arg His Leu His
            180                 185                 190

Ala Met Arg Arg Ala Arg Gly Asn Gly Arg Phe Leu Asn Lys Lys
        195                 200                 205

Lys Leu Glu Asn Tyr Asn Ser Asp Ala Thr Ser Asp Ile Gly Gln Asn
    210                 215                 220

Thr Gly Ala Asn Pro Ser Thr Asn Ser Pro Asn Thr Gln His Leu Phe
225                 230                 235                 240

Thr Asn Asn Glu Asn Leu Gly Ser Ser Asn Ala Ser Gln Ala Thr Val
                245                 250                 255

Gln Asp Met His Arg Val Glu Ser Phe Asn Ile Gly Tyr His Asn Gly
            260                 265                 270

Asn Gly Leu Ala Glu Leu Tyr His Ser Gln Ala Asn Gly Lys Lys Glu
        275                 280                 285

Gly Asn Cys Phe Gly Lys Glu Arg Asp Pro Asn Asn Gly Ala Phe Lys
290                 295                 300
```

<210> SEQ ID NO 61
<211> LENGTH: 1401
<212> TYPE: DNA
<213> ORGANISM: Glycine max

<400> SEQUENCE: 61

```
gaagtcttta tgtgacctgg gtggaatgat tctgtgtctg catgtgtgaa ttctggcaag      60
ggaactaggg atctgaagat aagatatgca atctaaatct gaaactgcaa atcaactgag     120
gtctgatcca cattccttta cacctaacaa tgcttattct gaaccctggt ggcgaggtat     180
tcagtacaat cctgtccccc aagcaatgtt aggagtgaat gcatctaatt catcttcact     240
tgaacgccct aatggtgatt cggaatccag tgaagaggat gatgatgcca ctaaagaatc     300
acaacccact gctcctaatc aatcaggaaa ttatggacag gaccaccaag cgatgcaaca     360
ttcttcatca tctgcacctt tggtacgtga tgattgcctt acacaggctc acaagtggaa     420
acttgttggc cactcaattg gatacactcc ttttatagga atgccccatg ccagaatggc     480
tttgcccctt gagatggctc aagagcctgt ttatgtgaat gccaaacaat accaaggaat     540
tctgagacga agacaggctc gtgctaaagc agagcttgaa aagaaattaa taaaagtcag     600
aaagccatat cttcatgaat cccggcatca gcatgctata agaagagcac gaggtaatgg     660
agggcgtttt gcaaagaaaa ctgaagttga ggcttcaaac cacatgaaca aggaaaagga     720
tatgggtact ggccaggtcc cattgtcacg gtcaattagt tcatctggtt ttggatcact     780
accctctgac tctgctgaga cctggaattc tcctagtgtg caacaagatg caagaggatc     840
tcaagtgcat gagagatttg aagaacgcaa ctatgcaaat gttttgcagt catcatctac     900
tttttgtttg cactcgggtg aaagagtgga ggaagggac tgttcaggtc aacaacgggg     960
aagcatcttg tcagagcaca cctcacagag gcgtcttgct attcagtaaa ccactgcatg    1020
tgttgatgct gaggttggta tatataattg agtgaactag taggttgagt accttggcta    1080
tctatctgta aacattggca atttgcatgc atgtcaagcg gcaaatcatt cttggctggg    1140
tttcagctgt tcatgatatg gggagaagaa tgattgattg ggccatcata cttgtgttgt    1200
tgaagtctac cagtccttca ttatatcctc ttttcatt ttctgtttt tgtacagaga    1260
tagtagttag caaagtcaag ccaacggatt agaagacttg atgaaacaaa ctactgactc    1320
```

```
actttcctct ggcggcttta ttttatgtta ctcaccggtt attaatgctt aatatgagac    1380
atcatatgag agatttgctg c                                              1401
```

<210> SEQ ID NO 62
<211> LENGTH: 307
<212> TYPE: PRT
<213> ORGANISM: Glycine max

<400> SEQUENCE: 62

```
Met Gln Ser Lys Ser Glu Thr Ala Asn Gln Leu Arg Ser Asp Pro His
 1               5                  10                  15

Ser Phe Thr Pro Asn Asn Ala Tyr Ser Glu Pro Trp Trp Arg Gly Ile
                20                  25                  30

Gln Tyr Asn Pro Val Pro Gln Ala Met Leu Gly Val Asn Ala Ser Asn
            35                  40                  45

Ser Ser Ser Leu Glu Arg Pro Asn Gly Asp Ser Glu Ser Ser Glu Glu
        50                  55                  60

Asp Asp Asp Ala Thr Lys Glu Ser Gln Pro Thr Ala Pro Asn Gln Ser
 65                  70                  75                  80

Gly Asn Tyr Gly Gln Asp His Gln Ala Met Gln His Ser Ser Ser Ser
                85                  90                  95

Ala Pro Leu Val Arg Asp Asp Cys Leu Thr Gln Ala Pro Gln Val Glu
            100                 105                 110

Leu Val Gly His Ser Ile Gly Tyr Thr Pro Phe Ile Gly Met Pro His
        115                 120                 125

Ala Arg Met Ala Leu Pro Leu Glu Met Ala Gln Glu Pro Val Tyr Val
130                 135                 140

Asn Ala Lys Gln Tyr Gln Gly Ile Leu Arg Arg Arg Gln Ala Arg Ala
145                 150                 155                 160

Lys Ala Glu Leu Glu Lys Lys Leu Ile Lys Val Arg Lys Pro Tyr Leu
                165                 170                 175

His Glu Ser Arg His Gln His Ala Ile Arg Arg Ala Arg Gly Asn Gly
            180                 185                 190

Gly Arg Phe Ala Lys Lys Thr Glu Val Glu Ala Ser Asn His Met Asn
        195                 200                 205

Lys Glu Lys Asp Met Gly Thr Gly Gln Val Pro Leu Ser Arg Ser Ile
210                 215                 220

Ser Ser Ser Gly Phe Gly Ser Leu Pro Ser Asp Ser Ala Glu Thr Trp
225                 230                 235                 240

Asn Ser Pro Ser Val Gln Gln Asp Ala Arg Gly Ser Gln Val His Glu
                245                 250                 255

Arg Phe Glu Glu Arg Asn Tyr Ala Asn Val Leu Gln Ser Ser Ser Thr
            260                 265                 270

Phe Cys Leu His Ser Gly Glu Arg Val Glu Glu Gly Asp Cys Ser Gly
        275                 280                 285

Gln Gln Arg Gly Ser Ile Leu Ser Glu His Thr Ser Gln Arg Arg Leu
    290                 295                 300

Ala Ile Gln
305
```

<210> SEQ ID NO 63
<211> LENGTH: 1241
<212> TYPE: DNA
<213> ORGANISM: Glycine max

<400> SEQUENCE: 63

```
gcacgaggtc ctaagttgta agaaacactc tcttctcctt tctcactatt gttctgttac     60
tgttttttgc agcaacactt cagttcaatt aacgaactac accactttct ttctcttctt    120
cgactgctct gtaaccgaaa acctcccttt cccagtttcg aatcttttgt ttctgccttt    180
ggttactgtt tttccgagcc atgctattca ttattgtcct tcgaatcgga ttgattggga    240
cactgtattg catgtaaatc aggaaatcat gacttctact catgacctct cagataatga    300
agctgatgac cagcagcagt cggaatcaca aatggagcct ttatctgcaa atggaatttc    360
ttatgcaggt attgctactc agaatgttca gtatgcaaca ccttcacagc ttggaactgg    420
gcatgctgtg gtaccgccca cttacccata tccagatcca tactacagaa gtatctttgc    480
tccctatgat gcacaaactt atccccccaca accctatggt ggaaatccaa tggtccacct    540
tcagttaatg ggaattcaac aagcaggtgt tcctttgcca actgatacag ttgaggagcc    600
tgtgtttgtc aatgcaaaac agtatcatgg tatattaaga cgcagacagt cccgtgctaa    660
agctgaatca gaaaaaaagg ctgcaaggaa tcggaagcca tacttgcatg aatctcgaca    720
tttgcatgca ctgagaagag caagaggatg tggaggtcgg ttttgaatt caaagaaaga    780
tgagaatcaa caggatgagg ttgcatcaac tgacgaatca cagtccacta tcaatctcaa    840
ttctgataaa aatgagcttg caccatcaga tagaacatcc taaaactaca gaatggtga    900
tgctgtagat tgcagggatc tgttgtgtat atctatattg ggagatgaat ctccaaccaa    960
cagtatcctc agatatctcc ctattattca ttctgtcgta caacgccata ggtataagta   1020
taggttgtgt agtaggtatg ttaggaggtt gcaaaataaa acaagtaaaa tgtaaattga   1080
agtgattcaa ctaagtctat ccccaatgtg gtcctttctt gccttttag gtatttttat   1140
tgtgtgggct tttctttgta ttatttggtg cctctgaggg aaagagaaga gattatccga   1200
aaaaaaaaaa aaaaaaaaaa aaaaaaaaaa aaaaaaaaa a                        1241
```

<210> SEQ ID NO 64
<211> LENGTH: 204
<212> TYPE: PRT
<213> ORGANISM: Glycine max

<400> SEQUENCE: 64

```
Met Thr Ser Thr His Asp Leu Ser Asp Asn Glu Ala Asp Asp Gln Gln
  1               5                  10                  15

Gln Ser Glu Ser Gln Met Glu Pro Leu Ser Ala Asn Gly Ile Ser Tyr
                 20                  25                  30

Ala Gly Ile Ala Thr Gln Asn Val Gln Tyr Ala Thr Pro Ser Gln Leu
             35                  40                  45

Gly Thr Gly His Ala Val Val Pro Pro Thr Tyr Pro Tyr Pro Asp Pro
         50                  55                  60

Tyr Tyr Arg Ser Ile Phe Ala Pro Tyr Asp Ala Gln Thr Tyr Pro Pro
 65                  70                  75                  80

Gln Pro Tyr Gly Gly Asn Pro Met Val His Leu Gln Leu Met Gly Ile
                 85                  90                  95

Gln Gln Ala Gly Val Pro Leu Pro Thr Asp Thr Val Glu Glu Pro Val
            100                 105                 110

Phe Val Asn Ala Lys Gln Tyr His Gly Ile Leu Arg Arg Arg Gln Ser
            115                 120                 125

Arg Ala Lys Ala Glu Ser Glu Lys Lys Ala Ala Arg Asn Arg Lys Pro
        130                 135                 140

Tyr Leu His Glu Ser Arg His Leu His Ala Leu Arg Arg Ala Arg Gly
```

```
                145                 150                 155                 160
Cys Gly Gly Arg Phe Leu Asn Ser Lys Lys Asp Glu Asn Gln Gln Asp
                    165                 170                 175

Glu Val Ala Ser Thr Asp Glu Ser Gln Ser Thr Ile Asn Leu Asn Ser
                180                 185                 190

Asp Lys Asn Glu Leu Ala Pro Ser Asp Arg Thr Ser
            195                 200

<210> SEQ ID NO 65
<211> LENGTH: 1716
<212> TYPE: DNA
<213> ORGANISM: Glycine max

<400> SEQUENCE: 65
gcacgaggta cgtaccgaca tgactccaac ctgatggggt taaacactgc ttctgcgtag      60
gattcgatgc cgctactcct tcttcagttt ctacaactga gtttcatatc tcctttctat     120
tgatgtttat gctgaagact gaataaaagt ctgagaaagc tgcttactac aaaccaacaa     180
gattaactaa gaaatcatct tttgggacga tgcaaactgt ttatcttaaa gagcacgaag     240
gaaatgcgca caattttgtg ggcacgttgt cttctgcagc ttcagcaccc tggtggagtg     300
cttttggatc tcaatctgtt catcagggag agtcttgtgg ccaagtgaaa ccctttttcat    360 tggagctgcc aaactgcata gaccaacttg ctgccactaa gccactagca agaggagctg     420
accaagtgtt gggtaaaggg cacataactc agtttacaat cttttccagat gattgtaaaa    480 tgtcagatga tgcgcaaaag cttcagacaa ccatgtcact gcagtcatcg cttactgatc     540
cacagtctcg ttttgagata gggtttagtc tgcccacgat atgtgcaaaa tatccttata     600
cggatcaatt ttatggactc ttctcagctt atgcacctca aatttcggga cgtataatgc     660
tgccacttaa catgacatct gatgatgaac caatttacgt aaatgctaag cagtaccatg     720
gaatcattag acgtcggcag tcccgtgcca agctgtact tgatcacaaa ttgactaaac      780
gtcgcaagcc ctatatgcac gaatcacgcc atctccatgc aatgcggcga ccaagaggat     840 gtggggtcg cttcttgaac actaagaatt ctgttgacgg aaatggtaaa attggaaatg      900
aagtgcataa aactgttggt gaacaattgc agtctagtgg ctctcagagt tctgaattcc     960
ttcaatctga ggttggaact tttaattcat caaagagac taatgaagc agtccaaata      1020 tttctggttc agaggtgact agcatgtatt cgcggggagg tcttgacagc ttttctctca    1080
atcatcttgg atctgctgtc cactctttg cagacatgat agatggtggg cgcggtatga     1140
tcatacccac caaatgggtt gcagcagcag gtaactgctg caaccttaaa gtttgatttg    1200
caaagaatca agggtgggct tgctgtagca ttgcaccagg cccatcctcg atgaggccag     1260
atgaagaagc ttcgtttcag ttgcgtgtgc tgactgtgac aagtttcgct cggtaagatc    1320
gtcctcacat ctggtctagg caatccatcc ttggctcata ctttggcaat ccatccttgg    1380
ctcattgtaa ctgaaggcaa ctcatccttg cttgatgta cttgcagtaa tttgtctttc     1440
tgcacaggaa tgttgttggc atggtacaaa ctaatgactt gatatcctga tgcagaagac    1500
aactatgttt ctgtctttgt gtgaaaatga aagcatgaaa ctctagttat gtgtgcttcg    1560
aataatgtct aaacgtggtg ttgtattttg tatttctgac ttcgaggaac aatgtattat    1620
agaaccttgt tctgtggtct ttgttagaaa aaataaagca ttggtgtgtt tttctccaaa    1680
aaaaaaaaaa aaaaaaaaaa aaaaaaaaaa aaaaag                              1716

<210> SEQ ID NO 66
```

<211> LENGTH: 328
<212> TYPE: PRT
<213> ORGANISM: Glycine max

<400> SEQUENCE: 66

```
Met Gln Thr Val Tyr Leu Lys Glu His Glu Gly Asn Ala His Asn Phe
  1               5                  10                  15

Val Gly Thr Leu Ser Ser Ala Ala Ser Ala Pro Trp Trp Ser Ala Phe
             20                  25                  30

Gly Ser Gln Ser Val His Gln Gly Glu Ser Cys Gly Gln Val Lys Pro
         35                  40                  45

Phe Ser Leu Glu Leu Pro Asn Cys Ile Asp Gln Leu Ala Ala Thr Lys
     50                  55                  60

Pro Leu Ala Arg Gly Ala Asp Gln Val Leu Gly Lys Gly His Ile Thr
 65                  70                  75                  80

Gln Phe Thr Ile Phe Pro Asp Asp Cys Lys Met Ser Asp Asp Ala Gln
                 85                  90                  95

Lys Leu Gln Thr Thr Met Ser Leu Gln Ser Ser Leu Thr Asp Pro Gln
            100                 105                 110

Ser Arg Phe Glu Ile Gly Phe Ser Leu Pro Thr Ile Cys Ala Lys Tyr
        115                 120                 125

Pro Tyr Thr Asp Gln Phe Tyr Gly Leu Phe Ser Ala Tyr Ala Pro Gln
    130                 135                 140

Ile Ser Gly Arg Ile Met Leu Pro Leu Asn Met Thr Ser Asp Asp Glu
145                 150                 155                 160

Pro Ile Tyr Val Asn Ala Lys Gln Tyr His Gly Ile Ile Arg Arg Arg
                165                 170                 175

Gln Ser Arg Ala Lys Ala Val Leu Asp His Lys Leu Thr Lys Arg Arg
            180                 185                 190

Lys Pro Tyr Met His Glu Ser Arg His Leu His Ala Met Arg Arg Pro
        195                 200                 205

Arg Gly Cys Gly Gly Arg Phe Leu Asn Thr Lys Asn Ser Val Asp Gly
    210                 215                 220

Asn Gly Lys Ile Gly Asn Glu Val His Lys Thr Val Gly Glu Gln Leu
225                 230                 235                 240

Gln Ser Ser Gly Ser Gln Ser Ser Glu Phe Leu Gln Ser Glu Val Gly
                245                 250                 255

Thr Phe Asn Ser Ser Lys Glu Thr Asn Gly Ser Ser Pro Asn Ile Ser
            260                 265                 270

Gly Ser Glu Val Thr Ser Met Tyr Ser Arg Gly Gly Leu Asp Ser Phe
        275                 280                 285

Ser Leu Asn His Leu Gly Ser Ala Val His Ser Phe Ala Asp Met Ile
    290                 295                 300

Asp Gly Gly Arg Gly Met Ile Ile Pro Thr Lys Trp Val Ala Ala Ala
305                 310                 315                 320

Gly Asn Cys Cys Asn Leu Lys Val
                325
```

<210> SEQ ID NO 67
<211> LENGTH: 1103
<212> TYPE: DNA
<213> ORGANISM: Glycine max

<400> SEQUENCE: 67
gcacgaggaa atgaagaatt agagggagtg agaggaggaa gaagaagaag aagattccag    60

-continued

```
aatccagagt gagaaacatt aggcttatca gaggagacat gcccgagttg aaccgacaat        120
tctattacta ctctttgctt ctttcttcat gcctcatcaa atcccaaagg atataattga        180
aggttttggg aactaaggct gcaatattgt atacattcta ctcaaggaat ggctcatact        240
tcttatcctt gtggtgatcc ttattttggt agttcaatag ttgcttatgg aacacaggct        300
attactcaac aaatggtgcc ccagatgctg ggattagcat ccaccagaat tgcattacca        360
gttgagcttg cagaagatgg gcccatttat gtcaatgcca acaatacca tggtatactg         420 agaaggcgac agtcacgagc aaagcttaag gctcaaaaca aactcatcaa agtcgtaag         480 ccatatcttc atgagtctcg gcaccgccac gcattgaaaa gggttagggg aactgggggg        540
cgctttctta gtgccaaaca gcttcaacag tttaatgcag aacttgtcac cgatgcccat        600
tcaggcccgg gccctgtcaa tgtttatcaa agaaagatg catctgaggc agaaagtcat         660
ccctcaagaa ctggaaaaaa tgcatctatc acattcacag caatctctgg cttgacaagt        720
atgtccggta acagtgtcag tttcaggcgg cctgagcaca acttcttggg gaactctcct        780
aatataggtg gatcgtcgca atgcagtggg ggactcacct ttggtggtgg agctcggcaa        840
tgtacttcag ttggccggtg agaggtggaa ccaatcaaaa tcaagttcac tggtctggca        900
aatcatcctt ggcttagtca ctttactttc tgtgtttcat gtgttgttac ggaaatgttg        960
tcttttggaa gactctgcat tagcactcag acttttgcta gtgctttccc atgtattttg       1020
aaagttgctc ttgtttctgt tgttgaactg gaccagaaag tttgtgcttg aaaatttaac       1080
tttttaaaaa aaaaaaaaaa aaa                                               1103
```

<210> SEQ ID NO 68
<211> LENGTH: 210
<212> TYPE: PRT
<213> ORGANISM: Glycine max

<400> SEQUENCE: 68

```
Met Ala His Thr Ser Tyr Pro Cys Gly Asp Pro Tyr Phe Gly Ser Ser
  1               5                  10                  15

Ile Val Ala Tyr Gly Thr Gln Ala Ile Thr Gln Gln Met Val Pro Gln
             20                  25                  30

Met Leu Gly Leu Ala Ser Thr Arg Ile Ala Leu Pro Val Glu Leu Ala
         35                  40                  45

Glu Asp Gly Pro Ile Tyr Val Asn Ala Lys Gln Tyr His Gly Ile Leu
     50                  55                  60

Arg Arg Arg Gln Ser Arg Ala Lys Leu Lys Ala Gln Asn Lys Leu Ile
 65                  70                  75                  80

Lys Ser Arg Lys Pro Tyr Leu His Glu Ser Arg His Arg His Ala Leu
                 85                  90                  95

Lys Arg Val Arg Gly Thr Gly Gly Arg Phe Leu Ser Ala Lys Gln Leu
            100                 105                 110

Gln Gln Phe Asn Ala Glu Leu Val Thr Asp Ala His Ser Gly Pro Gly
        115                 120                 125

Pro Val Asn Val Tyr Gln Lys Lys Asp Ala Ser Glu Ala Glu Ser His
    130                 135                 140

Pro Ser Arg Thr Gly Lys Asn Ala Ser Ile Thr Phe Thr Ala Ile Ser
145                 150                 155                 160

Gly Leu Thr Ser Met Ser Gly Asn Ser Val Ser Phe Arg Arg Pro Glu
                165                 170                 175

His Asn Phe Leu Gly Asn Ser Pro Asn Ile Gly Gly Ser Ser Gln Cys
            180                 185                 190
```

Ser Gly Gly Leu Thr Phe Gly Gly Ala Arg Gln Cys Thr Ser Val
    195                 200                 205

Gly Arg
    210

<210> SEQ ID NO 69
<211> LENGTH: 1128
<212> TYPE: DNA
<213> ORGANISM: Glycine max

<400> SEQUENCE: 69

| | | | | |
|---|---|---|---|---|
| gcacgagggg | tttgggtttc | aagagaggag | acatgcttaa | cttcaaccca acacttcaag | 60 |
| tacttgcttc | ttcatacct | taccagatcc | caaaggtcac | gatctaattt taagtgatta | 120 |
| gtctgatgag | cattttgaag | gttacatgaa | gcaatttctc | tttttgaatc ttcctgacac | 180 |
| cgagatcaat | tgttcacaag | ttgattgcaa | tcactcaatg | gctcattctt cttatcccta | 240 |
| cggcgatcca | attcttgctt | atggaccaca | agctattagt | catccccaaa tggtacccca | 300 |
| gatgctggga | ctagcatcca | ccagagtggc | attaccactt | gatcttgctg aagatggacc | 360 |
| gatttatgtc | aacgcgaaac | aataccatgg | tatactgaga | aggcgacagt cacgagcaaa | 420 |
| acttgaggct | cagaacaaac | ttatcaaaag | tcgtaagcca | tatcttcatg agtctcggca | 480 |
| ccgccatgct | ttgaataggg | ttaggggatc | tgggggtcga | tttctgagta ccaaacagct | 540 |
| tgcacagtct | aatgcagaat | ttgtcaccgg | tgcacattct | ggttctgacc ctaccaacat | 600 |
| atatcagaaa | gaacatccat | tagaggtgga | aagtcattcc | tcaaaagatg gagataatgc | 660 |
| atcattcata | caacctact | ccgaccggcc | atgtttatct | ggcaacaacc tcaattttcg | 720 |
| gcagcaggag | tgcatgtttc | tggggaattc | tgcaaacatg | agtggagcac cacagtgcag | 780 |
| tgggggactc | acctttggcg | gagcaaagca | acgcacttca | gttgtccggt gagagaagaa | 840 |
| actgatcgaa | accgacttca | ccggtcaggc | aaatcatcct | tggcttagtc acttttgtct | 900 |
| gtgtcttaat | gtgttcgtac | taaatgatca | ttttgagaga | ctcttcagtc tgcattagca | 960 |
| ctaataagac | ctttccaatt | gctttggcat | gtattttaaa | gttgctattg tactggattc | 1020 |
| tgaactggat | tggaatagtc | tgtgcatgga | actagtatgt | ttgtgttagt tactgttgaa | 1080 |
| tttccttctt | taaaaaaaaa | aaaaaaaaaa | aaaaaaaaaa | aaaaaaaa | 1128 |

<210> SEQ ID NO 70
<211> LENGTH: 228
<212> TYPE: PRT
<213> ORGANISM: Glycine max

<400> SEQUENCE: 70

Met Lys Gln Phe Leu Phe Leu Asn Leu Pro Asp Thr Glu Ile Asn Cys
1               5                   10                  15

Ser Gln Val Asp Cys Asn His Ser Met Ala His Ser Ser Tyr Pro Tyr
            20                  25                  30

Gly Asp Pro Ile Leu Ala Tyr Gly Pro Gln Ala Ile Ser His Pro Gln
        35                  40                  45

Met Val Pro Gln Met Leu Gly Leu Ala Ser Thr Arg Val Ala Leu Pro
    50                  55                  60

Leu Asp Leu Ala Glu Asp Gly Pro Ile Tyr Val Asn Ala Lys Gln Tyr
65                  70                  75                  80

His Gly Ile Leu Arg Arg Arg Gln Ser Arg Ala Lys Leu Glu Ala Gln
                85                  90                  95

```
Asn Lys Leu Ile Lys Ser Arg Lys Pro Tyr Leu His Glu Ser Arg His
                100                 105                 110

Arg His Ala Leu Asn Arg Val Arg Gly Ser Gly Arg Phe Leu Ser
        115                 120                 125

Thr Lys Gln Leu Ala Gln Ser Asn Ala Glu Phe Val Thr Gly Ala His
    130                 135                 140

Ser Gly Ser Asp Pro Thr Asn Ile Tyr Gln Lys Glu His Pro Leu Glu
145                 150                 155                 160

Val Glu Ser His Ser Ser Lys Asp Gly Asp Asn Ala Ser Phe Ile Thr
                165                 170                 175

Thr Tyr Ser Asp Arg Pro Cys Leu Ser Gly Asn Asn Leu Asn Phe Arg
            180                 185                 190

Gln Gln Glu Cys Met Phe Leu Gly Asn Ser Ala Asn Met Ser Gly Ala
        195                 200                 205

Pro Gln Cys Ser Gly Gly Leu Thr Phe Gly Gly Ala Lys Gln Arg Thr
    210                 215                 220

Ser Val Val Arg
225

<210> SEQ ID NO 71
<211> LENGTH: 1286
<212> TYPE: DNA
<213> ORGANISM: Helianthus sp.

<400> SEQUENCE: 71
gcacgagctt ctagattttc tctccgattc gtcgccccaa attttagggt ttttactttt      60
cgtcctctat actcgtagat cttggtgtaa cagtattgca taagtttcat gtcctcttct     120
gccatgcgag cgaattcatc tgattcgtct cctccagaac agtcgttaga cagggaatca     180
cagtctgatg aagttcttag tgaggaagaa gatgatgcaa gcaaagaaac acaaaatgct     240
tcgtcttttc gttcagataa aagttatcag cagcagggag taccaaatat ccttccaaat     300
aatggcgaaa ccgtagggca ggtcccacaa ctagaacttg tcggtcacac tattgcctgt     360
gctccaaatc cttattgtga tccatattat ggtggaatga tggcagctta tggtcagcct     420
tttgttcatc ctcagtttct tgagcaagca aggatgcctt tgccacttga aatggcgcaa     480
gagcctgttt acgtgaatgc caaacaatac catgcgatat aaggcgaag gcaatcccgt     540 gcaaaagcag agcttgagaa gaaacttata aaagacagaa agccttatct tcatgaatca     600
cggcatcagc atgctttgag aagggtaagg ggcaccggtg gtcgttttgc aaagaaaact     660
gacgttaata agaacacaac aggttcgggt tcaggttctg ccatgtcatc atcccagtcg     720
gtgaattcaa accgggtgca ctcagaatct gccgagagct tggacacacc aagggggtgga    780 ttggtaaatt cacacaatac tcgcacgtat cttgataacg gaggttcttt aggccagcag     840
tggataaaca tttcatctaa ccaatcttca cagagggctg ttgccatgaa gtgatgtcga     900
gtgtttaaca ccctttgtgt ctatccgtgg cttctaagct ggccggcaaa tcattcttgg     960
ctcatgttaa tatgagggac aaacaggtaa atgtaccttt tggtgtcctc tttggttttat   1020 ctttcaggat ttctttcttc ggaactgatg ttatgtacaa agtttgcttt tggggataga    1080
agaattggtt gggttgggtt tgtgtgttct tttctgaatg tttggtatat ttggaggtga    1140
agcatggagt ttaagatgtg cttatgtcta tcgtctaatt gtaggggcat atagtgctcc    1200
acagcctcca gcacatgtgt aatgtcgtgg ctgttgaaaa ttggagcttc atatttactg    1260
ttttgcaaaa aaaaaaaaaa aaaaaa                                        1286
```

-continued

<210> SEQ ID NO 72
<211> LENGTH: 261
<212> TYPE: PRT
<213> ORGANISM: Helianthus sp.

<400> SEQUENCE: 72

Met Ser Ser Ser Ala Met Arg Ala Asn Ser Ser Asp Ser Ser Pro Pro
1               5                   10                  15

Glu Gln Ser Leu Asp Arg Glu Ser Gln Ser Asp Glu Val Leu Ser Glu
            20                  25                  30

Glu Glu Asp Asp Ala Ser Lys Glu Thr Gln Asn Ala Ser Ser Phe Arg
        35                  40                  45

Ser Asp Lys Ser Tyr Gln Gln Gln Gly Val Pro Asn Ile Leu Pro Asn
    50                  55                  60

Asn Gly Glu Thr Val Gly Gln Val Pro Gln Leu Glu Leu Val Gly His
65                  70                  75                  80

Thr Ile Ala Cys Ala Pro Asn Pro Tyr Cys Asp Pro Tyr Tyr Gly Gly
                85                  90                  95

Met Met Ala Ala Tyr Gly Gln Pro Phe Val His Pro Gln Phe Leu Glu
            100                 105                 110

Gln Ala Arg Met Pro Leu Pro Leu Glu Met Ala Gln Glu Pro Val Tyr
        115                 120                 125

Val Asn Ala Lys Gln Tyr His Ala Ile Leu Arg Arg Arg Gln Ser Arg
    130                 135                 140

Ala Lys Ala Glu Leu Glu Lys Lys Leu Ile Lys Asp Arg Lys Pro Tyr
145                 150                 155                 160

Leu His Glu Ser Arg His Gln His Ala Leu Arg Arg Val Arg Gly Thr
                165                 170                 175

Gly Gly Arg Phe Ala Lys Lys Thr Asp Val Asn Lys Asn Thr Thr Gly
            180                 185                 190

Ser Gly Ser Gly Ser Ala Met Ser Ser Gln Ser Val Asn Ser Asn
        195                 200                 205

Arg Val His Ser Glu Ser Ala Glu Ser Leu Asp Thr Pro Arg Gly Gly
    210                 215                 220

Leu Val Asn Ser His Asn Thr Arg Thr Tyr Leu Asp Asn Gly Gly Ser
225                 230                 235                 240

Leu Gly Gln Gln Trp Ile Asn Ile Ser Ser Asn Gln Ser Ser Gln Arg
                245                 250                 255

Ala Val Ala Met Lys
            260

<210> SEQ ID NO 73
<211> LENGTH: 1306
<212> TYPE: DNA
<213> ORGANISM: Triticum aestivum

<400> SEQUENCE: 73
ggagaaacgg aaacagagac agagggagag gagacttgca gaggagagga gagaagaggc      60
ggaacaaggg aggagggagg ggtcgccgga aggggacat gctccctccg catctcacat      120
ctcgcagctt gaactgagag caagagcaga agcccatgag atgagacgca agcaaaatat     180
gcaagaaaat ggcacaatca tgattcagtt tggtcagcaa gtgcctaact gcgagtcctc     240
agctagcgat tctcctcaag aagtgtccgg aatgagcgaa gggagcttta atgagcagaa     300
tgatcaatct ggtaatcgcg atggctatac gaagagtagt gatgaaggca agatgatgtc     360

-continued

```
ggctttgtct ctgggcaatt cagaaatggc atacacaccg ccaaaacctg accgcactca    420
tccctttgcc atatcatacc catatgctga tccttactat ggtggtgcag tggcagccta    480
tggcgcacat gctattatgc accccagat ggtgggcatg gtaccatcct ctcgagtgcc     540
actaccgatt gaaccagctg ccgccgaaga gcccatttat gtgaatgcga agcaatacca    600
tgccattctc cgaaggagac agctccgcgc aaaattagag gctgaaaata agctggtcaa    660
aagccgtaag ccgtacctgc atgagtcccg gcaccagcac gcgatgaagc gggctcgggg    720
aacaggcggg cggttcctca acgcaaagga gaagtctgaa gcttcaggcg gcggcaatgc    780
atcagcgagg tctggccacg ccggcgttcc cccggatggc ggcatgttct cgaagcacga    840 ccacaccta ccatccggtg acttccatta ccgcgcgaga gggggcgcct agggtgggca     900
cgcagttgcc ccctggcaaa tcatccttgg cttatgtgtg tggcgaatga ccgtcaactc    960
ggtccagtga tattgtaaaa ctgaatttag agtctgtgca attgtgttac ttgggggttt   1020
ggtagacagc ccttgtgttt ggggagggga cgatgcagct gcagctgcag ccggttctct   1080
tgttgtggta ggtttgtgtg gcatggcagg tgctgctaag ctggagcctg cttgaactgt   1140
tttcctgtca ctttgttgtt tggggtaata atgaccatct tgtatgatat tagtactgac   1200
ttggagtaag taataaccat tcccggcgtg atgcatttgc gcccgtggtg gtgtttctgt   1260
tgaaaaaaaa aaaaaaaaaa aaaaaaaaaa aaaaaaaaaa aaaaaa                  1306
```

<210> SEQ ID NO 74
<211> LENGTH: 243
<212> TYPE: PRT
<213> ORGANISM: Triticum aestivum

<400> SEQUENCE: 74

```
Met Arg Arg Lys Gln Asn Met Gln Glu Asn Gly Thr Ile Met Ile Gln
  1               5                  10                  15

Phe Gly Gln Gln Val Pro Asn Cys Glu Ser Ser Ala Ser Asp Ser Pro
             20                  25                  30

Gln Glu Val Ser Gly Met Ser Glu Gly Ser Phe Asn Glu Gln Asn Asp
         35                  40                  45

Gln Ser Gly Asn Arg Asp Gly Tyr Thr Lys Ser Ser Asp Glu Gly Lys
     50                  55                  60

Met Met Ser Ala Leu Ser Leu Gly Asn Ser Glu Met Ala Tyr Thr Pro
 65                  70                  75                  80

Pro Lys Pro Asp Arg Thr His Pro Phe Ala Ile Ser Tyr Pro Tyr Ala
                 85                  90                  95

Asp Pro Tyr Tyr Gly Gly Ala Val Ala Ala Tyr Gly Ala His Ala Ile
            100                 105                 110

Met His Pro Gln Met Val Gly Met Val Pro Ser Ser Arg Val Pro Leu
        115                 120                 125

Pro Ile Glu Pro Ala Ala Ala Glu Pro Ile Tyr Val Asn Ala Lys
    130                 135                 140

Gln Tyr His Ala Ile Leu Arg Arg Gln Leu Arg Ala Lys Leu Glu
145                 150                 155                 160

Ala Glu Asn Lys Leu Val Lys Ser Arg Lys Pro Tyr Leu His Glu Ser
                165                 170                 175

Arg His Gln His Ala Met Lys Arg Ala Arg Gly Thr Gly Gly Arg Phe
            180                 185                 190

Leu Asn Ala Lys Glu Lys Ser Glu Ala Ser Gly Gly Asn Ala Ser
        195                 200                 205
```

```
Ala Arg Ser Gly His Ala Gly Val Pro Pro Asp Gly Met Phe Ser
    210                 215                 220

Lys His Asp His Thr Leu Pro Ser Gly Asp Phe His Tyr Arg Ala Arg
225                 230                 235                 240

Gly Gly Ala
```

<210> SEQ ID NO 75
<211> LENGTH: 1077
<212> TYPE: DNA
<213> ORGANISM: Triticum aestivum

<400> SEQUENCE: 75

```
gcacgaggtt ggaaagtaac aaaccatgac ttctgtcacc gacggtgttt caggtgatca    60
tagagctgat gagcagcaga agcaagctgc tgctcaaggg aaccaggaag aggccccagc   120
tactagtata ggtagtcagg caatggtggc aacaccttcc acagattatg tcacaccta    180
tggccaccag gaagcttgcc atgcaatggg tcaaattgct tacccaactg tcgatccatt   240
ctatggaagc ctttatgcag cctacggtgg acaacctatg atgcatccac caatggtcgg   300
aatgcatgca gccgcaatac cgttgcctac tgatgcaatt gaagagcctg tgtatgtgaa   360
tgcaaagcaa tataatgcca tattaaggcg gcgccaatct cgggctaaag cagagtcaga   420
aaggaagctt atcaagggcc gcaagccata tctccatgag tcgcggcatc aacatgcctt   480
gaaaagggcc aggggagccg aggccggtt tcttaacgca aagtcagacg acaatgaaga   540
gcattctgat tccagctcca aagataagca gaatggcgtt gcaccccgca gcagtggcca   600
atcctcccaa tctcccaaag cgcgacttc ggctgataag tcagcaaacc atgaatgaga   660
tgctagaagg tccgccggac gcgacgatcc atgccaacag ttttgtacag tatatatatg   720
ctagtgagcg agagagagtc gcgccggcgg gtgccatagg atatatccgc tctgctctat   780
agtagtgata gacttatcga cagatttttt tgcagcattg gtccgtgttt gctcggtttg   840
gtttctacat tctgtacaat gagtagtttt ttttgtggtt tttgtgttcc ggggttagcc   900
gcgggtttgg tcaggaggct tttgtagctt ataaaagaag tataattagt gctacattgt   960
tttctttggt gtggatttgg tctcttagct gtgctgcatc ctcattcgtg gtgcagaaaa  1020
taatatctgg gtatacataa taatagctct gcctgcagct ttctttgcca aaaaaaa    1077
```

<210> SEQ ID NO 76
<211> LENGTH: 210
<212> TYPE: PRT
<213> ORGANISM: Triticum aestivum

<400> SEQUENCE: 76

```
Met Thr Ser Val Thr Asp Gly Val Ser Gly Asp His Arg Ala Asp Glu
  1               5                  10                  15

Gln Gln Lys Gln Ala Ala Ala Gln Gly Asn Gln Glu Glu Ala Pro Ala
             20                  25                  30

Thr Ser Ile Gly Ser Gln Ala Met Val Ala Thr Pro Ser Thr Asp Tyr
         35                  40                  45

Val Thr Pro Tyr Gly His Gln Glu Ala Cys His Ala Met Gly Gln Ile
     50                  55                  60

Ala Tyr Pro Thr Val Asp Pro Phe Tyr Gly Ser Leu Tyr Ala Ala Tyr
 65                  70                  75                  80

Gly Gly Gln Pro Met Met His Pro Pro Met Val Gly Met His Ala Ala
                 85                  90                  95

Ala Ile Pro Leu Pro Thr Asp Ala Ile Glu Glu Pro Val Tyr Val Asn
```

```
            100                 105                 110
Ala Lys Gln Tyr Asn Ala Ile Leu Arg Arg Gln Ser Arg Ala Lys
        115                 120                 125

Ala Glu Ser Glu Arg Lys Leu Ile Lys Gly Arg Lys Pro Tyr Leu His
    130                 135                 140

Glu Ser Arg His Gln His Ala Leu Lys Arg Ala Arg Gly Ala Gly Gly
145                 150                 155                 160

Arg Phe Leu Asn Ala Lys Ser Asp Asp Asn Glu His Ser Asp Ser
                165                 170                 175

Ser Ser Lys Asp Lys Gln Asn Gly Val Ala Pro Arg Ser Ser Gly Gln
        180                 185                 190

Ser Ser Gln Ser Pro Lys Gly Ala Thr Ser Ala Asp Lys Ser Ala Asn
    195                 200                 205

His Glu
    210

<210> SEQ ID NO 77
<211> LENGTH: 1378
<212> TYPE: DNA
<213> ORGANISM: Triticum aestivum

<400> SEQUENCE: 77
gcacgaggag attcccctct ccgcggcgca gacgaccacc cgccggccgc ccctgccgtc      60
gctctgctag gcagcgatga tgagcttcaa gggccacgac ggattcgggc aggcctccaa     120
tggtggtggt ggtggtggag cctccgtgcc atggtgacg tgtcccaga tgctgtacgg      180 ggagccgggg gccgccttgt cgtcgtcgcc ggaggcggag cctcgccggg acgcccagtt     240
ccaggtcgtg cccagagctc agggcatcct ggatccactg ccggcgccca gagcggggc      300 tcctgaggtc ctcaagttct cggtgttcca agggaatttg gagtcgggag caacaaagg      360 agagaagccc atggagcact ccgccaccat cgcactgcag tcgccgctcc cggaatacaa     420
cagtcgcttc gaatttggcc cgggtccttc catgatgtct tctggttatc cttcagccga     480
gcagtgctat ggcctgctta ccacttacgc gatgaaatct acgcctggtg ccgattgct      540 cttgccactg aatgcaacag ctgacgcgcc gatttacgtg aatgcgaagc agtatgaagg     600
catccttcgc cgccgccgtg ctcgtgccaa ggtggagcga gagaatcagc tggtgaaagg     660
aagaaagccg tatcttcacg aatcacgcca ccgccacgcg atgcgccggg cgaggggcac     720
gggagggcgc ttcctcaaca ccaagaagga ggggaatggc aaggacgctg gaggaggagg     780
caagagggca gagtgcgccc cgcccacgcg cttcgccacg tctccgagct ccgtcatccc     840
gagcaacccg cactcccgga gcagcatctc gagcctctcc ggctcggagg tgtcgagcat     900
gtacgaccac gacgacgtgg accactacaa cagcatcgag cacctccgga cgcccttctt     960 cacccccgctg ccgatcatca tggacggcga gcacggggca tccgccccct tcaagtgggc    1020
cacggccgcc gacggctgct gtgagctcct caaggcgtga cttgaggggg gtacacgcag    1080
gcacccagat caagagccgg ccatggccgg tctggctcc gtctggttgt ctgcaggcaa     1140
atcattcttg gctctactgc attggggtgt ccttccacgt cgcattacct cttccctgag    1200
aactccggtg ctggttctca gggatcttgt gatgatgggg ctccccatat gcctgtaaaa    1260
tagtatcgga agcactagca gtgtactacg ggtatgaact ctgtggtact atcaggtatc    1320
tgtgtcagaa ctcagaataa gtatcaaact tcagggtcta aaaaaaaaa aaaaaaaa      1378

<210> SEQ ID NO 78
```

<211> LENGTH: 327
<212> TYPE: PRT
<213> ORGANISM: Triticum aestivum

<400> SEQUENCE: 78

```
Met Met Ser Phe Lys Gly His Asp Gly Phe Gly Gln Ala Ser Asn Gly
1               5                   10                  15

Gly Gly Gly Gly Ala Ser Val Pro Trp Trp Thr Val Ser Gln Met
            20                  25                  30

Leu Tyr Gly Glu Pro Gly Ala Ala Leu Ser Ser Pro Glu Ala Glu
        35                  40                  45

Pro Arg Arg Asp Ala Gln Phe Gln Val Val Pro Arg Ala Gln Gly Ile
    50                  55                  60

Leu Asp Pro Leu Pro Ala Pro Lys Ser Gly Ala Pro Glu Val Leu Lys
65                  70                  75                  80

Phe Ser Val Phe Gln Gly Asn Leu Glu Ser Gly Asn Lys Gly Glu
                85                  90                  95

Lys Pro Met Glu His Ser Ala Thr Ile Ala Leu Gln Ser Pro Leu Pro
            100                 105                 110

Glu Tyr Asn Ser Arg Phe Glu Phe Gly Pro Gly Pro Ser Met Met Ser
        115                 120                 125

Ser Gly Tyr Pro Ser Ala Glu Gln Cys Tyr Gly Leu Leu Thr Thr Tyr
    130                 135                 140

Ala Met Lys Ser Thr Pro Gly Gly Arg Leu Leu Leu Pro Leu Asn Ala
145                 150                 155                 160

Thr Ala Asp Ala Pro Ile Tyr Val Asn Ala Lys Gln Tyr Glu Gly Ile
                165                 170                 175

Leu Arg Arg Arg Arg Ala Arg Ala Lys Val Glu Arg Glu Asn Gln Leu
            180                 185                 190

Val Lys Gly Arg Lys Pro Tyr Leu His Glu Ser Arg His Arg His Ala
        195                 200                 205

Met Arg Arg Ala Arg Gly Thr Gly Gly Arg Phe Leu Asn Thr Lys Lys
    210                 215                 220

Glu Gly Asn Gly Lys Asp Ala Gly Gly Gly Lys Arg Ala Glu Cys
225                 230                 235                 240

Ala Pro Pro Thr Arg Phe Ala Thr Ser Pro Ser Ser Val Ile Pro Ser
                245                 250                 255

Asn Pro His Ser Arg Ser Ser Ile Ser Ser Leu Ser Gly Ser Glu Val
            260                 265                 270

Ser Ser Met Tyr Asp His Asp Val Asp His Tyr Asn Ser Ile Glu
        275                 280                 285

His Leu Arg Thr Pro Phe Thr Pro Leu Pro Ile Ile Met Asp Gly
    290                 295                 300

Glu His Gly Ala Ser Ala Pro Phe Lys Trp Ala Thr Ala Ala Asp Gly
305                 310                 315                 320

Cys Cys Glu Leu Leu Lys Ala
                325
```

<210> SEQ ID NO 79
<211> LENGTH: 1192
<212> TYPE: DNA
<213> ORGANISM: Triticum aestivum

<400> SEQUENCE: 79
gcacgaggga gtgacgcggt cgaggagggg cgtgcggggg gcagacagag agggagcgca      60

-continued

```
aagggacggc ggaggcaagc tagcttcccg ggggcggacg caccgagaga gggcggcggg      120
agggaggagg cgcgtgggag ccatgcttct cccctcttct tcgtcttcct cctacgatcc      180
caaaggtgac tcctttggga atcggttga cgatcatatg aggtcaactt tgacttttgg      240
tgataagcat tctgtatatg caggtcaaaa cactgactat ggccacccaa tggcttgcat      300
ttcatacccg ttcaacgatt ctggttctgg agtttgggcg gcctatggt cacgggctat      360 gttccagccc ctcatggcgg gcggaggggc atctgcaacg caagagttc cattgcccgt      420 cgaactagca gcggatgagc ccatatttgt caatcccaaa caatataatg ggattctccg      480
gcgaaggcag ctgcgcgcta agttagaggc ccagaataaa ctcaccaaaa acagaaagcc      540
ctacctccac gagtcgcgcc atcttcacgc gatgaagcgg gcaagaggtt ccggggacg      600 tttcctcaat tccaaacagc tgaagcagca gcagcagtct ggcagtgcct gcaccaaggc      660
cattgcggat ggcgcgaatt ccctgggttc gacccatcta cggctaggca gcggcgcagc      720
cggagaccga accaactcgg tgtccaaggc gatgtcctcc caagagaaca gcaagagagt      780
cgccgccccg gctcccgcct tcaccatgat tcaagcggcg cgcaaagacg acgacttctt      840
ccaccatcac gcccaccatc tcagcttctc cggtcatttt ggccagtcaa gcgaccgata      900
tacgtaataa ggggtcctcc gcgccccgt gtggtcaggc aactcatcct tggctttatt      960
tctggcgtgt taggacttca gagatagttt atctcacagt gctttgcagc ccatagttct     1020
cggcttgatg ttcggtatgc aaatgttggt gtactggtgc gttggaacaa agtttgatg     1080 tgttcacatg acgattggtc gcggaactca tcttgtgttc tgctcgaccc taaaaaaaaa     1140
aaaaaaaaaa aaaaaaaaaa aaaaaaaaaa aaaaaaaaaa aaaaaaaaaa ac           1192
```

<210> SEQ ID NO 80
<211> LENGTH: 254
<212> TYPE: PRT
<213> ORGANISM: Triticum aestivum

<400> SEQUENCE: 80

```
Met Leu Leu Pro Ser Ser Ser Ser Tyr Asp Pro Lys Gly Asp
  1               5                  10                  15

Ser Phe Gly Lys Ser Val Asp Asp His Met Arg Ser Thr Leu Thr Phe
                 20                  25                  30

Gly Asp Lys His Ser Val Tyr Ala Gly Gln Asn Thr Asp Tyr Gly His
             35                  40                  45

Pro Met Ala Cys Ile Ser Tyr Pro Phe Asn Asp Ser Gly Ser Gly Val
         50                  55                  60

Trp Ala Ala Tyr Gly Ser Arg Ala Met Phe Gln Pro Leu Met Ala Gly
 65                  70                  75                  80

Gly Gly Ala Ser Ala Thr Ala Arg Val Pro Leu Pro Val Glu Leu Ala
                 85                  90                  95

Ala Asp Glu Pro Ile Phe Val Asn Pro Lys Gln Tyr Asn Gly Ile Leu
                100                 105                 110

Arg Arg Arg Gln Leu Arg Ala Lys Leu Glu Ala Gln Asn Lys Leu Thr
            115                 120                 125

Lys Asn Arg Lys Pro Tyr Leu His Glu Ser Arg His Leu His Ala Met
        130                 135                 140

Lys Arg Ala Arg Gly Ser Gly Gly Arg Phe Leu Asn Ser Lys Gln Leu
145                 150                 155                 160

Lys Gln Gln Gln Gln Ser Gly Ser Ala Cys Thr Lys Ala Ile Ala Asp
                165                 170                 175
```

```
Gly Ala Asn Ser Leu Gly Ser Thr His Leu Arg Leu Gly Ser Gly Ala
            180                 185                 190

Ala Gly Asp Arg Thr Asn Ser Val Ser Lys Ala Met Ser Ser Gln Glu
        195                 200                 205

Asn Ser Lys Arg Val Ala Ala Pro Ala Pro Ala Phe Thr Met Ile Gln
    210                 215                 220

Ala Ala Arg Lys Asp Asp Phe Phe His His Ala His His Leu
225                 230                 235                 240

Ser Phe Ser Gly His Phe Gly Gln Ser Ser Asp Arg Tyr Thr
                245                 250
```

<210> SEQ ID NO 81
<211> LENGTH: 1260
<212> TYPE: DNA
<213> ORGANISM: Triticum aestivum

<400> SEQUENCE: 81

```
gcacgagaag attatctctg taaactataa gttctgacag gtcttttgct ttattagtgg     60
ctcttctctc tgatgatgtt cacatcgccg aagccccatt tacagtgagg tgaattgatg    120
cgattatatc ttcatgctaa cagtaacacc ctttttgttt cagacaatga caatgatcat    180
gggaagcccg atcagcacat ggtaaagccg cttttatctt tggggaaccc agagactgtt    240
gctcccccac caatgcttga ttgtagccaa tcatttgcat atattcctta tactgctgat    300
gcttatgctg ggatctttcc aggatatgcc tcgcacgcta ttgttcatcc ccaattgaat    360
gctgcaacaa actctcgtgt gccgctccct gttgagcctg cagcagaaga gccaatgttt    420
gttaatgcaa agcagtacca tgcaattctt aggaggaggc agatacgtgc taaattggag    480
gcccaaaata agctggtgaa agcccggaag ccataccttc atgaatctcg gcaccgccat    540
gccatgaagc gagctcgtgg aacaggaggg cggttcctca acacaaagca actcgaggag    600
cagaagcaga agcaggcttc agtggtgca agctgtacaa aggtccttgg caagaataca    660
ctccttcaga gtagccccgc cttcgcacct tcggcatcag ctccctccaa catgtcaagc    720
ttttcaacaa ccggcatgtt ggctaatcaa gagcgcacct gcttccctc ggttggcttc    780
cgtcccacgg ttagcttcag tgcactgaat ggcaacggga agctggcccc aaacggcatg    840
caccagcgcg cttccatgat gaggtaaagc aaagcaccct ctggtgcgct gccggtggca    900
attcatcctt ggcttatgaa gatgttccgg aaatgtggtt gcaatatcag ctggaccaag    960
acattgttat gagtcctttt gagtttcatc tagttgaaag cactggtgtg ctgatgcaga   1020
ctgaaatctt catcacattt cttttgtgtg tacttattca ataaggcac accttgatta   1080
tcccagagac cggagttggg catggttgcg aaaccatagg cctatacttc cttacctgtt   1140
gtgaatgtat ctggtaatgt acttaagaga tggttgagcc tcgagctttg atgaatgctg   1200
ttgcagttca tcaactttgc aacctggttt gcctgatttc aaaaaaaaaa aaaaaaaaa   1260
```

<210> SEQ ID NO 82
<211> LENGTH: 249
<212> TYPE: PRT
<213> ORGANISM: Triticum aestivum

<400> SEQUENCE: 82

```
Met Arg Leu Tyr Leu His Ala Asn Ser Asn Thr Leu Phe Val Ser Asp
  1               5                  10                  15

Asn Asp Asn Asp His Gly Lys Pro Asp Gln His Met Val Lys Pro Leu
             20                  25                  30
```

```
Leu Ser Leu Gly Asn Pro Glu Thr Val Ala Pro Pro Met Leu Asp
         35                  40                  45
Cys Ser Gln Ser Phe Ala Tyr Ile Pro Tyr Thr Ala Asp Ala Tyr Ala
     50                  55                  60
Gly Ile Phe Pro Gly Tyr Ala Ser His Ala Ile Val His Pro Gln Leu
 65                  70                  75                  80
Asn Ala Ala Thr Asn Ser Arg Val Pro Leu Pro Val Glu Pro Ala Ala
                 85                  90                  95
Glu Glu Pro Met Phe Val Asn Ala Lys Gln Tyr His Ala Ile Leu Arg
             100                 105                 110
Arg Arg Gln Ile Arg Ala Lys Leu Glu Ala Gln Asn Lys Leu Val Lys
         115                 120                 125
Ala Arg Lys Pro Tyr Leu His Glu Ser Arg His Arg His Ala Met Lys
     130                 135                 140
Arg Ala Arg Gly Thr Gly Gly Arg Phe Leu Asn Thr Lys Gln Leu Glu
145                 150                 155                 160
Glu Gln Lys Gln Lys Gln Ala Ser Gly Gly Ala Ser Cys Thr Lys Val
                 165                 170                 175
Leu Gly Lys Asn Thr Leu Leu Gln Ser Ser Pro Ala Phe Ala Pro Ser
             180                 185                 190
Ala Ser Ala Pro Ser Asn Met Ser Ser Phe Ser Thr Thr Gly Met Leu
         195                 200                 205
Ala Asn Gln Glu Arg Thr Cys Phe Pro Ser Val Gly Phe Arg Pro Thr
     210                 215                 220
Val Ser Phe Ser Ala Leu Asn Gly Asn Gly Lys Leu Ala Pro Asn Gly
225                 230                 235                 240
Met His Gln Arg Ala Ser Met Met Arg
                 245
```

<210> SEQ ID NO 83
<211> LENGTH: 887
<212> TYPE: DNA
<213> ORGANISM: Canna edulis

<400> SEQUENCE: 83

```
gcacgagatt cactcccagt tcttctcccc ggttttccgc ctctctccgc aggttttcga     60
cgtctggttt gccctaaatc agctgaatgg atcagccgcc tggccacccc gccgtccctc    120
cggtgatggg cgtcgccgct ggagtgcctt atgcaactgc cgctgccgcc ggacccctatc    180
aggcctacca gaacctctac caccagcagc aacagcagca gcagcaacaa ctccagatgt    240
tctgggccga ccagtaccgt gagatcgagc aaactaccga cttccggaac cacagcctgc    300
cgctcgcgcg gatcaagaag atcatgaagg ccgacgagga cgtgcgtatg atcgctgccg    360
aggcgcctgt ggtgttcgcc cgcgcctgcg agatgttcat cctggaactc acccaccggt    420
cgtgggctca cgccgaggag aacaagcgcc ggacactgca agaacgat atagccgcgg       480
ccatcagccg caccgacgtg ttcgattttc tcattgatat cgtgccaagg gaggagggga    540
aggaagatgt tgcccacgcc ctcggacccc cagctggtgg tgacccctc gcttactatt     600
atgtccagaa gtagaagctg ctgctgtgtg agtctttaat taaatgtctc catgttctca    660
atttcataaa tgcctagtg tgattataaa cataggggcat ggggtttggt ttgttacctg    720
aagtgcactg aatttaatct ctagtgaact tgctttgcat agctggtgat gtgttcttgt    780
tagtaagttt atattgtttg ggtattgtcc atctaactac atgtatgctt atggcaagca    840
tcattacatt gatatggatg ggcatttacg ctgctctcat tcgcgcc                  887
```

```
<210> SEQ ID NO 84
<211> LENGTH: 175
<212> TYPE: PRT
<213> ORGANISM: Canna edulis

<400> SEQUENCE: 84

Met Asp Gln Pro Pro Gly His Pro Ala Val Pro Pro Val Met Gly Val
1               5                   10                  15

Ala Ala Gly Val Pro Tyr Ala Thr Ala Ala Ala Gly Pro Tyr Gln
            20                  25                  30

Ala Tyr Gln Asn Leu Tyr His Gln Gln Gln Gln Gln Gln Gln Gln
        35                  40                  45

Leu Gln Met Phe Trp Ala Asp Gln Tyr Arg Glu Ile Glu Gln Thr Thr
    50                  55                  60

Asp Phe Arg Asn His Ser Leu Pro Leu Ala Arg Ile Lys Lys Ile Met
65                  70                  75                  80

Lys Ala Asp Glu Asp Val Arg Met Ile Ala Ala Glu Ala Pro Val Val
                85                  90                  95

Phe Ala Arg Ala Cys Glu Met Phe Ile Leu Glu Leu Thr His Arg Ser
            100                 105                 110

Trp Ala His Ala Glu Glu Asn Lys Arg Arg Thr Leu Gln Lys Asn Asp
        115                 120                 125

Ile Ala Ala Ala Ile Ser Arg Thr Asp Val Phe Asp Phe Leu Ile Asp
    130                 135                 140

Ile Val Pro Arg Glu Glu Gly Lys Glu Asp Val Ala His Ala Leu Gly
145                 150                 155                 160

Pro Pro Ala Gly Gly Asp Pro Leu Ala Tyr Tyr Tyr Val Gln Lys
                165                 170                 175

<210> SEQ ID NO 85
<211> LENGTH: 988
<212> TYPE: DNA
<213> ORGANISM: Vitis sp.

<400> SEQUENCE: 85
caaaaaaaaa atcccaaaac aagcagagac accctcctcc ctcgaatcaa attacaaaga      60
aatggagaac aaccagcagg cccaatcctc cccatacccca ccacagcaac cctttcacca    120
tcttctgcag cagcaacagc agcagcttca gatgttttgg tcctaccaac gccaagagat    180
cgagcaggtg aacgacttca gaaccacca actgcctctg gcccgcatca agaagattat     240
gaaggcggat gaggatgtcc ggatgatctc ggcggaggcc ccaatcctct tcgccaaggc    300
ctgcgagctc ttcattctgg agctgacgat aaggtcgtgg ttgcacgcgg aggagaacaa    360
gaggaggaca ctgcagaaga tgatatcgc cgcggcgatt actaggacgg atatatttga     420
ttttttggtg gatattgtgc cgagggatga gatcaaggac gagggggct tggggatggt     480
agggtcgacg gccagtgggg tgccgtacta ttatccgccg atgggcagc ccgcgccggg     540
agtaatgatg ggaaggccgg cggttccggg ggtggatccg ggggtgtacg tgcagccgcc    600
gtcgcaggca tggcagtcgg tgtggcagac ggcagaggac gggtcgtacg ggagcggagg    660
gagcagtgga caggggaatc ttgatggcca aggttaagca aacgcccatt gtggatgttg    720
tggtgcttcc cggcatgatg gaaactatcg agctcgtgga cagaacttgg attttccttg    780
gctatgaatt gctctgttat tatttgtgaa aactagttgg ttttttaatgt aatggcttca   840
attagaaact tgttaaaaac cgtgatttgg accagtgcag tgatatgact caactaatcc    900
```

-continued

| | |
|---|---|
| tatgtgcagt tctaaatgta aggtccatgt ttttcattt aactgaatga ttctagttat | 960 |
| ctgattaaaa aaaaaaaaaa aaaaaaaa | 988 |

<210> SEQ ID NO 86
<211> LENGTH: 211
<212> TYPE: PRT
<213> ORGANISM: Vitis sp.

<400> SEQUENCE: 86

```
Met Glu Asn Asn Gln Gln Ala Gln Ser Ser Pro Tyr Pro Pro Gln Gln
  1               5                  10                  15
Pro Phe His His Leu Leu Gln Gln Gln Gln Gln Leu Gln Met Phe
                 20                  25                  30
Trp Ser Tyr Gln Arg Gln Glu Ile Glu Gln Val Asn Asp Phe Lys Asn
             35                  40                  45
His Gln Leu Pro Leu Ala Arg Ile Lys Lys Ile Met Lys Ala Asp Glu
         50                  55                  60
Asp Val Arg Met Ile Ser Ala Glu Ala Pro Ile Leu Phe Ala Lys Ala
 65                  70                  75                  80
Cys Glu Leu Phe Ile Leu Glu Leu Thr Ile Arg Ser Trp Leu His Ala
                 85                  90                  95
Glu Glu Asn Lys Arg Arg Thr Leu Gln Lys Asn Asp Ile Ala Ala Ala
            100                 105                 110
Ile Thr Arg Thr Asp Ile Phe Asp Phe Leu Val Asp Ile Val Pro Arg
        115                 120                 125
Asp Glu Ile Lys Asp Glu Gly Gly Leu Gly Met Val Gly Ser Thr Ala
    130                 135                 140
Ser Gly Val Pro Tyr Tyr Tyr Pro Pro Met Gly Gln Pro Ala Pro Gly
145                 150                 155                 160
Val Met Met Gly Arg Pro Ala Val Pro Gly Val Asp Pro Gly Val Tyr
                165                 170                 175
Val Gln Pro Pro Ser Gln Ala Trp Gln Ser Val Trp Gln Thr Ala Glu
            180                 185                 190
Asp Gly Ser Tyr Gly Ser Gly Ser Ser Gly Gln Gly Asn Leu Asp
        195                 200                 205
Gly Gln Gly
    210
```

<210> SEQ ID NO 87
<211> LENGTH: 1572
<212> TYPE: DNA
<213> ORGANISM: Zea mays

<400> SEQUENCE: 87

| | |
|---|---|
| ccacgcgtcc gcataagaaa aaaatgaag cttgccattt cgctcagggc cctgcagcgg | 60 |
| cggcagctgg cgggagagag gcttgggact gggccgcccg ccgcgagga ataaactcac | 120 |
| tcctgtcttc atacgtatcc atagccggca ggcggcagta cctgtatgtg gttttagcta | 180 |
| tacgcgacct cagttcgggc gcaagctaca accccgacca ggcgagaaga agcatcgata | 240 |
| gtgtgacgag ctaacccacc accagcaacg taatccaaat ccatggacaa ccagccgctg | 300 |
| ccctactcca caggccagcc cctgccccc ggaggagccc cggtggcggg catgcctggc | 360 |
| gcggccggcc tcccacccgt gccgcaccac cacctgctcc agcagcagca ggcccagctg | 420 |
| caggcgttct gggcgtacca gcgccaggag gcggagcgcg cgtccgcgtc ggacttcaag | 480 |

-continued

```
aaccaccagc tgcctctggc ccggatcaag aagatcatga aggccgacga ggacgtgcgc    540
atgatctccg ccgaggcgcc cgtgctgttc gccaaggcct gcgagctctt catcctcgag    600
ctcactatcc gctcctggct ccacgccgag gagaacaagc gccgcaccct gcagcgcaac    660
gacgtcgccg cggccatcgc gcgcaccgac gtcttcgatt tcctcgtcga catcgtgccc    720
cgcgaggagg ccaaggagga gcccggcagc gccctcggct cgcggcgcc tggtaccggc    780 gtcgtcgggg ctggcgcccc gggcggggcg ccagccgccg ggatgcccta ctactatccg    840
ccgatggggc agccggcgcc gatgatgccg gcctggcatg ttccggcctg ggacccggcc    900
tggcagcaag gggcagcgga tgtcgatcag agcggcagct tcagcgagga aggacaaggg    960
tttggagcag gccatggcgg cgccgctagc ttccctcctg cgcctccgac ctccgagtga   1020
tcgatcggcg cgtctcttgg tcctggcctc ctggcttagc tacatgtgca tgatgtcaat   1080
cgttcaatgt gccatgctgt gtatactcta cagcaaacgt ggtaatggag ctgctatgca   1140
tacagaacga ataaggcgtg acgtgtgaga ccgtaagagt acgtagtact aatatgtaga   1200
tgcacgtgac gtgccaatta atcaaagatt aacatgcagt taattaatta gtcctcctac   1260
cgaggtgcct catctatatt ttttttccat ttatatatcg agttcacaca atccataaga   1320
atacaaactt cggcaaggtt taggatttgg ggaacttgag gcttggggag ttagggttcc   1380
atggctaccg gtcgtgatga cacatggggc atcaaggtag attaagggtc tgtttgtttg   1440 aactttttaga gttttttga aaagttgttg ttgaactttt gatactgaga agccaattca   1500
acgatgttat tagttcctga aaaaaaaaa aaaaaaaaa aaaaaaaaaa aaaaaaaaa   1560 aaaaaaaaaa ag                                                       1572
```

<210> SEQ ID NO 88
<211> LENGTH: 245
<212> TYPE: PRT
<213> ORGANISM: Zea mays

<400> SEQUENCE: 88

```
Met Asp Asn Gln Pro Leu Pro Tyr Ser Thr Gly Gln Pro Pro Ala Pro
  1               5                  10                  15

Gly Gly Ala Pro Val Ala Gly Met Pro Gly Ala Ala Gly Leu Pro Pro
             20                  25                  30

Val Pro His His His Leu Leu Gln Gln Gln Ala Gln Leu Gln Ala
         35                  40                  45

Phe Trp Ala Tyr Gln Arg Gln Glu Ala Glu Arg Ala Ser Ala Ser Asp
     50                  55                  60

Phe Lys Asn His Gln Leu Pro Leu Ala Arg Ile Lys Lys Ile Met Lys
 65                  70                  75                  80

Ala Asp Glu Asp Val Arg Met Ile Ser Ala Glu Ala Pro Val Leu Phe
                 85                  90                  95

Ala Lys Ala Cys Glu Leu Phe Ile Leu Glu Leu Thr Ile Arg Ser Trp
            100                 105                 110

Leu His Ala Glu Glu Asn Lys Arg Arg Thr Leu Gln Arg Asn Asp Val
        115                 120                 125

Ala Ala Ala Ile Ala Arg Thr Asp Val Phe Asp Phe Leu Val Asp Ile
    130                 135                 140

Val Pro Arg Glu Glu Ala Lys Glu Glu Pro Gly Ser Ala Leu Gly Phe
145                 150                 155                 160

Ala Ala Pro Gly Thr Gly Val Val Gly Ala Gly Ala Pro Gly Gly Ala
                165                 170                 175
```

```
Pro Ala Ala Gly Met Pro Tyr Tyr Pro Met Gly Gln Pro Ala
            180                 185                 190

Pro Met Met Pro Ala Trp His Val Pro Ala Trp Asp Pro Ala Trp Gln
            195                 200                 205

Gln Gly Ala Ala Asp Val Asp Gln Ser Gly Ser Phe Ser Glu Glu Gly
        210                 215                 220

Gln Gly Phe Gly Ala Gly His Gly Gly Ala Ala Ser Phe Pro Pro Ala
225                 230                 235                 240

Pro Pro Thr Ser Glu
            245

<210> SEQ ID NO 89
<211> LENGTH: 1164
<212> TYPE: DNA
<213> ORGANISM: Zea mays

<400> SEQUENCE: 89
gcacgagtct ccccccattc tccaatccgt gccctagtcg agccagccgc gaggaaggag      60
gcgtctcgcc tagcgcccgc ccgtcggccg accttctgct gcaccttcga actctggaaa    120
gatcatagat ttttgggcaa tagcaagtgg acatggaacc atcctctcag cctcagcctg    180
cgatgggtgt cgccgccggt gggtcacaag tgtatcctgc gtctgcctac ccgcctgcag    240
caacagtagc tcctcctgct gttgcatctg ctggtttaca gtcagtgcaa ccattcccag    300
ccaaccctgc ccatatgagt gctcagcacc agattgtcta ccaacaagct caacagttcc    360
accaacagct ccagcagcag caacagcagc agcttcagca gttctgggtc gaacgcatga    420
ctgaaatcga ggcaacagct gatttcagga accacaactt gccacttgcg aggataaaga    480
agatcatgaa ggccgacgaa gatgtccgca tgatctcagc cgaagctccc gtggtcttcg    540
caaaagcttg cgagatattc atactggagc tgacgctgag gtcgtggatg cacaccgagg    600
agaacaagcg ccgcaccttg cagaagaacg acattgccgc agccatcacc aggaccgaca    660
tttacgactt cttggtcgac attgttccca gggatgagat gaaggacgac ggaatcgggc    720
ttcctaggcc cgggctgcca cccatgggag ccccagctga cgcatatcca tactactaca    780
tgccacagca gcaggtgcct ggtcctggga tggtttatgg cgcccagcaa ggccacccgg    840
tgacgtatct gtggcaggat cctcaggaac agcaggagca agctcctgaa gagcagcagt    900
ctctgcatga aagggactga ggatgtcgct caagctatca cctgattttt cagagctctc    960
attttaggtt ctctaaactg caggttttcg ttggctaata tcgttgggta tcaaactgaa   1020
acaggtaggg tgtagcatca tggtagtttg atttctgctg tggtgttagt tggagggata   1080
atgattagcg gctagtggat taaagttacc cataccgttt cctttcgttc caaaaaaaa    1140 aaaaaaaaaa aaaaaaaaaa aaaa                                         1164

<210> SEQ ID NO 90
<211> LENGTH: 255
<212> TYPE: PRT
<213> ORGANISM: Zea mays

<400> SEQUENCE: 90

Met Glu Pro Ser Ser Gln Pro Gln Pro Ala Met Gly Val Ala Ala Gly
  1               5                  10                  15

Gly Ser Gln Val Tyr Pro Ala Ser Ala Tyr Pro Pro Ala Ala Thr Val
             20                  25                  30

Ala Pro Pro Ala Val Ala Ser Ala Gly Leu Gln Ser Val Gln Pro Phe
         35                  40                  45
```

```
Pro Ala Asn Pro Ala His Met Ser Ala Gln His Gln Ile Val Tyr Gln
         50                  55                  60

Gln Ala Gln Gln Phe His Gln Leu Gln Gln Gln Gln Gln Gln
 65                  70                  75                  80

Leu Gln Gln Phe Trp Val Glu Arg Met Thr Glu Ile Glu Ala Thr Ala
                 85                  90                  95

Asp Phe Arg Asn His Asn Leu Pro Leu Ala Arg Ile Lys Lys Ile Met
            100                 105                 110

Lys Ala Asp Glu Asp Val Arg Met Ile Ser Ala Glu Ala Pro Val Val
        115                 120                 125

Phe Ala Lys Ala Cys Glu Ile Phe Ile Leu Glu Leu Thr Leu Arg Ser
130                 135                 140

Trp Met His Thr Glu Glu Asn Lys Arg Arg Thr Leu Gln Lys Asn Asp
145                 150                 155                 160

Ile Ala Ala Ala Ile Thr Arg Thr Asp Ile Tyr Asp Phe Leu Val Asp
                165                 170                 175

Ile Val Pro Arg Asp Glu Met Lys Asp Asp Gly Ile Gly Leu Pro Arg
            180                 185                 190

Pro Gly Leu Pro Pro Met Gly Ala Pro Ala Asp Ala Tyr Pro Tyr Tyr
        195                 200                 205

Tyr Met Pro Gln Gln Gln Val Pro Gly Pro Gly Met Val Tyr Gly Ala
210                 215                 220

Gln Gln Gly His Pro Val Thr Tyr Leu Trp Gln Asp Pro Gln Glu Gln
225                 230                 235                 240

Gln Glu Gln Ala Pro Glu Glu Gln Gln Ser Leu His Glu Arg Asp
                245                 250                 255

<210> SEQ ID NO 91
<211> LENGTH: 1270
<212> TYPE: DNA
<213> ORGANISM: Zea mays

<400> SEQUENCE: 91
gcacgaggac gagacagaga gagaaggcca agaggcttcc tctccccatt cctcccttcc      60
gtgccctagc cgagccagcc gcgaggaagg aggcatcccg ccgtctcgcc tggcgcccgc     120
ccgtcggccg accttctgcc gcagcttcca attgtaaaaa gatcatagat ttttgtgcaa     180
gagcgagtgg atatggaacc atcccctcag cctatgggtg tcgctgccgg tgggtcacaa     240
gtgtatcctg cctctgccta tccgcctgca gcaacagtag ctcctgcttc tgttgtatct     300
gctggtttac agtcagggca gccattccca gccaatcctg tcatatgag tgctcagcac      360 cagattgtct accaacaagc tcaacaattc caccaacagc tccagcagca acaacaacag     420
cagcttcagc agttctgggt tgaacgcatg actgaaattg aggcgacgac tgatttcaag     480
aaccacaact tgccacttgc gaggataaag aagatcatga aggccgatga agatgttcgc     540
atgatctcag ctgaagctcc tgtagtcttt gcaaaagctt gtgagatatt catactggag     600
ctgacactta ggtcgtggat gcacactgag gagaacaagc gccgcacctt gcaaaagaat     660
gacattgcag cagcgatcac taggactgac atttatgact tcttggtcga cattgttccc     720
agggatgaga tgaaggagga cggaattggg cttcctaggg ctggtctgcc acccatggga     780
gccccagctg atgcatatcc atactactac atgccacagc agcaggtgcc tggttctgga     840
atggtttatg gtgcccagca agggcaccca gtgacttatt tgtggcagga gcctcagcaa     900
cagcaggagc aagctcctga agagcagcaa tctgcatgaa gtggctgag aatattgctc      960
```

-continued

```
agaagctatc acctgattca gagttctcat tttaggttgt ccaaactgca ggttttctta    1020
gtaatatcgt tggttatcaa actgaaacag gcgattctaa gtagggtgta gcatcatggt    1080
agtttcattt ctgcttgtga tgttagttga aaggataatg attagtggct agtggattaa    1140
agttaccata ccatttcctt ctattccgaa agtttgcctc catgaggcct ctgatatgac    1200
gtgctagttg ttaatgcttc aaaaaaaaaa aaaaaaaaaa aaaaaaaaaa aaaaaaaaaa    1260
aaaaaaaaaa                                                          1270
```

<210> SEQ ID NO 92
<211> LENGTH: 248
<212> TYPE: PRT
<213> ORGANISM: Zea mays

<400> SEQUENCE: 92

```
Met Glu Pro Ser Pro Gln Pro Met Gly Val Ala Ala Gly Gly Ser Gln
 1               5                  10                  15

Val Tyr Pro Ala Ser Ala Tyr Pro Pro Ala Ala Thr Val Ala Pro Ala
                20                  25                  30

Ser Val Val Ser Ala Gly Leu Gln Ser Gly Gln Pro Phe Pro Ala Asn
            35                  40                  45

Pro Gly His Met Ser Ala Gln His Gln Ile Val Tyr Gln Gln Ala Gln
        50                  55                  60

Gln Phe His Gln Gln Leu Gln Gln Gln Gln Gln Gln Gln Leu Gln Gln
    65                  70                  75                  80

Phe Trp Val Glu Arg Met Thr Glu Ile Glu Ala Thr Thr Asp Phe Lys
                    85                  90                  95

Asn His Asn Leu Pro Leu Ala Arg Ile Lys Lys Ile Met Lys Ala Asp
                100                 105                 110

Glu Asp Val Arg Met Ile Ser Ala Glu Ala Pro Val Val Phe Ala Lys
            115                 120                 125

Ala Cys Glu Ile Phe Ile Leu Glu Leu Thr Leu Arg Ser Trp Met His
        130                 135                 140

Thr Glu Glu Asn Lys Arg Arg Thr Leu Gln Lys Asn Asp Ile Ala Ala
145                 150                 155                 160

Ala Ile Thr Arg Thr Asp Ile Tyr Asp Phe Leu Val Asp Ile Val Pro
                    165                 170                 175

Arg Asp Glu Met Lys Glu Asp Gly Ile Gly Leu Pro Arg Ala Gly Leu
                180                 185                 190

Pro Pro Met Gly Ala Pro Ala Asp Ala Tyr Pro Tyr Tyr Tyr Met Pro
            195                 200                 205

Gln Gln Gln Val Pro Gly Ser Gly Met Val Tyr Gly Ala Gln Gln Gly
        210                 215                 220

His Pro Val Thr Tyr Leu Trp Gln Glu Pro Gln Gln Gln Gln Glu Gln
225                 230                 235                 240

Ala Pro Glu Glu Gln Gln Ser Ala
                245
```

<210> SEQ ID NO 93
<211> LENGTH: 511
<212> TYPE: DNA
<213> ORGANISM: Zea mays
<220> FEATURE:
<221> NAME/KEY: unsure
<222> LOCATION: (442)
<223> OTHER INFORMATION: n = A, C, G, or T
<220> FEATURE:

```
<221> NAME/KEY: unsure
<222> LOCATION: (452)
<223> OTHER INFORMATION: n = A, C, G, or T
<220> FEATURE:
<221> NAME/KEY: unsure
<222> LOCATION: (474)
<223> OTHER INFORMATION: n = A, C, G, or T
<220> FEATURE:
<221> NAME/KEY: unsure
<222> LOCATION: (497)
<223> OTHER INFORMATION: n = A, C, G, or T
<220> FEATURE:
<221> NAME/KEY: unsure
<222> LOCATION: (504)
<223> OTHER INFORMATION: n = A, C, G, or T

<400> SEQUENCE: 93
gactcaactc agtgctcagc accagatggt gtaccagcag gctcagcaat ttcatcaaca      60
acttcagcaa cagcaggaac aacagctcag ggagttctgg actacccaga tggatgagat     120
caagcaagca aatgacttca agatccacac cttgccactt gcaaggataa agaagataat     180
gaaggctgat gaggatgtgc ggatgatctc tgcagaagct cctgttgtgt ttgcgaaggc     240
atgcgaggta ttcatattag agctgacatt gaggtcatgg atgcacacag aggagaacaa     300
gcgccggacc ttgcagaaga acgacattgc agctgccatc accaggactg atatatatga     360
cttcttggtg gacataatcc cgagggatga aatgaaagag gaaggcttc ggacataatc      420 ccatagttgg cctgccgcct gntatggggg cntccagctt gatcatggt cttnatccat      480 tattactatg tggccantta acangtgcca a                                    511

<210> SEQ ID NO 94
<211> LENGTH: 135
<212> TYPE: PRT
<213> ORGANISM: Zea mays

<400> SEQUENCE: 94

Thr Gln Leu Ser Ala Gln His Gln Met Val Tyr Gln Gln Ala Gln Gln
  1               5                  10                  15

Phe His Gln Gln Leu Gln Gln Gln Gln Glu Gln Gln Leu Arg Glu Phe
             20                  25                  30

Trp Thr Thr Gln Met Asp Glu Ile Lys Gln Ala Asn Asp Phe Lys Ile
         35                  40                  45

His Thr Leu Pro Leu Ala Arg Ile Lys Lys Ile Met Lys Ala Asp Glu
     50                  55                  60

Asp Val Arg Met Ile Ser Ala Glu Ala Pro Val Val Phe Ala Lys Ala
 65                  70                  75                  80

Cys Glu Val Phe Ile Leu Glu Leu Thr Leu Arg Ser Trp Met His Thr
                 85                  90                  95

Glu Glu Asn Lys Arg Arg Thr Leu Gln Lys Asn Asp Ile Cys Ser Cys
            100                 105                 110

His His Pro Gly Leu Ile Tyr Met Thr Ser Leu Val Asp Ile Ile Pro
        115                 120                 125

Arg Asp Glu Met Lys Glu Glu
    130                 135

<210> SEQ ID NO 95
<211> LENGTH: 499
<212> TYPE: DNA
<213> ORGANISM: Zea mays
<220> FEATURE:
<221> NAME/KEY: unsure
<222> LOCATION: (278)
```

```
<223> OTHER INFORMATION: n = A, C, G, or T
<220> FEATURE:
<221> NAME/KEY: unsure
<222> LOCATION: (368)
<223> OTHER INFORMATION: n = A, C, G, or T
<220> FEATURE:
<221> NAME/KEY: unsure
<222> LOCATION: (390)..(391)
<223> OTHER INFORMATION: n = A, C, G, or T
<220> FEATURE:
<221> NAME/KEY: unsure
<222> LOCATION: (452)
<223> OTHER INFORMATION: n = A, C, G, or T
<220> FEATURE:
<221> NAME/KEY: unsure
<222> LOCATION: (468)
<223> OTHER INFORMATION: n = A, C, G, or T
<220> FEATURE:
<221> NAME/KEY: unsure
<222> LOCATION: (474)
<223> OTHER INFORMATION: n = A, C, G, or T
<220> FEATURE:
<221> NAME/KEY: unsure
<222> LOCATION: (480)
<223> OTHER INFORMATION: n = A, C, G, or T
<220> FEATURE:
<221> NAME/KEY: unsure
<222> LOCATION: (486)
<223> OTHER INFORMATION: n = A, C, G, or T

<400> SEQUENCE: 95
ctttctcccc tgttgttgtt gatccaaaaa gccacctccc cccaacccaa tcccgtcgtc      60
actctctcac tccactgcct ccggaacacc ctagcaatgg atcccaactc cagcatccct     120 ccccggtga tgggcgcggc ggtggcgtac cctccggcgg ccggcgccgc gtactccgcc     180
gggccgtacg cgcacgcgca cgcggcgttg ggcgcgctgt accgcctcc cccgcgccg      240 ggtcccccct cctcgcacca gggcggcgcg gcggcggngc agctgcagct gttctgggcg    300
gagcagtacc gcgagatcga ggcgacgacg gacttcaaga accacaacct gccgctgggc    360
cgcatcanga agatcatgaa ggcggacgan ngactgcgca tgatcgccgc cgaggcgccg    420
gtggtgttcg cccgcgcctg cgagatgttc ancctggagc tgaccaancg cggntgggcn    480
cacgcngagg aaaaaaaac                                                  499

<210> SEQ ID NO 96
<211> LENGTH: 134
<212> TYPE: PRT
<213> ORGANISM: Zea mays
<220> FEATURE:
<221> NAME/KEY: UNSURE
<222> LOCATION: (61)
<223> OTHER INFORMATION: Xaa = any amino acid
<220> FEATURE:
<221> NAME/KEY: UNSURE
<222> LOCATION: (91)
<223> OTHER INFORMATION: Xaa = any amino acid
<220> FEATURE:
<221> NAME/KEY: UNSURE
<222> LOCATION: (98)..(99)
<223> OTHER INFORMATION: Xaa = any amino acid
<220> FEATURE:
<221> NAME/KEY: UNSURE
<222> LOCATION: (119)
<223> OTHER INFORMATION: Xaa = any amino acid
<220> FEATURE:
<221> NAME/KEY: UNSURE
<222> LOCATION: (124)
<223> OTHER INFORMATION: Xaa = any amino acid

<400> SEQUENCE: 96

Met Asp Pro Asn Ser Ser Ile Pro Pro Pro Val Met Gly Ala Ala Val
```

```
                1               5              10              15
              Ala Tyr Pro Pro Ala Gly Ala Ala Tyr Ser Ala Gly Pro Tyr Ala
                             20                  25                  30

His Ala His Ala Ala Leu Gly Ala Leu Tyr Pro Pro Pro Ala Pro
                             35                  40                  45

Gly Pro Pro Ser Ser His Gln Gly Gly Ala Ala Ala Xaa Gln Leu Gln
                         50                  55                  60

Leu Phe Trp Ala Glu Gln Tyr Arg Glu Ile Glu Ala Thr Thr Asp Phe
               65                  70                  75                  80

Lys Asn His Asn Leu Pro Leu Gly Arg Ile Xaa Lys Ile Met Lys Ala
                             85                  90                  95

Asp Xaa Xaa Leu Arg Met Ile Ala Ala Glu Ala Pro Val Val Phe Ala
                            100                 105                 110

Arg Ala Cys Glu Met Phe Xaa Leu Glu Leu Thr Xaa Arg Gly Trp Ala
                            115                 120                 125

His Ala Glu Glu Lys Lys
                      130

<210> SEQ ID NO 97
<211> LENGTH: 1060
<212> TYPE: DNA
<213> ORGANISM: Zea mays

<400> SEQUENCE: 97
gcacgagaag caccttcctc ttcctcttcc tccgccccccc aatcccctc gtctcacaac      60
cctagctgcc cccgaatcca tggatcccaa caaatccagc accccgccgc cgcctccagt    120
catgggtgcc cccgttgcct accctccgcc ggcgtaccct ccggtgtgg ccgccggcgc     180
cggcgcctac ccgccgcagc tctacgcgcc gccggctgct gccgcggccc agcaggcggc    240
ggccgcgcag cagcagcagc tgcagatatt ctgggcggag cagtaccgcg agatcgaggc    300
cactaccgac ttcaagaatc acaacctccc gctcgcccgc atcaagaaga tcatgaaagc    360
cgacgaggac gtccgcatga tcgccgccga ggctcccgtg gtgttcgccc gggcctgcga    420
gatgttcatc ctcgagctca cccatcgcgg ctgggcgcac gccgaagaga acaagcgccg    480
cacgctccag aaatccgaca ttgccgctgc catcgcccgc accgaggtat tcgacttcct    540
tgtggacatc gttccgcgcg acgacggtaa agacgctgat gcggcggccg ccgcagctgc    600
cgcggctgcc gggatcccgc gccccgccgc cggagtacca gccaccgacc ctctcgccta    660
ctactacgtg cctcagcagt aatgtatcat catcacgtta ttgttccgtc tatgtgcctg    720
agcaataatg tatcatcatt gccttattgt tccggggcag ttgtgttatt tgtgtctgtt    780
tagttgctgc tgctgttacc gcgtaatagc atatgtgtta tctgtgtctg tttagttgct    840
gctgctgttg ccgcgtaata aaacttggtc gtttacgggg ctccctcaag attaagaatt    900
gagttgtttg atggtagaat cctggtaagg ttgttgtaac tggggggcgc ctttgtttgg    960
gctggtagtg tatgcctagg cctcacttat ctgatgctgt aatgcgacaa gtattatgtg   1020
gttgtctggt aattattgtg caaaaaaaaa aaaaaaaaa                          1060

<210> SEQ ID NO 98
<211> LENGTH: 200
<212> TYPE: PRT
<213> ORGANISM: Zea mays

<400> SEQUENCE: 98

Met Asp Pro Asn Lys Ser Ser Thr Pro Pro Pro Pro Val Met Gly
```

```
                1               5              10              15
Ala Pro Val Ala Tyr Pro Pro Ala Tyr Pro Gly Val Ala Ala
                   20                  25                  30

Gly Ala Gly Ala Tyr Pro Pro Gln Leu Tyr Ala Pro Ala Ala Ala
                   35                  40                  45

Ala Ala Gln Gln Ala Ala Ala Gln Gln Gln Gln Leu Gln Ile Phe
                   50                  55                  60

Trp Ala Glu Gln Tyr Arg Glu Ile Glu Ala Thr Thr Asp Phe Lys Asn
 65                  70                  75                  80

His Asn Leu Pro Leu Ala Arg Ile Lys Lys Ile Met Lys Ala Asp Glu
                    85                  90                  95

Asp Val Arg Met Ile Ala Ala Glu Ala Pro Val Val Phe Ala Arg Ala
                   100                 105                 110

Cys Glu Met Phe Ile Leu Glu Leu Thr His Arg Gly Trp Ala His Ala
                   115                 120                 125

Glu Glu Asn Lys Arg Arg Thr Leu Gln Lys Ser Asp Ile Ala Ala Ala
                   130                 135                 140

Ile Ala Arg Thr Glu Val Phe Asp Phe Leu Val Asp Ile Val Pro Arg
145                 150                 155                 160

Asp Asp Gly Lys Asp Ala Asp Ala Ala Ala Ala Ala Ala Ala Ala
                   165                 170                 175

Ala Gly Ile Pro Arg Pro Ala Ala Gly Val Pro Ala Thr Asp Pro Leu
                   180                 185                 190

Ala Tyr Tyr Tyr Val Pro Gln Gln
                   195                 200

<210> SEQ ID NO 99
<211> LENGTH: 901
<212> TYPE: DNA
<213> ORGANISM: Zea mays

<400> SEQUENCE: 99
gcacgagtga ccgccggaac accctaggca atggagccca aatccaccac ccctcccccg      60 cccccgtga tgggcgcgcc catcgcgtat cctcccccgc ccggcgccgc gtaccccgcc     120
gggccgtacg tgcacgcgcc ggcggccgcg ctctaccctc ctcctcccct gccgccggcg     180
cccccctcct cgcagcaggg cgccgcggcg gcgcaccagc agcagctatt ctgggcggag     240
caataccgcg agatcgaggc caccaccgac ttcaagaacc acaacctgcc gctcgcccgc     300
atcaagaaga tcatgaaggc cgacgaggac gtgcgcatga tcgccgccga ggcgcccgtc     360
gtcttctccc gcgcctgcga gatgttcatc ctcgagctca cccaccgcgg ctgggcacac     420
gccgaggaga caagcgccg cacgctgcag aagtccgaca tcgccgccgc cgtcgcgcgc     480
accgaggtct tcgacttcct cgtcgacatc gtgccgcggg acgaggccaa ggacgccgac     540
tccgccgcca tgggagcagc cgggatcccg caccccgccg ccggcctgcc cgccgccgat     600
cccatgggct actactacgt ccagccgcag taacgaattt gcttccttat catggtttcg     660
cttccatgca gcctttgcgg ttttttagta aactattatt attactgaga gtgccctgtt     720
gttacccatg ctctgttgtt gccacccaat aactcgatga cctgatgatc atctgatgtg     780
cctcccgttc cgtaacaagt gattccattt ctgattaaaa aaaaaaaaa aaaaaaaaa      840 aaaaaaaaaa aaaaaaaaaa aaaaaaaaaa aaaaaccaa aaaaaaaaaa aaaaaaaaaa     900
a                                                                     901
```

<210> SEQ ID NO 100
<211> LENGTH: 200
<212> TYPE: PRT
<213> ORGANISM: Zea mays

<400> SEQUENCE: 100

```
Met Glu Pro Lys Ser Thr Thr Pro Pro Pro Val Met Gly Ala
  1               5                  10                  15
Pro Ile Ala Tyr Pro Pro Pro Gly Ala Ala Tyr Pro Ala Gly Pro
             20                  25                  30
Tyr Val His Ala Pro Ala Ala Ala Leu Tyr Pro Pro Pro Leu Pro
         35                  40                  45
Pro Ala Pro Pro Ser Ser Gln Gln Gly Ala Ala Ala His Gln Gln
     50                  55                  60
Gln Leu Phe Trp Ala Glu Gln Tyr Arg Glu Ile Glu Ala Thr Thr Asp
 65                  70                  75                  80
Phe Lys Asn His Asn Leu Pro Leu Ala Arg Ile Lys Lys Ile Met Lys
                 85                  90                  95
Ala Asp Glu Asp Val Arg Met Ile Ala Ala Glu Ala Pro Val Val Phe
                100                 105                 110
Ser Arg Ala Cys Glu Met Phe Ile Leu Glu Leu Thr His Arg Gly Trp
            115                 120                 125
Ala His Ala Glu Glu Asn Lys Arg Arg Thr Leu Gln Lys Ser Asp Ile
        130                 135                 140
Ala Ala Ala Val Ala Arg Thr Glu Val Phe Asp Phe Leu Val Asp Ile
145                 150                 155                 160
Val Pro Arg Asp Glu Ala Lys Asp Ala Asp Ser Ala Ala Met Gly Ala
                165                 170                 175
Ala Gly Ile Pro His Pro Ala Ala Gly Leu Pro Ala Ala Asp Pro Met
            180                 185                 190
Gly Tyr Tyr Tyr Val Gln Pro Gln
        195                 200
```

<210> SEQ ID NO 101
<211> LENGTH: 1118
<212> TYPE: DNA
<213> ORGANISM: Oryza sativa

<400> SEQUENCE: 101

```
cacacacagc tacaaatcga ctgtaattaa ggtacgtata tataggtgac aatggacaac    60
cagcagctac cctacgccgg tcagccggcg ccgcaggcg  ccggagcccc ggtgccgggc   120
gtgcctggcg cgggcgggcc gccggcggtg ccgcaccacc acctgctcca gcagcagcag   180
gcgcagctgc aggcgttctg gcgtaccag  cggcaggagg cggagcgcgc gtcggcgtcg   240
gacttcaaga accaccagct gccgctggcg cggatcaaga agatcatgaa ggcggacgag   300
gacgtgcgca tgatctcggc ggaggcgccc gtgctgttcg ccaaggcgtg cgagctcttc   360
atcctggagc tcaccatccg ctcgtggctg cacgccgagg agaacaagcg ccgcaccctg   420
cagcgcaacg acgtcgccgc cgccatcgcg cgcaccgacg tgttcgactt cctcgtcgac   480
atcgtgccgc gggaggaggc caaggaggag cccggcagcg cgctcgggtt cgcggcggga   540
gggcccgccg cgccgttgg  agcggccggc cccgccgcgg ggctgccgta ctactacccg   600
ccgatgggc  agccggcgcc gatgatgccg gcgtggcatg ttccggcgtg ggacccggcg   660
tggcagcaag agcagcgcc  ggatgtggac caggcgccg  ccggcagctt cagcgaggaa   720
gggcagcaag gttttgcagg ccatggcggt gcggcagcta gcttccctcc tgcacctcca   780
```

```
agctccgaat agtgatgatc catatggttc catgcatgca tcgctgaggt gctagctagc    840
tactatagct gctcaaatca aatgctcaat gtgtcggtaa ttaattaatg tggtacgtat    900
taacttaacc gatgtacgta atggacgctc aagctaatta agggatgtac aatttactaa    960
ttaatttaat ttgtaatata tagccgatta actagcaagg tgacccagta ctatttgtaa   1020
tttcttttcc cgttatgcta ctaattgtgg acgcacaaac cattaccgga acagaaatta   1080
ctactgatga attactataa aaaaaaaaaa aaaaaaa                            1118
```

<210> SEQ ID NO 102
<211> LENGTH: 246
<212> TYPE: PRT
<213> ORGANISM: Oryza sativa

<400> SEQUENCE: 102

```
Met Asp Asn Gln Gln Leu Pro Tyr Ala Gly Gln Pro Ala Ala Gly
  1               5                  10                  15

Ala Gly Ala Pro Val Pro Gly Val Pro Gly Ala Gly Gly Pro Pro Ala
                 20                  25                  30

Val Pro His His His Leu Leu Gln Gln Gln Ala Gln Leu Gln Ala
             35                  40                  45

Phe Trp Ala Tyr Gln Arg Gln Glu Ala Glu Arg Ala Ser Ala Ser Asp
     50                  55                  60

Phe Lys Asn His Gln Leu Pro Leu Ala Arg Ile Lys Lys Ile Met Lys
 65                  70                  75                  80

Ala Asp Glu Asp Val Arg Met Ile Ser Ala Glu Ala Pro Val Leu Phe
                 85                  90                  95

Ala Lys Ala Cys Glu Leu Phe Ile Leu Glu Leu Thr Ile Arg Ser Trp
            100                 105                 110

Leu His Ala Glu Glu Asn Lys Arg Arg Thr Leu Gln Arg Asn Asp Val
        115                 120                 125

Ala Ala Ala Ile Ala Arg Thr Asp Val Phe Asp Phe Leu Val Asp Ile
    130                 135                 140

Val Pro Arg Glu Glu Ala Lys Glu Glu Pro Gly Ser Ala Leu Gly Phe
145                 150                 155                 160

Ala Ala Gly Gly Pro Ala Gly Ala Val Gly Ala Ala Gly Pro Ala Ala
                165                 170                 175

Gly Leu Pro Tyr Tyr Tyr Pro Pro Met Gly Gln Pro Ala Pro Met Met
            180                 185                 190

Pro Ala Trp His Val Pro Ala Trp Asp Pro Ala Trp Gln Gln Gly Ala
        195                 200                 205

Ala Pro Asp Val Asp Gln Gly Ala Ala Gly Ser Phe Ser Glu Glu Gly
    210                 215                 220

Gln Gln Gly Phe Ala Gly His Gly Gly Ala Ala Ala Ser Phe Pro Pro
225                 230                 235                 240

Ala Pro Pro Ser Ser Glu
                245
```

<210> SEQ ID NO 103
<211> LENGTH: 1343
<212> TYPE: DNA
<213> ORGANISM: Oryza sativa

<400> SEQUENCE: 103

```
tctgacccaa gggcgaccgc gtctccctct ctctctctct ctccgccgcc gacgccgagg     60
```

-continued

```
gctccacgag agggaggtgg gcggcgcggc ccttcgccgg agggagcgct ctccgccgcc    120
gccgctcccg ctcccgccgg cgcgggagat ccgggcgtcg tctctcgggc ctttggcttt    180
ggacggacaa gagctgacat ggaaccatcc tcacagcctc agcctgtgat gggtgttgcc    240
actggtgggt cacaagcata tcctcctcct gctgctgcat atccacctca agccatggtt    300
cctggagctc ctgctgttgt tcctcctggc tcacagccat cagcaccatt ccccactaat    360
ccagctcaac tcagtgctca gcaccagcta gtctaccaac aagcccagca atttcatcag    420
cagctgcagc aacagcaaca gcagcaactc cgtgagttct gggctaacca aatggaagag    480
attgagcaaa caaccgactt caagaaccac agcttgccac tcgcaaggat aaagaagata    540
atgaaggctg atgaggatgt ccggatgatc tcggcagaag cccccgttgt cttcgcaaag    600
gcatgcgagg tattcatatt agagttaaca ttgaggtcgt ggatgcacac ggaggagaac    660
aagcgccgga ccttgcagaa gaatgacatt gcagctgcca tcaccaggac tgatatctat    720
gacttcttgg tggacatagt tcccagggat gaaatgaaag aagaagggct tgggcttccg    780
agggttggcc taccgcctaa tgtgggggc gcagcagaca catatccata ttactacgtg    840
ccagcgcagc aggggcctgg atcaggaatg atgtacggtg acagcaagg tcacccggtg    900
acgtatgtgt ggcagcagcc tcaagagcaa caggaagagg ccctgaaga gcagcactct    960
ctgccagaaa gtagctaaag atgatacagt gaagttgtga cattgatata cattgtcctg   1020
tgaacttagg gcctctaaaa ctcagtgctc ttgtcaaaac tattcccatg attgttggct   1080
gaaacgggta atctgattag gtcttaggct ttcctaatgt tagttctgct ctgctatggc   1140
agcagtagaa aaaaaaaaga ttgtgatttg gtaggtgatt gcaactaat gtagtaactg    1200
taccttacct ttcatcagtt tctaatccaa tactcaaaag tgctggcatg tggagaccct   1260
tgtatgaatt gagtgtttgt tcatgtcatg catcagtctg ttgcctcatt tatcagtcat   1320
catgcctcct gctttgcaaa aaa                                           1343
```

<210> SEQ ID NO 104
<211> LENGTH: 259
<212> TYPE: PRT
<213> ORGANISM: Oryza sativa

<400> SEQUENCE: 104

```
Met Glu Pro Ser Ser Gln Pro Gln Pro Val Met Gly Val Ala Thr Gly
  1               5                  10                  15

Gly Ser Gln Ala Tyr Pro Pro Ala Ala Ala Tyr Pro Pro Gln Ala
             20                  25                  30

Met Val Pro Gly Ala Pro Ala Val Val Pro Pro Gly Ser Gln Pro Ser
         35                  40                  45

Ala Pro Phe Pro Thr Asn Pro Ala Gln Leu Ser Ala Gln His Gln Leu
     50                  55                  60

Val Tyr Gln Gln Ala Gln Gln Phe His Gln Leu Gln Gln Gln Gln
 65                  70                  75                  80

Gln Gln Gln Leu Arg Glu Phe Trp Ala Asn Gln Met Glu Glu Ile Glu
                 85                  90                  95

Gln Thr Thr Asp Phe Lys Asn His Ser Leu Pro Leu Ala Arg Ile Lys
            100                 105                 110

Lys Ile Met Lys Ala Asp Glu Asp Val Arg Met Ile Ser Ala Glu Ala
        115                 120                 125

Pro Val Val Phe Ala Lys Ala Cys Glu Val Phe Ile Leu Glu Leu Thr
    130                 135                 140
```

```
Leu Arg Ser Trp Met His Thr Glu Glu Asn Lys Arg Arg Thr Leu Gln
145                 150                 155                 160

Lys Asn Asp Ile Ala Ala Ala Ile Thr Arg Thr Asp Ile Tyr Asp Phe
                165                 170                 175

Leu Val Asp Ile Val Pro Arg Asp Glu Met Lys Glu Glu Gly Leu Gly
            180                 185                 190

Leu Pro Arg Val Gly Leu Pro Pro Asn Val Gly Gly Ala Ala Asp Thr
        195                 200                 205

Tyr Pro Tyr Tyr Tyr Val Pro Ala Gln Gln Gly Pro Gly Ser Gly Met
    210                 215                 220

Met Tyr Gly Gly Gln Gln Gly His Pro Val Thr Tyr Val Trp Gln Gln
225                 230                 235                 240

Pro Gln Glu Gln Gln Glu Glu Ala Pro Glu Glu Gln His Ser Leu Pro
                245                 250                 255

Glu Ser Ser
```

<210> SEQ ID NO 105
<211> LENGTH: 1085
<212> TYPE: DNA
<213> ORGANISM: Oryza sativa

<400> SEQUENCE: 105

```
gcacgagaag gaatctacgt tgcatgcata agacgtgttg gaaatatcat aagttttggg     60
acaagcaaga gaggacatgg agccatcatc acaacctcag ccggcaattg gtgttgttgc    120
tggtggatca caagtgtacc ctgcataccg gcctgcagca acagtgccta cagctcctgc    180
tgtcattcct gccggttcac agccagcacc gtcgttccct gccaacccctg atcaactgag    240
tgctcagcac cagctcgtct atcagcaagc cagcaatttt caccagcagc ttcagcagca    300
gcaacagcgt caactccagc agttttgggc tgaacgtctg gtcgatattg aacaaactac    360
tgacttcaag aaccacagct tgccacttgc taggataaag aagatcatga aggcagatga    420
ggacgttcgc atgatctccg cagaggctcc tgtgatcttt gcgaaagcat gtgagatatt    480
catactggag ctgaccctga gatcatggat gcacacggag gagaacaagc gccgtacctt    540
gcagaagaat gacatagcag ctgccatcac caggacggat atgtacgatt cttggtaga    600
tatagttccc agggatgact tgaaggagga gggagttggg ctccctaggg ctggattgcc    660
gcccttgggt gtccctgctg actcatatcc gtatggctac tatgtgccac agcagcaggt    720
cccaggtgca ggaatagcgt atggtggtca gcaaggtcat ccggggtatc tgtggcagga    780
tcctcaggaa cagcaggaag agcctcctgc agagcagcaa agtgattaag aagagtaaat    840
gatccctgtg aattgtcaag aagcttacca cctgattcag aatttttactt ttagccaggt    900
tgtcgtctat tctgaattta tgaataggat taggattctc tcatggtagt tgcatttctg    960
ctgtagtgga aaaggattta tgacatgaga gtatgagact aatgggtttc agttactata   1020
ccgtttcctg tcaatccaaa agttggcctt tgcgaggcca ttgatataaa aaaaaaaaa   1080
aaaaa                                                              1085
```

<210> SEQ ID NO 106
<211> LENGTH: 250
<212> TYPE: PRT
<213> ORGANISM: Oryza sativa

<400> SEQUENCE: 106

```
Met Glu Pro Ser Ser Gln Pro Gln Pro Ala Ile Gly Val Val Ala Gly
1               5                  10                  15
```

Gly Ser Gln Val Tyr Pro Ala Tyr Arg Pro Ala Thr Val Pro Thr
            20                  25                  30

Ala Pro Ala Val Ile Pro Ala Gly Ser Gln Pro Ala Pro Ser Phe Pro
        35                  40                  45

Ala Asn Pro Asp Gln Leu Ser Ala Gln His Gln Leu Val Tyr Gln Gln
    50                  55                  60

Ala Gln Gln Phe His Gln Leu Gln Gln Gln Gln Arg Gln Leu
65                  70                  75                  80

Gln Gln Phe Trp Ala Glu Arg Leu Val Asp Ile Glu Gln Thr Thr Asp
                85                  90                  95

Phe Lys Asn His Ser Leu Pro Leu Ala Arg Ile Lys Lys Ile Met Lys
            100                 105                 110

Ala Asp Glu Asp Val Arg Met Ile Ser Ala Glu Ala Pro Val Ile Phe
        115                 120                 125

Ala Lys Ala Cys Glu Ile Phe Ile Leu Glu Leu Thr Leu Arg Ser Trp
    130                 135                 140

Met His Thr Glu Glu Asn Lys Arg Arg Thr Leu Gln Lys Asn Asp Ile
145                 150                 155                 160

Ala Ala Ala Ile Thr Arg Thr Asp Met Tyr Asp Phe Leu Val Asp Ile
                165                 170                 175

Val Pro Arg Asp Asp Leu Lys Glu Glu Val Gly Leu Pro Arg Ala
            180                 185                 190

Gly Leu Pro Pro Leu Gly Val Pro Ala Asp Ser Tyr Pro Tyr Gly Tyr
        195                 200                 205

Tyr Val Pro Gln Gln Gln Val Pro Gly Ala Gly Ile Ala Tyr Gly Gly
    210                 215                 220

Gln Gln Gly His Pro Gly Tyr Leu Trp Gln Asp Pro Gln Glu Gln Gln
225                 230                 235                 240

Glu Glu Pro Pro Ala Glu Gln Gln Ser Asp
                245                 250

<210> SEQ ID NO 107
<211> LENGTH: 893
<212> TYPE: DNA
<213> ORGANISM: Oryza sativa

<400> SEQUENCE: 107
gcacgagaaa gagagagctt ttccatcccc aaatcccctc ctcctcctca aaccctagct      60
aagctccgct cgcagcagcc atggatccca ccaaatccag cacgccgccg ccggtgatgg     120
gcgcgcccgt cggcttcccg cctggcgcgt accctccgcc tcccccggc ggcgcagcag      180 cagctgcaga tgttctgggc ggagcagtac cgcgagatcg aggccaccac cgacttcaag     240
aaccacaacc tccccctggc ccgcatcaag aagatcatga aggccgacga ggacgtccgc     300
atgatcgccg ccgaggcccc cgtcgtgttc gcccgcgcct gcgagatgtt catcctcgag     360
ctcacccacc gcggctgggc gcacgccgag gagaacaagc gccgtacgct gcagaagtcc     420
gacattgccg ccgccatcgc gcgcaccgag gtgttcgact cctcgtcga catcgtgccc      480 cgcgacgacg ccaaggacgc cgacgccgcc gcggccgcgg cggcggccgg catccccgc      540 cccgccgccg gtgtgccggc caccgatccg ctcgcctact actatgtgcc ccagcagtaa     600
tgtatctgat taacccctt caagccttt ctaagcgaag gatgtgttgt tgtttgttgt       660
tgctgttgct gttcttgttg ttgttgttgc cgcgtaataa gatatgttga taatttatgg     720
cttcccctga gcttaaagaa tttgagcttt tggttctaga atctgggtaa aattgttgta    780

```
atgggaaga ctgtatgact gtatttgtag tgcatgtctt aacttgtcgg atagtgtaat    840
ccgataatta ttatgcggtt agctggttac ctctcaaaaa aaaaaaaaaa aaa           893
```

<210> SEQ ID NO 108
<211> LENGTH: 172
<212> TYPE: PRT
<213> ORGANISM: Oryza sativa

<400> SEQUENCE: 108

```
Met Asp Pro Thr Lys Ser Ser Thr Pro Pro Val Met Gly Ala Pro
 1               5                  10                  15

Val Gly Phe Pro Pro Gly Ala Tyr Pro Pro Pro Pro Ala Ala Gln
                20                  25                  30

Gln Gln Leu Gln Met Phe Trp Ala Glu Gln Tyr Arg Glu Ile Glu Ala
            35                  40                  45

Thr Thr Asp Phe Lys Asn His Asn Leu Pro Leu Ala Arg Ile Lys Lys
     50                  55                  60

Ile Met Lys Ala Asp Glu Asp Val Arg Met Ile Ala Ala Glu Ala Pro
 65                  70                  75                  80

Val Val Phe Ala Arg Ala Cys Glu Met Phe Ile Leu Glu Leu Thr His
                85                  90                  95

Arg Gly Trp Ala His Ala Glu Gly Asn Lys Arg Thr Leu Gln Lys
            100                 105                 110

Ser Asp Ile Ala Ala Ala Ile Ala Arg Thr Glu Val Phe Asp Phe Leu
        115                 120                 125

Val Asp Ile Val Pro Arg Asp Asp Ala Lys Asp Ala Asp Ala Ala
    130                 135                 140

Ala Ala Ala Ala Ala Gly Ile Pro Arg Pro Ala Ala Gly Val Pro Ala
145                 150                 155                 160

Thr Asp Pro Leu Ala Tyr Tyr Tyr Val Pro Gln Gln
                165                 170
```

<210> SEQ ID NO 109
<211> LENGTH: 1054
<212> TYPE: DNA
<213> ORGANISM: Glycine max

<400> SEQUENCE: 109

```
gcacgagggg tctctctgtc tctctcggat catcaaaatc agaaagaatt ggggggaatgg    60 agaacaacca gcaacaaggc gctcaagccc aatcgggacc gtaccccggc ggcgccggtg   120
gaagtgcagg tgcaggtgca ggtgcaggcg cggccccgtt ccagcacctg ctccagcagc   180
agcagcagca gctgcagatg ttctggtcgt accagcggca agagatcgag cacgtgaacg   240
acttcaagaa ccaccagctc cccttggccc gcatcaagaa gatcatgaag gccgacgagg   300
acgtccgcat gatctccgcc gaggcccca tcctcttcgc caaggcctgc gagctcttca   360
tcctcgagct caccatccgc tcctggctcc acgccgacga gaacaagcgc cgcaccctcc   420
agaagaacga catccgccgc cgcatcactc gcaccgacat tttcgacttc ctcgtcgaca   480 tcgtccccg cgacgagatc aaggacgacg ccgcgctcgt cggggcaacg gccagtgggg   540
tgccttacta ctaccgccc attggccagc ctgccgggat gatgattggc cgccccgccg   600
tcgatcccgc caccggagtt tatgtccagc cgccctccca ggcctggcag tccgtctggc   660
agtccgccgc cgaggacacg ccctacggca ccggtgccca ggggaacctt gatgccagca   720
gctgagcgac aaccatgccg aaacggactg tcaggagtta tgaagattct gaacttgctt   780
```

```
ggaattttga ttgcttgcaa tttggaaatg gttttgttaa ctaaatttt atgggatgac    840 actatgaacc tgttaactcg atgaacagca tgatttaact acttctgtac aaaaatttaa    900
aactaaacaa tgatccttct gtgtgaactt gtttgatcat ctgctaatac tatttatttc    960
ctcgtaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaa                               1054
```

<210> SEQ ID NO 110
<211> LENGTH: 222
<212> TYPE: PRT
<213> ORGANISM: Glycine max

<400> SEQUENCE: 110

```
Met Glu Asn Asn Gln Gln Gln Gly Ala Gln Ala Gln Ser Gly Pro Tyr
  1               5                  10                  15

Pro Gly Gly Ala Gly Gly Ser Ala Gly Ala Gly Ala Gly Ala Gly Ala
             20                  25                  30

Ala Pro Phe Gln His Leu Leu Gln Gln Gln Gln Gln Gln Leu Gln Met
         35                  40                  45

Phe Trp Ser Tyr Gln Arg Gln Glu Ile Glu His Val Asn Asp Phe Lys
     50                  55                  60

Asn His Gln Leu Pro Leu Ala Arg Ile Lys Lys Ile Met Lys Ala Asp
 65                  70                  75                  80

Glu Asp Val Arg Met Ile Ser Ala Glu Ala Pro Ile Leu Phe Ala Lys
                 85                  90                  95

Ala Cys Glu Leu Phe Ile Leu Glu Leu Thr Ile Arg Ser Trp Leu His
            100                 105                 110

Ala Asp Glu Asn Lys Arg Arg Thr Leu Gln Lys Asn Asp Ile Ala Ala
        115                 120                 125

Ala Ile Thr Arg Thr Asp Ile Phe Asp Phe Leu Val Asp Ile Val Pro
    130                 135                 140

Arg Asp Glu Ile Lys Asp Asp Ala Ala Leu Val Gly Ala Thr Ala Ser
145                 150                 155                 160

Gly Val Pro Tyr Tyr Tyr Pro Pro Ile Gly Gln Pro Ala Gly Met Met
                165                 170                 175

Ile Gly Arg Pro Ala Val Asp Pro Ala Thr Gly Val Tyr Val Gln Pro
            180                 185                 190

Pro Ser Gln Ala Trp Gln Ser Val Trp Gln Ser Ala Ala Glu Asp Thr
        195                 200                 205

Pro Tyr Gly Thr Gly Ala Gln Gly Asn Leu Asp Gly Gln Ser
    210                 215                 220
```

<210> SEQ ID NO 111
<211> LENGTH: 1036
<212> TYPE: DNA
<213> ORGANISM: Glycine max

<400> SEQUENCE: 111

```
gcacgagccc acacacactc tttctctctc tctctttccc tgatcatcaa aatcagaaaa     60
aattggggga atggagacca acaaccagca acaacaacaa caaggagctc aagcccaatc    120
gggaccctac cccgtcgccg gcgccggcgg cagtgcaggt gcaggtgcag gcgctcctcc    180 cccttccag caccttctcc agcagcagca gcagcagctc cagatgttct ggtcttacca    240
gcgtcaagaa atcgagcacg tgaacgactt taagaatcac cagctccctc ttgcccgcat    300
```

-continued

```
caagaagatc atgaaggccg acgaggatgt ccgcatgatc tccgccgagg ccccatcct    360 cttcgccaag gcctgcgagc tcttcatcct cgagctcacc atccgctcct ggctccacgc    420
cgaggagaac aagcgccgca ccctccagaa gaacgacatc gccgccgcca tcacccgcac    480
cgacattttc gacttcctcg ttgatattgt cccccgcgac gagatcaagg acgacgctgc    540
tcttgtgggg gccaccgcca gtggggtgcc ttactactac ccgcccattg gacagcctgc    600 cggggatgatg attggccgcc ccgccgtcga tcccgccacc ggggtttatg tccagccgcc    660
ctcccaggca tggcagtccg tctggcagtc cgctgccgag gacgcttcct atggcaccgg    720
cggggccggt gcccagcgga gccttgatgg ccagagttga gtgacatcga tgccgatgat    780
ggacagtcag gagttatgaa gattctgaac ttgctgcaat ttagaaatgg ttttgtttac    840
taaattttta tgggatgaca ctgtgaacct gttaactcga tgaacagcat gatttaacta    900
cttttgtaca aaaatttaaa actaaacact gatccttctg tgtgaaacat gtatgatcat    960
ctgccaatac tgtttatttc ctcataagtc atgataccac tcgtatactt tgctaaaaaa    1020
aaaaaaaaaa aaaaaa                                                     1036
```

<210> SEQ ID NO 112
<211> LENGTH: 229
<212> TYPE: PRT
<213> ORGANISM: Glycine max

<400> SEQUENCE: 112

```
Met Glu Thr Asn Asn Gln Gln Gln Gln Gln Gly Ala Gln Ala Gln
  1               5                  10                  15

Ser Gly Pro Tyr Pro Val Ala Gly Gly Ser Ala Gly Ala Gly
             20                  25                  30

Ala Gly Ala Pro Pro Pro Phe Gln His Leu Leu Gln Gln Gln Gln
         35                  40                  45

Gln Leu Gln Met Phe Trp Ser Tyr Gln Arg Gln Glu Ile Glu His Val
     50                  55                  60

Asn Asp Phe Lys Asn His Gln Leu Pro Leu Ala Arg Ile Lys Lys Ile
 65                  70                  75                  80

Met Lys Ala Asp Glu Asp Val Arg Met Ile Ser Ala Glu Ala Pro Ile
                 85                  90                  95

Leu Phe Ala Lys Ala Cys Glu Leu Phe Ile Leu Glu Leu Thr Ile Arg
            100                 105                 110

Ser Trp Leu His Ala Glu Glu Asn Lys Arg Arg Thr Leu Gln Lys Asn
            115                 120                 125

Asp Ile Ala Ala Ala Ile Thr Arg Thr Asp Ile Phe Asp Phe Leu Val
130                 135                 140

Asp Ile Val Pro Arg Asp Glu Ile Lys Asp Asp Ala Ala Leu Val Gly
145                 150                 155                 160

Ala Thr Ala Ser Gly Val Pro Tyr Tyr Tyr Pro Pro Ile Gly Gln Pro
                165                 170                 175

Ala Gly Met Met Ile Gly Arg Pro Ala Val Asp Pro Thr Gly Val
            180                 185                 190

Tyr Val Gln Pro Pro Ser Gln Ala Trp Gln Ser Val Trp Gln Ser Ala
            195                 200                 205

Ala Glu Asp Ala Ser Tyr Gly Thr Gly Gly Ala Gly Ala Gln Arg Ser
        210                 215                 220

Leu Asp Gly Gln Ser
225
```

```
<210> SEQ ID NO 113
<211> LENGTH: 514
<212> TYPE: DNA
<213> ORGANISM: Glycine max
<220> FEATURE:
<221> NAME/KEY: unsure
<222> LOCATION: (424)
<223> OTHER INFORMATION: n = A, C, G, or T
<220> FEATURE:
<221> NAME/KEY: unsure
<222> LOCATION: (430)
<223> OTHER INFORMATION: n = A, C, G, or T
<220> FEATURE:
<221> NAME/KEY: unsure
<222> LOCATION: (464)
<223> OTHER INFORMATION: n = A, C, G, or T
<220> FEATURE:
<221> NAME/KEY: unsure
<222> LOCATION: (506)
<223> OTHER INFORMATION: n = A, C, G, or T

<400> SEQUENCE: 113
tagggttttc tcctccccca ttgacccacc gtccatcgca aaggaagtcg cgcccaattt      60
ccatggtttg tagattaaat cttaaagcag taagtcatca tggataaatc agagcagact     120
cagcagcaac atcagcatgg gatgggcgtt gccacaggtg ctagccaaat ggcctattct     180
tctcactacc cgactgctcc catggtggct tctggcacgc ctgctgtagc tgttccttcc     240
ccaactcagg ctccagctgc cttctctagt tctgctcacc agcttgcata ccagcaagca     300
cagcatttcc accaccaaca gcagcaacac caacaacagc agcttcaaat gttctggtca     360
aaccaaatgc aagaaattga gcaaacaatt gactttaaaa accacagtct tcctcttgct     420
cggntaaaan agataatgaa agctgatgaa gatgtccgga tganttctgc aagaagctcc     480
aagtcaatat ttgcaaaagc atgtgnaatg gtca                                  514

<210> SEQ ID NO 114
<211> LENGTH: 126
<212> TYPE: PRT
<213> ORGANISM: Glycine max
<220> FEATURE:
<221> NAME/KEY: UNSURE
<222> LOCATION: (109)
<223> OTHER INFORMATION: Xaa = any amino acid
<220> FEATURE:
<221> NAME/KEY: UNSURE
<222> LOCATION: (111)
<223> OTHER INFORMATION: Xaa = any amino acid
<220> FEATURE:
<221> NAME/KEY: UNSURE
<222> LOCATION: (122)
<223> OTHER INFORMATION: Xaa = any amino acid

<400> SEQUENCE: 114

Met Asp Lys Ser Glu Gln Thr Gln Gln Gln His Gln His Gly Met Gly
  1               5                  10                  15

Val Ala Thr Gly Ala Ser Gln Met Ala Tyr Ser Ser His Tyr Pro Thr
                 20                  25                  30

Ala Pro Met Val Ala Ser Gly Thr Pro Ala Val Ala Val Pro Ser Pro
             35                  40                  45

Thr Gln Ala Pro Ala Ala Phe Ser Ser Ser Ala His Gln Leu Ala Tyr
         50                  55                  60

Gln Gln Ala Gln His Phe His His Gln Gln Gln His Gln Gln Gln
 65                  70                  75                  80

Gln Leu Gln Met Phe Trp Ser Asn Gln Met Gln Glu Ile Glu Gln Thr
                 85                  90                  95
```

```
Ile Asp Phe Lys Asn His Ser Leu Pro Leu Ala Arg Xaa Lys Xaa Ile
            100                 105                 110

Met Lys Ala Asp Glu Asp Val Arg Met Xaa Ser Ala Arg Ser
        115                 120                 125
```

<210> SEQ ID NO 115
<211> LENGTH: 1363
<212> TYPE: DNA
<213> ORGANISM: Glycine max

<400> SEQUENCE: 115

```
ttcggcacga gttgaaacca aaccaaacca aaccaaacca aacctctctt tctcagtttc      60
tctctcttag ggttttctcc tcccccattg acccaccgtc catcgcaaag gaagtcgcgc     120
ccaatttcca tggaactgta aagagattat agtttgtaga ttaaatctta aagcagtaag     180
tcatcatgga taaatcagag cagactcagc agcaacatca gcatgggatg ggcgttgcca     240
caggtgctag ccaaatggcc tattcttctc actacccgac tgctcccatg gtggcttctg     300
gcacgcctgc tgtagctgtt ccttccccaa ctcaggctcc agctgccttc tctagttctg     360
ctcaccagct tgcataccag caagcacagc atttccacca ccaacagcag caacaccaac     420
aacagcagct tcaaatgttc tggtcaaacc aaatgcaaga aattgagcaa acaattgact     480
ttaaaaacca cagtcttcct cttgctcgga taaaaaagat aatgaaagct gatgaagatg     540
tccggatgat ttctgcagaa gctccagtca tatttgcaaa agcatgtgaa atgttcatat     600
tagagttgac gttgagatct tggatccaca cagaagagaa caagaggaga actctacaaa     660
agaatgatat agcagctgct atttcgagaa acgatgtttt tgatttcttg gttgatatta     720
tcccaagaga tgagttgaaa gaggaaggac ttggaataac caaggctact attccattgg     780
tgaattctcc agctgatatg ccatattact atgtccctcc acagcatcct gttgtaggac     840
ctcctgggat gatcatgggc aagcccgttg gtgctgagca agcaacgctg tattctacac     900
agcagcctcg acctcccatg gcgttcatgc catggcccca tacacaaccc cagcaacagc     960
agccaccccca acatcaacaa acagactcat gatgaccatg caattcaatt aggtcggaaa    1020
gtagcatgca ccttatgatt attacaaatt tacttaatgc ctttaagtca gctgtagttt    1080
agtgttttgc attgaaaaat gccaaagatt gtttgaggtt tcttgcactc atttatgatt    1140
gtatgagctc ttatgctgag ttacttttgg ttgtgtttat ttgaggtact ggtgtggtag    1200
ttaaattagt ttgtagctgt ccataagtaa acagcgtagc tgcttaatta ggaggtctga    1260
aatgatgaaa tagtttgtat tgttattgca gaaggtaggt tttattcagt atttcattct    1320
attgcaatgg ctgaattta tgctcaaaaa aaaaaaaaaa aaa                       1363
```

<210> SEQ ID NO 116
<211> LENGTH: 268
<212> TYPE: PRT
<213> ORGANISM: Glycine max

<400> SEQUENCE: 116

```
Met Asp Lys Ser Glu Gln Thr Gln Gln Gln His Gln His Gly Met Gly
 1               5                  10                  15

Val Ala Thr Gly Ala Ser Gln Met Ala Tyr Ser Ser His Tyr Pro Thr
            20                  25                  30

Ala Pro Met Val Ala Ser Gly Thr Pro Ala Val Ala Val Pro Ser Pro
        35                  40                  45

Thr Gln Ala Pro Ala Ala Phe Ser Ser Ser Ala His Gln Leu Ala Tyr
```

```
                  50                  55                  60
Gln Gln Ala Gln His Phe His His Gln Gln Gln His Gln Gln Gln
 65                  70                  75                  80
Gln Leu Gln Met Phe Trp Ser Asn Gln Met Gln Glu Ile Glu Gln Thr
                 85                  90                  95
Ile Asp Phe Lys Asn His Ser Leu Pro Leu Ala Arg Ile Lys Lys Ile
                100                 105                 110
Met Lys Ala Asp Glu Asp Val Arg Met Ile Ser Ala Glu Ala Pro Val
            115                 120                 125
Ile Phe Ala Lys Ala Cys Glu Met Phe Ile Leu Glu Leu Thr Leu Arg
        130                 135                 140
Ser Trp Ile His Thr Glu Glu Asn Lys Arg Arg Thr Leu Gln Lys Asn
145                 150                 155                 160
Asp Ile Ala Ala Ala Ile Ser Arg Asn Asp Val Phe Asp Phe Leu Val
                165                 170                 175
Asp Ile Ile Pro Arg Asp Glu Leu Lys Glu Glu Gly Leu Gly Ile Thr
            180                 185                 190
Lys Ala Thr Ile Pro Leu Val Asn Ser Pro Ala Asp Met Pro Tyr Tyr
        195                 200                 205
Tyr Val Pro Pro Gln His Pro Val Val Gly Pro Pro Gly Met Ile Met
    210                 215                 220
Gly Lys Pro Val Gly Ala Glu Gln Ala Thr Leu Tyr Ser Thr Gln Gln
225                 230                 235                 240
Pro Arg Pro Pro Met Ala Phe Met Pro Trp Pro His Thr Gln Pro Gln
                245                 250                 255
Gln Gln Gln Pro Pro Gln His Gln Gln Thr Asp Ser
            260                 265
```

<210> SEQ ID NO 117
<211> LENGTH: 1505
<212> TYPE: DNA
<213> ORGANISM: Glycine max

<400> SEQUENCE: 117

```
gcacgagctc caccgtccat tgcaaagtct tgcgcccaat ttccatggaa ctgtaaagag    60
aggatagtta aagattaaa tcttaaagca gtaagtcatc atggataaat cagagcagac   120
tcaacagcag cagcagcaac aacagcatgt gatgggagtt gccgcagggg ctagccaaat   180
ggcctattct tctcactacc cgactgcttc catggtggct tctggcacgc ccgctgtaac   240
tgctccttcc ccaactcagg ctccagctgc cttctctagt tctgctcacc agcttgcata   300
ccagcaagca cagcatttcc accaccaaca gcagcaacac caacaacagc agcttcaaat   360
gttctggtca aaccaaatgc aagaaattga gcaaacaatt gactttaaaa accatagcct   420
tcctcttgct cggataaaaa agataatgaa agctgatgaa gatgtccgga tgatttcagc   480
agaagctccg gtcatatttg caaagcttg tgaaatgttc atattagagt tgacgttgcg   540
atcttggatc cacacagaag agaacaagag gagaactcta caaaagaatg atatagcagc   600
tgctatttcg agaaacgatg ttttttgattt cttggttgat attattccaa gagatgagtt   660
gaaagaggaa ggacttggaa taccaaggc tactattccg ttagtgggtt ctccagctga   720
tatgccatat tactatgtcc ctccacagca tcctgttgta ggaccacctg ggatgatcat   780
gggcaagccc attggcgctg agcaagcaac actatattct acacagcagc ctcgacctcc   840
tgtggcgttc atgccatggc ctcatacaca accctgcaa cagcagccac cccaacatca   900
```

```
acaaacagac tcatgatgac tatgcaattc aattaggttg gaaagtagcc tgcacctttt      960
gattattaca aatttactta atgcctttca gccagctgta gtttagtgtt gtgcattgaa     1020
aaaaagcaaa agattgtttt gaggtttctt gcactcattt atgattgtat gagctcttgt     1080
gatgagttac ttttggttgt gtttactatt ggtgtagtgg ttaaattatt tggcagctgt     1140
ccataaccag agagcgtagc tgcttaatta ggaggtttga tatgatgaaa tagtttgtat     1200
tgttattgca gaaggtaggt ttaattcagt attccattct actgcaatgg ctgaatttat     1260
tgctcatctg catagtacta gttgatgttt tttcctgtga ctcgttatgt gttagagtgc     1320
gaagaagaat gagtgtgcca tatttattct tcccctgttc ttgcgccaca ctctcggaaa     1380
aacaaatgtt tccgatcatt tcaattattt ccaggaacat caatatagtg gttgatgttt     1440
aatgctgtca ctgcaaaaaa aaatatgttt tttacagttg gaaaaaaaaa aaaaaaaaa      1500 aaaaa                                                                 1505
```

<210> SEQ ID NO 118
<211> LENGTH: 271
<212> TYPE: PRT
<213> ORGANISM: Glycine max

<400> SEQUENCE: 118

```
Met Asp Lys Ser Glu Gln Thr Gln Gln Gln Gln Gln Gln Gln Gln His
  1               5                  10                  15

Val Met Gly Val Ala Ala Gly Ala Ser Gln Met Ala Tyr Ser Ser His
                 20                  25                  30

Tyr Pro Thr Ala Ser Met Val Ala Ser Gly Thr Pro Ala Val Thr Ala
             35                  40                  45

Pro Ser Pro Thr Gln Ala Pro Ala Ala Phe Ser Ser Ala His Gln
         50                  55                  60

Leu Ala Tyr Gln Gln Ala Gln His Phe His His Gln Gln Gln Gln His
 65                  70                  75                  80

Gln Gln Gln Gln Leu Gln Met Phe Trp Ser Asn Gln Met Gln Glu Ile
                 85                  90                  95

Glu Gln Thr Ile Asp Phe Lys Asn His Ser Leu Pro Leu Ala Arg Ile
            100                 105                 110

Lys Lys Ile Met Lys Ala Asp Glu Asp Val Arg Met Ile Ser Ala Glu
        115                 120                 125

Ala Pro Val Ile Phe Ala Lys Ala Cys Glu Met Phe Ile Leu Glu Leu
    130                 135                 140

Thr Leu Arg Ser Trp Ile His Thr Glu Glu Asn Lys Arg Arg Thr Leu
145                 150                 155                 160

Gln Lys Asn Asp Ile Ala Ala Ala Ile Ser Arg Asn Asp Val Phe Asp
                165                 170                 175

Phe Leu Val Asp Ile Ile Pro Arg Asp Glu Leu Lys Glu Glu Gly Leu
            180                 185                 190

Gly Ile Thr Lys Ala Thr Ile Pro Leu Val Gly Ser Pro Ala Asp Met
        195                 200                 205

Pro Tyr Tyr Tyr Val Pro Pro Gln His Pro Val Val Gly Pro Pro Gly
    210                 215                 220

Met Ile Met Gly Lys Pro Ile Gly Ala Glu Gln Ala Thr Leu Tyr Ser
225                 230                 235                 240

Thr Gln Gln Pro Arg Pro Pro Val Ala Phe Met Pro Trp Pro His Thr
                245                 250                 255

Gln Pro Leu Gln Gln Gln Pro Pro Gln His Gln Gln Thr Asp Ser
            260                 265                 270
```

-continued

```
                260             265             270
```

<210> SEQ ID NO 119
<211> LENGTH: 730
<212> TYPE: DNA
<213> ORGANISM: Glycine max

<400> SEQUENCE: 119

```
gcacgagtga ctttaaaaac catagccttc ctcttgctcg gataaaaaag ataatgaaag    60
ctgatgaaga tgtccggatg atttcagcag aagctccggt catatttgca aaagcttgtg   120
aaatgttcat attagagttg acgttgcgat cttggatcca cacagaagag aacaagagga   180
gaactctaca aagaatgat atagcagctg ctatttcgag aaacgatgtt tttgatttct    240
tggttgatat tattccaaga gatgagttga agaggaagg acttggaata accaggcta     300
ctattccgtt agtgggttct ccagctgata tgccatatta ctatgtccct ccacagcatc   360
ctgttgtagg accacctggg atgatcatgg caagcccat ggcgctgag caagcaacac     420
tatattctac acagcagcct cgacctcctg tggcgttcat gccatggcct catacacaac   480
ccctgcaaca gcagccaccc caacatcaac aaacagactc atgatgacta tgcaattcaa   540
ttaggttgga aagtagcctg cacctttga ttattacaaa tttacttaat gcctttcagc    600
cagctgtagt ttagtgttgt gcattgaaaa aaagcaaaag attgttttga ggtttcttgc   660
actcatttat gattgtatga gctcttgtga tgagttactt ttggttgtgt ttaaaaaaaa   720
aaaaaaaaaa                                                          730
```

<210> SEQ ID NO 120
<211> LENGTH: 171
<212> TYPE: PRT
<213> ORGANISM: Glycine max

<400> SEQUENCE: 120

```
Asp Phe Lys Asn His Ser Leu Pro Leu Ala Arg Ile Lys Lys Ile Met
 1               5                  10                  15

Lys Ala Asp Glu Asp Val Arg Met Ile Ser Ala Glu Ala Pro Val Ile
            20                  25                  30

Phe Ala Lys Ala Cys Glu Met Phe Ile Leu Glu Leu Thr Leu Arg Ser
        35                  40                  45

Trp Ile His Thr Glu Glu Asn Lys Arg Arg Thr Leu Gln Lys Asn Asp
    50                  55                  60

Ile Ala Ala Ala Ile Ser Arg Asn Asp Val Phe Asp Phe Leu Val Asp
65                  70                  75                  80

Ile Ile Pro Arg Asp Glu Leu Lys Glu Glu Gly Leu Gly Ile Thr Lys
                85                  90                  95

Ala Thr Ile Pro Leu Val Gly Ser Pro Ala Asp Met Pro Tyr Tyr Tyr
            100                 105                 110

Val Pro Pro Gln His Pro Val Gly Pro Pro Gly Met Ile Met Gly
        115                 120                 125

Lys Pro Ile Gly Ala Glu Gln Ala Thr Leu Tyr Ser Thr Gln Gln Pro
    130                 135                 140

Arg Pro Pro Val Ala Phe Met Pro Trp Pro His Thr Gln Pro Leu Gln
145                 150                 155                 160

Gln Gln Pro Pro Gln His Gln Gln Thr Asp Ser
                165                 170
```

<210> SEQ ID NO 121

<211> LENGTH: 1139
<212> TYPE: DNA
<213> ORGANISM: Glycine max

<400> SEQUENCE: 121

```
gcacgagaca cagcttttgt tctcgcactt cgctgtctga ggttctggat tctcagtgtt      60
tgcgaagcgc tgcatcatcc tttggggaag aatggatcat caagggcata gccagaaccc     120
atctatgggg gtggttggta gtggagctca attagcatat ggttctaacc catatcagcc     180
aggccaaata actgggccac cggggtctgt tgtgacatca gttggtacca ttcaatccac     240
acctgctgga gctcagctag acagcatca acttgcttat cagcatattc atcagcaaca     300
acaacaccag cttcagcaac agctccaaca attttggtca aaccagtacc aagaaattga     360
gaaggttact gatttcaaga accacagtct cccctggca aggatcaaga agattatgaa     420
ggctgacgag gatgttagga tgatatcagc cgaagcacca gtcatctttg caagggcatg     480
tgaaatgttc atattagagt taaccctgcg ttccttggaat cacactgaag agaacaaaag     540
gcgaacactt caaaaaaatg atattgctgc tgcaatcaca aggactgaca tctttgattt     600
cttggttgac attgtgcctc gtgaggactt gaaagatgaa gtgcttgcat caatcccaag     660
aggaacaatg cctgttgcag ggcctgctga tgcccttcca tattgctaca tgccgcctca     720
gcatgcgtcc caagttggag ctgctggtgt tataatgggt aagcctgtga tggacccaaa     780
catgtatgct cagcagtctc accctacat ggcaccacaa atgtggccac agccaccaga     840
ccaacgacag tcgtccccag aacattagct gatgtgtcgt ggaaattaag ataaccaggc     900
accggaatca gttgtgaatg tcaaactgaa tggttggaa gatccatact acattgcgag     960
cagaagctgt agctgatagt ttacatgcaa tgcagactat aaacatatgt agataatgtg    1020
ctagggaaaa cttaacctta tctttgattt agctggataa aatggtattt ttcatgttta    1080
aatttacagg tcatcagatg ataatattta tttactggtg caaaaaaaaa aaaaaaaaa    1139
```

<210> SEQ ID NO 122
<211> LENGTH: 258
<212> TYPE: PRT
<213> ORGANISM: Glycine max

<400> SEQUENCE: 122

```
Met Asp His Gln Gly His Ser Gln Asn Pro Ser Met Gly Val Val Gly
 1               5                  10                  15

Ser Gly Ala Gln Leu Ala Tyr Gly Ser Asn Pro Tyr Gln Pro Gly Gln
            20                  25                  30

Ile Thr Gly Pro Pro Gly Ser Val Val Thr Ser Val Gly Thr Ile Gln
        35                  40                  45

Ser Thr Pro Ala Gly Ala Gln Leu Gly Gln His Gln Leu Ala Tyr Gln
    50                  55                  60

His Ile His Gln Gln Gln Gln His Gln Leu Gln Gln Leu Gln Gln
65                  70                  75                  80

Phe Trp Ser Asn Gln Tyr Gln Glu Ile Glu Lys Val Thr Asp Phe Lys
                85                  90                  95

Asn His Ser Leu Pro Leu Ala Arg Ile Lys Lys Ile Met Lys Ala Asp
            100                 105                 110

Glu Asp Val Arg Met Ile Ser Ala Glu Ala Pro Val Ile Phe Ala Arg
        115                 120                 125

Ala Cys Glu Met Phe Ile Leu Glu Leu Thr Leu Arg Ser Trp Asn His
    130                 135                 140
```

```
Thr Glu Glu Asn Lys Arg Arg Thr Leu Gln Lys Asn Asp Ile Ala Ala
145                 150                 155                 160

Ala Ile Thr Arg Thr Asp Ile Phe Asp Phe Leu Val Asp Ile Val Pro
                165                 170                 175

Arg Glu Asp Leu Lys Asp Glu Val Leu Ala Ser Ile Pro Arg Gly Thr
            180                 185                 190

Met Pro Val Ala Gly Pro Ala Asp Ala Leu Pro Tyr Cys Tyr Met Pro
        195                 200                 205

Pro Gln His Ala Ser Gln Val Gly Ala Ala Gly Val Ile Met Gly Lys
    210                 215                 220

Pro Val Met Asp Pro Asn Met Tyr Ala Gln Gln Ser His Pro Tyr Met
225                 230                 235                 240

Ala Pro Gln Met Trp Pro Gln Pro Pro Asp Gln Arg Gln Ser Ser Pro
                245                 250                 255

Glu His

<210> SEQ ID NO 123
<211> LENGTH: 1493
<212> TYPE: DNA
<213> ORGANISM: Triticum aestivum

<400> SEQUENCE: 123
ggcaccagct ctggcttcca agtctataca taatataggg accgagcttg cggttttgcc        60
aagggtgatg gggaccgagc aagggaagga aggaacggga gcggggggagg ggcgcgtgga      120 ggtgcgcacg gggccgaggc cagcgctgcc ggcgccgcag cagcgggcgg tggacgggtt      180
ctggagggag cggcaggagg agatggaggc gacggcggac ttcaacgacc gcatactgcc      240
catggcccgc ctcaagaggc tcatccgcgc cgaggaggac ggcatgatga tcgccgccga      300
cacgccggcg tacctggcca agctctgcga gctcttcgtg caggagctcg ccgtgcgcgc      360
ctgggcgtgc gcccaatccc accaccgccg catcatactg gaatcggaca tcgccgaggc      420
catcgccttc acccagtcgt acgacttcct cgccaccgtg ctcctcgagc caacgggaa       480 ggcgcggctg gccggccgtg ctgctatccc gacaacggtt ccggtgacgg cggcgagggc      540
aaggctcatc accaggaagc gccacatgcc ggacccgaat cctccacggc cggtgcatgg      600
ggtgcggaga attcgtcctc gtgcgcttcc tatcccgccg ccgtcggact ttcgctacgt      660
gccggttcca tttccgttca cctcggcgcc gataggagcc gcagcgatgg cggaggggct      720
gatgattctc ccacccatca accacgcgac taccgagcgc gtgttcttcc tggacaggaa      780
cagcggcact gacttcgcag gtgaaaactc tgctgctgaa actatagcat ctccgcctcc      840
tccggcaggg cctgcaggag cagtggcgct gcccactgtc catcctgctg cttactactt      900
gtgcgcttac ccggtgacca acgacgttga ggcctttgcc gttggcaaca ctgatcctga      960
tgtcatccca ccggagattg tagtgggaga cgtcgccatc ccaccggaga ttatagaggg     1020
aaacgtcgcc gatggcaacg cgacggcgg acagcagcag cagcagagcg aaaaccttgg     1080
tggtaatggt gagagtgtgg tggtgtcgca aagcaatggt gtgcaggaag atggtgcaga     1140
tgggatgttt ctgaaggaga tcctcatgga tgaagacctg atgtttcccg acgctgagct     1200
ttttccgttg gtgggcgctg cacctggtcc agaggatttc atcgtcgacc aagatgttct     1260
cgacgacgtc ttcgccaacc cgagcagcag cgcaagcagc gactgaaccg aaagaagatc     1320
agagcgggac gcagcatcgg ttgattcatc tatcgtctct cgacctgcta ctctatgcta     1380
gccgctatat cggttaataa atttgggaat aagtttgtgt tcgtgcgtgt gacatggact     1440
```
gtatggttcg ccctgaattt atcgtattgc aatatatagc cgtgattgtg tgt 1493

<210> SEQ ID NO 124
<211> LENGTH: 434
<212> TYPE: PRT
<213> ORGANISM: Triticum aestivum

<400> SEQUENCE: 124

```
Ala Pro Ala Leu Ala Ser Lys Ser Ile His Asn Ile Gly Thr Glu Leu
 1               5                  10                  15

Ala Val Leu Pro Arg Val Met Gly Thr Glu Gln Gly Lys Glu Gly Thr
            20                  25                  30

Gly Ala Gly Glu Gly Arg Val Glu Val Arg Thr Gly Pro Arg Pro Ala
        35                  40                  45

Leu Pro Ala Pro Gln Gln Arg Ala Val Asp Gly Phe Trp Arg Glu Arg
    50                  55                  60

Gln Glu Glu Met Glu Ala Thr Ala Asp Phe Asn Asp Arg Ile Leu Pro
65                  70                  75                  80

Met Ala Arg Leu Lys Arg Leu Ile Arg Ala Glu Glu Asp Gly Met Met
                85                  90                  95

Ile Ala Ala Asp Thr Pro Ala Tyr Leu Ala Lys Leu Cys Glu Leu Phe
            100                 105                 110

Val Gln Glu Leu Ala Val Arg Ala Trp Ala Cys Ala Gln Ser His His
        115                 120                 125

Arg Arg Ile Ile Leu Glu Ser Asp Ile Ala Glu Ala Ile Ala Phe Thr
    130                 135                 140

Gln Ser Tyr Asp Phe Leu Ala Thr Val Leu Leu Glu His Gln Arg Glu
145                 150                 155                 160

Ala Arg Leu Ala Gly Arg Ala Ala Ile Pro Thr Thr Val Pro Val Thr
                165                 170                 175

Ala Ala Arg Ala Arg Leu Ile Thr Arg Lys Arg His Met Pro Asp Pro
            180                 185                 190

Asn Pro Pro Arg Pro Val His Gly Val Arg Arg Ile Arg Pro Arg Ala
        195                 200                 205

Leu Pro Ile Pro Pro Ser Asp Phe Arg Tyr Val Pro Val Pro Phe
    210                 215                 220

Pro Phe Thr Ser Ala Pro Ile Gly Ala Ala Ala Met Ala Glu Gly Leu
225                 230                 235                 240

Met Ile Leu Pro Pro Ile Asn His Ala Thr Thr Glu Arg Val Phe Phe
                245                 250                 255

Leu Asp Arg Asn Ser Gly Thr Asp Phe Ala Gly Glu Asn Ser Ala Ala
            260                 265                 270

Glu Thr Ile Ala Ser Pro Pro Pro Ala Gly Pro Ala Gly Ala Val
        275                 280                 285

Ala Leu Pro Thr Val His Pro Ala Ala Tyr Tyr Leu Cys Ala Tyr Pro
    290                 295                 300

Val Thr Asn Asp Val Glu Ala Phe Ala Val Gly Asn Thr Asp Pro Asp
305                 310                 315                 320

Val Ile Pro Pro Glu Ile Val Val Gly Asp Val Ala Ile Pro Pro Glu
                325                 330                 335

Ile Ile Glu Gly Asn Val Ala Asp Gly Asn Gly Asp Gly Gly Gln Gln
            340                 345                 350

Gln Gln Gln Ser Glu Asn Leu Gly Gly Asn Gly Glu Ser Val Val Val
        355                 360                 365
```

```
Ser Gln Ser Asn Gly Val Gln Glu Asp Gly Ala Asp Gly Met Phe Leu
    370                 375                 380

Lys Glu Ile Leu Met Asp Glu Asp Leu Met Phe Pro Asp Ala Glu Leu
385                 390                 395                 400

Phe Pro Leu Val Gly Ala Ala Pro Gly Pro Glu Asp Phe Ile Val Asp
                405                 410                 415

Gln Asp Val Leu Asp Asp Val Phe Ala Asn Pro Ser Ser Ser Ala Ser
            420                 425                 430

Ser Asp
```

```
<210> SEQ ID NO 125
<211> LENGTH: 660
<212> TYPE: DNA
<213> ORGANISM: Triticum aestivum
<220> FEATURE:
<221> NAME/KEY: unsure
<222> LOCATION: (483)
<223> OTHER INFORMATION: n = A, C, G, or T
<220> FEATURE:
<221> NAME/KEY: unsure
<222> LOCATION: (614)
<223> OTHER INFORMATION: n = A, C, G, or T
<220> FEATURE:
<221> NAME/KEY: unsure
<222> LOCATION: (630)
<223> OTHER INFORMATION: n = A, C, G, or T
<220> FEATURE:
<221> NAME/KEY: unsure
<222> LOCATION: (644)
<223> OTHER INFORMATION: n = A, C, G, or T
<220> FEATURE:
<221> NAME/KEY: unsure
<222> LOCATION: (647)
<223> OTHER INFORMATION: n = A, C, G, or T

<400> SEQUENCE: 125
ggcaccgagc tagcttggca atggccgcga gggcgtgtcc tgctgcttct ggttaccgtg     60
tgtgctgaag catctgacgc gcttgcgccg agcagcagga gctagccgtt catgctcttc    120
ttccctcccc ttggcatctg aagcagtaag agctcaagtt cacagagggc gttcgtccga    180
tctacaaagc ccagctgtac atcgccttag ctagcttgca gatcgcaagc tagatagtaa    240
tggagaacca ccagctgccc tacaccaccc agccgccggc aacgggcgcg gccggaggag    300
ccccggtgcc tggcgtgcct gggccaccgc cggtgccaca ccaccacctg ctccagcagc    360
agcaggccca gctgcaggcg ttctgggcgt accagcggca ggaggcggag cgcgcatcgg    420
cgtccgactt caagaaccac cagctgccgc tggctcggat caagaagatc atgaaggccg    480
acnaagacgt gcgcatgatc tccgcggagg cgcccgtgct cttcgccaag gcctgcgagc    540
tctttattct cgaagctcac cattccgctt cctggctgca cgcccgagga agaacaagcc    600
gccgcacaac ttgnagcgca aacgacgttn cccgcttgcc aatnggngcc gccacccgac    660
```

```
<210> SEQ ID NO 126
<211> LENGTH: 147
<212> TYPE: PRT
<213> ORGANISM: Triticum aestivum
<220> FEATURE:
<221> NAME/KEY: UNSURE
<222> LOCATION: (82)
<223> OTHER INFORMATION: Xaa = any amino acid
<220> FEATURE:
<221> NAME/KEY: UNSURE
<222> LOCATION: (125)
<223> OTHER INFORMATION: Xaa = any amino acid
<220> FEATURE:
<221> NAME/KEY: UNSURE
```

-continued

<222> LOCATION: (131)
<223> OTHER INFORMATION: Xaa = any amino acid
<220> FEATURE:
<221> NAME/KEY: UNSURE
<222> LOCATION: (135)
<223> OTHER INFORMATION: Xaa = any amino acid
<220> FEATURE:
<221> NAME/KEY: UNSURE
<222> LOCATION: (142)
<223> OTHER INFORMATION: Xaa = any amino acid
<220> FEATURE:
<221> NAME/KEY: UNSURE
<222> LOCATION: (145)
<223> OTHER INFORMATION: Xaa = any amino acid

<400> SEQUENCE: 126

Met Glu Asn His Gln Leu Pro Tyr Thr Thr Gln Pro Pro Ala Thr Gly
 1               5                  10                  15

Ala Ala Gly Gly Ala Pro Val Pro Gly Val Pro Gly Pro Pro Pro Val
            20                  25                  30

Pro His His His Leu Leu Gln Gln Gln Ala Gln Leu Gln Ala Phe
        35                  40                  45

Trp Ala Tyr Gln Arg Gln Glu Ala Glu Arg Ala Ser Ala Ser Asp Phe
 50                  55                  60

Lys Asn His Gln Leu Pro Leu Ala Arg Ile Lys Lys Ile Met Lys Ala
 65                  70                  75                  80

Asp Xaa Asp Val Arg Met Ile Ser Ala Glu Ala Pro Val Leu Phe Ala
                 85                  90                  95

Lys Ala Cys Glu Leu Phe Ile Leu Glu Ala His Ser Ala Ser Trp
            100                 105                 110

Leu His Ala Arg Gly Arg Thr Ser Arg Arg Thr Thr Xaa Ser Ala Asn
            115                 120                 125

Asp Val Xaa Arg Leu Pro Xaa Gly Ala Ala Thr Arg Arg Xaa Phe Glu
        130                 135                 140

Xaa Phe Leu
145

<210> SEQ ID NO 127
<211> LENGTH: 1874
<212> TYPE: DNA
<213> ORGANISM: Triticum aestivum

<400> SEQUENCE: 127
gcacgagccc acccacaacc ctagctcccc cgaacccatg gatcccacca aatccagcac     60
cccgccgccg cccccgtcc tgggcgcgcc cgtcggctac ccgccggggg cgtaccctcc    120
tccgccgggc gccccgcgg ccgcctaccc gccgcagctc tacgccgccgc cgggcgccgc    180 cgccgcccag caggccgcgg cgcagcagca gcagcagctg caggtgttct gggcggagca    240
gtaccgcgag atcgaggcca ccaccgactt caagaaccac aacctcccgc tggcccggat    300
caagaagatc atgaaggccg acgaggacgt ccgcatgatc gccgccgagg ccccgtcgt    360 cttcgcccgc gcctgcgaga tgttcatcct cgagctcacc caccgcggct gggcgcacgc    420
cgaggagaac aagcgccgca cgctccagaa gtccgacatt gcggccgcca tcgcccgcac    480
cgaggtcttc gacttcctcg tggacatcgt gccccgggac gacgccaagg acgccgaggc    540
ggccgccgcc gcggccatgg ccacggcggc ggccgggatc ccgcgcccgg ccgccggcgt    600
gcctgccacc gacccgagta tggcatacta ctatgtcccc cagcagtaat gtatcatcga    660
tctaaacttg cgcatttcta atcggagaat gtgttgttgt tctgtgactg tccttggtgc    720

-continued

```
tgttgttgct gcggcgtaat aagatttatg ggcctcccct gagcttatga attgagctgt    780
tcggttctag tattacagta ggattgttgt aatgggggag gccgtatgat tgcttccgta    840
gtgcatgact aactggccac ccagtgtaat ctgataacta ttatctggcg cctcccatgg    900
ttactatgta tttatgttct tcacacagtc ctctttgtct ctaccacttc gaggagttct    960
tcggaaggat gggctccaag atgcttctgg tcaccgctct cttggtgggc atagcctctc   1020
agagctatgc caccaggagc cttgacgaa accacttggc tgatcagaag tacggcggcg   1080
gcggctacgg aggtggcggt gggggctccg gaggtggtgg tggctacgga ggaggtggca   1140
gcggcggcgg gggtggctat ggaggaggcg gcggcggtgg ctacgaggga ggaggcggcg   1200
gttacacacc gatgccaaca ccgtcgaccc ccagccacag cggatcctgc gactactgga   1260
agggccaccc ggagaagatc atcgactgca tcggcagcct gggcagcatc ctgggctccc   1320
tcggagaggt gtgccactcc ttcttcggca gcaagatcca taccctgcag acgcgctgt   1380
gcaacacccg gaccgactgc tacgcgacc tgctgcgcga gggcgccgcc gcctacatca   1440
acgccatcgc cgccaagaag gagaagttcg cctacaccgc ctaccaggtc aaggagtgcg   1500
tcgccgtcgg gctcacctcc gagttcgccg ccgccgcgca ggccgccatg ttgaagaagg   1560
ccaactacgc ctgccactac taggaggcta ggctaccggc cggccgcccc agctggtggt   1620
cgtcggtggc taaataagtc catatatgca tgcacgtgtc gtgcatgttt tcatgcagtt   1680
tcccggatgc gcgcgcgcgt gtcctccgct atgcctttat gtgtttgctt gccgtttgat   1740
gatgcatgcc atgccgtctc atatatacgt agtgatgctt aatgctttgc ttgcttttct   1800
tatcttcgtt ggtgatgtaa gaataatttg attgaggagt tattagtgaa agacatagta   1860
tgcaaaaaaa aaaa                                                    1874
```

<210> SEQ ID NO 128
<211> LENGTH: 203
<212> TYPE: PRT
<213> ORGANISM: Triticum aestivum

<400> SEQUENCE: 128

```
Met Asp Pro Thr Lys Ser Ser Thr Pro Pro Pro Pro Val Leu Gly
 1               5                  10                  15

Ala Pro Val Gly Tyr Pro Pro Gly Ala Tyr Pro Pro Pro Gly Ala
                20                  25                  30

Pro Ala Ala Ala Tyr Pro Pro Gln Leu Tyr Ala Pro Gly Ala Ala
                35                  40                  45

Ala Ala Gln Ala Ala Ala Gln Gln Gln Gln Leu Gln Val Phe
     50                  55                  60

Trp Ala Glu Gln Tyr Arg Glu Ile Glu Ala Thr Thr Asp Phe Lys Asn
 65                  70                  75                  80

His Asn Leu Pro Leu Ala Arg Ile Lys Lys Ile Met Lys Ala Asp Glu
                85                  90                  95

Asp Val Arg Met Ile Ala Ala Glu Ala Pro Val Phe Ala Arg Ala
                100                 105                 110

Cys Glu Met Phe Ile Leu Glu Leu Thr His Arg Gly Trp Ala His Ala
            115                     120                 125

Glu Glu Asn Lys Arg Arg Thr Leu Gln Lys Ser Asp Ile Ala Ala Ala
        130                 135                 140

Ile Ala Arg Thr Glu Val Phe Asp Phe Leu Val Asp Ile Val Pro Arg
145                 150                 155                 160

Asp Asp Ala Lys Asp Ala Glu Ala Ala Ala Ala Ala Met Ala Thr
```

```
                   165                 170                 175
Ala Ala Ala Gly Ile Pro Arg Pro Ala Ala Gly Val Pro Ala Thr Asp
            180                 185                 190

Pro Ser Met Ala Tyr Tyr Val Pro Gln Gln
        195                 200
```

<210> SEQ ID NO 129
<211> LENGTH: 629
<212> TYPE: DNA
<213> ORGANISM: Amaranthus retroflexus
<220> FEATURE:
<221> NAME/KEY: unsure
<222> LOCATION: (566)..(567)..(568)
<223> OTHER INFORMATION: n = A, C, G, or T
<220> FEATURE:
<221> NAME/KEY: unsure
<222> LOCATION: (606)..(607)..(608)
<223> OTHER INFORMATION: n = A, C, G, or T
<220> FEATURE:
<221> NAME/KEY: unsure
<222> LOCATION: (626)..(627)..(628)..(629)
<223> OTHER INFORMATION: n = A, C, G, or T

<400> SEQUENCE: 129

```
gcacgaggat ggatcatcat catcgtggag ggttccatgg ttaccgcaaa caacatcccc      60
tttctaagtc ctcctcttct gaaatgagat tgacatcgga ggtgttaccg gctgagatga     120
atcacatacg cccaactagc aatggaaaag gagtatcaca tgacatgaac aaccatacca     180
ataaccatca tccctacaac aatagcaaca acaacaacaa tggtttcagc aacggaaata     240
gtaatcactc agcatcaacc gatcaagata caatgagtg cactgtacgc gagcaagatc      300
gctttatgcc catcgccaat gtcattagga tcatgcgcaa gattcttcct cctcatgcca     360
aaatctccga tgatgctaag gaaactatcc aggagtgtgt atcagagtac atcagcttca     420
taacaggtga agccaacgag aggtgccaaa gggaacaacg taagaccata actgctgaag     480
atgttctttg ggcgatgagc aagttgggat tcgatgacta catcgaaccc ctcacactgt     540
acttgcatcg atacagggaa ctcgannngg aacgtggttc catccgcact tgtgagccac     600
tcctcnnnct cagtcgtgct gccatnnnn                                       629
```

<210> SEQ ID NO 130
<211> LENGTH: 198
<212> TYPE: PRT
<213> ORGANISM: Amaranthus retroflexus
<220> FEATURE:
<221> NAME/KEY: UNSURE
<222> LOCATION: (186)..(187)
<223> OTHER INFORMATION: Xaa = any amino acid

<400> SEQUENCE: 130

```
Met Asp His His His Arg Gly Gly Phe His Gly Tyr Arg Lys Gln His
 1               5                  10                  15

Pro Leu Ser Lys Ser Ser Ser Glu Met Arg Leu Thr Ser Glu Val
            20                  25                  30

Leu Pro Ala Glu Met Asn His Ile Arg Pro Thr Ser Asn Gly Lys Gly
        35                  40                  45

Val Ser His Asp Met Asn Asn His Thr Asn Asn His His Pro Tyr Asn
    50                  55                  60

Asn Ser Asn Asn Asn Asn Asn Gly Phe Ser Asn Gly Asn Ser Asn His
65                  70                  75                  80

Ser Ala Ser Thr Asp Gln Asp Asn Asn Glu Cys Thr Val Arg Glu Gln
                85                  90                  95
```

```
Asp Arg Phe Met Pro Ile Ala Asn Val Ile Arg Ile Met Arg Lys Ile
            100                 105                 110

Leu Pro Pro His Ala Lys Ile Ser Asp Asp Ala Lys Glu Thr Ile Gln
        115                 120                 125

Glu Cys Val Ser Glu Tyr Ile Ser Phe Ile Thr Gly Glu Ala Asn Glu
    130                 135                 140

Arg Cys Gln Arg Glu Gln Arg Lys Thr Ile Thr Ala Glu Asp Val Leu
145                 150                 155                 160

Trp Ala Met Ser Lys Leu Gly Phe Asp Asp Tyr Ile Glu Pro Leu Thr
                165                 170                 175

Leu Tyr Leu His Arg Tyr Arg Glu Leu Xaa Xaa Glu Arg Gly Ser Ile
            180                 185                 190

Arg Thr Cys Glu Pro Leu
        195
```

<210> SEQ ID NO 131
<211> LENGTH: 625
<212> TYPE: DNA
<213> ORGANISM: Momordica charantia
<220> FEATURE:
<221> NAME/KEY: unsure
<222> LOCATION: (597)..(598)..(599)
<223> OTHER INFORMATION: n = A, C, G, or T
<220> FEATURE:
<221> NAME/KEY: unsure
<222> LOCATION: (620)..(621)..(622)..(623)
<223> OTHER INFORMATION: n = A, C, G, or T

<400> SEQUENCE: 131

```
gcacgaggct agctagctag gtctctctac tcagttagag agagaaagaa aaagaaaaca    60
aggggaagag agagagagag gcatggaata tggaggagga ggaggagatg ggttccatag   120
ctacagaagg cagcagccaa acacaaaacc aagctctgct ttgaacatgt tgctgaccac   180
aaacaagcca tccgccaaca accaccacca ccacttaaac ggccaaaacg ccaccaccac   240
caccaactcc tctgctgctg ccgccccgac cctggcccg gccgctgctg ccaacaacaa   300
cgagcagcag tgcgtcgtgc gggagcaaga ccaatacatg ccgatcgcca acgtgatacg   360
catcatgcgg cggatcttac cctcccatgc aaagatatcc gacgatgcca aggagaccat   420
ccaagagtgt gtgtcggagt acattagctt catcaccggc gaggccaacg agcggtgcca   480
gcgagagcag cgcaagacgg tgacggcgga ggacgtcctt tgggccatgg ggaagcttgg   540
cttcgacgac tacatcgagc cactcaccgt gttcctcaac cgctaccggg agtcagnnng   600
cgatcgaatc cgaacggagn nnntc                                         625
```

<210> SEQ ID NO 132
<211> LENGTH: 179
<212> TYPE: PRT
<213> ORGANISM: Momordica charantia
<220> FEATURE:
<221> NAME/KEY: UNSURE
<222> LOCATION: (172)..(173)
<223> OTHER INFORMATION: Xaa = any amino acid

<400> SEQUENCE: 132

```
Met Glu Tyr Gly Gly Gly Gly Asp Gly Phe His Ser Tyr Arg Arg
  1               5                  10                  15

Gln Gln Pro Asn Thr Lys Pro Ser Ser Ala Leu Asn Met Leu Leu Thr
            20                  25                  30

Thr Asn Lys Pro Ser Ala Asn Asn His His His His Leu Asn Gly Gln
```

```
                35              40              45
Asn Ala Thr Thr Thr Thr Asn Ser Ser Ala Ala Ala Pro Thr Leu
         50              55              60
Ala Pro Ala Ala Ala Ala Asn Asn Asn Glu Gln Gln Cys Val Val Arg
 65              70              75              80
Glu Gln Asp Gln Tyr Met Pro Ile Ala Asn Val Ile Arg Ile Met Arg
                 85              90              95
Arg Ile Leu Pro Ser His Ala Lys Ile Ser Asp Asp Ala Lys Glu Thr
             100             105             110
Ile Gln Glu Cys Val Ser Glu Tyr Ile Ser Phe Ile Thr Gly Glu Ala
         115             120             125
Asn Glu Arg Cys Gln Arg Glu Gln Arg Lys Thr Val Thr Ala Glu Asp
     130             135             140
Val Leu Trp Ala Met Gly Lys Leu Gly Phe Asp Asp Tyr Ile Glu Pro
145             150             155             160
Leu Thr Val Phe Leu Asn Arg Tyr Arg Glu Ser Xaa Xaa Asp Arg Ile
                 165             170             175
Arg Thr Glu

<210> SEQ ID NO 133
<211> LENGTH: 1173
<212> TYPE: DNA
<213> ORGANISM: Zea mays

<400> SEQUENCE: 133
ccacgcgtcc gccaccacac cacgagcgcg cgataaccct agctagcttc aggtagtagc      60
gagagccaat ggactccagc agcttcctcc ctgccgccgg cgcggagaat ggctcggcgg     120
cgggcggcgc caacaatggc ggcgctgctc agcagcatgc ggcgccggcg atccgcgagc     180
aggaccggct gatgccgatc gcgaacgtga tccgcatcat gcggcgcgtg ctgccggcgc     240
acgccaagat ctcggacgac gccaaggaga cgatccagga gtgcgtgtcg gagtacatca     300
gcttcatcac gggggaggcc aacgagcggt gccagcggga gcagcgcaag accatcaccg     360
ccgaggacgt gctgtgggcc atgagccgcc tcggcttcga cgactacgtc gagccgctcg     420
gcgcctacct ccaccgctac cgcgagttcg agggcgacgc gcgcggcgtc gggctcgtcc     480
cgggggccgc cccatcgcgc ggcggcgacc accaccccgca ctccatgtcg ccagcggcga     540
tgctcaagtc ccgcgggcca gtctccggag ccgccatgct accgcaccac caccaccacc     600
acgacatgca gatgcacgcc gccatgtacg ggggaacggc cgtgcccccg ccggccgggc     660
ctcctcacca cggcgggttc ctcatgccac acccacaggg tagtagccac tacctgcctt     720
acgcgtacga gcccacgtac ggcggtgagc acgccatggc tgcatactat ggaggcgccg     780
cgtacgcgcc cggcaacggc gggagcggcg acggcagtgg cagtggcggc ggtggcggga     840
gcgcgtcgca cacaccgcag ggcagcggcg gcttggagca cccgcacccg ttcgcgtaca     900
agtagctagt tcgtacgtcg ttcgacttga gcaagccatc gatctgctga tctgaacgta     960
cgctgtattg tacacgcatg cacgtacgta tcggcggcta gctctcctgt ttaagttgta    1020
ctgtgattct gtcccggccg gctagcaact tagtatcttc cttcagtctc tagtttctta    1080
gcagtcgtag aagtgttcaa tgcttgccag tgtgttgttt tagggccggg gtaaaccatc    1140
cgatgagatt atttcaaaaa aaaaaaaaa aaa                                  1173

<210> SEQ ID NO 134
<211> LENGTH: 278
```

<212> TYPE: PRT
<213> ORGANISM: Zea mays

<400> SEQUENCE: 134

```
Met Asp Ser Ser Phe Leu Pro Ala Ala Gly Ala Glu Asn Gly Ser
 1               5                  10                  15

Ala Ala Gly Gly Ala Asn Asn Gly Gly Ala Ala Gln Gln His Ala Ala
             20                  25                  30

Pro Ala Ile Arg Glu Gln Asp Arg Leu Met Pro Ile Ala Asn Val Ile
         35                  40                  45

Arg Ile Met Arg Arg Val Leu Pro Ala His Ala Lys Ile Ser Asp Asp
     50                  55                  60

Ala Lys Glu Thr Ile Gln Glu Cys Val Ser Glu Tyr Ile Ser Phe Ile
 65                  70                  75                  80

Thr Gly Glu Ala Asn Glu Arg Cys Gln Arg Glu Gln Arg Lys Thr Ile
                 85                  90                  95

Thr Ala Glu Asp Val Leu Trp Ala Met Ser Arg Leu Gly Phe Asp Asp
            100                 105                 110

Tyr Val Glu Pro Leu Gly Ala Tyr Leu His Arg Tyr Arg Glu Phe Glu
        115                 120                 125

Gly Asp Ala Arg Gly Val Gly Leu Val Pro Gly Ala Ala Pro Ser Arg
    130                 135                 140

Gly Gly Asp His His Pro His Ser Met Ser Pro Ala Ala Met Leu Lys
145                 150                 155                 160

Ser Arg Gly Pro Val Ser Gly Ala Ala Met Leu Pro His His His
                165                 170                 175

His His Asp Met Gln Met His Ala Ala Met Tyr Gly Gly Thr Ala Val
            180                 185                 190

Pro Pro Pro Ala Gly Pro Pro His His Gly Gly Phe Leu Met Pro His
        195                 200                 205

Pro Gln Gly Ser Ser His Tyr Leu Pro Tyr Ala Tyr Glu Pro Thr Tyr
    210                 215                 220

Gly Gly Glu His Ala Met Ala Ala Tyr Tyr Gly Gly Ala Ala Tyr Ala
225                 230                 235                 240

Pro Gly Asn Gly Gly Ser Gly Asp Gly Ser Gly Ser Gly Gly Gly Gly
                245                 250                 255

Gly Ser Ala Ser His Thr Pro Gln Gly Ser Gly Gly Leu Glu His Pro
            260                 265                 270

His Pro Phe Ala Tyr Lys
        275
```

<210> SEQ ID NO 135
<211> LENGTH: 1269
<212> TYPE: DNA
<213> ORGANISM: Zea mays

<400> SEQUENCE: 135

```
ccacgcgtcc gcatgaataa tccccaaaac cctaaagcca gtgctccttg caccttgcca      60
ccggagcttc ccaaagaagc agtggcgacc gacgaagcac cgccgccaat gggcaacaac     120
aacaacacgg aatcggcgac ggcgacgatg gtccgggagc aggaccggct gatgcccgtg     180
gccaacgtgt cccgcatcat gcgccaagtg ctgcctccgt acgccaagat ctccgacgac     240
gccaaggagg tgatccagga gtgcgtgtcg gagttcatca gcttcgtcac tggcgaggcg     300
aacgagcggt gccacaccga gcgccgcaag accgtcacct ccgaggacat cgtgtgggcc     360
```

```
atgagccgcc tcggcttcga cgactacgtc gcgcccctcg gcgccttcct ccagcgcatg    420
cgcgacgaca gcgaccacgg cggtgaagag cgcggcggcc ctgcagggcg tggtggctcg    480
cgccgcggct cgtcgtcctt gccgctccac tgcccgcagc agatgcacca cctgcaccca    540
gccgtctgcc ggcgtccgca ccagagcgtg tcgcctgctg caggatacgc cgtccggccc    600
gttccccgcc cgatgccagc cagtgggtac cgcatgcagg gcggagacca ccgcagcgtg    660
ggcggcgtgg ctccctgcag ctacggaggg gcgctcgtcc aggccggtgg aacccaacac    720
gttgttggat ccacgacga cgaggcaagc tcttcgagtg aaaatccgcc gccggagggg    780
cgtgccgctg gctcgaacta gcctagcttc tcagttcccc gtgtacaata gagggggcgg    840
tcgcggcgcc gcgccgcgcc cttgggttgg gccgggcgct atgctgcagt ttggtttgta    900
aactaacgag cctagggtag ctggtgcacg cgcgccacct cgccggacgt cgccgtcgtc    960
gtcggcatgg acttaaccgg cgggccctgt tgttatttct caagtttgta gccaacgcac   1020
tgttcggtgc gttccataat ttaatttacc atgttgctct cgaaatgaaa aaaaaaaaa   1080
aaaaaagggc ggccgcccctt ttttttttttt tttttttttt tcctcttaag gcaaggcaac   1140
tcctgtttgt aggggaatcg ttatggttct gcttctgatt gctcctagtt cttccatcat   1200
tttcgtgttc aaagagaagg ctcccagaaa ataaaataac gattgctatg aaaaaaaaaa   1260
aaaaaaag                                                            1269
```

<210> SEQ ID NO 136
<211> LENGTH: 262
<212> TYPE: PRT
<213> ORGANISM: Zea mays

<400> SEQUENCE: 136

```
Met Asn Asn Pro Gln Asn Pro Lys Ala Ser Ala Pro Cys Thr Leu Pro
  1               5                  10                  15

Pro Glu Leu Pro Lys Glu Ala Val Ala Thr Asp Glu Ala Pro Pro Pro
             20                  25                  30

Met Gly Asn Asn Asn Thr Glu Ser Ala Thr Ala Thr Met Val Arg
         35                  40                  45

Glu Gln Asp Arg Leu Met Pro Val Ala Asn Val Ser Arg Ile Met Arg
 50                  55                  60

Gln Val Leu Pro Pro Tyr Ala Lys Ile Ser Asp Ala Lys Glu Val
 65                  70                  75                  80

Ile Gln Glu Cys Val Ser Glu Phe Ile Ser Phe Val Thr Gly Glu Ala
                 85                  90                  95

Asn Glu Arg Cys His Thr Glu Arg Arg Lys Thr Val Thr Ser Glu Asp
            100                 105                 110

Ile Val Trp Ala Met Ser Arg Leu Gly Phe Asp Asp Tyr Val Ala Pro
        115                 120                 125

Leu Gly Ala Phe Leu Gln Arg Met Arg Asp Asp Ser Asp His Gly Gly
    130                 135                 140

Glu Glu Arg Gly Gly Pro Ala Gly Arg Gly Ser Arg Arg Gly Ser
145                 150                 155                 160

Ser Ser Leu Pro Leu His Cys Pro Gln Gln Met His Leu His Pro
                165                 170                 175

Ala Val Cys Arg Arg Pro His Gln Ser Val Ser Pro Ala Ala Gly Tyr
            180                 185                 190

Ala Val Arg Pro Val Pro Arg Pro Met Pro Ala Ser Gly Tyr Arg Met
        195                 200                 205
```

```
Gln Gly Gly Asp His Arg Ser Val Gly Gly Val Ala Pro Cys Ser Tyr
    210                 215                 220
Gly Gly Ala Leu Val Gln Ala Gly Gly Thr Gln His Val Val Gly Phe
225                 230                 235                 240
His Asp Asp Glu Ala Ser Ser Ser Ser Glu Asn Pro Pro Pro Glu Gly
                245                 250                 255
Arg Ala Ala Gly Ser Asn
            260
```

<210> SEQ ID NO 137
<211> LENGTH: 481
<212> TYPE: DNA
<213> ORGANISM: Argemone mexicana
<220> FEATURE:
<221> NAME/KEY: unsure
<222> LOCATION: (410)
<223> OTHER INFORMATION: n = A, C, G, or T
<220> FEATURE:
<221> NAME/KEY: unsure
<222> LOCATION: (471)
<223> OTHER INFORMATION: n = A, C, G, or T

<400> SEQUENCE: 137

```
cgagagaaag agttggtgaa gaagaagaag aagttgaaaa gagatggaac gtggtggtgg    60
tggtggtggt agtggtggtg gtttccatgg atatcagaaa ctcccaaaat caaactccgc   120
tggaatgatg ctctcggagc tatcgaataa caacaacaat attgacgtaa actctacatg   180
tactgtacga gagcaagatc gatacatgcc aattgctaat gtgatcagga tcatgcgtaa   240
ggtacttcct actcatgcca agatctctga cgatgccaaa gaaactatcc aagaatgtgt   300
ctcagaatac atcagtttca tcacaagtga agccaatgat cgttgccaac gtgaacaaag   360
aaagacaatc acagctgaag atgttttatg ggcgatgagc aaactagggn ttgatgagta   420
cattgaacct ctaactcttt accttcaacg ttatcgtgag tttgaaggtg nacgttggtc   480
a                                                                  481
```

<210> SEQ ID NO 138
<211> LENGTH: 146
<212> TYPE: PRT
<213> ORGANISM: Argemone mexicana
<220> FEATURE:
<221> NAME/KEY: UNSURE
<222> LOCATION: (123)
<223> OTHER INFORMATION: Xaa = any amino acid
<220> FEATURE:
<221> NAME/KEY: UNSURE
<222> LOCATION: (143)
<223> OTHER INFORMATION: Xaa = any amino acid

<400> SEQUENCE: 138

```
Met Glu Arg Gly Gly Gly Gly Gly Ser Gly Gly Gly Phe His Gly
  1               5                  10                  15
Tyr Gln Lys Leu Pro Lys Ser Asn Ser Ala Gly Met Met Leu Ser Glu
                 20                  25                  30
Leu Ser Asn Asn Asn Asn Asn Ile Asp Val Asn Ser Thr Cys Thr Val
             35                  40                  45
Arg Glu Gln Asp Arg Tyr Met Pro Ile Ala Asn Val Ile Arg Ile Met
         50                  55                  60
Arg Lys Val Leu Pro Thr His Ala Lys Ile Ser Asp Asp Ala Lys Glu
 65                  70                  75                  80
Thr Ile Gln Glu Cys Val Ser Glu Tyr Ile Ser Phe Ile Thr Ser Glu
                 85                  90                  95
```

```
Ala Asn Asp Arg Cys Gln Arg Glu Gln Arg Lys Thr Ile Thr Ala Glu
            100                 105                 110

Asp Val Leu Trp Ala Met Ser Lys Leu Gly Xaa Asp Glu Tyr Ile Glu
        115                 120                 125

Pro Leu Thr Leu Tyr Leu Gln Arg Tyr Arg Glu Phe Glu Gly Xaa Arg
    130                 135                 140

Trp Ser
145

<210> SEQ ID NO 139
<211> LENGTH: 1154
<212> TYPE: DNA
<213> ORGANISM: Glycine max
<220> FEATURE:
<221> NAME/KEY: unsure
<222> LOCATION: (3)
<223> OTHER INFORMATION: n = A, C, G, or T

<400> SEQUENCE: 139
atnacacaca cctaccttat aactatggaa actggaggct ttcatggcta ccgcaagctc      60
cccaacacaa cctctgggtt gaagctgtca gtgtcagaca tgaacatgaa catgaggcag    120
cagcaggtag catcatcaga tcagaactgc agcaaccaca gtgcagcagg agaggagaac    180
gaatgcacgg tgagggagca agacaggttc atgccaatcg ctaacgtgat acggatcatg    240
cgcaagattc tccctccaca cgcaaaaatc tccgatgatg caaggagac aatccaagag     300 tgcgtgtcgg agtacatcag cttcatcacc ggggaggcca acgagcgttg ccagagggag    360
cagcgcaaga ccataaccgc agaggacgtg cttttgggcaa tgagtaagct tggattcgac    420
gactacatcg aaccgttaac catgtaccttt caccgctacc gtgagctgga gggtgaccgc    480
acctctatga ggggtgaacc gctcgggaag aggactgtgg aatatgccac gcttgctact    540
gcttttgtgc cgccacccctt tcatcaccac aatggctact tggtgctgc catgcccatg    600 gggacttacg ttagggaaac gccaccaaat gctgcgtcat ctcatcacca tcatggaatc    660
tccaatgctc atgaaccaaa tgctcgctcc atataaaatt aatgaagagt actgttcagt    720
aggagaacaa gacttcttgg acttgattag cttaactctc agtgattggt gttagagtac    780
tgttgttgag gatggttaat tttataatta agggctggga attggggagt tagtatatat    840
tcctaatcct aattatgtgc atctttaatt tatggaataa cttttgtttttt tgttttaact    900 tctgataatt tggattttct gatgttaatt gtggttttgt ctatccctta ttaacagtgc    960
caagcttaag gttttagcca tgctccaaaa tggaatactt gtactgttat gttgttctgg    1020
tagtgatggt gatgaaacct gcaagttatg tttatgtata aagccactat tgatcaaaat    1080
tagagaaatt atcatttaat aagtatcctc ccatgttaat tttaaaaaaa aaaaaaaaaa    1140
actcgagacc ggca                                                      1154

<210> SEQ ID NO 140
<211> LENGTH: 223
<212> TYPE: PRT
<213> ORGANISM: Glycine max

<400> SEQUENCE: 140

Met Glu Thr Gly Gly Phe His Gly Tyr Arg Lys Leu Pro Asn Thr Thr
  1               5                  10                  15

Ser Gly Leu Lys Leu Ser Val Ser Asp Met Asn Met Asn Met Arg Gln
            20                  25                  30
```

```
Gln Gln Val Ala Ser Ser Asp Gln Asn Cys Ser Asn His Ser Ala Ala
         35                  40                  45
Gly Glu Glu Asn Glu Cys Thr Val Arg Glu Gln Asp Arg Phe Met Pro
 50                  55                  60
Ile Ala Asn Val Ile Arg Ile Met Arg Lys Ile Leu Pro Pro His Ala
 65                  70                  75                  80
Lys Ile Ser Asp Asp Ala Lys Glu Thr Ile Gln Glu Cys Val Ser Glu
                 85                  90                  95
Tyr Ile Ser Phe Ile Thr Gly Glu Ala Asn Glu Arg Cys Gln Arg Glu
            100                 105                 110
Gln Arg Lys Thr Ile Thr Ala Glu Asp Val Leu Trp Ala Met Ser Lys
        115                 120                 125
Leu Gly Phe Asp Asp Tyr Ile Glu Pro Leu Thr Met Tyr Leu His Arg
130                 135                 140
Tyr Arg Glu Leu Glu Gly Asp Arg Thr Ser Met Arg Gly Glu Pro Leu
145                 150                 155                 160
Gly Lys Arg Thr Val Glu Tyr Ala Thr Leu Ala Thr Ala Phe Val Pro
                165                 170                 175
Pro Pro Phe His His Asn Gly Tyr Phe Gly Ala Ala Met Pro Met
            180                 185                 190
Gly Thr Tyr Val Arg Glu Thr Pro Pro Asn Ala Ala Ser Ser His His
        195                 200                 205
His His Gly Ile Ser Asn Ala His Glu Pro Asn Ala Arg Ser Ile
    210                 215                 220

<210> SEQ ID NO 141
<211> LENGTH: 942
<212> TYPE: DNA
<213> ORGANISM: Glycine max

<400> SEQUENCE: 141
gcacgagctc tcttataatc acacacacac ctaccttaat agctatggaa actggaggct    60
ttcacggcta ccgcaagctc cccaacacca ccgctgggtt gaagctgtca gtgtcagaca   120
tgaacatgag gcagcaggta gcatcatcag atcacagtgc agccacagga gaggagaacg   180
aatgcacggt gagggagcaa gacaggttca tgccaatcgc caacgtgatt aggatcatgc   240
gcaagattct ccctccacac gcaaaaatct cggacgatgc aaaagaaaca atccaagagt   300
gcgtgtctga gtacatcagc ttcatcacag gtgaggcgaa cgagcgttgc cagagggagc   360
agcggaagac cataaccgca gaggacgtgc tttgggccat gagcaagctt ggattcgacg   420
actacatcga accgttgacc atgtaccttc accgctaccg tgaacttgag ggtgaccgca   480
cctctatgag gggtgaacca ctcgggaaga ggactgtgga atacgccacg cttggtgttg   540
ctactgcttt tgtccctcca ccctatcatc accacaatgg gtactttggt gctgccatgc   600
ccatggggac ttacgttagg gaagcgccac caaatacagc ctcctcccat caccaccacc   660
accaccacca ccaccatgct cgtggaatct ccaatgctca tgaaccaaat gctcgctcca   720
tataaaatta taattatatg actaggattc agaacaagac ttgatgatga ttagcttaac   780
tctcagtaat tggtgctaga gtactactgt tgttgaggat actttatttt ataattaagg   840
gctgggaagg gagttagtat attcctaatc ctaactatgt gcatctttaa tttatgaaat   900
cactttgttt taacctttga tgaaaaaaaa aaaaaaaaaa aa                      942

<210> SEQ ID NO 142
<211> LENGTH: 240
```

<212> TYPE: PRT
<213> ORGANISM: Glycine max

<400> SEQUENCE: 142

```
Thr Ser Ser Leu Ile Ile Thr His Thr Pro Thr Leu Ile Ala Met Glu
1               5                   10                  15

Thr Gly Gly Phe His Gly Tyr Arg Lys Leu Pro Asn Thr Thr Ala Gly
            20                  25                  30

Leu Lys Leu Ser Val Ser Asp Met Asn Met Arg Gln Val Ala Ser
        35                  40                  45

Ser Asp His Ser Ala Ala Thr Gly Glu Glu Asn Glu Cys Thr Val Arg
    50                  55                  60

Glu Gln Asp Arg Phe Met Pro Ile Ala Asn Val Ile Arg Ile Met Arg
65                  70                  75                  80

Lys Ile Leu Pro Pro His Ala Lys Ile Ser Asp Ala Lys Glu Thr
                85                  90                  95

Ile Gln Glu Cys Val Ser Glu Tyr Ile Ser Phe Ile Thr Gly Glu Ala
                100                 105                 110

Asn Glu Arg Cys Gln Arg Glu Gln Arg Lys Thr Ile Thr Ala Glu Asp
            115                 120                 125

Val Leu Trp Ala Met Ser Lys Leu Gly Phe Asp Asp Tyr Ile Glu Pro
130                 135                 140

Leu Thr Met Tyr Leu His Arg Tyr Arg Glu Leu Glu Gly Asp Arg Thr
145                 150                 155                 160

Ser Met Arg Gly Glu Pro Leu Gly Lys Arg Thr Val Glu Tyr Ala Thr
                165                 170                 175

Leu Gly Val Ala Thr Ala Phe Val Pro Pro Tyr His His His Asn
            180                 185                 190

Gly Tyr Phe Gly Ala Ala Met Pro Met Gly Thr Tyr Val Arg Glu Ala
        195                 200                 205

Pro Pro Asn Thr Ala Ser Ser His His His His His His His
    210                 215                 220

His Ala Arg Gly Ile Ser Asn Ala His Glu Pro Asn Ala Arg Ser Ile
225                 230                 235                 240
```

<210> SEQ ID NO 143
<211> LENGTH: 796
<212> TYPE: DNA
<213> ORGANISM: Glycine max

<400> SEQUENCE: 143

```
gcacgagcaa tggcgggagt gagggaacag gaccagtaca tgccgatagc gaacgtgata    60
aggatcatgc gtcggattct gccagcgcac gcgaagatct cagacgacgc gaaggagacg   120
atccaggagt gcgtgtctga gtacatcagt tcatcacgg cggaggcgaa cgagcggtgc    180
cagcgggagc agcggaagac ggtgaccgca gaggatgtgt tgtgggcgat ggagaagctt   240
ggctttgaca actacgctca ccctctctct ctttaccttc accgctaccg cgagagtgaa   300
ggagaacctg cttctgtcag acgcgcttct tctgcaatgg ggatcaataa taatatggtg   360
cacccacctt atattaattc tcatggcttt ggaatgtttg attttgaccc atcatcgcaa   420
gggttttaca gggacgatca taacgctgct tctggatctg gtggttttgt tgcgcctttt   480
gatccttatg ctaacatcaa acgtgatgcc ctgtgatcat gtaagaacaa caactagtgc   540
atgctgcttt ttcacttggt tagttatatt caagcacaag cacatgcagg tgcagctgca   600
actatttagc ttcatctaca aatctttttt cctctcttct tctcatgctt taattattta   660
```

```
gagacaatac ttgttattca ttgttatgct caattgctag cttctattca tcgtcgactg      720
tctgtattgt tgatgttcat tacagtaaca gataagatgg taactgcttt actacttcaa      780
aaaaaaaaaa aaaaa                                                       796
```

<210> SEQ ID NO 144
<211> LENGTH: 171
<212> TYPE: PRT
<213> ORGANISM: Glycine max

<400> SEQUENCE: 144

```
Ala Arg Ala Met Ala Gly Val Arg Glu Gln Asp Gln Tyr Met Pro Ile
 1               5                  10                  15

Ala Asn Val Ile Arg Ile Met Arg Arg Ile Leu Pro Ala His Ala Lys
             20                  25                  30

Ile Ser Asp Asp Ala Lys Glu Thr Ile Gln Glu Cys Val Ser Glu Tyr
         35                  40                  45

Ile Ser Phe Ile Thr Ala Glu Ala Asn Glu Arg Cys Gln Arg Glu Gln
     50                  55                  60

Arg Lys Thr Val Thr Ala Glu Asp Val Leu Trp Ala Met Glu Lys Leu
 65                  70                  75                  80

Gly Phe Asp Asn Tyr Ala His Pro Leu Ser Leu Tyr Leu His Arg Tyr
                 85                  90                  95

Arg Glu Ser Glu Gly Glu Pro Ala Ser Val Arg Arg Ala Ser Ser Ala
            100                 105                 110

Met Gly Ile Asn Asn Asn Met Val His Pro Pro Tyr Ile Asn Ser His
        115                 120                 125

Gly Phe Gly Met Phe Asp Phe Asp Pro Ser Ser Gln Gly Phe Tyr Arg
    130                 135                 140

Asp Asp His Asn Ala Ala Ser Gly Ser Gly Gly Phe Val Ala Pro Phe
145                 150                 155                 160

Asp Pro Tyr Ala Asn Ile Lys Arg Asp Ala Leu
                165                 170
```

<210> SEQ ID NO 145
<211> LENGTH: 905
<212> TYPE: DNA
<213> ORGANISM: Vernonia mespilifolia

<400> SEQUENCE: 145

```
gcacgagcca atttctagag agagaacgag agagaattct ctaaagagga aaaatagatg       60
gaacgtggag gaggtttcca tggctaccac aggctcccca tccaccctac atctggaatc      120
caacaatcgg atatgaagct aaagctacca gaaatgacca caataactc gtccactgat       180 gacaatgagt gcaccgttcg agaacaggac cgcttcatgc cgatagcaaa cgtgatccgc      240
atcatgcgga gatccttcc tccacatgcc aagatctctg atgatgccaa agagacgatc       300
caagaatgtg tttcagagta cattagcttt gtcacaggcg aggcaaatga ccgctgccag      360
cgtgagcaaa ggaagaccat cacagctgaa gatgtgctct gggctatgag caaactggga      420
tttgatgatt atatcgagcc cttgactgtg tatctccatc gctacaggga gtttgatggt      480
ggcgaacgtg gatccataag gggtgagccc cttgtgaaga ggagtacttc tgatcctggt      540
cactttggga tggcttcttt tgtgcctgct tttcatatgg gtcatcataa cggcttcttt      600
ggtcctgcaa gcattggtgg tttcctgaaa gacccatcga gtgctggccc ttcgggacct      660
gcagtcgctg ggtttgagcc gtatgctcag tgtaaagagt aactgcaaaa agtagggggtt     720
```

```
gggatgagat gatgatgatg gtggtggtgg tggtggtttg ttttgttttg ttctttcttt      780
ttttttcttt ctttcttttc ttggtcattg aggaacaaac ttacattggt tcactttggc      840
taggcatgta acggttaac atgcttatca agtagtagtt ttcgatcaaa aaaaaaaaa        900 aaaaa                                                                  905
```

```
<210> SEQ ID NO 146
<211> LENGTH: 214
<212> TYPE: PRT
<213> ORGANISM: Vernonia mespilifolia

<400> SEQUENCE: 146
```

| Met | Glu | Arg | Gly | Gly | Gly | Phe | His | Gly | Tyr | His | Arg | Leu | Pro | Ile | His |
|---|---|---|---|---|---|---|---|---|---|---|---|---|---|---|---|
| 1 | | | | 5 | | | | | 10 | | | | | 15 | |

Pro Thr Ser Gly Ile Gln Gln Ser Asp Met Lys Leu Lys Leu Pro Glu
            20                  25                  30

Met Thr Asn Asn Asn Ser Ser Thr Asp Asp Asn Glu Cys Thr Val Arg
        35                  40                  45

Glu Gln Asp Arg Phe Met Pro Ile Ala Asn Val Ile Arg Ile Met Arg
    50                  55                  60

Lys Ile Leu Pro Pro His Ala Lys Ile Ser Asp Asp Ala Lys Glu Thr
65                  70                  75                  80

Ile Gln Glu Cys Val Ser Glu Tyr Ile Ser Phe Val Thr Gly Glu Ala
                85                  90                  95

Asn Asp Arg Cys Gln Arg Glu Gln Arg Lys Thr Ile Thr Ala Glu Asp
            100                 105                 110

Val Leu Trp Ala Met Ser Lys Leu Gly Phe Asp Asp Tyr Ile Glu Pro
        115                 120                 125

Leu Thr Val Tyr Leu His Arg Tyr Arg Glu Phe Asp Gly Gly Glu Arg
    130                 135                 140

Gly Ser Ile Arg Gly Glu Pro Leu Val Lys Arg Ser Thr Ser Asp Pro
145                 150                 155                 160

Gly His Phe Gly Met Ala Ser Phe Val Pro Ala Phe His Met Gly His
                165                 170                 175

His Asn Gly Phe Phe Gly Pro Ala Ser Ile Gly Gly Phe Leu Lys Asp
            180                 185                 190

Pro Ser Ser Ala Gly Pro Ser Gly Pro Ala Val Ala Gly Phe Glu Pro
        195                 200                 205

Tyr Ala Gln Cys Lys Glu
    210

```
<210> SEQ ID NO 147
<211> LENGTH: 1098
<212> TYPE: DNA
<213> ORGANISM: Triticum aestivum

<400> SEQUENCE: 147
```

```
gcacgagcaa gtgcgagtgc gactacctgc attgcaccctt ggctagccct agacatggag     60
aacgacggcg tccccaacgg accagcggcg ccggcaccta cccagggac gccggtggtg       120 cgggagcagg accggctgat gccgatcgcg aacgtgatcc gcatcatgcg ccgtgcgctc      180
cctgcccacg ccaagatctc cgacgacgcc aaggaggcga ttcaggaatg cgtgtccgag      240
ttcatcagct cgtcaccgg cgaggccaac gaacggtgcc gcatgcagca ccgcaagacc       300
gtcaacgccg aagacatcgt gtgggcccta accgcctcg gcttcgacga ctacgtcgtg       360
```

-continued

```
cccctcagcg tcttcctgca ccgcatgcgc gaccccgagg cggggacagg tggtgccgct    420
gcaggcgaca gccgcgccgt gacgagtgcg cctccccgcg cggccccgcc cgtgatccac    480
gccgtgccgc tgcaggctca cgcccgatg tacgcgcccc cggctccgtt gcaggttgag    540
aatcagatgc agcggcctgt gtacgctccc ccggctccgg tgcaggttca gatgcagcgg    600
ggcatctatg gccccgggc tccagtgcac gggtacgccg tcggaatggc gcccgtgcgg    660
gccaacgtcg gcgggcagta ccaggtgttc ggcggagagg gtgtcatggc ccagcaatac    720
tacgggtacg gtacgagga aggagcgtac ggcgcaggta gcagcaacgg aggagccgcc    780
attggcgacg aggagagctc gtccaacggc gtgccgcac cggggagggg catgggggag    840
ccagagccag agccagcagc agaagaatcg catgacaagc ccgtccaatc tggctagtcg    900
cgtgcgcggc gcgcgttagc ttctgcgtcc tgtgtactgt aataatttgc cgtgtcgatc    960
cggccatggt ttgtgtgtgc gtagtgctta tctaatgtgg gcttgtcctc tagtaattca   1020
tgtattgctt atctaatgtg gacttgtcct ctagtaattc atgtactctt tgctgttgaa   1080
aaaaaaaaaa aaaaaaa                                                  1098
```

<210> SEQ ID NO 148
<211> LENGTH: 280
<212> TYPE: PRT
<213> ORGANISM: Triticum aestivum

<400> SEQUENCE: 148

```
Met Glu Asn Asp Gly Val Pro Asn Gly Pro Ala Ala Pro Ala Pro Thr
  1               5                  10                  15

Gln Gly Thr Pro Val Val Arg Glu Gln Asp Arg Leu Met Pro Ile Ala
             20                  25                  30

Asn Val Ile Arg Ile Met Arg Arg Ala Leu Pro Ala His Ala Lys Ile
         35                  40                  45

Ser Asp Asp Ala Lys Glu Ala Ile Gln Glu Cys Val Ser Glu Phe Ile
     50                  55                  60

Ser Phe Val Thr Gly Glu Ala Asn Glu Arg Cys Arg Met Gln His Arg
 65                  70                  75                  80

Lys Thr Val Asn Ala Glu Asp Ile Val Trp Ala Leu Asn Arg Leu Gly
                 85                  90                  95

Phe Asp Asp Tyr Val Val Pro Leu Ser Val Phe Leu His Arg Met Arg
            100                 105                 110

Asp Pro Glu Ala Gly Thr Gly Gly Ala Ala Gly Asp Ser Arg Ala
        115                 120                 125

Val Thr Ser Ala Pro Pro Arg Ala Ala Pro Val Ile His Ala Val
    130                 135                 140

Pro Leu Gln Ala Gln Arg Pro Met Tyr Ala Pro Ala Pro Leu Gln
145                 150                 155                 160

Val Glu Asn Gln Met Gln Arg Pro Val Tyr Ala Pro Ala Pro Val
                165                 170                 175

Gln Val Gln Met Gln Arg Gly Ile Tyr Gly Pro Arg Ala Pro Val His
            180                 185                 190

Gly Tyr Ala Val Gly Met Ala Pro Val Arg Ala Asn Val Gly Gly Gln
        195                 200                 205

Tyr Gln Val Phe Gly Gly Glu Gly Val Met Ala Gln Gln Tyr Tyr Gly
    210                 215                 220

Tyr Gly Tyr Glu Glu Gly Ala Tyr Gly Ala Gly Ser Ser Asn Gly Gly
225                 230                 235                 240
```

```
Ala Ala Ile Gly Asp Glu Glu Ser Ser Ser Asn Gly Val Pro Ala Pro
            245                 250                 255

Gly Glu Gly Met Gly Glu Pro Glu Pro Glu Pro Ala Ala Glu Glu Ser
            260                 265                 270

His Asp Lys Pro Val Gln Ser Gly
            275                 280

<210> SEQ ID NO 149
<211> LENGTH: 932
<212> TYPE: DNA
<213> ORGANISM: Canna edulis

<400> SEQUENCE: 149
gcaccagctc aaatctccga attagggttt ctgtgccttg tctccaatgg cggaatcggg      60
ggccccgggc acgcccgaga gcggacattc cggcggcgga tctggcgcgc gggagcagga     120
ccgctgcctc cccattgcca acattgggcg gattatgagg aaggccgtac ccgagaacgg     180
caagatcgcc aaggacgcca aggaatccgt ccaggagtgc gtctccgagt tcatcagctt     240
cgtcaccagc gaggcgagcg ataagtgccg ccgcgagaaa aggaagacga tcaacgcga     300 tgatcttctg tgggctatgc ggatgcttgg cttcgaagag tacgtcgagc ctcttaagct     360
ctacttgcag ctctcacagag agatggaggg aaacgtcatg gtttcacgtc ccgctgatca     420
atgatcaacc aggaaaaaga gatggagcaa ttaacaggca gcccacagat tcgttcaatg     480
gcatgtagga tggttctcaa gaaagcaaac ttttgcttac tatttcaagg tgtaggccct     540
ttgttagtgt agtaataag ttatagttgc tgcaggttat ttttgttctt atttgtactc      600
ttgtccaata ccttttcctc taagtgaaca acattcagag aatggctctt ctctaggact     660
tggacgaagg cacgaagcac tgatctgaag ttatgatcca ttcaaccatc taaaattaat     720
tttaaatttt aaattgagac aatgttttga cccttgtttc gacatttccc gacagcccta     780
ctgtaatgta aagatgactt ggatagcaaa attgttaaaa aggtacaatt cctgcaatgt     840
tttacaagtc aaaaaaaaaa aaaaaaaaaa aaaaaaaaaa aaaaaaaaaa aaaaaaaaaa     900
aaaaaaaaaa aaaaaaaaaa aaaaaaaaaa aa                                    932

<210> SEQ ID NO 150
<211> LENGTH: 121
<212> TYPE: PRT
<213> ORGANISM: Canna edulis

<400> SEQUENCE: 150

Met Ala Glu Ser Gly Ala Pro Gly Thr Pro Glu Ser Gly His Ser Gly
 1               5                  10                  15

Gly Gly Ser Gly Ala Arg Glu Gln Asp Arg Cys Leu Pro Ile Ala Asn
            20                  25                  30

Ile Gly Arg Ile Met Arg Lys Ala Val Pro Glu Asn Gly Lys Ile Ala
        35                  40                  45

Lys Asp Ala Lys Glu Ser Val Gln Glu Cys Val Ser Glu Phe Ile Ser
    50                  55                  60

Phe Val Thr Ser Glu Ala Ser Asp Lys Cys Arg Arg Glu Lys Arg Lys
65                  70                  75                  80

Thr Ile Asn Gly Asp Asp Leu Leu Trp Ala Met Arg Met Leu Gly Phe
                85                  90                  95

Glu Glu Tyr Val Glu Pro Leu Lys Leu Tyr Leu Gln Leu Tyr Arg Glu
            100                 105                 110

Met Glu Gly Asn Val Met Val Ser Arg
            115                 120
```

<210> SEQ ID NO 151
<211> LENGTH: 863
<212> TYPE: DNA
<213> ORGANISM: Momordica charantia

<400> SEQUENCE: 151

```
gcacgagcag gatctcgctc acatggcgga ggctccgacg agtccagccg gcggcagcca      60
cgagagcggc ggcgagcaga gccccaatac cggtggggtt cgggagcagg accgatacct     120
cccgatcgct aacattagcc ggatcatgaa gaaggccttg cccgctaatg caagatcgc     180
caaggacgcc aaggacaccg tccaggaatg cgtctccgaa ttcatcagct tcatcactag     240
cgaggcgagc gataagtgcc agaaggagaa gagaaagacc attaatgggg atgatttgct     300
gtgggcaatg gcgacattgg gtttcgagga ctatattgat ccgcttaagt cgtatctaac     360
taggtacaga gagttggagt gtgatgctaa gggatcttct aggggtggtg atgagtctgc     420
taaaagagat gcagttgggg ccttgcctgg ccaaaattcc cagcagtaca tgcagccggg     480
agcaatgacc tacattaaca cccaaggaca gcatttgatc attccttcaa tgcagaataa     540
tgaataggag actcctgcat tccctcttgg attgtctgaa atctgaggct ggtagaagcg     600
ttcaacacct atatagcatc tttacaatcg atttggctaa tttattatga aatgatgata     660
ttatatatat ttctggggtt tctgtgttgg ttctggattt gattttggtt tgggctttta     720
aggtgggctt cgatttttatt gatgctctcg tcatctaaag ttattgtaaa tttgggacct     780
tcaatttagt atagttgctt tggtaatttg gaaactggaa aaaaaaaaa aaaaaaaaaa     840
aaaaaaaaaa aaaaaaaaaa aaa                                             863
```

<210> SEQ ID NO 152
<211> LENGTH: 174
<212> TYPE: PRT
<213> ORGANISM: Momordica charantia

<400> SEQUENCE: 152

```
Met Ala Glu Ala Pro Thr Ser Pro Ala Gly Gly Ser His Glu Ser Gly
 1               5                  10                  15

Gly Glu Gln Ser Pro Asn Thr Gly Gly Val Arg Glu Gln Asp Arg Tyr
            20                  25                  30

Leu Pro Ile Ala Asn Ile Ser Arg Ile Met Lys Lys Ala Leu Pro Ala
        35                  40                  45

Asn Gly Lys Ile Ala Lys Asp Ala Lys Asp Thr Val Gln Glu Cys Val
    50                  55                  60

Ser Glu Phe Ile Ser Phe Ile Thr Ser Glu Ala Ser Asp Lys Cys Gln
 65                  70                  75                  80

Lys Glu Lys Arg Lys Thr Ile Asn Gly Asp Asp Leu Leu Trp Ala Met
                85                  90                  95

Ala Thr Leu Gly Phe Glu Asp Tyr Ile Asp Pro Leu Lys Ser Tyr Leu
            100                 105                 110

Thr Arg Tyr Arg Glu Leu Glu Cys Asp Ala Lys Gly Ser Ser Arg Gly
        115                 120                 125

Gly Asp Glu Ser Ala Lys Arg Asp Ala Val Gly Ala Leu Pro Gly Gln
    130                 135                 140

Asn Ser Gln Gln Tyr Met Gln Pro Gly Ala Met Thr Tyr Ile Asn Thr
145                 150                 155                 160

Gln Gly Gln His Leu Ile Ile Pro Ser Met Gln Asn Asn Glu
                165                 170
```

165                 170

<210> SEQ ID NO 153
<211> LENGTH: 1179
<212> TYPE: DNA
<213> ORGANISM: Eucalyptus grandis

<400> SEQUENCE: 153

```
gcaccagttt cccccgccc cccgatcgc cgccctccc gccggggccg gcggcggcgg      60
ggcgtcggcg gcggcggcgg aggatgtggg gagctttctc acggaggatg aggtttcttc     120
tcttctatgt ttttttttt gcagctgctc ggcttgcctg ccctctcggg cgacgacgcg     180
atggcggagg ctccggcgag tcccggcggc ggcggcagcc acgagagcgg cgagcacagc     240
ccccggtccg gcggcgccgt ccgcgagcag gacaggtacc tccccatcgc caacatcagc     300
cgcatcatga agaaggccct ccccgccaac ggcaagatcg ccaaggacgc caaggagacc     360
gtgcaggagt gcgtctccga gttcatcagc ttcatcacca gcgaggcgag cgacaagtgc     420
cagagggaga agaggaagac gatcaacggc gacgacttgc tctggcccat ggcgacctta     480
gggtttgagg attacctcga tccgcttaag atttacctgg ccagatacag ggagatggag     540
ggggatacca agggtcagc taaagtgggg gaagcatcta ctaaaagaga tggcgccgca     600
gttcagtcag ttcctaatgc acagattgct catcaaggtt ctttctctca ggcaccaac     660
tattcgcatt ctcaagttca ccatcctgcg cttccgatgc atggctcaga atgacatgtt     720
ccagcccttg ttgcatgaga tgaagaagtc atcacacttg ttccaggcgt ttgactcatc     780
tcggcatcaa gatattcata agatgtgctg ctgacatttt agggtggtct ctgccaattg     840
tgttcatttg gagttgtttt ccagtgggct gtatatttta gcatctgcat catatttgct     900
ttcagcctta catatgtctg gtttagattt acttgataat gtagaaaggt aagcccccct     960
gcgagtattt atcttattgt catttagatt cgacacccaa ggaggacgag aatgaagttt    1020
cttttttagct ctctgtttcg ttggagttgt cttgtgtatt cttgagttag aaacttgtga   1080
acaaattggt atgcacagtc catgtttatg tgacaatgtc gaggtctgag tgtataatcc    1140
agagtccaat tcagatcgta aaaaaaaaaa aaaaaaaaa                           1179
```

<210> SEQ ID NO 154
<211> LENGTH: 177
<212> TYPE: PRT
<213> ORGANISM: Eucalyptus grandis

<400> SEQUENCE: 154

Met Ala Glu Ala Pro Ala Ser Pro Gly Gly Gly Ser His Glu Ser
1               5                   10                  15

Gly Glu His Ser Pro Arg Ser Gly Gly Ala Val Arg Glu Gln Asp Arg
                20                  25                  30

Tyr Leu Pro Ile Ala Asn Ile Ser Arg Ile Met Lys Lys Ala Leu Pro
            35                  40                  45

Ala Asn Gly Lys Ile Ala Lys Asp Ala Lys Glu Thr Val Gln Glu Cys
        50                  55                  60

Val Ser Glu Phe Ile Ser Phe Ile Thr Ser Glu Ala Ser Asp Lys Cys
65                  70                  75                  80

Gln Arg Glu Lys Arg Lys Thr Ile Asn Gly Asp Asp Leu Leu Trp Pro
                85                  90                  95

Met Ala Thr Leu Gly Phe Glu Asp Tyr Leu Asp Pro Leu Lys Ile Tyr
            100                 105                 110

```
Leu Ala Arg Tyr Arg Glu Met Glu Gly Asp Thr Lys Gly Ser Ala Lys
        115                 120                 125

Val Gly Glu Ala Ser Thr Lys Arg Asp Gly Ala Ala Val Gln Ser Val
    130                 135                 140

Pro Asn Ala Gln Ile Ala His Gln Gly Ser Phe Ser His Gly Thr Asn
145                 150                 155                 160

Tyr Ser His Ser Gln Val His His Pro Ala Leu Pro Met His Gly Ser
                165                 170                 175

Glu

<210> SEQ ID NO 155
<211> LENGTH: 983
<212> TYPE: DNA
<213> ORGANISM: Zea mays

<400> SEQUENCE: 155
gcacgagccg agcgcctcc tcttctccag cgtccgatcc ccattcccca cctctcctcc      60
ctccgccgcc agctcccgcc cccttctctc cctcctcgc ctcccgcgc gcgcgttttt     120 ataagggttt cggcggaggc gcccggtcgc tggcgatggc cgacgacggc gggagccacg     180
agggcagcgg cggcggcgga ggcgtccggg agcaggaccg gttcctgccc atcgccaaca     240
tcagccggat catgaagaag gccgtcccgg ccaacggcaa gatcgccaag gacgctaagg     300
agaccctgca ggagtgcgtc tccgagttca tcattcgt gaccagcgag ccagcgaca     360 aatgccagaa ggagaaacga agacaatca acggggacga tttgctctgg gcgatggcca     420
ctttaggatt cgaggagtac gtcgagcctc tcaagattta cctacaaaag tacaaagaga     480
tggagggtga tagcaagctg tctacaaagg ctggcgaggg ctctgtaaag aaggatgcaa     540
ttagtcccca tggtggcacc agtagctcaa gtaatcagtt ggttcagcat ggagtctaca     600
accaagggat gggctatatg cagccacagt accacaatgg ggaaacctaa taagggcta     660 atacagcagc aatttatgct agggaagtct ctgcattgct taccatgtgt attggcagaa     720
aacaggaggc acttacaaag ggtgttaatc tctgcgatgg ctgcctctca ggtgtaaatt     780
ggcttcggtt tagcgctgct tttgtccgta tatttaggat gatttgactg ttgctacttt     840
tggcaacctt ttacatttac agatatgtat tattcagcat aaatataata tagtagtcct     900
aggcctaaat aatggtgatt aacataccaa gtcttttatc aggctactcg ttttctggaa     960
caaaaaaaaa aaaaaaaaa aaa                                              983

<210> SEQ ID NO 156
<211> LENGTH: 164
<212> TYPE: PRT
<213> ORGANISM: Zea mays

<400> SEQUENCE: 156

Met Ala Asp Asp Gly Gly Ser His Glu Gly Ser Gly Gly Gly Gly Gly
  1               5                  10                  15

Val Arg Glu Gln Asp Arg Phe Leu Pro Ile Ala Asn Ile Ser Arg Ile
             20                  25                  30

Met Lys Lys Ala Val Pro Ala Asn Gly Lys Ile Ala Lys Asp Ala Lys
         35                  40                  45

Glu Thr Leu Gln Glu Cys Val Ser Glu Phe Ile Ser Phe Val Thr Ser
     50                  55                  60

Glu Ala Ser Asp Lys Cys Gln Lys Glu Lys Arg Lys Thr Ile Asn Gly
 65                  70                  75                  80
```

```
Asp Asp Leu Leu Trp Ala Met Ala Thr Leu Gly Phe Glu Glu Tyr Val
            85                  90                  95

Glu Pro Leu Lys Ile Tyr Leu Gln Lys Tyr Lys Glu Met Glu Gly Asp
            100                 105                 110

Ser Lys Leu Ser Thr Lys Ala Gly Glu Gly Ser Val Lys Lys Asp Ala
            115                 120                 125

Ile Ser Pro His Gly Gly Thr Ser Ser Ser Asn Gln Leu Val Gln
130                 135                 140

His Gly Val Tyr Asn Gln Gly Met Gly Tyr Met Gln Pro Gln Tyr His
145                 150                 155                 160

Asn Gly Glu Thr

<210> SEQ ID NO 157
<211> LENGTH: 1021
<212> TYPE: DNA
<213> ORGANISM: Zea mays

<400> SEQUENCE: 157
ggcacgagcg ctcctgttct tctcgcatcc ccagcccagg tggtgtcccc tgtcgcgttg      60
atgcatgctc cctcggcggt ggccttgagc tgaggcggcg gagcgatgcc ggactcggac     120
aacgactccg gcgggccgag caacgccggg ggcgagctgt cgtcgccgcg ggagcaggac     180
cggttcctgc ccatcgccaa cgtgagccgg atcatgaaga aggcgctccc ggccaacgcc     240
aagatcagca aggacgccaa ggagacggtg caggagtgcg tgtccgagtt catctccttc     300
atcaccggcg aggcctccga caagtgccag cgcgagaagc gcaagaccat caacggcgac     360
gacctgctgt gggccatgac cacgctcggc ttcgaggact acgtcgagcc gctcaagcac     420
tacctgcaca agttccgcga gatcgagggc gagagggccg ccgcgtccgc cggcgcctcg     480
ggctcgcagc agcagcagca gcagggcgag ctgcccagag cgccgccaa tgccgccggg     540
tacgccgggt acgcgcgcc tggctccggc ggcatgatga tgatgatgat ggggcagccc     600
atgtacggcg gctcgcagcc gcagcaacag ccgccgccgc ctcagccgcc acagcagcag     660
cagcaacatc aacagcatca catggcaata ggaggcagag aggattcgg ccaacaaggc     720
ggcggcggcg gctcctcgtc gtcgtcaggg cttggccggc aagacagggc gtgagttgcg     780
acgatacgtt cagaatcaga atcgctgata ctcctacgta gaattatacc tcctacctaa     840
ttgatgacac cgcaccgcac ctcgttgtgc tgcctgtcct tgtacgtta ctaattactg     900
ctgcctgtat gtaaatcaaa atctgaggct cccatttcga aacggacggt gaactactct     960
tcccgtttcg tttcatacga gaatcgaact cgttttcaat taaaaaaaaa aaaaaaaaa    1020
a                                                                  1021

<210> SEQ ID NO 158
<211> LENGTH: 222
<212> TYPE: PRT
<213> ORGANISM: Zea mays

<400> SEQUENCE: 158

Met Pro Asp Ser Asp Asn Asp Ser Gly Gly Pro Ser Asn Ala Gly Gly
1               5                   10                  15

Glu Leu Ser Ser Pro Arg Glu Gln Asp Arg Phe Leu Pro Ile Ala Asn
            20                  25                  30

Val Ser Arg Ile Met Lys Lys Ala Leu Pro Ala Asn Ala Lys Ile Ser
        35                  40                  45

Lys Asp Ala Lys Glu Thr Val Gln Glu Cys Val Ser Glu Phe Ile Ser
```

```
                     50                  55                  60
        Phe Ile Thr Gly Glu Ala Ser Asp Lys Cys Gln Arg Glu Lys Arg Lys
        65                  70                  75                  80

Thr Ile Asn Gly Asp Asp Leu Leu Trp Ala Met Thr Thr Leu Gly Phe
                        85                  90                  95

Glu Asp Tyr Val Glu Pro Leu Lys His Tyr Leu His Lys Phe Arg Glu
                        100                 105                 110

Ile Gly Glu Arg Ala Ala Ala Ser Ala Gly Ala Ser Gly Ser Gln
                    115                 120                 125

Gln Gln Gln Gln Gly Glu Leu Pro Arg Gly Ala Ala Asn Ala Ala
            130                 135                 140

Gly Tyr Ala Gly Tyr Gly Ala Pro Gly Ser Gly Gly Met Met Met Met
        145                 150                 155                 160

Met Met Gly Gln Pro Met Tyr Gly Gly Ser Gln Pro Gln Gln Pro
                        165                 170                 175

Pro Pro Pro Gln Pro Pro Gln Gln Gln Gln His Gln His His
                    180                 185                 190

Met Ala Ile Gly Gly Arg Gly Gly Phe Gly Gln Gly Gly Gly
                    195                 200                 205

Gly Ser Ser Ser Ser Gly Leu Gly Arg Gln Asp Arg Ala
            210                 215                 220

<210> SEQ ID NO 159
<211> LENGTH: 1055
<212> TYPE: DNA
<213> ORGANISM: Oryza sativa

<400> SEQUENCE: 159
gcacgagctt acatctctct ctctcctctc ttctcttctt cctcccagac tagtcagtct      60
ctcccaagaa cacccactcc tctagtctct ctctcgagag agagaaaatt gatgattctt     120
gggatgattt tgaggcgtct gatttgctga agaggaggag gaggatgccg gactcggaca     180
acgactccgg cgggccgagc aactacgcgc gaggggagct gtcgtcgccg cgggagcagg     240
acaggttcct gccgatcgcg aacgtgagca ggatcatgaa gaaggcgctg ccggcgaacg     300
ccaagatcag caaggacgcc aaggagacgt gcaggagtg cgtctccgag ttcatctcct     360
tcatcaccgg cgaggcctcc gacaagtgcc agcgcgagaa gcgcaagacc atcaacggcg     420
acgacctgct ctgggccatg accaccctcg gcttcgagga ctacgtcgac ccctcaagc      480 actacctcca caagttccgc gagatcgagg gcgagcgcgc cgccgcctcc accaccggcg     540
ccggcaccag cgccgcctcc accagccgcc gcagcagca gcacaccgcc aatgccgccg      600
gcggctacgc cgggtacgcc gccccgggag ccggccccgg cggcatgatg atgatgatgg     660
ggcagcccat gtacggctcg ccgccaccgc cgccacagca gcagcagcag caacaccacc     720
acatggcaat gggaggaaga ggcggcttcg gtcatcatcc cggcggcggc ggcggcgggt     780
cgtcgtcgtc gtcggggcac ggtcggcaaa cagggggcgc ttgacatcgc tccgagacga     840
gtagcatgca ccatggtaca tatatacagt aatcagcagc tgttcatttt tctatgatta     900
ctagttgact taagcttgca aatttgctaa tctgagctcc tgagtttttt ttttggtca     960 gcaatttcaa gatggtcaga agctaaattt gtctatttgt tactgataaa ttatttgttc    1020
tctcaaaaaa aaaaaaaaaa aaaaaaaaaa aaaaa                                1055

<210> SEQ ID NO 160
<211> LENGTH: 219
```

<212> TYPE: PRT
<213> ORGANISM: Oryza sativa

<400> SEQUENCE: 160

```
Met Pro Asp Ser Asp Asn Asp Ser Gly Gly Pro Ser Asn Tyr Ala Gly
 1               5                  10                  15
Gly Glu Leu Ser Ser Pro Arg Glu Gln Asp Arg Phe Leu Pro Ile Ala
             20                  25                  30
Asn Val Ser Arg Ile Met Lys Lys Ala Leu Pro Ala Asn Ala Lys Ile
         35                  40                  45
Ser Lys Asp Ala Lys Glu Thr Val Gln Glu Cys Val Ser Glu Phe Ile
 50                  55                  60
Ser Phe Ile Thr Gly Glu Ala Ser Asp Lys Cys Gln Arg Glu Lys Arg
 65                  70                  75                  80
Lys Thr Ile Asn Gly Asp Asp Leu Leu Trp Ala Met Thr Thr Leu Gly
                 85                  90                  95
Phe Glu Asp Tyr Val Asp Pro Leu Lys His Tyr Leu His Lys Phe Arg
            100                 105                 110
Glu Ile Glu Gly Glu Arg Ala Ala Ala Ser Thr Thr Gly Ala Gly Thr
        115                 120                 125
Ser Ala Ala Ser Thr Thr Pro Pro Gln Gln Gln His Thr Ala Asn Ala
130                 135                 140
Ala Gly Gly Tyr Ala Gly Tyr Ala Ala Pro Gly Ala Gly Pro Gly Gly
145                 150                 155                 160
Met Met Met Met Met Gly Gln Pro Met Tyr Ser Pro Pro Pro
                165                 170                 175
Pro Gln Gln Gln Gln Gln His His His Met Ala Met Gly Gly Arg
            180                 185                 190
Gly Gly Phe Gly His His Pro Gly Gly Gly Gly Ser Ser Ser
        195                 200                 205
Ser Ser Gly His Gly Arg Gln Asn Arg Gly Ala
210                 215
```

<210> SEQ ID NO 161
<211> LENGTH: 873
<212> TYPE: DNA
<213> ORGANISM: Oryza sativa

<400> SEQUENCE: 161

```
gtttttggag ggcggcgcgg ggatggcgga cgcggggcac gacgagagcg ggagcccgcc      60
gaggagcggc ggggtgaggg agcaggacag gttcctgccc atcgccaaca tcagccgcat     120
catgaagaag gccgtcccgg cgaacggcaa gatcgccaag gacgccaagg agaccctgca     180
ggagtgcgtc tcggagttca tctccttcgt caccagcgag gcgagcgaca atgtcagaa      240
ggagaagcgc aagaccatca acggggaaga tctcctcttt gcgatgggta cgcttggctt     300
tgaggagtac gttgatccgt tgaagatcta tttacacaag tacagagaga tggagggtga     360
tagtaagctg tcctcaaagg ctggtgatgg ttcagtaaag aaggatacaa ttggtccgca     420
cagtggcgct agtagctcaa gtgcgcaagg gatggttggg gcttacaccc aagggatggg     480
ttatatgcaa cctcagtatc ataatgggga cacctaaaga tgaggacagt gaaaattttc     540
agtaactggt gtcctctgtg agttattatc catctgttaa ggaagaaccc acattagggc     600
catatttatt agtagaagac taaagcactt gaagggtgtt ggtttagaaa gggtgttaac     660
agttggctgt ggcgattgct tcacagatgt aaattgcttc ataagtggtt taatgcttgt     720
```

-continued

```
ttttgcctgt atattcagag caattttcac atattggtag ttctgcaatc ttttgcattc      780
ccatacatgt atcaggtggc acaaatctat tgcaagtacc ctagcattga ataatgctgg      840
ttaacatata aaaaaaaaaa aaaaaaaaaa aaa                                   873
```

<210> SEQ ID NO 162
<211> LENGTH: 164
<212> TYPE: PRT
<213> ORGANISM: Oryza sativa

<400> SEQUENCE: 162

```
Met Ala Asp Ala Gly His Asp Glu Ser Gly Ser Pro Pro Arg Ser Gly
 1               5                  10                  15

Gly Val Arg Glu Gln Asp Arg Phe Leu Pro Ile Ala Asn Ile Ser Arg
            20                  25                  30

Ile Met Lys Lys Ala Val Pro Ala Asn Gly Lys Ile Ala Lys Asp Ala
        35                  40                  45

Lys Glu Thr Leu Gln Glu Cys Val Ser Glu Phe Ile Ser Phe Val Thr
    50                  55                  60

Ser Glu Ala Ser Asp Lys Cys Gln Lys Glu Lys Arg Lys Thr Ile Asn
65                  70                  75                  80

Gly Glu Asp Leu Leu Phe Ala Met Gly Thr Leu Gly Phe Glu Glu Tyr
                85                  90                  95

Val Asp Pro Leu Lys Ile Tyr Leu His Lys Tyr Arg Glu Met Glu Gly
            100                 105                 110

Asp Ser Lys Leu Ser Ser Lys Ala Gly Asp Gly Ser Val Lys Lys Asp
        115                 120                 125

Thr Ile Gly Pro His Ser Gly Ala Ser Ser Ser Ala Gln Gly Met
    130                 135                 140

Val Gly Ala Tyr Thr Gln Gly Met Gly Tyr Met Gln Pro Gln Tyr His
145                 150                 155                 160

Asn Gly Asp Thr
```

<210> SEQ ID NO 163
<211> LENGTH: 799
<212> TYPE: DNA
<213> ORGANISM: Glycine max

<400> SEQUENCE: 163

```
gcacgagacg aaagcaacgg tgaagatgaa taatgagtga ggcaatccaa tggtgagaaa       60
ggagtccgtg aaagcagaga cttatcgaga acaacggca cagaaggttc cacgtgggaa      120
gcagataaag gaatattaag cagagagatc caacggacac tgctagtgaa ggcagaagaa      180
gaagattcct ggattgattg tgaagatggc tgagtcggac aacgactcgg gagggcgca      240 gaacgcggga acagtggaa acttgagcga gttgtcgcct cgggaacagg accggtttct      300
ccccatagcg aacgtgagca ggatcatgaa gaaggccttg ccggcgaacg cgaagatctc      360
gaaggacgcg aaggagacgg tgcaggaatg cgtgtcggag ttcatcagct tcataacggg      420
tgaggcgtcg acaagtgcc agagggagaa gcgcaagacc atcaacggcg acgatcttct      480
ctgggccatg acaaccctgg gattcgaaga gtacgtggag cctctgaaga tttacctcca      540
gcgcttccgc gagatggagg gagagaagac cgtggccgcc cgcgactctt ctaaggactc      600
ggcctccgcc tcctcctatc atcagggaca cgtgtacggc tcccctgcct accatcatca      660
agtgcctggg cccacttatc ctgccccctgg tagacccaga tgacgtgctc ctctattcgc      720
cactccctag acttttttata ttatattatt taattaaact ctcttctcca ctcaaccttt      780
```

-continued

```
gcaaaaaaaa aaaaaaaaa                                                799
```

<210> SEQ ID NO 164
<211> LENGTH: 165
<212> TYPE: PRT
<213> ORGANISM: Glycine max

<400> SEQUENCE: 164

```
Met Ala Glu Ser Asp Asn Asp Ser Gly Gly Ala Gln Asn Ala Gly Asn
 1               5                  10                  15

Ser Gly Asn Leu Ser Glu Leu Ser Pro Arg Glu Gln Asp Arg Phe Leu
             20                  25                  30

Pro Ile Ala Asn Val Ser Arg Ile Met Lys Lys Ala Leu Pro Ala Asn
         35                  40                  45

Ala Lys Ile Ser Lys Asp Ala Lys Glu Thr Val Gln Glu Cys Val Ser
     50                  55                  60

Glu Phe Ile Ser Phe Ile Thr Gly Glu Ala Ser Asp Lys Cys Gln Arg
 65                  70                  75                  80

Glu Lys Arg Lys Thr Ile Asn Gly Asp Asp Leu Leu Trp Ala Met Thr
                 85                  90                  95

Thr Leu Gly Phe Glu Glu Tyr Val Glu Pro Leu Lys Ile Tyr Leu Gln
            100                 105                 110

Arg Phe Arg Glu Met Glu Gly Glu Lys Thr Val Ala Ala Arg Asp Ser
        115                 120                 125

Ser Lys Asp Ser Ala Ser Ala Ser Ser Tyr His Gln Gly His Val Tyr
    130                 135                 140

Gly Ser Pro Ala Tyr His His Gln Val Pro Gly Pro Thr Tyr Pro Ala
145                 150                 155                 160

Pro Gly Arg Pro Arg
                165
```

<210> SEQ ID NO 165
<211> LENGTH: 644
<212> TYPE: DNA
<213> ORGANISM: Glycine max

<400> SEQUENCE: 165

```
gcacgagcag tttctggggc atctcaaaat caatggaaga tattggaggc agttcctcaa    60
acgacaacaa caacaatggt ggcatcatca aggaacagga ccggttgctg ccaatagcca   120
atgttggtcg gctcatgaag cggattcttc ctcagaacgc caaaatctcg aaggaggcga   180
aggagacgat gcaggaatgt gtgtcggagt tcataagctt cgtgacgagt gaggcttcgg   240
agaagtgcag gaaggagagg aggaagacag tgaatggtga tgacatttgt tgggccttgg   300
caacactagg ctttgataac tatgctgaac caatgagaag gtacttgcat agatatagag   360
aggttgaggt agatcataat aaggtcaatc ttcaagaaaa agggaatagt cctgaagaga   420
aagacgatga attatttaaa ttgagcaata gaggggttgg gctttgacca attattatgc   480
ttatagtaga caggaactcg ttaatccatt catactcatc actgattact gattagatga   540
attagtaatt ttaaggtttt tgtgaggatg agataatata tgtaataatt ttcttgtctt   600
aattggaatt tatcgagctt agaacaaaaa aaaaaaaaaa aaaa                    644
```

<210> SEQ ID NO 166
<211> LENGTH: 152
<212> TYPE: PRT
<213> ORGANISM: Glycine max

<400> SEQUENCE: 166

```
Ser Phe Trp Gly Ile Ser Lys Ser Met Glu Asp Ile Gly Gly Ser Ser
1               5                   10                  15

Ser Asn Asp Asn Asn Asn Gly Gly Ile Ile Lys Glu Gln Asp Arg
            20                  25                  30

Leu Leu Pro Ile Ala Asn Val Gly Arg Leu Met Lys Arg Ile Leu Pro
            35                  40                  45

Gln Asn Ala Lys Ile Ser Lys Glu Ala Lys Glu Thr Met Gln Glu Cys
        50                  55                  60

Val Ser Glu Phe Ile Ser Phe Val Thr Ser Glu Ala Ser Glu Lys Cys
65                  70                  75                  80

Arg Lys Glu Arg Arg Lys Thr Val Asn Gly Asp Asp Ile Cys Trp Ala
                85                  90                  95

Leu Ala Thr Leu Gly Phe Asp Asn Tyr Ala Glu Pro Met Arg Arg Tyr
            100                 105                 110

Leu His Arg Tyr Arg Glu Val Glu Val Asp His Asn Lys Val Asn Leu
        115                 120                 125

Gln Glu Lys Gly Asn Ser Pro Glu Glu Lys Asp Asp Glu Leu Phe Lys
    130                 135                 140

Leu Ser Asn Arg Gly Val Gly Leu
145                 150
```

<210> SEQ ID NO 167
<211> LENGTH: 879
<212> TYPE: DNA
<213> ORGANISM: Glycine max

<400> SEQUENCE: 167

```
gcacgagaag gaacgtgaaa gtaaaacgga cggtggcgat agaagcgtct ctcatctcca      60
tcgtctcctc actcctctct tctccagcgt tcatttttc tcgcgcccaa atacaaaatc      120
acatcacaac agggttccgg cgaccatgtc cgatgctccg gcgagtccat gcggcggcgg      180
cggcggaggc agccacgaga gcggcgagca cagtccccgc tccaatttcc gcgagcagga      240
ccgcttcctc cccatcgcca acatcagccg catcatgaag aaagcgcttc ctcccaacgg      300
gaaaatcgcc aaggacgcca aggaaaccgt gcaggaatgc gtctccgagt tcatcagctt      360
cgtcaccagc gaagcgagcg ataagtgtca gagagagaag aggaagacca tcaacggcga      420
cgatttgctt tgggctatga ccactttagg tttcgaggag tatattgatc cgctcaaggt      480
ttacctcgcc gcttacagag agattgaggg tgattcaaag ggttcggcca agggtggaga      540
tgcatctgct aagagagatg tttatcagag tcctaatggc caggttgctc atcaaggttc      600
tttctcacaa ggtgttaatt atacgaattc ttagcccag gctcaacata tgatagttcc      660
gatgcaaggc caagagtaga tattgatcct ctccttcagt gtttgacatg tgtgatctaa      720
atgccagtgg aactttatg tcaatatgtg cccttggtat aatgaatgca tttatgtta      780
tgtaaacact acatgcgggg atgttggttc ttgtgaccag atattattta ttaagactta      840
catttatctt tggaaaaaaa aaaaaaaaaa aaaaaaaa                              879
```

<210> SEQ ID NO 168
<211> LENGTH: 162
<212> TYPE: PRT
<213> ORGANISM: Glycine max

<400> SEQUENCE: 168

```
Met Ser Asp Ala Pro Ala Ser Pro Cys Gly Gly Gly Gly Gly Ser
1               5                   10                  15

His Glu Ser Gly Glu His Ser Pro Arg Ser Asn Phe Arg Glu Gln Asp
            20                  25                  30

Arg Phe Leu Pro Ile Ala Asn Ile Ser Arg Ile Met Lys Lys Ala Leu
            35                  40                  45

Pro Pro Asn Gly Lys Ile Ala Lys Asp Ala Lys Glu Thr Val Gln Glu
    50                  55                  60

Cys Val Ser Glu Phe Ile Ser Phe Val Thr Ser Glu Ala Ser Asp Lys
65                  70                  75                  80

Cys Gln Arg Glu Lys Arg Lys Thr Ile Asn Gly Asp Asp Leu Leu Trp
                85                  90                  95

Ala Met Thr Thr Leu Gly Phe Glu Glu Tyr Ile Asp Pro Leu Lys Val
            100                 105                 110

Tyr Leu Ala Ala Tyr Arg Glu Ile Glu Gly Asp Ser Lys Gly Ser Ala
            115                 120                 125

Lys Gly Gly Asp Ala Ser Ala Lys Arg Asp Val Tyr Gln Ser Pro Asn
    130                 135                 140

Gly Gln Val Ala His Gln Gly Ser Phe Ser Gln Gly Val Asn Tyr Thr
145                 150                 155                 160

Asn Ser
```

<210> SEQ ID NO 169
<211> LENGTH: 771
<212> TYPE: DNA
<213> ORGANISM: Glycine max

<400> SEQUENCE: 169

```
gcacgagagt ctttagaaaa gatatccatg gctgagtccg acaacgagtc aggaggtcac      60
acggggaacg cgagcgggag caacgagttg tccggttgca gggagcaaga caggttcctc     120
ccaatagcaa acgtgagcag gatcatgaag aaggcgttgc cggcgaacgc gaagatatcg     180
aaggaggcga aggagacggt gcaggagtgc gtgtcggagt tcatcagctt cataacagga     240
gaggcttccg ataagtgcca gaaggagaag aggaagacga tcaacggcga cgatcttctc     300
tgggccatga ctaccctggg cttcgaggac tacgtggatc ctctcaagat ttacctgcac     360
aagtataggg agatggaggg ggagaaaacc gctatgatgg aaggccaca tgagagggat     420
gagggttatg ccatggcca tggtcatgca actcctatga tgacgatgat gatggggcat     480
cagccccagc accagcacca gcaccagcac cagcaccagc accagggaca cgtgtatgga     540
tctggatcag catcttctgc aagaactaga tagcatgtgt catctgttta agcttaattg     600
attttattat gaggatgata tgatataaga tttatattcg tatatgtttg gttttagaaa     660
tacaccagct ccagcttgta attgcttgaa acttccttgt tgagagaata tagacattat     720
tgtggatggt gatgtggcaa aaaaaaaaaa aaaaaaaaa aaaaaaaaa a                771
```

<210> SEQ ID NO 170
<211> LENGTH: 181
<212> TYPE: PRT
<213> ORGANISM: Glycine max

<400> SEQUENCE: 170

```
Met Ala Glu Ser Asp Asn Glu Ser Gly Gly His Thr Gly Asn Ala Ser
1               5                   10                  15

Gly Ser Asn Glu Leu Ser Gly Cys Arg Glu Gln Asp Arg Phe Leu Pro
            20                  25                  30
```

Ile Ala Asn Val Ser Arg Ile Met Lys Lys Ala Leu Pro Ala Asn Ala
            35                  40                  45

Lys Ile Ser Lys Glu Ala Lys Glu Thr Val Gln Glu Cys Val Ser Glu
        50                  55                  60

Phe Ile Ser Phe Ile Thr Gly Glu Ala Ser Asp Lys Cys Gln Lys Glu
65                  70                  75                  80

Lys Arg Lys Thr Ile Asn Gly Asp Asp Leu Leu Trp Ala Met Thr Thr
                85                  90                  95

Leu Gly Phe Glu Asp Tyr Val Asp Pro Leu Lys Ile Tyr Leu His Lys
            100                 105                 110

Tyr Arg Glu Met Glu Gly Glu Lys Thr Ala Met Met Gly Arg Pro His
        115                 120                 125

Glu Arg Asp Glu Gly Tyr Gly His Gly His Gly Ala Thr Pro Met
    130                 135                 140

Met Thr Met Met Met Gly His Gln Pro Gln His Gln His Gln His Gln
145                 150                 155                 160

His Gln His Gln His Gln Gly His Val Tyr Gly Ser Gly Ser Ala Ser
                165                 170                 175

Ser Ala Arg Thr Arg
            180

<210> SEQ ID NO 171
<211> LENGTH: 848
<212> TYPE: DNA
<213> ORGANISM: Glycine max

<400> SEQUENCE: 171
gcgccaaata caaattcgtg tcaacccaac ccagggttcc ggcgagcatg gccgacggtc      60
cggctagccc aggcggcggc agccacgaga gcggcgacca cagccctcgc tctaacgtgc     120
gcgagcagga caggtaccct cctatcgcta acataagccg catcatgaag aaggcacttc     180
ctgccaacgg taaaatcgca aggacgcca aagagaccgt tcaggaatgc gtctccgagt      240
tcatcagctt catcaccagc gagttatgtc agagagaaaa gagaaagact attaacggcg     300
atgatttgct ctgggcgatg gccactctcg gtttcgagga ttatatggat cctcttaaaa     360
tttacctcac tagataccga gagatggagg gtgatacgaa gggctctgcc aagggtggag     420
actcatctgc taagagagat gttcagccaa gtcctaatgc tcagcttgct catcaaggtt     480
ctttctcaca aaatgttact tacccgaatt ctcagggtcg acatatgatg gttccaatgc     540
aaggcccgga gtaggtatca agtttattat tgaccctctt gttgtaacgt atgttttcta     600
cgccagttac caagtgctca cggcatattg aatgtctttt tatgttatgt gaatactgac     660
aggagatgtt ggttcttgtg tccgtttttt ttttttaaa ttaaggtttg tatattatct      720
ttggattcga attattattt gaaagttatt attatattgt aaatcctaga gccctgttgt     780
ctgaatccat caggcggctt ggtaaagacc gagattttag gactgattgt aagcataaat     840
ccgaatat                                                              848

<210> SEQ ID NO 172
<211> LENGTH: 168
<212> TYPE: PRT
<213> ORGANISM: Glycine max

<400> SEQUENCE: 172

Met Ala Asp Gly Pro Ala Ser Pro Gly Gly Gly Ser His Glu Ser Gly
1               5                   10                  15

```
Asp His Ser Pro Arg Ser Asn Val Arg Glu Gln Asp Arg Tyr Leu Pro
             20                  25                  30

Ile Ala Asn Ile Ser Arg Ile Met Lys Lys Ala Leu Pro Ala Asn Gly
         35                  40                  45

Lys Ile Ala Lys Asp Ala Lys Glu Thr Val Gln Glu Cys Val Ser Glu
 50                  55                  60

Phe Ile Ser Phe Ile Thr Ser Glu Leu Cys Gln Arg Glu Lys Arg Lys
 65                  70                  75                  80

Thr Ile Asn Gly Asp Asp Leu Leu Trp Ala Met Ala Thr Leu Gly Phe
                 85                  90                  95

Glu Asp Tyr Met Asp Pro Leu Lys Ile Tyr Leu Thr Arg Tyr Arg Glu
            100                 105                 110

Met Glu Gly Asp Thr Lys Gly Ser Ala Lys Gly Asp Ser Ser Ala
            115                 120                 125

Lys Arg Asp Val Gln Pro Ser Pro Asn Ala Gln Leu Ala His Gln Gly
130                 135                 140

Ser Phe Ser Gln Asn Val Thr Tyr Pro Asn Ser Gln Gly Arg His Met
145                 150                 155                 160

Met Val Pro Met Gln Gly Pro Glu
            165
```

<210> SEQ ID NO 173
<211> LENGTH: 1097
<212> TYPE: DNA
<213> ORGANISM: Triticum aestivum

<400> SEQUENCE: 173

```
gcacgaggcg ccgccttctc ttctccagcg tcggatcttc ccccactcgc cgccctcacc      60
gcacctccat tcccctccac caccttccct ccctccacgc gctcctctat ataagggga     120
gggccggatg tcggacgagg cggcgagccc ccgggcggc ggcggcggcg gaggaggcgg     180
cggcagcgac gacggcggcg gcggcggcg cttcggcggc gtcagggagc aggacaggtt     240
cctgcccatc gccaacatca gccgcatcat gaagaaggcc atcccggcca acggcaagat     300
cgccaaggac gccaaggaga ccgtgcagga gtgcgtctcc gagttcatct ccttcatcac     360
cagcgaggcg agcgacaagt gccagaggga gaagcgcaag accatcaacg gcgacgacct     420
gctctgggcg atggccacgc tgggcttcga ggagtacatc gagcccctca aggtttatct     480
gcagaagtac agagagacgg aggtgatag taagctagct gggaagtctg gtgatgtctc     540
tgttaaaaag gatgcactgg gtcctcatgg aggagcaagt ggcacaagtg cgcaagggat     600
gggccaacaa gtagcataca atccaggaat ggtttatatg caacctcagt accataatgg     660
ggacatctca aactgaagat atggaccatc tccgagactg ctgctactct gctaggcggg     720
ttttcgtcat gtggagagca ctaagcagtt aaagaaaact cttagtaccc ccattagtct     780
cgtgttgttg ggtctgccag aactgatgct caaaggctgc ttcccagatg taaattgctt     840
tttcctgaga atagattcag ttgtggttta gcatggttgt tgttgttgtc tgtatattta     900
tgatgattag cctcgtcgtg ctgtcattc ggttccatat aatctgggta tttgggggag     960
acataactcc tccaggtgta gtttgtcctg aactagctgt atcagactct tgagaagagt    1020
tgctattagc cctccaaaaa aaaaaaaaa aaaaaaaaa aaaaaaaaa aaaaaaaaa      1080
aaaaaaaaaa aaaaaa                                                    1097
```

<210> SEQ ID NO 174

```
<211> LENGTH: 182
<212> TYPE: PRT
<213> ORGANISM: Triticum aestivum

<400> SEQUENCE: 174

Met Ser Asp Glu Ala Ala Ser Pro Pro Gly Gly Gly Gly Gly Gly Gly
 1               5                  10                  15

Gly Gly Gly Ser Asp Asp Gly Gly Gly Gly Gly Phe Gly Gly Val
            20                  25                  30

Arg Glu Gln Asp Arg Phe Leu Pro Ile Ala Asn Ile Ser Arg Ile Met
         35                  40                  45

Lys Lys Ala Ile Pro Ala Asn Gly Lys Ile Ala Lys Asp Ala Lys Glu
     50                  55                  60

Thr Val Gln Glu Cys Val Ser Glu Phe Ile Ser Phe Ile Thr Ser Glu
 65                  70                  75                  80

Ala Ser Asp Lys Cys Gln Arg Glu Lys Arg Lys Thr Ile Asn Gly Asp
                 85                  90                  95

Asp Leu Leu Trp Ala Met Ala Thr Leu Gly Phe Glu Glu Tyr Ile Glu
            100                 105                 110

Pro Leu Lys Val Tyr Leu Gln Lys Tyr Arg Glu Thr Gly Asp Ser
        115                 120                 125

Lys Leu Ala Gly Lys Ser Gly Asp Val Ser Val Lys Lys Asp Ala Leu
    130                 135                 140

Gly Pro His Gly Gly Ala Ser Gly Thr Ser Ala Gln Gly Met Gly Gln
145                 150                 155                 160

Gln Val Ala Tyr Asn Pro Gly Met Val Tyr Met Gln Pro Gln Tyr His
                165                 170                 175

Asn Gly Asp Ile Ser Asn
            180

<210> SEQ ID NO 175
<211> LENGTH: 1016
<212> TYPE: DNA
<213> ORGANISM: Triticum aestivum

<400> SEQUENCE: 175
ctcgtgccgc aaagattgaa ttttcgtaca agtgtccttc cttccagtta acttcatgct    60
cctgcttgat caggctagag tggtttgatt gcttcttgat ttgagacaca gatcggggag   120
aggagccatg ccggagtcgg acaacgactc cggcgggccg agcaacaccg gcggggaggg   180
ggagctgtcg tcgccgcggg agcaggaccg cttcctgccc atcgccaacg tgagccgcat   240
catgaagaag gcgctcccgg ccaacgccaa gatcagcaag gacgccaagg agacggtgca   300
ggagtgcgtc tccgagttca tctccttcat caccggcgag gcctccgaca agtgccagcg   360
cgagaagcgc aagaccatca acggcgacga cctcctctgg gccatgacca ccctcggctt   420
cgaggactac gtcgaccccc tcaagcacta cctccacaaa ttccgcgaga tcagggcga   480
gagggccgcc gccacgtcga cgtcaaccgc ccgcagcac ctgcccgaca ataatgccac   540
cggttacgcc gactatggtg gcgccgctgt cccgcccg gccccgggag gcatgatgat   600
gatgggcag cccatgtacg gctcaccgcc gccgcagcag cagcaccaac atcaggttgc   660
aatgggaggg agagcgggct ttccctatca cggaggcagc agcggtggcg gcgggtcgtc   720
ttcttcgtcg gggttcggac ggaaagaggg gtgacatctt ttcttttctt ttcgttttga   780
gctgaccaaa gtgagtgatt tcaacatatg ttcctctctt ggatgaagcc gtgacttgta   840
gcttagggaa atccattcag tacaaggagg aataattgtt cagcaaatca gttttcttct   900
```

```
ataaacagga ggaatgtata actacgagtc tacaaatcat acctgggaag ctctccatga      960
attacttgtt taacaacatg gcgagacaca ataccaatat attgatgtta aaaaaa         1016

<210> SEQ ID NO 176
<211> LENGTH: 208
<212> TYPE: PRT
<213> ORGANISM: Triticum aestivum

<400> SEQUENCE: 176

Met Pro Glu Ser Asp Asn Asp Ser Gly Gly Pro Ser Asn Thr Gly Gly
  1               5                  10                  15

Glu Gly Glu Leu Ser Ser Pro Arg Glu Gln Asp Arg Phe Leu Pro Ile
             20                  25                  30

Ala Asn Val Ser Arg Ile Met Lys Lys Ala Leu Pro Ala Asn Ala Lys
         35                  40                  45

Ile Ser Lys Asp Ala Lys Glu Thr Val Gln Glu Cys Val Ser Glu Phe
     50                  55                  60

Ile Ser Phe Ile Thr Gly Glu Ala Ser Asp Lys Cys Gln Arg Glu Lys
 65                  70                  75                  80

Arg Lys Thr Ile Asn Gly Asp Asp Leu Leu Trp Ala Met Thr Thr Leu
                 85                  90                  95

Gly Phe Glu Asp Tyr Val Asp Pro Leu Lys His Tyr Leu His Lys Phe
            100                 105                 110

Arg Glu Ile Glu Gly Glu Arg Ala Ala Ala Thr Ser Thr Ser Thr Ala
        115                 120                 125

Pro Gln His Leu Pro Asp Asn Asn Ala Thr Gly Tyr Ala Asp Tyr Gly
    130                 135                 140

Gly Ala Ala Val Pro Ala Pro Ala Pro Gly Gly Met Met Met Met Gly
145                 150                 155                 160

Gln Pro Met Tyr Gly Ser Pro Pro Gln Gln Gln His Gln His Gln
                165                 170                 175

Val Ala Met Gly Gly Arg Ala Gly Phe Pro Tyr His Gly Gly Ser Ser
            180                 185                 190

Gly Gly Gly Gly Ser Ser Ser Ser Gly Phe Gly Arg Lys Glu Gly
        195                 200                 205

<210> SEQ ID NO 177
<211> LENGTH: 982
<212> TYPE: DNA
<213> ORGANISM: Triticum aestivum

<400> SEQUENCE: 177
gcacgaggca ttccccaccc ctcctcgcag cgccaaccac cgtctcctcc tcccccctcc       60
cttctctccc ctccgctcct ccccccccgc gcgcgcgttt tttataaggg tttcggggcg      120
cgggatggcc gacgacgaca gcgggagccc cggggcggc ggcggggtca gggagcagga      180
ccgcttcctc cccatcgcca acatcagccg catcatgaag aaggccgtgc cggccaacgg      240
caagatcgcc aaggacgcca aggagaccct ccaggagtgc gtctccgagt tcatctcctt      300
cgtcaccagc gaggccagcg acaagtgcca gaaggagaag cgcaagacca tcaacgggga      360
cgatctgctc tgggccatgg ccacgctcgg attcgaggag tacgtagacc ccctcaagat      420
ctacctgcaa aagtacagag atatggaggg tgatagtaaa ttgacctcaa aatctggtga      480
aggatccgtg aagaaagata taattggtgc tcatagtggt gcgactagct caaacgccca      540
agcgatggtt cagcatggag cttacgccca agggatgggt tatatgcaac cccagtacca      600
```

```
taatgggggac acctgaaact gaagatcagg caattttcgg caatgggtat tgctccatga    660
gtggttatct atctgttaag gaagccgccc caacattagg ttcatgatga tcattggctg    720
gaaactaaag cacctggaag ggtgcttaac agttggttgt gatggctgcc tccaagatgt    780
aaattgcttc cgagagaata gattcaccta ttatggttta gtgcttgttt ttatctgtac    840
attcagaata attcagccgt tggtagtttg gcaatctttt gtttcagata tttgtattag    900
gaagcataaa tatattacaa ctgggtatta acttataaaa aaaaaaaaaa aaaaaaaaa    960 aaaaaaaaaa aaaaaaaaaa aa                                            982
```

<210> SEQ ID NO 178
<211> LENGTH: 163
<212> TYPE: PRT
<213> ORGANISM: Triticum aestivum

<400> SEQUENCE: 178

```
Met Ala Asp Asp Asp Ser Gly Ser Pro Arg Gly Gly Gly Val Arg
 1               5                  10                  15

Glu Gln Asp Arg Phe Leu Pro Ile Ala Asn Ile Ser Arg Ile Met Lys
                20                  25                  30

Lys Ala Val Pro Ala Asn Gly Lys Ile Ala Lys Asp Ala Lys Glu Thr
            35                  40                  45

Leu Gln Glu Cys Val Ser Glu Phe Ile Ser Phe Val Thr Ser Glu Ala
        50                  55                  60

Ser Asp Lys Cys Gln Lys Glu Lys Arg Lys Thr Ile Asn Gly Asp Asp
    65                  70                  75                  80

Leu Leu Trp Ala Met Ala Thr Leu Gly Phe Glu Glu Tyr Val Asp Pro
                85                  90                  95

Leu Lys Ile Tyr Leu Gln Lys Tyr Arg Asp Met Glu Gly Asp Ser Lys
            100                 105                 110

Leu Thr Ser Lys Ser Gly Glu Gly Ser Val Lys Lys Asp Ile Ile Gly
        115                 120                 125

Ala His Ser Gly Ala Thr Ser Ser Asn Ala Gln Ala Met Val Gln His
    130                 135                 140

Gly Ala Tyr Ala Gln Gly Met Gly Tyr Met Gln Pro Gln Tyr His Asn
145                 150                 155                 160

Gly Asp Thr
```

<210> SEQ ID NO 179
<211> LENGTH: 272
<212> TYPE: PRT
<213> ORGANISM: Arabidopsis thaliana
<220> FEATURE:
<221> NAME/KEY: misc_feature
<222> LOCATION:
<223> OTHER INFORMATION: gi 11282597

<400> SEQUENCE: 179

```
Met Gln Ser Lys Pro Gly Arg Glu Asn Glu Glu Val Asn Asn His
 1               5                  10                  15

His Ala Val Gln Gln Pro Met Met Tyr Ala Glu Pro Trp Trp Lys Asn
                20                  25                  30

Asn Ser Phe Gly Val Val Pro Gln Ala Arg Pro Ser Gly Ile Pro Ser
            35                  40                  45

Asn Ser Ser Ser Leu Asp Cys Pro Asn Gly Ser Glu Ser Asn Asp Val
        50                  55                  60
```

```
His Ser Ala Ser Glu Asp Gly Ala Leu Asn Gly Glu Asn Asp Gly Thr
 65                  70                  75                  80

Trp Lys Asp Ser Gln Ala Ala Thr Ser Ser Arg Ser Val Asp Asn His
                 85                  90                  95

Gly Met Glu Gly Asn Asp Pro Ala Leu Ser Ile Arg Asn Met His Asp
            100                 105                 110

Gln Pro Leu Val Gln Pro Glu Leu Val Gly His Tyr Ile Ala Cys
        115                 120                 125

Val Pro Asn Pro Tyr Gln Asp Pro Tyr Tyr Gly Gly Leu Met Gly Ala
    130                 135                 140

Tyr Gly His Gln Gln Leu Gly Phe Arg Pro Tyr Leu Gly Met Pro Arg
145                 150                 155                 160

Glu Arg Thr Ala Leu Pro Leu Asp Met Ala Gln Glu Pro Val Tyr Val
                165                 170                 175

Asn Ala Lys Gln Tyr Glu Gly Ile Leu Arg Arg Arg Lys Ala Arg Ala
            180                 185                 190

Lys Ala Glu Leu Glu Arg Lys Val Ile Arg Asp Arg Lys Pro Tyr Leu
        195                 200                 205

His Glu Ser Arg His Lys His Ala Met Arg Arg Ala Arg Ala Ser Gly
    210                 215                 220

Gly Arg Phe Ala Lys Lys Ser Glu Val Glu Ala Gly Glu Asp Ala Gly
225                 230                 235                 240

Gly Arg Asp Arg Glu Arg Gly Ser Ala Thr Asn Ser Ser Gly Ser Glu
                245                 250                 255

Gln Val Glu Thr Asp Ser Asn Glu Thr Leu Asn Ser Ser Gly Ala Pro
            260                 265                 270

<210> SEQ ID NO 180
<211> LENGTH: 215
<212> TYPE: PRT
<213> ORGANISM: Vitis riparia
<220> FEATURE:
<221> NAME/KEY: misc_feature
<222> LOCATION:
<223> OTHER INFORMATION: gi 7141243

<400> SEQUENCE: 180

Met Met Pro Met Thr Met Ala Glu Tyr His Leu Ala Pro Pro Ser Gln
  1               5                  10                  15

Leu Glu Leu Val Gly His Ser Ile Val Gln Ser Gln Phe Leu Gly Val
                 20                  25                  30

Asn Val Ala Arg Met Ala Leu Pro Ile Glu Met Ala Glu Glu Pro Val
             35                  40                  45

Tyr Val Asn Ala Lys Gln Tyr His Gly Ile Leu Arg Arg Arg Gln Ser
     50                  55                  60

Arg Ala Lys Ala Glu Leu Glu Lys Lys Leu Ile Lys Val Arg Lys Pro
 65                  70                  75                  80

Tyr Leu His Glu Ser Arg His Gln His Ala Met Arg Arg Ala Arg Gly
                 85                  90                  95

Cys Gly Gly Arg Phe Leu Asn Thr Lys Lys Leu Asp Ser Asn Ala Ser
            100                 105                 110

Tyr Asp Met Pro Asp Lys Gly Ser Asp Pro Asp Val Asn Leu Ser Thr
        115                 120                 125

Arg Pro Ile Ser Ser Ser Val Ser Glu Ser Leu Pro Phe Asn Ser Ser
    130                 135                 140

Arg Asn Glu Asp Ser Pro Thr Ser His Leu Asp Ala Arg Gly Pro Ser
```

```
                145                 150                 155                 160
Val Gln Glu Leu His Asn Arg Gln Thr Ser Ser Met Glu Met Ala Thr
                    165                 170                 175

Ser Leu Leu Ser Thr Gln Pro Gly Ile Ser Val Gly Arg Thr Tyr His
                180                 185                 190

Ser Leu Lys Met Met Ile Gly Val Glu Arg Arg Pro Arg Lys Ala
            195                 200                 205

Ala Ser Ile Arg Glu Phe Trp
    210                 215

<210> SEQ ID NO 181
<211> LENGTH: 238
<212> TYPE: PRT
<213> ORGANISM: Oryza sativa
<220> FEATURE:
<221> NAME/KEY: misc_feature
<222> LOCATION:
<223> OTHER INFORMATION: gi 7489565

<400> SEQUENCE: 181

Met Leu Pro Pro His Leu Thr Glu Asn Gly Thr Val Met Ile Gln Phe
  1                 5                  10                  15

Gly His Lys Met Pro Asp Tyr Glu Ser Ser Ala Thr Gln Ser Thr Ser
                 20                  25                  30

Gly Ser Pro Arg Glu Val Ser Gly Met Ser Glu Gly Ser Leu Asn Glu
             35                  40                  45

Gln Asn Asp Gln Ser Gly Asn Leu Asp Gly Tyr Thr Lys Ser Asp Glu
     50                  55                  60

Gly Lys Met Met Ser Ala Leu Ser Leu Gly Lys Ser Glu Thr Val Tyr
 65                  70                  75                  80

Ala His Ser Glu Pro Asp Arg Ser Gln Pro Phe Gly Ile Ser Tyr Pro
                 85                  90                  95

Tyr Ala Asp Ser Phe Tyr Gly Gly Ala Val Ala Thr Tyr Gly Thr His
                100                 105                 110

Ala Ile Met His Pro Gln Ile Val Gly Val Met Ser Ser Ser Arg Val
            115                 120                 125

Pro Leu Pro Ile Glu Pro Ala Thr Glu Glu Pro Ile Tyr Val Asn Ala
130                 135                 140

Lys Gln Tyr His Ala Ile Leu Arg Arg Arg Gln Leu Arg Ala Lys Leu
145                 150                 155                 160

Glu Ala Glu Asn Lys Leu Val Lys Asn Arg Lys Pro Tyr Leu His Glu
                165                 170                 175

Ser Arg His Gln His Ala Met Lys Arg Ala Arg Gly Thr Gly Gly Arg
            180                 185                 190

Phe Leu Asn Thr Lys Gln Gln Pro Glu Ala Ser Asp Gly Gly Thr Pro
        195                 200                 205

Arg Leu Val Ser Ala Asn Gly Val Val Phe Ser Lys His Glu His Ser
    210                 215                 220

Leu Ser Ser Ser Asp Leu His His Arg Ala Lys Glu Gly Ala
225                 230                 235

<210> SEQ ID NO 182
<211> LENGTH: 197
<212> TYPE: PRT
<213> ORGANISM: Arabidopsis thaliana
<220> FEATURE:
<221> NAME/KEY: misc_feature
<222> LOCATION:
```

-continued

<223> OTHER INFORMATION: gi 6634774

<400> SEQUENCE: 182

```
Met Thr His Thr Thr Glu Asn Thr Asn Lys Asn Arg Ala Thr Gly Arg
  1               5                  10                  15

Asp Asn Ile Gly Ser His Glu Lys Gln Glu Gln Arg Asp Ser His Phe
             20                  25                  30

Gln Pro Pro Ile Pro Ser Ala Arg Asn Tyr Glu Ser Ile Val Thr Ser
         35                  40                  45

Leu Val Tyr Ser Asp Pro Gly Thr Thr Asn Ser Met Ala Pro Gly Gln
     50                  55                  60

Tyr Pro Tyr Pro Asp Pro Tyr Arg Ser Ile Phe Ala Pro Pro Pro
 65                  70                  75                  80

Gln Pro Tyr Thr Gly Val His Leu Gln Leu Met Gly Val Gln Gln Gln
                 85                  90                  95

Gly Val Pro Leu Pro Ser Asp Ala Val Glu Glu Pro Val Phe Val Asn
            100                 105                 110

Ala Lys Gln Tyr His Gly Ile Leu Arg Arg Arg Gln Ser Arg Ala Arg
        115                 120                 125

Leu Glu Ser Gln Asn Lys Val Ile Lys Ser Arg Lys Pro Tyr Leu His
    130                 135                 140

Glu Ser Arg His Leu His Ala Ile Arg Arg Pro Arg Gly Cys Gly Gly
145                 150                 155                 160

Arg Phe Leu Asn Ala Lys Lys Glu Asp Glu His His Glu Asp Ser Ser
                165                 170                 175

His Glu Glu Lys Ser Asn Leu Ser Ala Gly Lys Ser Ala Met Ala Ala
            180                 185                 190

Ser Ser Gly Thr Ser
        195
```

<210> SEQ ID NO 183
<211> LENGTH: 298
<212> TYPE: PRT
<213> ORGANISM: Arabidopsis thaliana
<220> FEATURE:
<221> NAME/KEY: misc_feature
<222> LOCATION:
<223> OTHER INFORMATION: gi 9293997

<400> SEQUENCE: 183

```
Met His Ser Lys Ser Asp Ser Gly Gly Asn Lys Val Asp Ser Glu Val
  1               5                  10                  15

His Gly Thr Val Ser Ser Ser Ile Asn Ser Leu Asn Pro Trp His Arg
             20                  25                  30

Ala Ala Ala Ala Cys Asn Ala Asn Ser Ser Val Glu Ala Gly Asp Lys
         35                  40                  45

Ser Ser Lys Ser Ile Ala Leu Ala Leu Glu Ser Asn Gly Ser Lys Ser
     50                  55                  60

Pro Ser Asn Arg Asp Asn Thr Val Asn Lys Glu Ser Gln Val Thr Thr
 65                  70                  75                  80

Ser Pro Gln Ser Ala Gly Asp Tyr Ser Asp Lys Asn Gln Glu Ser Leu
                 85                  90                  95

His His Gly Ile Thr Gln Pro Pro His Pro Gln Leu Val Gly His
            100                 105                 110

Thr Val Gly Trp Ala Ser Ser Asn Pro Tyr Gln Asp Pro Tyr Tyr Ala
        115                 120                 125
```

```
Gly Val Met Gly Ala Tyr Gly His His Pro Leu Gly Phe Val Pro Tyr
        130                 135                 140

Gly Gly Met Pro His Ser Arg Met Pro Leu Pro Pro Glu Met Ala Gln
145                 150                 155                 160

Glu Pro Val Phe Val Asn Ala Lys Gln Tyr Gln Ala Ile Leu Arg Arg
                165                 170                 175

Arg Gln Ala Arg Ala Lys Ala Glu Leu Glu Lys Lys Leu Ile Lys Ser
            180                 185                 190

Arg Lys Pro Tyr Leu His Glu Ser Arg His Gln His Ala Met Arg Arg
            195                 200                 205

Pro Arg Gly Thr Gly Gly Arg Phe Ala Lys Lys Thr Asn Thr Glu Ala
        210                 215                 220

Ser Lys Arg Lys Ala Glu Glu Lys Ser Asn Gly His Val Thr Gln Ser
225                 230                 235                 240

Pro Ser Ser Asn Ser Asp Gln Gly Glu Ala Trp Asn Gly Asp Tyr
                245                 250                 255

Arg Thr Pro Gln Gly Asp Glu Met Gln Ser Ser Ala Tyr Lys Arg Arg
                260                 265                 270

Glu Glu Gly Glu Cys Ser Gly Gln Gln Trp Asn Ser Leu Ser Ser Asn
            275                 280                 285

His Pro Ser Gln Ala Arg Leu Ala Ile Lys
        290                 295

<210> SEQ ID NO 184
<211> LENGTH: 340
<212> TYPE: PRT
<213> ORGANISM: Arabidopsis thaliana
<220> FEATURE:
<221> NAME/KEY: misc_feature
<222> LOCATION:
<223> OTHER INFORMATION: gi 5903072

<400> SEQUENCE: 184

Met Met His Gln Met Leu Asn Lys Lys Asp Ser Ala Thr His Ser Thr
1               5                   10                  15

Leu Pro Tyr Leu Asn Thr Ser Ile Ser Trp Gly Val Val Pro Thr Asp
            20                  25                  30

Ser Val Ala Asn Arg Arg Gly Ser Ala Glu Ser Leu Ser Leu Lys Val
        35                  40                  45

Asp Ser Arg Pro Gly His Ile Gln Thr Thr Lys Gln Ile Ser Phe Gln
    50                  55                  60

Asp Gln Asp Ser Ser Ser Thr Gln Ser Thr Gly Gln Ser Tyr Thr Glu
65                  70                  75                  80

Val Ala Ser Ser Gly Asp Asp Asn Pro Ser Arg Gln Ile Ser Phe Ser
                85                  90                  95

Ala Lys Ser Gly Ser Glu Ile Thr Gln Arg Lys Gly Phe Ala Ser Asn
            100                 105                 110

Pro Lys Gln Gly Ser Met Thr Gly Phe Pro Asn Ile His Phe Ala Pro
        115                 120                 125

Ala Gln Ala Asn Phe Ser Phe His Tyr Ala Asp Pro His Tyr Gly Gly
    130                 135                 140

Leu Leu Ala Ala Thr Tyr Leu Pro Gln Ala Pro Thr Cys Asn Pro Gln
145                 150                 155                 160

Met Val Ser Met Ile Pro Gly Arg Val Pro Leu Pro Ala Glu Leu Thr
                165                 170                 175

Glu Thr Asp Pro Val Phe Val Asn Ala Lys Gln Tyr His Ala Ile Met
```

```
                    180                 185                 190
Arg Arg Arg Gln Gln Arg Ala Lys Leu Glu Ala Gln Asn Lys Leu Ile
                195                 200                 205

Arg Ala Arg Lys Pro Tyr Leu His Glu Ser Arg His Val His Ala Leu
    210                 215                 220

Lys Arg Pro Arg Gly Ser Gly Arg Phe Leu Asn Thr Lys Lys Leu
225                 230                 235                 240

Leu Gln Glu Ser Glu Gln Ala Ala Arg Glu Gln Glu Gln Asp Lys
                245                 250                 255

Leu Gly Gln Gln Val Asn Arg Lys Thr Asn Met Ser Arg Phe Glu Ala
                260                 265                 270

His Met Leu Gln Asn Asn Lys Asp Arg Ser Ser Thr Thr Ser Gly Ser
                275                 280                 285

Asp Ile Thr Ser Val Ser Asp Gly Ala Asp Ile Phe Gly His Thr Glu
                290                 295                 300

Phe Gln Phe Ser Gly Phe Pro Thr Pro Ile Asn Arg Ala Met Leu Val
305                 310                 315                 320

His Gly Gln Ser Asn Asp Met His Gly Gly Asp Met His His Phe
                325                 330                 335

Ser Val His Ile
            340

<210> SEQ ID NO 185
<211> LENGTH: 355
<212> TYPE: PRT
<213> ORGANISM: Arabidopsis thaliana
<220> FEATURE:
<221> NAME/KEY: misc_feature
<222> LOCATION:
<223> OTHER INFORMATION: gi 8778470

<400> SEQUENCE: 185

Met Asp Lys Lys Val Ser Phe Thr Ser Ser Val Ala His Ser Thr Pro
1               5                   10                  15

Pro Tyr Leu Ser Thr Ser Ile Ser Trp Gly Leu Pro Thr Lys Ser Asn
                20                  25                  30

Gly Val Thr Glu Ser Leu Ser Leu Lys Val Val Asp Ala Arg Pro Glu
            35                  40                  45

Arg Leu Ile Asn Thr Lys Asn Ile Ser Phe Gln Asp Gln Asp Ser Ser
        50                  55                  60

Ser Thr Leu Ser Ser Ala Gln Ser Ser Asn Asp Val Thr Ser Ser Gly
65                  70                  75                  80

Asp Asp Asn Pro Ser Arg Gln Ile Ser Phe Leu Ala His Ser Asp Val
                85                  90                  95

Cys Lys Gly Phe Glu Glu Thr Gln Arg Lys Arg Phe Ala Ile Lys Ser
                100                 105                 110

Gly Ser Ser Thr Ala Gly Ile Ala Asp Ile His Ser Ser Pro Ser Lys
            115                 120                 125

Val Pro Val Tyr Leu Leu Arg Val Thr Ile Ser Ser Thr Cys Asp Cys
        130                 135                 140

Leu Leu Thr Ser Cys Val Ile Leu Trp Phe Gln Ala Asn Phe Ser Phe
145                 150                 155                 160

His Tyr Ala Asp Pro His Phe Gly Gly Leu Met Pro Ala Ala Tyr Leu
                165                 170                 175

Pro Gln Ala Thr Ile Trp Asn Pro Gln Met Thr Arg Val Pro Leu Pro
            180                 185                 190
```

```
Phe Asp Leu Ile Glu Asn Glu Pro Val Phe Val Asn Ala Lys Gln Phe
            195                 200                 205

His Ala Ile Met Arg Arg Gln Gln Arg Ala Lys Leu Glu Ala Gln
    210                 215                 220

Asn Lys Leu Ile Lys Ala Arg Lys Pro Tyr Leu His Glu Ser Arg His
225                 230                 235                 240

Val His Ala Leu Lys Arg Pro Arg Gly Ser Gly Gly Arg Phe Leu Asn
                245                 250                 255

Thr Lys Lys Leu Gln Glu Ser Thr Asp Pro Lys Gln Asp Met Pro Ile
            260                 265                 270

Gln Gln Gln His Ala Thr Gly Asn Met Ser Arg Phe Val Leu Tyr Gln
            275                 280                 285

Leu Gln Asn Ser Asn Asp Cys Asp Cys Ser Thr Thr Ser Arg Ser Asp
        290                 295                 300

Ile Thr Ser Ala Ser Asp Ser Val Asn Leu Phe Gly His Ser Glu Phe
305                 310                 315                 320

Leu Ile Ser Asp Cys Pro Ser Gln Thr Asn Pro Thr Met Tyr Val His
                325                 330                 335

Gly Gln Ser Asn Asp Met His Gly Gly Arg Asn Thr His His Phe Ser
            340                 345                 350

Val His Ile
        355

<210> SEQ ID NO 186
<211> LENGTH: 271
<212> TYPE: PRT
<213> ORGANISM: Arabidopsis thaliana
<220> FEATURE:
<221> NAME/KEY: misc_feature
<222> LOCATION:
<223> OTHER INFORMATION: gi 2398521

<400> SEQUENCE: 186

Met Gln Ser Lys Pro Gly Arg Glu Asn Glu Glu Val Asn Asn His
1               5                   10                  15

His Ala Val Gln Gln Pro Met Met Tyr Ala Glu Pro Trp Trp Lys Asn
                20                  25                  30

Asn Ser Phe Gly Val Val Pro Gln Ala Arg Pro Ser Gly Ile Pro Ser
            35                  40                  45

Asn Ser Ser Leu Asp Cys Pro Asn Gly Ser Glu Ser Asn Asp Val
    50                  55                  60

His Ser Ala Ser Glu Asp Gly Ala Leu Asn Gly Glu Asn Asp Gly Thr
65                  70                  75                  80

Trp Lys Asp Ser Gln Ala Ala Thr Ser Ser Arg Ser Asp Asn His Gly
                85                  90                  95

Met Glu Gly Asn Asp Pro Ala Leu Ser Ile Arg Asn Met His Asp Gln
            100                 105                 110

Pro Leu Val Gln Pro Pro Glu Leu Val Gly His Tyr Ile Ala Cys Val
        115                 120                 125

Pro Asn Pro Tyr Gln Asp Pro Tyr Tyr Gly Gly Leu Met Gly Ala Tyr
    130                 135                 140

Gly His Gln Gln Leu Gly Phe Arg Pro Tyr Leu Gly Met Pro Arg Glu
145                 150                 155                 160

Arg Thr Ala Leu Pro Leu Asp Met Ala Gln Glu Pro Val Tyr Val Asn
                165                 170                 175
```

```
Ala Lys Gln Tyr Glu Gly Ile Leu Arg Arg Lys Ala Arg Ala Lys
            180                 185                 190

Ala Glu Leu Glu Arg Lys Val Ile Arg Asp Arg Lys Pro Tyr Leu His
            195                 200                 205

Glu Ser Arg His Lys His Ala Met Arg Arg Ala Arg Ala Ser Gly Gly
            210                 215                 220

Arg Phe Ala Lys Lys Ser Glu Val Glu Ala Gly Glu Asp Ala Gly Gly
225                 230                 235                 240

Arg Asp Arg Glu Arg Gly Ser Ala Thr Asn Ser Ser Gly Ser Glu Gln
                245                 250                 255

Val Glu Thr Asp Ser Asn Glu Thr Leu Asn Ser Ser Gly Ala Pro
            260                 265                 270

<210> SEQ ID NO 187
<211> LENGTH: 315
<212> TYPE: PRT
<213> ORGANISM: Brassica napus
<220> FEATURE:
<221> NAME/KEY: misc_feature
<222> LOCATION:
<223> OTHER INFORMATION: gi 1586551

<400> SEQUENCE: 187

Met Ile Ser Leu Thr Val Thr Thr Pro Ser Leu Arg Met Glu Thr Glu
1               5                   10                  15

Asp Met His Ser Lys Ser Glu Ser Gly Asn Gln Ile Val Ser Glu Ala
                20                  25                  30

His His His Thr Ser Ser Thr Ser Ile Asn Ser Leu Asn Pro Trp Leu
            35                  40                  45

Arg Ala Ala Ser Cys Asn Ala Asn Ser Ser Val Glu Glu Ala Gly
        50                  55                  60

Asp Lys Ser Ile Ala Leu Glu Asn Gln Thr Asn Leu Glu Ser Ser Asn
65                  70                  75                  80

Gly Ser Lys Ser Pro Ser Asn Arg Asp Glu Asn Gly Asn Lys Glu Ser
                85                  90                  95

Gln Val Thr Ala Ser Pro Gln Gln Ser Ala Ala Asp Tyr Ser Glu Lys
            100                 105                 110

Ser Gln Glu Leu Val His Pro Gly Ser Thr Pro Pro His Pro Gln
        115                 120                 125

Leu Val Ser His Thr Val Gly Trp Ala Ser Ser Asn Pro Tyr Gln Asp
    130                 135                 140

Ser Tyr Tyr Ala Gly Met Met Gly Ala Tyr Pro Leu Thr Tyr Val Pro
145                 150                 155                 160

His Gly Gly Met Pro His Ser Arg Met Gln Leu Pro Pro Glu Met Ala
                165                 170                 175

Gln Glu Pro Val Tyr Val Asn Ala Lys Gln Tyr Gln Ala Ile Met Arg
            180                 185                 190

Arg Arg Gln Ala Arg Ala Lys Ala Glu Leu Glu Lys Lys Leu Ile Lys
        195                 200                 205

Ser Arg Lys Arg Tyr Leu His Glu Ser Arg His His Ala Met Arg
    210                 215                 220

Arg Pro Arg Gly Thr Gly Gly Arg Phe Ala Lys Lys Thr Asn Thr Glu
225                 230                 235                 240

Ala Ser Gln Gln Lys Asp Gly Glu Lys Arg Asn Ala Cys Ala Thr Gln
                245                 250                 255

Ser Pro Thr Ser Ser His Ser Asp Gln His Glu Gly Cys Ser Asp Glu
```

-continued

```
                    260                 265                 270
Tyr Arg Thr Asn Gln Ser Asp Glu Met Gln Ser Ser Ala Tyr Lys Ile
            275                 280                 285

Arg Glu Glu Ala Asp Cys Ser Gly Gln Gln Trp Asn Asn Ile Ser Ser
        290                 295                 300

Asn His Pro Ser Gln Pro Leu Leu Ala Ile Lys
305                 310                 315

<210> SEQ ID NO 188
<211> LENGTH: 295
<212> TYPE: PRT
<213> ORGANISM: Arabidopsis thaliana
<220> FEATURE:
<221> NAME/KEY: misc_feature
<222> LOCATION:
<223> OTHER INFORMATION: gi 6714441

<400> SEQUENCE: 188

Met Ala Met Gln Thr Val Arg Glu Gly Leu Phe Ser Ala Pro Gln Thr
  1               5                  10                  15

Ser Trp Trp Thr Ala Phe Gly Ser Gln Pro Leu Ala Pro Glu Ser Leu
             20                  25                  30

Ala Gly Asp Ser Asp Ser Phe Ala Gly Val Lys Val Gly Ser Val Gly
         35                  40                  45

Glu Thr Gly Gln Arg Val Asp Lys Gln Ser Asn Ser Ala Thr His Leu
     50                  55                  60

Ala Phe Ser Leu Gly Asp Val Lys Ser Pro Arg Leu Val Pro Lys Pro
 65                  70                  75                  80

His Gly Ala Thr Phe Ser Met Gln Ser Pro Cys Leu Glu Leu Gly Phe
                 85                  90                  95

Ser Gln Pro Pro Ile Tyr Thr Lys Tyr Pro Tyr Gly Glu Gln Gln Tyr
            100                 105                 110

Tyr Gly Val Val Ser Ala Tyr Gly Ser Gln Ser Arg Val Met Leu Pro
        115                 120                 125

Leu Asn Met Glu Thr Glu Asp Ser Thr Ile Tyr Val Asn Ser Lys Gln
130                 135                 140

Tyr His Gly Ile Ile Arg Arg Gln Ser Arg Ala Lys Ala Ala
145                 150                 155                 160

Val Leu Asp Gln Lys Lys Leu Ser Ser Arg Cys Arg Lys Pro Tyr Met
                165                 170                 175

His His Ser Arg His Leu His Ala Leu Arg Arg Pro Arg Gly Ser Gly
            180                 185                 190

Gly Arg Phe Leu Asn Thr Lys Ser Gln Asn Leu Glu Asn Ser Gly Thr
        195                 200                 205

Asn Ala Lys Lys Gly Asp Gly Ser Met Gln Ile Gln Ser Gln Pro Lys
    210                 215                 220

Pro Gln Gln Ser Asn Ser Gln Asn Ser Glu Val Val His Pro Glu Asn
225                 230                 235                 240

Gly Thr Met Asn Leu Ser Asn Gly Leu Asn Val Ser Gly Ser Glu Val
                245                 250                 255

Thr Ser Met Asn Tyr Phe Leu Ser Ser Pro Val His Ser Leu Gly Gly
            260                 265                 270

Met Val Met Pro Ser Lys Trp Ile Ala Ala Ala Ala Met Asp Asn
        275                 280                 285

Gly Cys Cys Asn Phe Lys Thr
    290                 295
```

```
<210> SEQ ID NO 189
<211> LENGTH: 205
<212> TYPE: PRT
<213> ORGANISM: Oryza sativa
<220> FEATURE:
<221> NAME/KEY: misc_feature
<222> LOCATION:
<223> OTHER INFORMATION: gi 5257260

<400> SEQUENCE: 189

Met Glu Pro Lys Ser Thr Thr Pro Pro Pro Pro Pro Pro Pro Val
 1               5                  10                  15

Leu Gly Ala Pro Val Pro Tyr Pro Pro Ala Gly Ala Tyr Pro Pro
                20                  25                  30

Val Gly Pro Tyr Ala His Ala Pro Pro Leu Tyr Ala Pro Pro Pro
            35                  40                  45

Ala Ala Ala Ala Ala Ser Ala Ala Thr Ala Ala Ser Gln Gln Ala
        50                  55                  60

Ala Ala Ala Gln Leu Gln Asn Phe Trp Ala Glu Gln Tyr Arg Glu Ile
65                  70                  75                  80

Glu His Thr Thr Asp Phe Lys Asn His Asn Leu Pro Leu Ala Arg Ile
                85                  90                  95

Lys Lys Ile Met Lys Ala Asp Glu Asp Val Arg Met Ile Ala Ala Glu
               100                 105                 110

Ala Pro Val Val Phe Ala Arg Ala Cys Glu Met Phe Ile Leu Glu Leu
           115                 120                 125

Thr His Arg Gly Trp Ala His Ala Glu Glu Asn Lys Arg Arg Thr Leu
       130                 135                 140

Gln Lys Ser Asp Ile Ala Ala Ile Ala Arg Thr Glu Val Phe Asp
145                 150                 155                 160

Phe Leu Val Asp Ile Val Pro Arg Asp Glu Ala Lys Asp Ala Glu Ala
                165                 170                 175

Ala Ala Ala Val Ala Ala Gly Ile Pro His Pro Ala Ala Gly Leu Pro
            180                 185                 190

Ala Thr Asp Pro Met Ala Tyr Tyr Tyr Val Gln Pro Gln
        195                 200                 205

<210> SEQ ID NO 190
<211> LENGTH: 234
<212> TYPE: PRT
<213> ORGANISM: Arabidopsis thaliana
<220> FEATURE:
<221> NAME/KEY: misc_feature
<222> LOCATION:
<223> OTHER INFORMATION: gi 6523090

<400> SEQUENCE: 190

Met Asp Thr Asn Asn Gln Gln Pro Pro Ser Ala Ala Gly Ile Pro
 1               5                  10                  15

Pro Pro Pro Pro Gly Thr Thr Ile Ser Ala Ala Gly Gly Ala Ser
                20                  25                  30

Tyr His His Leu Leu Gln Gln Gln Gln Gln Leu Gln Leu Phe Trp
            35                  40                  45

Thr Tyr Gln Arg Gln Glu Ile Glu Gln Val Asn Asp Phe Lys Asn His
        50                  55                  60

Gln Leu Pro Leu Ala Arg Ile Lys Lys Ile Met Lys Ala Asp Glu Asp
65                  70                  75                  80
```

```
Val Arg Met Ile Ser Ala Glu Ala Pro Ile Leu Phe Ala Lys Ala Cys
                85                  90                  95

Glu Leu Phe Ile Leu Glu Leu Thr Ile Arg Ser Trp Leu His Ala Glu
            100                 105                 110

Glu Asn Lys Arg Arg Thr Leu Gln Lys Asn Asp Ile Ala Ala Ala Ile
        115                 120                 125

Thr Arg Thr Asp Ile Phe Asp Phe Leu Val Asp Ile Val Pro Arg Asp
130                 135                 140

Glu Ile Lys Asp Glu Ala Ala Val Leu Gly Gly Met Val Val Ala
145                 150                 155                 160

Pro Thr Ala Ser Gly Val Pro Tyr Tyr Tyr Pro Pro Met Gly Gln Pro
                165                 170                 175

Ala Gly Pro Gly Gly Met Met Ile Gly Arg Pro Ala Met Asp Pro Asn
            180                 185                 190

Gly Val Tyr Val Gln Pro Pro Ser Gln Ala Trp Gln Ser Val Trp Gln
        195                 200                 205

Thr Ser Thr Gly Thr Gly Asp Asp Val Ser Tyr Gly Ser Gly Gly Ser
210                 215                 220

Ser Gly Gln Gly Asn Leu Asp Gly Gln Gly
225                 230
```

<210> SEQ ID NO 191
<211> LENGTH: 217
<212> TYPE: PRT
<213> ORGANISM: Arabidopsis thaliana
<220> FEATURE:
<221> NAME/KEY: misc_feature
<222> LOCATION:
<223> OTHER INFORMATION: gi 3776575

<400> SEQUENCE: 191

```
Met Asp Gln Gln Gly Gln Ser Ser Ala Met Asn Tyr Gly Ser Asn Pro
1               5                   10                  15

Tyr Gln Thr Asn Ala Met Thr Thr Thr Pro Thr Gly Ser Asp His Pro
            20                  25                  30

Ala Tyr His Gln Ile His Gln Gln Gln Gln Gln Leu Thr Gln Gln
        35                  40                  45

Leu Gln Ser Phe Trp Glu Thr Gln Phe Lys Glu Ile Glu Lys Thr Thr
50                  55                  60

Asp Phe Lys Asn His Ser Leu Pro Leu Ala Arg Ile Lys Lys Ile Met
65                  70                  75                  80

Lys Ala Asp Glu Asp Val Arg Met Ile Ser Ala Glu Ala Pro Val Val
                85                  90                  95

Phe Ala Arg Ala Cys Glu Met Phe Ile Leu Glu Leu Thr Leu Arg Ser
            100                 105                 110

Trp Asn His Thr Glu Glu Asn Lys Arg Arg Thr Leu Gln Lys Asn Asp
        115                 120                 125

Ile Ala Ala Ala Val Thr Arg Thr Asp Ile Phe Asp Phe Leu Val Asp
130                 135                 140

Ile Val Pro Arg Glu Asp Leu Arg Asp Glu Val Leu Gly Gly Val Gly
145                 150                 155                 160

Ala Glu Ala Ala Thr Ala Ala Gly Tyr Pro Tyr Gly Tyr Leu Pro Pro
                165                 170                 175

Gly Thr Ala Pro Ile Gly Asn Pro Gly Met Val Met Gly Asn Pro Gly
            180                 185                 190

Ala Tyr Pro Pro Asn Pro Tyr Met Gly Gln Pro Met Trp Gln Gln Pro
```

```
                195                 200                 205
Gly Pro Glu Gln Gln Asp Pro Asp Asn
    210                 215

<210> SEQ ID NO 192
<211> LENGTH: 231
<212> TYPE: PRT
<213> ORGANISM: Arabidopsis thaliana
<220> FEATURE:
<221> NAME/KEY: misc_feature
<222> LOCATION:
<223> OTHER INFORMATION: gi 6289057

<400> SEQUENCE: 192

Met Asp Gln Gln Asp His Gly Gln Ser Gly Ala Met Asn Tyr Gly Thr
  1               5                  10                  15

Asn Pro Tyr Gln Thr Asn Pro Met Ser Thr Ala Ala Thr Val Ala
                 20                  25                  30

Gly Gly Ala Ala Gln Pro Gly Gln Leu Ala Phe His Gln Ile His Gln
             35                  40                  45

Gln Gln Gln Gln Gln Leu Ala Gln Leu Gln Ala Phe Trp Glu
         50                  55                  60

Asn Gln Phe Lys Glu Ile Glu Lys Thr Thr Asp Phe Lys Lys His Ser
 65                  70                  75                  80

Leu Pro Leu Ala Arg Ile Lys Lys Ile Met Lys Ala Asp Glu Asp Val
                 85                  90                  95

Arg Met Ile Ser Ala Glu Ala Pro Val Val Phe Ala Arg Ala Cys Glu
                100                 105                 110

Met Phe Ile Leu Glu Leu Thr Leu Arg Ser Trp Asn His Thr Glu Glu
            115                 120                 125

Asn Lys Arg Arg Thr Leu Gln Lys Asn Asp Ile Ala Ala Ala Val Thr
        130                 135                 140

Arg Thr Asp Ile Phe Asp Phe Leu Val Asp Ile Val Pro Arg Glu Asp
145                 150                 155                 160

Leu Arg Asp Glu Val Leu Gly Ser Ile Pro Arg Gly Thr Val Pro Glu
                165                 170                 175

Ala Ala Ala Ala Gly Tyr Pro Tyr Gly Tyr Leu Pro Ala Gly Thr Ala
            180                 185                 190

Pro Ile Gly Asn Pro Gly Met Val Met Gly Asn Pro Gly Gly Ala Tyr
        195                 200                 205

Pro Pro Asn Pro Tyr Met Gly Gln Pro Met Trp Gln Gln Gln Ala Pro
    210                 215                 220

Asp Gln Pro Asp Gln Glu Asn
225                 230

<210> SEQ ID NO 193
<211> LENGTH: 137
<212> TYPE: PRT
<213> ORGANISM: Arabidopsis thaliana
<220> FEATURE:
<221> NAME/KEY: misc_feature
<222> LOCATION:
<223> OTHER INFORMATION: gi 6056368

<400> SEQUENCE: 193

Met Gln Glu Ile Glu His Thr Thr Asp Phe Lys Asn His Thr Leu Pro
  1               5                  10                  15

Leu Ala Arg Ile Lys Lys Ile Met Lys Ala Asp Glu Asp Val Arg Met
                 20                  25                  30
```

```
Ile Ser Ala Glu Ala Pro Val Ile Phe Ala Lys Ala Cys Glu Met Phe
         35                  40                  45

Ile Leu Glu Leu Thr Leu Arg Ala Trp Ile His Thr Glu Glu Asn Lys
 50                  55                  60

Arg Arg Thr Leu Gln Lys Asn Asp Ile Ala Ala Ile Ser Arg Thr
 65                  70                  75                  80

Asp Val Phe Asp Phe Leu Val Asp Ile Ile Pro Arg Asp Glu Leu Lys
                 85                  90                  95

Glu Glu Gly Leu Gly Val Thr Lys Gly Thr Ile Pro Ser Val Val Gly
                100                 105                 110

Ser Pro Pro Tyr Tyr Tyr Leu Gln Gln Gln Gly Met Met Gln His Trp
            115                 120                 125

Pro Gln Glu Gln His Pro Asp Glu Ser
130                 135
```

<210> SEQ ID NO 194
<211> LENGTH: 250
<212> TYPE: PRT
<213> ORGANISM: Arabidopsis thaliana
<220> FEATURE:
<221> NAME/KEY: misc_feature
<222> LOCATION:
<223> OTHER INFORMATION: gi 9758288

<400> SEQUENCE: 194

```
Met Asp Asn Asn Asn Asn Asn Asn Gln Gln Pro Pro Pro Thr Ser
 1               5                  10                  15

Val Tyr Pro Pro Gly Ser Ala Val Thr Thr Val Ile Pro Pro Pro
             20                  25                  30

Ser Gly Ser Ala Ser Ile Val Thr Gly Gly Gly Ala Thr Tyr His His
         35                  40                  45

Leu Leu Gln Gln Gln Gln Gln Leu Gln Met Phe Trp Thr Tyr Gln
 50                  55                  60

Arg Gln Glu Ile Glu Gln Val Asn Asp Phe Lys Asn His Gln Leu Pro
 65                  70                  75                  80

Leu Ala Arg Ile Lys Lys Ile Met Lys Ala Asp Glu Asp Val Arg Met
                 85                  90                  95

Ile Ser Ala Glu Ala Pro Ile Leu Phe Ala Lys Ala Cys Glu Leu Phe
                100                 105                 110

Ile Leu Glu Leu Thr Ile Arg Ser Trp Leu His Ala Glu Glu Asn Lys
            115                 120                 125

Arg Arg Thr Leu Gln Lys Asn Asp Ile Ala Ala Ile Thr Arg Thr
130                 135                 140

Asp Ile Phe Asp Phe Leu Val Asp Ile Val Pro Arg Glu Glu Ile Lys
145                 150                 155                 160

Glu Glu Glu Asp Ala Ala Ser Ala Leu Gly Gly Gly Met Val Ala
                165                 170                 175

Pro Ala Ala Ser Gly Val Pro Tyr Tyr Tyr Pro Pro Met Gly Gln Pro
            180                 185                 190

Ala Val Pro Gly Gly Met Met Ile Gly Arg Pro Ala Met Asp Pro Ser
        195                 200                 205

Gly Val Tyr Ala Gln Pro Pro Ser Gln Ala Trp Gln Ser Val Trp Gln
    210                 215                 220

Asn Ser Ala Gly Gly Gly Asp Asp Val Ser Tyr Gly Ser Gly Gly Ser
225                 230                 235                 240
```

```
Ser Gly His Gly Asn Leu Asp Ser Gln Gly
            245                 250
```

<210> SEQ ID NO 195
<211> LENGTH: 208
<212> TYPE: PRT
<213> ORGANISM: Arabidopsis thaliana
<220> FEATURE:
<221> NAME/KEY: misc_feature
<222> LOCATION:
<223> OTHER INFORMATION: gi 6552738

<400> SEQUENCE: 195

```
Met Thr Ser Val Val Ala Gly Ala Gly Asp Lys Asn Asn Gly
 1               5                  10                  15

Ile Val Gln Gln Gln Pro Pro Cys Val Ala Arg Glu Gln Asp Gln
                20              25                  30

Tyr Met Pro Ile Ala Asn Val Ile Arg Ile Met Arg Lys Thr Leu Pro
        35                  40                  45

Ser His Ala Lys Ile Ser Asp Asp Ala Lys Glu Thr Ile Gln Glu Cys
    50                  55                  60

Val Ser Glu Tyr Ile Ser Phe Val Thr Gly Glu Ala Asn Glu Arg Cys
65                  70                  75                  80

Gln Arg Glu Gln Arg Lys Thr Ile Thr Ala Glu Asp Ile Leu Trp Ala
                85                  90                  95

Met Ser Lys Leu Gly Phe Asp Asn Tyr Val Asp Pro Leu Thr Val Phe
            100                 105                 110

Ile Asn Arg Tyr Arg Glu Ile Glu Thr Asp Arg Gly Ser Ala Leu Arg
        115                 120                 125

Gly Glu Pro Pro Ser Leu Arg Gln Thr Tyr Gly Asn Gly Ile Gly
    130                 135                 140

Phe His Gly Pro Ser His Gly Leu Pro Pro Gly Pro Tyr Gly Tyr
145                 150                 155                 160

Gly Met Leu Asp Gln Ser Met Val Met Gly Gly Arg Tyr Tyr Gln
                165                 170                 175

Asn Gly Ser Ser Gly Gln Asp Glu Ser Ser Val Gly Gly Ser Ser
            180                 185                 190

Ser Ser Ile Asn Gly Met Pro Ala Phe Asp His Tyr Gly Gln Tyr Lys
        195                 200                 205
```

<210> SEQ ID NO 196
<211> LENGTH: 205
<212> TYPE: PRT
<213> ORGANISM: Arabidopsis thaliana
<220> FEATURE:
<221> NAME/KEY: misc_feature
<222> LOCATION:
<223> OTHER INFORMATION: gi 9758795

<400> SEQUENCE: 196

```
Met Ala Glu Gly Ser Met Arg Pro Pro Glu Phe Asn Gln Pro Asn Lys
 1               5                  10                  15

Thr Ser Asn Gly Gly Glu Glu Cys Thr Val Arg Glu Gln Asp Arg
                20              25                  30

Phe Met Pro Ile Ala Asn Val Ile Arg Ile Met Arg Arg Ile Leu Pro
        35                  40                  45

Ala His Ala Lys Ile Ser Asp Asp Ser Lys Glu Thr Ile Gln Glu Cys
    50                  55                  60

Val Ser Glu Tyr Ile Ser Phe Ile Thr Gly Glu Ala Asn Glu Arg Cys
```

```
                 65                  70                  75                  80
Gln Arg Glu Gln Arg Lys Thr Ile Thr Ala Glu Asp Val Leu Trp Ala
                 85                  90                  95

Met Ser Lys Leu Gly Phe Asp Asp Tyr Ile Glu Pro Leu Thr Leu Tyr
                100                 105                 110

Leu His Arg Tyr Arg Glu Leu Glu Gly Glu Arg Gly Val Ser Cys Ser
                115                 120                 125

Ala Gly Ser Val Ser Met Thr Asn Gly Leu Val Val Lys Arg Pro Asn
                130                 135                 140

Gly Thr Met Thr Glu Tyr Gly Ala Tyr Gly Pro Val Pro Gly Ile His
145                 150                 155                 160

Met Ala Gln Tyr His Tyr Arg His Gln Asn Gly Phe Val Phe Ser Gly
                165                 170                 175

Asn Glu Pro Asn Ser Lys Met Ser Gly Ser Ser Gly Ala Ser Gly
                180                 185                 190

Ala Arg Val Glu Val Phe Pro Thr Gln Gln His Lys Tyr
                195                 200                 205

<210> SEQ ID NO 197
<211> LENGTH: 178
<212> TYPE: PRT
<213> ORGANISM: Zea mays
<220> FEATURE:
<221> NAME/KEY: misc_feature
<222> LOCATION:
<223> OTHER INFORMATION: gi 22380

<400> SEQUENCE: 197

Met Ala Glu Ala Pro Ala Ser Pro Gly Gly Gly Gly Ser His Glu
1               5                   10                  15

Ser Gly Ser Pro Arg Gly Gly Gly Gly Gly Ser Val Arg Glu Gln
                20                  25                  30

Asp Arg Phe Leu Pro Ile Ala Asn Ile Ser Arg Ile Met Lys Lys Ala
                35                  40                  45

Ile Pro Ala Asn Gly Lys Ile Ala Lys Asp Ala Lys Glu Thr Val Gln
50                  55                  60

Glu Cys Val Ser Glu Phe Ile Ser Phe Ile Thr Ser Glu Ala Ser Asp
65                  70                  75                  80

Lys Cys Gln Arg Glu Lys Arg Lys Thr Ile Asn Gly Asp Asp Leu Leu
                85                  90                  95

Trp Ala Met Ala Thr Leu Gly Phe Glu Asp Tyr Ile Glu Pro Leu Lys
                100                 105                 110

Val Tyr Leu Gln Lys Tyr Arg Glu Met Glu Gly Asp Ser Lys Leu Thr
                115                 120                 125

Ala Lys Ser Ser Asp Gly Ser Ile Lys Lys Asp Ala Leu Gly His Val
                130                 135                 140

Gly Ala Ser Ser Ser Ala Ala Glu Gly Met Gly Gln Gln Gly Ala Tyr
145                 150                 155                 160

Asn Gln Gly Met Gly Tyr Met Gln Pro Gln Tyr His Asn Gly Asp Ile
                165                 170                 175

Ser Asn

<210> SEQ ID NO 198
<211> LENGTH: 228
<212> TYPE: PRT
<213> ORGANISM: Arabidopsis thaliana
<220> FEATURE:
```

```
<221> NAME/KEY: misc_feature
<222> LOCATION:
<223> OTHER INFORMATION: gi 6729485

<400> SEQUENCE: 198
```

| | | | | | | | | | | | | | | | |
|---|---|---|---|---|---|---|---|---|---|---|---|---|---|---|---|
| Met | Ala | Glu | Ser | Gln | Thr | Gly | Gly | Gly | Gly | Ser | His | Glu | Ser |
| 1 | | | | 5 | | | | | 10 | | | | | 15 |
| Gly | Gly | Asp | Gln | Ser | Pro | Arg | Ser | Leu | Asn | Val | Arg | Glu | Gln | Asp | Arg |
| | | | 20 | | | | | 25 | | | | | 30 |
| Phe | Leu | Pro | Ile | Ala | Asn | Ile | Ser | Arg | Ile | Met | Lys | Arg | Gly | Leu | Pro |
| | | 35 | | | | | 40 | | | | | 45 |
| Leu | Asn | Gly | Lys | Ile | Ala | Lys | Asp | Ala | Lys | Glu | Thr | Met | Gln | Glu | Cys |
| 50 | | | | | 55 | | | | | 60 |
| Val | Ser | Glu | Phe | Ile | Ser | Phe | Val | Thr | Ser | Glu | Ala | Ser | Asp | Lys | Cys |
| 65 | | | | | 70 | | | | | 75 | | | | | 80 |
| Gln | Arg | Glu | Lys | Arg | Lys | Thr | Ile | Asn | Gly | Asp | Asp | Leu | Leu | Trp | Ala |
| | | | | 85 | | | | | 90 | | | | | 95 |
| Met | Ala | Thr | Leu | Gly | Phe | Glu | Asp | Tyr | Ile | Asp | Pro | Leu | Lys | Val | Tyr |
| | | | 100 | | | | | 105 | | | | | 110 |
| Leu | Met | Arg | Tyr | Arg | Glu | Met | Glu | Gly | Asp | Thr | Lys | Gly | Ser | Gly | Lys |
| | | 115 | | | | | 120 | | | | | 125 |
| Gly | Gly | Glu | Ser | Ser | Ala | Lys | Arg | Asp | Gly | Gln | Pro | Ser | Gln | Val | Ser |
| 130 | | | | | 135 | | | | | 140 |
| Gln | Phe | Ser | Gln | Val | Pro | Gln | Gln | Gly | Ser | Phe | Ser | Gln | Gly | Pro | Tyr |
| 145 | | | | | 150 | | | | | 155 | | | | | 160 |
| Gly | Asn | Ser | Gln | Ser | Leu | Arg | Phe | Gly | Asn | Ser | Ile | Glu | His | Leu | Glu |
| | | | | 165 | | | | | 170 | | | | | 175 |
| Val | Leu | Met | Ser | Ser | Thr | Arg | Thr | Leu | Phe | Ile | Thr | Ile | Phe | Arg | Asp |
| | | | 180 | | | | | 185 | | | | | 190 |
| Ser | Thr | Met | Pro | Val | Val | Ser | Glu | Asn | Leu | Ser | Asp | Pro | Leu | Ser | Ile |
| | | | 195 | | | | | 200 | | | | | 205 |
| Asp | Met | Asp | Cys | Glu | Ala | Ile | Tyr | His | His | Phe | Ile | Gly | Leu | Leu | Ile |
| 210 | | | | | 215 | | | | | 220 |
| Leu | Ser | Cys | Lys |
| 225 |

```
<210> SEQ ID NO 199
<211> LENGTH: 161
<212> TYPE: PRT
<213> ORGANISM: Arabidopsis thaliana
<220> FEATURE:
<221> NAME/KEY: misc_feature
<222> LOCATION:
<223> OTHER INFORMATION: gi 2244810

<400> SEQUENCE: 199
```

| | | | | | | | | | | | | | | | |
|---|---|---|---|---|---|---|---|---|---|---|---|---|---|---|---|
| Met | Ala | Asp | Ser | Asp | Asn | Asp | Ser | Gly | Gly | His | Lys | Asp | Gly | Gly | Asn |
| 1 | | | | 5 | | | | | 10 | | | | | 15 |
| Ala | Ser | Thr | Arg | Glu | Gln | Asp | Arg | Phe | Leu | Pro | Ile | Ala | Asn | Val | Ser |
| | | | 20 | | | | | 25 | | | | | 30 |
| Arg | Ile | Met | Lys | Lys | Ala | Leu | Pro | Ala | Asn | Ala | Lys | Ile | Ser | Lys | Asp |
| | | 35 | | | | | 40 | | | | | 45 |
| Ala | Lys | Glu | Thr | Val | Gln | Glu | Cys | Val | Ser | Glu | Phe | Ile | Ser | Phe | Ile |
| 50 | | | | | 55 | | | | | 60 |
| Thr | Gly | Glu | Ala | Ser | Asp | Lys | Cys | Gln | Arg | Glu | Lys | Arg | Lys | Thr | Ile |
| 65 | | | | | 70 | | | | | 75 | | | | | 80 |
| Asn | Gly | Asp | Asp | Leu | Leu | Trp | Ala | Met | Thr | Thr | Leu | Gly | Phe | Glu | Asp |

```
                        85                  90                  95
Tyr Val Glu Pro Leu Lys Val Tyr Leu Gln Lys Tyr Arg Glu Val Glu
                100                 105                 110

Gly Glu Lys Thr Thr Thr Ala Gly Arg Gln Gly Asp Lys Glu Gly Gly
            115                 120                 125

Gly Gly Gly Gly Gly Ala Gly Ser Gly Ser Gly Ala Pro Met Tyr
        130                 135                 140

Gly Gly Gly Met Val Thr Thr Met Gly His Gln Phe Ser His His Phe
145                 150                 155                 160

Ser

<210> SEQ ID NO 200
<211> LENGTH: 187
<212> TYPE: PRT
<213> ORGANISM: Arabidopsis thaliana
<220> FEATURE:
<221> NAME/KEY: misc_feature
<222> LOCATION:
<223> OTHER INFORMATION: gi 2398529

<400> SEQUENCE: 200

Arg Asp Arg Asp Ser Gly Gly Gly Gln Asn Gly Asn Gln Asn Gly
 1               5                  10                  15

Gln Ser Ser Leu Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Met Gln Glu Cys Val Ser Glu Phe Ile
    50                  55                  60

Ser Phe Val Thr Gly Glu Ala Ser Asp Lys Cys Gln Lys Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Val Tyr Leu Gln Arg Phe Arg
                100                 105                 110

Glu Ile Glu Gly Glu Arg Thr Gly Leu Gly Arg Pro Gln Thr Gly Gly
            115                 120                 125

Glu Val Gly Glu His Gln Arg Asp Ala Val Gly Asp Gly Gly Phe
        130                 135                 140

Tyr Gly Gly Gly Gly Met Gln Tyr His Gln His His Gln Phe Leu
145                 150                 155                 160

His Gln Gln Asn His Met Tyr Gly Ala Thr Gly Gly Gly Ser Asp Ser
                165                 170                 175

Gly Gly Gly Ala Ala Ser Gly Arg Thr Arg Thr
            180                 185

<210> SEQ ID NO 201
<211> LENGTH: 160
<212> TYPE: PRT
<213> ORGANISM: Arabidopsis thaliana
<220> FEATURE:
<221> NAME/KEY: misc_feature
<222> LOCATION:
<223> OTHER INFORMATION: gi 3738293

<400> SEQUENCE: 201

Met Ala Gly Asn Tyr His Ser Phe Gln Asn Pro Ile Pro Arg Tyr Gln
 1               5                  10                  15
```

```
Asn Tyr Asn Phe Gly Ser Ser Ser Asn His Gln His Glu His Asp
            20                  25                  30

Gly Leu Val Val Val Glu Asp Gln Gln Gln Glu Ser Met Met
        35                  40                  45

Val Lys Glu Gln Asp Arg Leu Leu Pro Ile Ala Asn Val Gly Arg Ile
50                      55                  60

Met Lys Asn Ile Leu Pro Ala Asn Ala Lys Val Ser Lys Glu Ala Lys
65                  70                  75                  80

Glu Thr Met Gln Glu Cys Val Ser Glu Phe Ile Ser Phe Val Thr Gly
                85                  90                  95

Glu Ala Ser Asp Lys Cys His Lys Glu Lys Arg Lys Thr Val Asn Gly
            100                 105                 110

Asp Asp Ile Cys Trp Ala Met Ala Asn Leu Gly Phe Asp Asp Tyr Ala
        115                 120                 125

Ala Gln Leu Lys Lys Tyr Leu His Arg Tyr Arg Val Leu Glu Gly Glu
130                 135                 140

Lys Pro Asn His His Gly Lys Gly Gly Pro Lys Ser Ser Pro Asp Asn
145                 150                 155                 160
```

<210> SEQ ID NO 202
<211> LENGTH: 308
<212> TYPE: PRT
<213> ORGANISM: Arabidopsis thaliana
<220> FEATURE:
<221> NAME/KEY: misc_feature
<222> LOCATION:
<223> OTHER INFORMATION: gi 4587559

<400> SEQUENCE: 202

```
Met Gln Val Phe Gln Arg Lys Glu Asp Ser Ser Trp Gly Asn Ser Met
1               5                   10                  15

Pro Thr Thr Asn Ser Asn Ile Gln Gly Ser Glu Ser Phe Ser Leu Thr
            20                  25                  30

Lys Asp Met Ile Met Ser Thr Thr Gln Leu Pro Ala Met Lys His Ser
        35                  40                  45

Gly Leu Gln Leu Gln Asn Gln Asp Ser Thr Ser Ser Gln Ser Thr Glu
    50                  55                  60

Glu Glu Ser Gly Gly Gly Glu Val Ala Ser Phe Gly Glu Tyr Lys Arg
65                  70                  75                  80

Tyr Gly Cys Ser Ile Val Asn Asn Asn Leu Ser Gly Tyr Ile Glu Asn
                85                  90                  95

Leu Gly Lys Pro Ile Glu Asn Tyr Thr Lys Ser Ile Thr Thr Ser Ser
            100                 105                 110

Met Val Ser Gln Asp Ser Val Phe Pro Ala Pro Thr Ser Gly Gln Ile
        115                 120                 125

Ser Trp Ser Leu Gln Cys Ala Glu Thr Ser His Phe Asn Gly Phe Leu
130                 135                 140

Ala Pro Glu Tyr Ala Ser Thr Pro Thr Ala Leu Pro His Leu Glu Met
145                 150                 155                 160

Met Gly Leu Val Ser Ser Arg Val Pro Leu Pro His Ile Gln Glu
                165                 170                 175

Asn Glu Pro Ile Phe Val Asn Ala Lys Gln Tyr His Ala Ile Leu Arg
            180                 185                 190

Arg Arg Lys His Arg Ala Lys Leu Glu Ala Gln Asn Lys Leu Ile Lys
        195                 200                 205

Cys Arg Lys Pro Tyr Leu His Glu Ser Arg His Leu His Ala Leu Lys
```

```
                210              215                220
Arg Ala Arg Gly Ser Gly Gly Arg Phe Leu Asn Thr Lys Lys Leu Gln
225                 230                 235                 240

Glu Ser Ser Asn Ser Leu Cys Ser Ser Gln Met Ala Asn Gly Gln Asn
                245                 250                 255

Phe Ser Met Ser Pro His Gly Gly Ser Gly Ile Gly Ser Ser Ser
            260                 265                 270

Ile Ser Pro Ser Ser Asn Ser Asn Cys Ile Asn Met Phe Gln Asn Pro
        275                 280                 285

Gln Phe Arg Phe Ser Gly Tyr Pro Ser Thr His His Ala Ser Ala Leu
    290                 295                 300

Met Ser Gly Thr
305

<210> SEQ ID NO 203
<211> LENGTH: 25
<212> TYPE: DNA
<213> ORGANISM: synthetic construct

<400> SEQUENCE: 203
acagtacagt acagtacagt acagt                                         25

<210> SEQ ID NO 204
<211> LENGTH: 25
<212> TYPE: DNA
<213> ORGANISM: synthetic construct

<400> SEQUENCE: 204
actgtactgt actgtacgtg actgt                                         25

<210> SEQ ID NO 205
<211> LENGTH: 765
<212> TYPE: DNA
<213> ORGANISM: Oryza sativa

<400> SEQUENCE: 205
atggaggccg gctacccggg cgcggcggcg aacggcgctg ccgccgacgg gaacggtggc     60
gcgcagcagg cggcggccgc gccggctata cgtgagcagg accggctgat gccgatcgcg    120
aacgtgatcc gcatcatgcg ccgcgtgctc ccggcgcacg ccaagatctc ggacgacgcc    180
aaggagacga tccaggagtg cgtgtcggag tacatcagct tcatcaccgg ggaggccaac    240
gagcggtgcc agcgcgagca gcgcaagacc atcaccgccg aggacgtgct ctgggccatg    300
agccgcctcg gcttcgacga ctacgtcgag ccccctcggcg tctacctcca ccgctaccgc    360
gagttcgagg gggagtcccg cggcgtcggc gtcggcgtcg cgccgcgcg cggcgaccac    420 caccatggtc acgtcggtgg gatgctcaag tcccgcgcgc agggctccat ggtgacgcac    480
cacgacatgc agatgcacgc ggccatgtac ggtggcggcg cggtgccgcc gccgccgcat    540
cctcctccgc accaccacgc gttccaccag ctcatgccgc cgcaccacgg ccagtacgcg    600
ccgccgtacg acatgtacgg cggcgagcac gggatggcgg cgtactacgg cgggatgtac    660
gcgcccggca gcggcggcga cgggagcggc agcagcggca gcggtggcgc cggcacgccg    720
cagaccgtca acttcgagca ccagcatccg ttcggataca agtag                    765

<210> SEQ ID NO 206
<211> LENGTH: 254
<212> TYPE: PRT
<213> ORGANISM: Oryza sativa
```

<400> SEQUENCE: 206

| | | | | | | | | | | | |
|---|---|---|---|---|---|---|---|---|---|---|---|
Met | Glu | Ala | Gly | Tyr | Pro | Gly | Ala | Ala | Asn | Gly | Ala | Ala | Asp
1 | | | | 5 | | | | | 10 | | | | 15

Gly Asn Gly Gly Ala Gln Gln Ala Ala Ala Pro Ala Ile Arg Glu
              20                  25                  30

Gln Asp Arg Leu Met Pro Ile Ala Asn Val Ile Arg Ile Met Arg Arg
            35                  40                  45

Val Leu Pro Ala His Ala Lys Ile Ser Asp Ala Lys Glu Thr Ile
 50                  55                  60

Gln Glu Cys Val Ser Glu Tyr Ile Ser Phe Ile Thr Gly Glu Ala Asn
65                  70                  75                  80

Glu Arg Cys Gln Arg Glu Gln Arg Lys Thr Ile Thr Ala Glu Asp Val
                85                  90                  95

Leu Trp Ala Met Ser Arg Leu Gly Phe Asp Asp Tyr Val Glu Pro Leu
               100                 105                 110

Gly Val Tyr Leu His Arg Tyr Arg Glu Phe Glu Gly Glu Ser Arg Gly
               115                 120                 125

Val Gly Val Gly Val Gly Ala Ala Arg Gly Asp His His His Gly His
               130                 135                 140

Val Gly Gly Met Leu Lys Ser Arg Ala Gln Gly Ser Met Val Thr His
145                 150                 155                 160

His Asp Met Gln Met His Ala Ala Met Tyr Gly Gly Gly Ala Val Pro
               165                 170                 175

Pro Pro Pro His Pro Pro His His Ala Phe His Gln Leu Met
               180                 185                 190

Pro Pro His His Gly Gln Tyr Ala Pro Pro Tyr Asp Met Tyr Gly Gly
               195                 200                 205

Glu His Gly Met Ala Ala Tyr Tyr Gly Gly Met Tyr Ala Pro Gly Ser
               210                 215                 220

Gly Gly Asp Gly Ser Gly Ser Ser Gly Ser Gly Ala Gly Thr Pro
225                 230                 235                 240

Gln Thr Val Asn Phe Glu His Gln His Pro Phe Gly Tyr Lys
               245                 250

<210> SEQ ID NO 207
<211> LENGTH: 1499
<212> TYPE: DNA
<213> ORGANISM: Catalpa speciosa

<400> SEQUENCE: 207
gcacgaggtg ctctttaaaa ttcacaagta catctgacct ctacatcaac acacattgac     60
tctaaattct ctctctaaat tctgtcaacc cccaaattct agggttttgt tttaattgtc    120
atcagatttc gccttaacag gacacattgg ttgatttctt tggagaaatt agggagcat    180 gcaatccaag tcccagagcg gcaaccaagg agaatccaac ctttataatg ttcctaactc    240
caaagtaaat ccggattctt ggtggaataa tactggatat aattcctttt cctcaacaat    300
gatgggtgga aatgcatcag attcatcatc cctagaacaa tctgtggatg gacagtcgca    360
gtctaaaggt ggtataaatg aggaagatga tgatactacc aaacgatcac caagtagtac    420
acctctgctg ccagatagaa actataggca ggagggtccg agtctccagc aagctccacc    480
taccatacat ccaagaaaca atgggatcgt taatcaggcc ccacagcttg agcttggtgg    540
gcattcagta gcttgtgggt caaatcctta tgatccatat tacggaggaa tgatggcagc    600

```
ttatggccag ccattggttc ctcctcattt atatgatatg catcatgcaa ggatggcact      660 gccctggag atgactcaag agcctgtata tgtgaatgcc aagcagtacc atggcattct      720
gcggaggcgg cagtctcgtg ctaaagctga gcttgaaaag aagttaataa aagttcggaa      780
gccttatctc catgagtctc gacaccaaca tgccttaagg agggcaaggg ggactggagg      840
acgatttgca aagaagtccg atgcagatac ttccaagggg actggacccg gctcatccat      900
cccatcgcag cttattagct catcacgagg ttctgagcca gtgcctgagg ctcagaattt      960
gtacaacgct gatgatggca attttagaag gcaaaccaac ttgcaggaac cggcacttca     1020
gttgggcaag acaggtgaag ggcccacttc aagtcacaag tggggaaata caacctcgaa     1080
ccatgcactt gctatgcagt aaagtcatac ttattggaag gtacaaatgc tggttacttg     1140
tttaaatctt ggctttccca agctgagcgg caattcattc ttggctgttt ctattttatc     1200
tcgtggagga ggaaggatga gagtctttgt ttcttagctt ctcttaatgt ctattgttct     1260
tcccttgtgt acaaaatgtc ttttagcatt agaggcaaag tttgagttag acaagacaa      1320 ccgaagtttg ggtagggaaa acttggttta taacttaaga ttcttgtaaa gttccgcaag     1380
gagtcgcatg catgtgtttg ctacttacat ttgttgcact ttcgaattgt gaacccaaaa     1440
gcatcaatgg tgtttgaata gaacttttaa aagccaaaaa aaaaaaaaaa aaaaaaaa      1499
```

<210> SEQ ID NO 208
<211> LENGTH: 307
<212> TYPE: PRT
<213> ORGANISM: Catalpa speciosa

<400> SEQUENCE: 208

```
Met Gln Ser Lys Ser Gln Ser Gly Asn Gln Gly Glu Ser Asn Leu Tyr
  1               5                  10                  15

Asn Val Pro Asn Ser Lys Val Asn Pro Asp Ser Trp Trp Asn Asn Thr
             20                  25                  30

Gly Tyr Asn Ser Phe Ser Ser Thr Met Met Gly Gly Asn Ala Ser Asp
         35                  40                  45

Ser Ser Ser Leu Glu Gln Ser Val Asp Gly Gln Ser Gln Ser Lys Gly
     50                  55                  60

Gly Ile Asn Glu Glu Asp Asp Thr Thr Lys Arg Ser Pro Ser Ser
 65                  70                  75                  80

Thr Pro Leu Leu Pro Asp Arg Asn Tyr Arg Gln Glu Gly Pro Ser Leu
                 85                  90                  95

Gln Gln Ala Pro Pro Thr Ile His Pro Arg Asn Asn Gly Ile Val Asn
            100                 105                 110

Gln Ala Pro Gln Leu Glu Leu Gly Gly His Ser Val Ala Cys Gly Ser
        115                 120                 125

Asn Pro Tyr Asp Pro Tyr Tyr Gly Gly Met Met Ala Ala Tyr Gly Gln
    130                 135                 140

Pro Leu Val Pro Pro His Leu Tyr Asp Met His Ala Arg Met Ala
145                 150                 155                 160

Leu Pro Leu Glu Met Thr Gln Glu Pro Val Tyr Val Asn Ala Lys Gln
                165                 170                 175

Tyr His Gly Ile Leu Arg Arg Arg Gln Ser Arg Ala Lys Ala Glu Leu
            180                 185                 190

Glu Lys Lys Leu Ile Lys Val Arg Lys Pro Tyr Leu His Glu Ser Arg
        195                 200                 205

His Gln His Ala Leu Arg Arg Ala Arg Gly Thr Gly Gly Arg Phe Ala
    210                 215                 220
```

```
Lys Lys Ser Asp Ala Asp Thr Ser Lys Gly Thr Gly Pro Gly Ser Ser
225                 230                 235                 240

Ile Pro Ser Gln Leu Ile Ser Ser Ser Arg Gly Ser Glu Pro Val Pro
                245                 250                 255

Glu Ala Gln Asn Leu Tyr Asn Ala Asp Asp Gly Asn Phe Arg Arg Gln
                260                 265                 270

Thr Asn Leu Gln Glu Pro Ala Leu Gln Leu Gly Lys Thr Gly Glu Gly
            275                 280                 285

Pro Thr Ser Ser His Lys Trp Gly Asn Thr Thr Ser Asn His Ala Leu
        290                 295                 300

Ala Met Gln
305

<210> SEQ ID NO 209
<211> LENGTH: 1626
<212> TYPE: DNA
<213> ORGANISM: Zea mays

<400> SEQUENCE: 209
ccacgcgtcc gcgatcagcg tcagttacca cgacgaccga tcttgctcgc cagcgagagc    60
gacccctccc ctccctactt cccatgctga tctcggcgcg cttctcttcc tcctccccca   120
gagccgggca ctgatttccc ttggctgctg ctgctggatt ctttggtgtt ccatcaggcc   180
aaggatcccg caaagagctc cggagccaag cctgctgcag ccgtcgcgtc gggtgaggca   240
ggcttcagct tcagtctcct actcgacgag gcaagcggat cggagcgggc ctccgctccg   300
ccatgatgag cttcaagggc cacgaggggt ttggccaggt ggccgccgcc ggtgccggga   360
gccaggctgc ctcccatggt ggagcaggcc cgctgccatg gtgggcgggg cccagctgc    420 tgttcggcga gccggcgccc ccgtcaccgg aggagacgcg ccgggacgcc cagttccagg   480
tcgtgccggg ggttcagggc acgccggatc cagcgccgcc caagacaggg acacctgagg   540
tcctcaaatt ctctgtcttt caagggaatt tggagtcggg tggtaaagga gagaaaaccc   600
caaagaactc taccactatt gctcttcagt caccgttccc agaatacaat ggccgtttcg   660
agattggtct tggtcaatct atgctggccc cttccaatta tccttgtgct gaccagtgct   720
atggcatgct tgcggcttat ggaatgagat cgatgtctgg tgggagaatg ctgttgccac   780
taaatgcgac agctgatgca cccatctatg tgaatccgaa gcagtacgaa ggcatcctcc   840
gccgtcgccg tgctcgcgcc aaggcggaga gcgagaacag gctcgccaaa gcagaaagc    900 cctatctcca cgagtcgcgc cacctccacg cgatgcgtcg ggtaagaggc accggcgggc   960
gcttcgtcaa cacgaagaaa gaagggcgtg cacgggcgt tgcttcgaac gggggcagca   1020
agacggctgc agcggcaccg tcgcgcctcg ccatgccccc tagcttccag agtagcgtcg   1080
ccagcctgtc tggctccgac gtgtcaaaca tgtacagcgg cggcttggag cagcaccttc   1140
gggcgccgca cttcttcacc ccgctgccac ccatcatgga ggacggcgac cacggtggtc   1200
cccccacccg catctcctcc tccttcaagt gggcagccag cgacggctgc tgcgagctcc   1260
tcaaggcgtg aaccgacgag gaggagggga tggctactca gacgaacggc cttctcgccg   1320
atggctggtc gtctgtaggc aaatcattct tggctgttcc gcattgggt gcaacctcat    1380 ccacatcatc tacctaccca gtaggccagt accccctgtt ccctgaacag tgcttgggtt   1440
acagggtgcc tcctgtgtgt gtgatgatgt ggtgtgcctc ccccacatgc atttgctgta   1500
acataatagt gtacccaaac cactgcttcg gactatcatt gtctgtctcg gtatggattc   1560
```

```
tctgttgtca cagtgtctga ataattgagg cgtcagactt caaagttaaa aaaaaaaaa     1620 aaaaaa                                                               1626
```

<210> SEQ ID NO 210
<211> LENGTH: 322
<212> TYPE: PRT
<213> ORGANISM: Zea mays

<400> SEQUENCE: 210

```
Met Met Ser Phe Lys Gly His Glu Gly Phe Gly Gln Val Ala Ala Ala
 1               5                  10                  15

Gly Ala Gly Ser Gln Ala Ala Ser His Gly Ala Gly Pro Leu Pro
                20                  25                  30

Trp Trp Ala Gly Pro Gln Leu Leu Phe Gly Glu Pro Ala Pro Pro Ser
            35                  40                  45

Pro Glu Glu Thr Arg Arg Asp Ala Gln Phe Gln Val Val Pro Gly Val
        50                  55                  60

Gln Gly Thr Pro Asp Pro Ala Pro Pro Lys Thr Gly Thr Pro Glu Val
 65                 70                  75                  80

Leu Lys Phe Ser Val Phe Gln Gly Asn Leu Glu Ser Gly Gly Lys Gly
                85                  90                  95

Glu Lys Thr Pro Lys Asn Ser Thr Thr Ile Ala Leu Gln Ser Pro Phe
            100                 105                 110

Pro Glu Tyr Asn Gly Arg Phe Glu Ile Gly Leu Gly Gln Ser Met Leu
        115                 120                 125

Ala Pro Ser Asn Tyr Pro Cys Ala Asp Gln Cys Tyr Gly Met Leu Ala
    130                 135                 140

Ala Tyr Gly Met Arg Ser Met Ser Gly Gly Arg Met Leu Leu Pro Leu
145                 150                 155                 160

Asn Ala Thr Ala Asp Ala Pro Ile Tyr Val Asn Pro Lys Gln Tyr Glu
                165                 170                 175

Gly Ile Leu Arg Arg Arg Arg Ala Arg Ala Lys Ala Glu Ser Glu Asn
            180                 185                 190

Arg Leu Ala Lys Gly Arg Lys Pro Tyr Leu His Glu Ser Arg His Leu
        195                 200                 205

His Ala Met Arg Arg Val Arg Gly Thr Gly Gly Arg Phe Val Asn Thr
    210                 215                 220

Lys Lys Glu Gly Arg Gly Thr Gly Val Ala Ser Asn Gly Gly Ser Lys
225                 230                 235                 240

Thr Ala Ala Ala Pro Ser Arg Leu Ala Met Pro Pro Ser Phe Gln
                245                 250                 255

Ser Ser Val Ala Ser Leu Ser Gly Ser Asp Val Ser Asn Met Tyr Ser
            260                 265                 270

Gly Gly Leu Glu Gln His Leu Arg Ala Pro His Phe Phe Thr Pro Leu
        275                 280                 285

Pro Pro Ile Met Glu Asp Gly Asp His Gly Gly Pro Pro Thr Arg Ile
    290                 295                 300

Ser Ser Ser Phe Lys Trp Ala Ala Ser Asp Gly Cys Cys Glu Leu Leu
305                 310                 315                 320

Lys Ala
```

<210> SEQ ID NO 211
<211> LENGTH: 1569
<212> TYPE: DNA
<213> ORGANISM: Oryza sativa -continued

```
<400> SEQUENCE: 211
gcacgaggcg atctttcccc agagagagag agagagagag agagagtctt gattgggggga        60 ggagagaggg agagagagaa agagagagga cagaaaatgt tgtggatct tgagtaatgc        120 cttctaataa tgataatgct gttgcaagaa atggagaatc atcctgtcca atgcatggcc        180
aagaccaact atgattttct tgccaggaat aactatccaa tgaaacagtt agttcagagg        240
aactctgatg gtgactcgtc accaacaaag tctggggagt ctcaccaaga agcatctgca        300
gtaagtgaca gcagtctcaa cggacaacac acctcaccac aatcagtgtt tgtcccctca        360
gatattaaca acaatgatag ttgtggggag cgggaccatg gcactaagtc ggtattgtct        420
ttgggcaaca cagaagctgc ctttcctcct tcaaagttcg attacaacca gccttttgca        480
tgtgtttctt atccatatgg tactgatcca tattatggtg gagtattaac aggatacact        540
tcacatgcat ttgttcatcc tcaaattact ggtgctgcaa actctaggat gccattgcct        600
gttgatcctt ctgtagaaga gcccatattt gtcaatgcaa agcaatacaa tgcgatcctt        660
agaagaaggc aaacgcgtgc aaaattggag gcccaaaata aggcggtgaa aggtcggaag        720
ccttacctcc atgaatctcg acatcatcat gctatgaagc gagcccgtgg atcaggtggt        780
cggyyactta ccaaaaagga gctgctggaa cagcagcagc agcagcagca gcagaagcca        840
ccaccggcat cagctcagtc tccaacaggt agagccagaa cgagcggcgg tgccgttgtc        900
cttggcaaga acctgtgccc agagaacagc acatcctgct cgccatcgac accgacaggc        960
tccgagatct ccagcatctc atttgggggc ggcatgctgg ctcaccaaga gcacatcagc       1020
ttcgcatccg ctgatcgcca ccccacaatg aaccagaacc accgtgtccc cgtcatgagg       1080
tgaaaacctc gggatcgcgg gacacgggcg gttctggttt accctcactg gcgcactccg       1140
gtgtgcccgt ggcaattcat ccttggctta tgaagtatct acctgataat agtctgctgt       1200
cagtttatat gcaatgcaac ctctgtcaga taaactctta tagtttgttt tattgtaagc       1260
tatgactgaa cgaactgtcg agcagatggc taatttgtat gttgtgggta cagaaatcct       1320
gaagcttttg atgtacctaa ttgccttttg cttatactct tggtgtatac ccattaccaa       1380
gttgccttaa aaaccctcca attatgtaat cagtcatggt tttatagaac cttgccacat       1440
gtaatcaatc acctgttttt gtaaattgat ctataaacgc taaaaaaaaa aaaaaaaaa        1500 aaaaaaaaa aaaaaaaaa aaaaaaaaa aaaaaaaaa aaaaaaaaa aaaaaaaaa            1560 aaaaaaaaa                                                             1569

<210> SEQ ID NO 212
<211> LENGTH: 317
<212> TYPE: PRT
<213> ORGANISM: Oryza sativa

<400> SEQUENCE: 212

Met Ile Met Leu Leu Gln Glu Met Glu Asn His Pro Val Gln Cys Met
 1               5                  10                  15

Ala Lys Thr Asn Tyr Asp Phe Leu Ala Arg Asn Asn Tyr Pro Met Lys
            20                  25                  30

Gln Leu Val Gln Arg Asn Ser Asp Gly Asp Ser Ser Pro Thr Lys Ser
        35                  40                  45

Gly Glu Ser His Gln Glu Ala Ser Ala Val Ser Asp Ser Ser Leu Asn
    50                  55                  60

Gly Gln His Thr Ser Pro Gln Ser Val Phe Val Pro Ser Asp Ile Asn
65                  70                  75                  80
```

Asn Asn Asp Ser Cys Gly Glu Arg Asp His Gly Thr Lys Ser Val Leu
            85                  90                  95

Ser Leu Gly Asn Thr Glu Ala Ala Phe Pro Pro Ser Lys Phe Asp Tyr
            100                 105                 110

Asn Gln Pro Phe Ala Cys Val Ser Tyr Pro Tyr Gly Thr Asp Pro Tyr
            115                 120                 125

Tyr Gly Gly Val Leu Thr Gly Tyr Thr Ser His Ala Phe Val His Pro
        130                 135                 140

Gln Ile Thr Gly Ala Ala Asn Ser Arg Met Pro Leu Pro Val Asp Pro
145                 150                 155                 160

Ser Val Glu Glu Pro Ile Phe Val Asn Ala Lys Gln Tyr Asn Ala Ile
                165                 170                 175

Leu Arg Arg Arg Gln Thr Arg Ala Lys Leu Glu Ala Gln Asn Lys Ala
                180                 185                 190

Val Lys Gly Arg Lys Pro Tyr Leu His Glu Ser Arg His His His Ala
            195                 200                 205

Met Lys Arg Ala Arg Gly Ser Gly Gly Arg Phe Leu Thr Lys Lys Glu
        210                 215                 220

Leu Leu Glu Gln Gln Gln Gln Gln Gln Gln Lys Pro Pro Pro Ala
225                 230                 235                 240

Ser Ala Gln Ser Pro Thr Gly Arg Ala Arg Thr Ser Gly Gly Ala Val
                245                 250                 255

Val Leu Gly Lys Asn Leu Cys Pro Glu Asn Ser Thr Ser Cys Ser Pro
            260                 265                 270

Ser Thr Pro Thr Gly Ser Glu Ile Ser Ser Ile Ser Phe Gly Gly Gly
        275                 280                 285

Met Leu Ala His Gln Glu His Ile Ser Phe Ala Ser Ala Asp Arg His
        290                 295                 300

Pro Thr Met Asn Gln Asn His Arg Val Pro Val Met Arg
305                 310                 315

<210> SEQ ID NO 213
<211> LENGTH: 1375
<212> TYPE: DNA
<213> ORGANISM: Glycine max

<400> SEQUENCE: 213
gcacgaggag gttgcagact tagaaagaga gagagagaga gaatgggtct catctcaatg    60
caatttaggt tctgaaaacc aaagcttttc ataggaaaag ttgtgctaag atgccaggga   120
aacctgacac tgatgattgg cgtgtagagc gtggggagca gattcagttt cagtcttcca   180
tttactctca tcatcagcct tggtggcgcg gagtggggga aaatgcctcc aaatcatctt   240
cagatgatca gttaaatggt tcaatcgtga atggtatcac gcggtctgag accaatgata   300
agtcaggcgg aggtgttgcc aaagaatacc aaaacatcaa acatgccatg ttgtcaaccc   360
catttaccat ggagaaacat cttgctccaa tccccagat ggaacttgtt ggtcattcag    420
ttgttttaac atctccttat tcagatgcac agtatggtca aatcttgact acttacgggc   480
aacaagttat gataaatcct cagttgtatg aatgcatca tgctagaatg ccttttgccac   540 ttgaaatgga agaggagcct gtttatgtca atgcgaagca gtatcatggt attttgaggc   600
gaagacagtc acgtgctaag gctgagattg aaagaaagt aatcaaaaac aggaagccat   660
acctccatga atcccgtcac cttcatgcaa tgaaagggc aagaggcaac ggtggtcgct   720
ttctcaacac aaagaagctt gaaaataaca attctaattc cacttcagac aaaggcaaca   780

```
atactcgtgc aaacgcctca acaaactcgc ctaacactca acttttgttc accaacaatt   840
tgaatctagg ctcatcaaat gtttcacaag ccacagttca gcacatgcac acagagcaga   900
gtttcactat aggttaccat aatggaaatg gtcttacagc actataccgt tcacaagcaa   960
atgggaaaaa ggagggaaac tgctttggta agagaggga ccctaatggg gatttcaaat  1020
aacacttccc tcagccatac agcaagagtg aagatgaagg gctttatctc atccaacttg  1080
tgatgctgta tagaaggcaa ttcattcttg cttagttaa gtggtgagac cagtgacatg  1140
gtgtacacta tggccttgtt tggtctctcc cttgcttttg tttctctcta caagtccata  1200
tgtaaaatgg ataacagaaa gaaaagaaa aatcactttg gtttgagaac ttttaaagt   1260 ttatattaac tgtgttaagg ttcataaaac tgtagactga tttgtgtgac atgctccaca  1320
gaaccttaaa ttttcctcta ttttgtccta aaaaaaaaaa aaaaaaaaaa aaaaa       1375
```

<210> SEQ ID NO 214
<211> LENGTH: 303
<212> TYPE: PRT
<213> ORGANISM: Glycine max

<400> SEQUENCE: 214

```
Met Pro Gly Lys Pro Asp Thr Asp Asp Trp Arg Val Glu Arg Gly Glu
  1               5                  10                  15

Gln Ile Gln Phe Gln Ser Ser Ile Tyr Ser His His Gln Pro Trp Trp
             20                  25                  30

Arg Gly Val Gly Glu Asn Ala Ser Lys Ser Ser Asp Asp Gln Leu
         35                  40                  45

Asn Gly Ser Ile Val Asn Gly Ile Thr Arg Ser Glu Thr Asn Asp Lys
 50                  55                  60

Ser Gly Gly Gly Val Ala Lys Glu Tyr Gln Asn Ile Lys His Ala Met
 65                  70                  75                  80

Leu Ser Thr Pro Phe Thr Met Glu Lys His Leu Ala Pro Asn Pro Gln
                 85                  90                  95

Met Glu Leu Val Gly His Ser Val Val Leu Thr Ser Pro Tyr Ser Asp
            100                 105                 110

Ala Gln Tyr Gly Gln Ile Leu Thr Thr Tyr Gly Gln Gln Val Met Ile
        115                 120                 125

Asn Pro Gln Leu Tyr Gly Met His His Ala Arg Met Pro Leu Pro Leu
130                 135                 140

Glu Met Glu Glu Glu Pro Val Tyr Val Asn Ala Lys Gln Tyr His Gly
145                 150                 155                 160

Ile Leu Arg Arg Arg Gln Ser Arg Ala Lys Ala Glu Ile Glu Lys Lys
                165                 170                 175

Val Ile Lys Asn Arg Lys Pro Tyr Leu His Glu Ser Arg His Leu His
            180                 185                 190

Ala Met Arg Arg Ala Arg Gly Asn Gly Gly Arg Phe Leu Asn Thr Lys
        195                 200                 205

Lys Leu Glu Asn Asn Ser Asn Ser Thr Ser Asp Lys Gly Asn Asn
    210                 215                 220

Thr Arg Ala Asn Ala Ser Thr Asn Ser Pro Asn Thr Gln Leu Leu Phe
225                 230                 235                 240

Thr Asn Asn Leu Asn Leu Gly Ser Ser Asn Val Ser Gln Ala Thr Val
                245                 250                 255

Gln His Met His Thr Glu Gln Ser Phe Thr Ile Gly Tyr His Asn Gly
            260                 265                 270
```

Asn Gly Leu Thr Ala Leu Tyr Arg Ser Gln Ala Asn Gly Lys Lys Glu
            275                 280                 285

Gly Asn Cys Phe Gly Lys Glu Arg Asp Pro Asn Gly Asp Phe Lys
        290                 295                 300

<210> SEQ ID NO 215
<211> LENGTH: 1192
<212> TYPE: DNA
<213> ORGANISM: Triticum aestivum

<400> SEQUENCE: 215

| | | | | | | |
|---|---|---|---|---|---|---|
| gcacgaggga | gtgacgcggt | cgaggagggg | cgtgcggggg | gcagacagag | agggagcgca | 60 |
| aagggacggc | ggaggcaagc | tagcttcccg | ggggcgacg | caccgagaga | gggcggcggg | 120 |
| agggaggagg | cgcgtgggag | ccatgcttct | cccctcttct | tcgtcttcct | cctacgatcc | 180 |
| caaaggtgac | tcctttggga | aatcggttga | cgatcatatg | aggtcaactt | tgacttttgg | 240 |
| tgataagcat | tctgtatttg | caagtcaaaa | cactgactat | ggccacccaa | tggcttgcat | 300 |
| ttcataccca | ttcaatgatt | ctggttctgt | ttgggcggcc | tatgggtcac | ggctatgtt | 360 |
| ccagcccctc | atggcggaag | gagggcatc | tgcgaccgca | agagttccat | tgcctgtcga | 420 |
| attagcagcg | gatgagccca | tatttgtcaa | tcccaaacaa | tataatggga | ttctccggcg | 480 |
| aaggcagctg | cgcgccaagt | tagaggccca | gaataaactc | acaaaaaaca | gaaagcccta | 540 |
| cctccacgag | tctcgccatc | ttcacgcgat | gaagcgggca | agaggttccg | ggggacgttt | 600 |
| cctcaattcc | aaacagctga | agcagcagca | gcagcagtct | ggcagtgcat | gcacgaaggc | 660 |
| cattgcggat | ggcgcgaatt | ccttgggttc | aacccatcta | cggctaggca | gcggcgcagc | 720 |
| cggagaccga | agcaactcgg | cgtccaaggc | gatgtcctcc | aagagaaca | gcaagagagt | 780 |
| cgccgccccg | gctcccgcct | tcaccatgat | tcaagcggcg | cgcaaagacg | acgacttctt | 840 |
| ccaccatcac | ggccaccatc | tcagcttctc | cgaccacttc | ggccagtcga | gcgaccggta | 900 |
| tacgtaacaa | ggggtcctct | gtgccccggt | gtggtctggc | aactcatcct | tggctttatt | 960 |
| tctggcgtgt | tagggtttca | gagatagtgt | atctcatagt | actactgttg | tactgctttg | 1020 |
| cacccacata | gttctctgct | tgatgttcgg | catgcaaatg | ttggtgtact | ggtgcgttgg | 1080 |
| gacaaaagtt | tgatgtgttt | acatgacaat | tggtcgcgga | actcatcttg | tgttctgctc | 1140 |
| gactctaatg | tgtgtgctca | catgtgaatt | ccgtaaaaaa | aaaaaaaaaa | aa | 1192 |

<210> SEQ ID NO 216
<211> LENGTH: 254
<212> TYPE: PRT
<213> ORGANISM: Triticum aestivum

<400> SEQUENCE: 216

Met Leu Leu Pro Ser Ser Ser Ser Ser Tyr Asp Pro Lys Gly Asp
1               5                   10                  15

Ser Phe Gly Lys Ser Val Asp Asp His Met Arg Ser Thr Leu Thr Phe
            20                  25                  30

Gly Asp Lys His Ser Val Phe Ala Ser Gln Asn Thr Asp Tyr Gly His
        35                  40                  45

Pro Met Ala Cys Ile Ser Tyr Pro Phe Asn Asp Ser Gly Ser Val Trp
    50                  55                  60

Ala Ala Tyr Gly Ser Arg Ala Met Phe Gln Pro Leu Met Ala Glu Gly
65                  70                  75                  80

Gly Ala Ser Ala Thr Ala Arg Val Pro Leu Pro Val Glu Leu Ala Ala

```
                    85                  90                  95
Asp Glu Pro Ile Phe Val Asn Pro Lys Gln Tyr Asn Gly Ile Leu Arg
            100                 105                 110
Arg Arg Gln Leu Arg Ala Lys Leu Glu Ala Gln Asn Lys Leu Thr Lys
            115                 120                 125
Asn Arg Lys Pro Tyr Leu His Glu Ser Arg His Leu His Ala Met Lys
            130                 135                 140
Arg Ala Arg Gly Ser Gly Arg Phe Leu Asn Ser Lys Gln Leu Lys
145                 150                 155                 160
Gln Gln Gln Gln Ser Gly Ser Ala Cys Thr Lys Ala Ile Ala Asp
                165                 170                 175
Gly Ala Asn Ser Leu Gly Ser Thr His Leu Arg Leu Gly Ser Gly Ala
            180                 185                 190
Ala Gly Asp Arg Ser Asn Ser Ala Ser Lys Ala Met Ser Ser Gln Glu
            195                 200                 205
Asn Ser Lys Arg Val Ala Ala Pro Ala Pro Ala Phe Thr Met Ile Gln
    210                 215                 220
Ala Ala Arg Lys Asp Asp Asp Phe Phe His His His Gly His His Leu
225                 230                 235                 240
Ser Phe Ser Asp His Phe Gly Gln Ser Ser Asp Arg Tyr Thr
                245                 250

<210> SEQ ID NO 217
<211> LENGTH: 298
<212> TYPE: PRT
<213> ORGANISM: Arabidopsis thaliana
<220> FEATURE:
<221> NAME/KEY: misc_feature
<222> LOCATION:
<223> OTHER INFORMATION: gi 9293997

<400> SEQUENCE: 217

Met His Ser Lys Ser Asp Ser Gly Gly Asn Lys Val Asp Ser Glu Val
1               5                   10                  15
His Gly Thr Val Ser Ser Ser Ile Asn Ser Leu Asn Pro Trp His Arg
            20                  25                  30
Ala Ala Ala Cys Asn Ala Asn Ser Ser Val Glu Ala Gly Asp Lys
        35                  40                  45
Ser Ser Lys Ser Ile Ala Leu Ala Leu Glu Ser Asn Gly Ser Lys Ser
    50                  55                  60
Pro Ser Asn Arg Asp Asn Thr Val Asn Lys Glu Ser Gln Val Thr Thr
65                  70                  75                  80
Ser Pro Gln Ser Ala Gly Asp Tyr Ser Asp Lys Asn Gln Glu Ser Leu
                85                  90                  95
His His Gly Ile Thr Gln Pro Pro His Pro Gln Leu Val Gly His
            100                 105                 110
Thr Val Gly Trp Ala Ser Ser Asn Pro Tyr Gln Asp Pro Tyr Tyr Ala
            115                 120                 125
Gly Val Met Gly Ala Tyr Gly His His Pro Leu Gly Phe Val Pro Tyr
        130                 135                 140
Gly Gly Met Pro His Ser Arg Met Pro Leu Pro Pro Glu Met Ala Gln
145                 150                 155                 160
Glu Pro Val Phe Val Asn Ala Lys Gln Tyr Gln Ala Ile Leu Arg Arg
                165                 170                 175
Arg Gln Ala Arg Ala Lys Ala Glu Leu Glu Lys Lys Leu Ile Lys Ser
            180                 185                 190
```

```
Arg Lys Pro Tyr Leu His Glu Ser Arg His Gln His Ala Met Arg Arg
            195                 200                 205

Pro Arg Gly Thr Gly Gly Arg Phe Ala Lys Lys Thr Asn Thr Glu Ala
210                 215                 220

Ser Lys Arg Lys Ala Glu Glu Lys Ser Asn Gly His Val Thr Gln Ser
225                 230                 235                 240

Pro Ser Ser Ser Asn Ser Asp Gln Gly Glu Ala Trp Asn Gly Asp Tyr
                245                 250                 255

Arg Thr Pro Gln Gly Asp Glu Met Gln Ser Ser Ala Tyr Lys Arg Arg
            260                 265                 270

Glu Glu Gly Glu Cys Ser Gly Gln Gln Trp Asn Ser Leu Ser Ser Asn
            275                 280                 285

His Pro Ser Gln Ala Arg Leu Ala Ile Lys
            290                 295

<210> SEQ ID NO 218
<211> LENGTH: 238
<212> TYPE: PRT
<213> ORGANISM: Oryza sativa
<220> FEATURE:
<221> NAME/KEY: misc_feature
<222> LOCATION:
<223> OTHER INFORMATION: gi 7489565

<400> SEQUENCE: 218

Met Leu Pro Pro His Leu Thr Glu Asn Gly Thr Val Met Ile Gln Phe
1               5                   10                  15

Gly His Lys Met Pro Asp Tyr Glu Ser Ser Ala Thr Gln Ser Thr Ser
            20                  25                  30

Gly Ser Pro Arg Glu Val Ser Gly Met Ser Glu Gly Ser Leu Asn Glu
        35                  40                  45

Gln Asn Asp Gln Ser Gly Asn Leu Asp Gly Tyr Thr Lys Ser Asp Glu
    50                  55                  60

Gly Lys Met Met Ser Ala Leu Ser Leu Gly Lys Ser Glu Thr Val Tyr
65                  70                  75                  80

Ala His Ser Glu Pro Asp Arg Ser Gln Pro Phe Gly Ile Ser Tyr Pro
                85                  90                  95

Tyr Ala Asp Ser Phe Tyr Gly Gly Ala Val Ala Thr Tyr Gly Thr His
            100                 105                 110

Ala Ile Met His Pro Gln Ile Val Gly Val Met Ser Ser Ser Arg Val
        115                 120                 125

Pro Leu Pro Ile Glu Pro Ala Thr Glu Glu Pro Ile Tyr Val Asn Ala
130                 135                 140

Lys Gln Tyr His Ala Ile Leu Arg Arg Arg Gln Leu Arg Ala Lys Leu
145                 150                 155                 160

Glu Ala Glu Asn Lys Leu Val Lys Asn Arg Lys Pro Tyr Leu His Glu
                165                 170                 175

Ser Arg His Gln His Ala Met Lys Arg Ala Arg Gly Thr Gly Gly Arg
            180                 185                 190

Phe Leu Asn Thr Lys Gln Gln Pro Glu Ala Ser Asp Gly Gly Thr Pro
        195                 200                 205

Arg Leu Val Ser Ala Asn Gly Val Val Phe Ser Lys His Glu His Ser
    210                 215                 220

Leu Ser Ser Ser Asp Leu His His Arg Ala Lys Glu Gly Ala
225                 230                 235
```

<210> SEQ ID NO 219
<211> LENGTH: 215
<212> TYPE: PRT
<213> ORGANISM: Vitis riparia
<220> FEATURE:
<221> NAME/KEY: misc_feature
<222> LOCATION:
<223> OTHER INFORMATION: gi 7141243

<400> SEQUENCE: 219

```
Met Met Pro Met Thr Met Ala Glu Tyr His Leu Ala Pro Pro Ser Gln
 1               5                  10                  15

Leu Glu Leu Val Gly His Ser Ile Val Gln Ser Gln Phe Leu Gly Val
             20                  25                  30

Asn Val Ala Arg Met Ala Leu Pro Ile Glu Met Ala Glu Glu Pro Val
         35                  40                  45

Tyr Val Asn Ala Lys Gln Tyr His Gly Ile Leu Arg Arg Arg Gln Ser
     50                  55                  60

Arg Ala Lys Ala Glu Leu Glu Lys Lys Leu Ile Lys Val Arg Lys Pro
 65                  70                  75                  80

Tyr Leu His Glu Ser Arg His Gln His Ala Met Arg Arg Ala Arg Gly
                 85                  90                  95

Cys Gly Gly Arg Phe Leu Asn Thr Lys Lys Leu Asp Ser Asn Ala Ser
            100                 105                 110

Tyr Asp Met Pro Asp Lys Gly Ser Asp Pro Asp Val Asn Leu Ser Thr
        115                 120                 125

Arg Pro Ile Ser Ser Ser Val Ser Glu Ser Leu Pro Phe Asn Ser Ser
    130                 135                 140

Arg Asn Glu Asp Ser Pro Thr Ser His Leu Asp Ala Arg Gly Pro Ser
145                 150                 155                 160

Val Gln Glu Leu His Asn Arg Gln Thr Ser Ser Met Glu Met Ala Thr
                165                 170                 175

Ser Leu Leu Ser Thr Gln Pro Gly Ile Ser Val Gly Arg Thr Tyr His
            180                 185                 190

Ser Leu Lys Met Met Ile Gly Val Glu Arg Arg Arg Pro Arg Lys Ala
        195                 200                 205

Ala Ser Ile Arg Glu Phe Trp
    210                 215
```

<210> SEQ ID NO 220
<211> LENGTH: 1329
<212> TYPE: DNA
<213> ORGANISM: Glycine max

<400> SEQUENCE: 220

```
gcacgagtag ggttttctcc tcccccattg acccaccgtc catcgcaaag gaagtcgcgc      60
ccaatttcca tggtttgtag attaaatctt aaagcagtaa gtcatcatgg ataaatcaga     120
gcagactcag cagcaacatc agcatgggat gggcgttgcc acaggtgcta gccaaatggc     180
ctattcttct cactacccga ctgctcccat ggtggcttct ggcacgcctg ctgtagctgt     240
tccttcccca actcaggctc cagctgcctt ctctagttct gctcaccagc ttgcatacca     300
gcaagcacag catttccacc accaacagca gcaacaccaa caacagcagc ttcaaatgtt     360
ctggtcaaac caaatgcaag aaattgagca acaattgac tttaaaaacc acagtcttcc     420
tcttgctcgg ataaaaaaga taatgaaagc tgatgaagat gtccggatga tttctgcaga     480
agctccagtc atatttgcaa aagcatgtga atgttcata ttagagttga cgttgagatc      540
```

-continued

```
ttggatccac acagaagaga acaagaggag aactctacaa aagaatgata tagcagctgc      600
tatttcgaga acgatgttt ttgatttctt ggttgatatt atcccaagag atgagttgaa       660
agaggaagga cttggaataa ccaaggctac tattccattg gtgaattctc cagctgatat      720
gccatattac tatgtccctc cacagcatcc tgttgtagga cctcctggga tgatcatggg      780
caagcccgtt ggtgctgagc aagcaacgct gtattctaca cagcagcctc gacctcccat      840
ggcgttcatg ccatggcccc atacacaacc ccagcaacag cagccacccc aacatcaaca      900
aacagactca tgatgacaat gcaattcaat taggtcggaa agtagcatgc accttatgat      960
tattacaaat ttacttaatg cctttaagtc agctgtagtt tagtgttttg cattgaaaaa     1020
tgccaaagat tgtttgaggt ttcttgcact catttatgat tgtatgagct cttatgctga     1080
gttacttttg gttgtgttta tttgaggtac tggtgtggta gttaaattag tttgtagctg     1140
tccataagta aacagcgtag ctgcttaatt aggaggtctg aaatgatgaa atagtttgta     1200
ttgttattgc agaaggtagg ttttattcag tatttcaaaa aaaaaaaaaa aaaaaaaaa      1260 aaaaaaaaaa aaaaaaaaaa aaaaaaaaaa aaaaaaaaaa aaaaaaaaaa aaaaaaaaaa     1320
aaaaaaaaaa                                                            1329
```

<210> SEQ ID NO 221
<211> LENGTH: 268
<212> TYPE: PRT
<213> ORGANISM: Glycine max

<400> SEQUENCE: 221

```
Met Asp Lys Ser Glu Gln Thr Gln Gln Gln His Gln His Gly Met Gly
  1               5                  10                  15

Val Ala Thr Gly Ala Ser Gln Met Ala Tyr Ser Ser His Tyr Pro Thr
             20                  25                  30

Ala Pro Met Val Ala Ser Gly Thr Pro Ala Val Ala Val Pro Ser Pro
         35                  40                  45

Thr Gln Ala Pro Ala Ala Phe Ser Ser Ser Ala His Gln Leu Ala Tyr
     50                  55                  60

Gln Gln Ala Gln His Phe His His Gln Gln Gln His Gln Gln Gln
 65                  70                  75                  80

Gln Leu Gln Met Phe Trp Ser Asn Gln Met Gln Glu Ile Glu Gln Thr
                 85                  90                  95

Ile Asp Phe Lys Asn His Ser Leu Pro Leu Ala Arg Ile Lys Lys Ile
            100                 105                 110

Met Lys Ala Asp Glu Asp Val Arg Met Ile Ser Ala Glu Ala Pro Val
        115                 120                 125

Ile Phe Ala Lys Ala Cys Glu Met Phe Ile Leu Glu Leu Thr Leu Arg
    130                 135                 140

Ser Trp Ile His Thr Glu Glu Asn Lys Arg Arg Thr Leu Gln Lys Asn
145                 150                 155                 160

Asp Ile Ala Ala Ala Ile Ser Arg Asn Asp Val Phe Asp Phe Leu Val
                165                 170                 175

Asp Ile Ile Pro Arg Asp Glu Leu Lys Glu Glu Gly Leu Gly Ile Thr
            180                 185                 190

Lys Ala Thr Ile Pro Leu Val Asn Ser Pro Ala Asp Met Pro Tyr Tyr
        195                 200                 205

Tyr Val Pro Pro Gln His Pro Val Val Gly Pro Pro Gly Met Ile Met
    210                 215                 220
```

-continued

```
Gly Lys Pro Val Gly Ala Glu Gln Ala Thr Leu Tyr Ser Thr Gln Gln
225                 230                 235                 240

Pro Arg Pro Pro Met Ala Phe Met Pro Trp Pro His Thr Gln Pro Gln
                245                 250                 255

Gln Gln Gln Pro Pro Gln His Gln Gln Thr Asp Ser
            260                 265

<210> SEQ ID NO 222
<211> LENGTH: 199
<212> TYPE: PRT
<213> ORGANISM: Arabidopsis thaliana
<220> FEATURE:
<221> NAME/KEY: misc_feature
<222> LOCATION:
<223> OTHER INFORMATION: gi 15223482

<400> SEQUENCE: 222

Met Glu Gln Ser Glu Glu Gly Gln Gln Gln Gln Gln Gln Gly Val Met
1               5                   10                  15

Asp Tyr Val Pro Pro His Ala Tyr Gln Ser Gly Pro Val Asn Ala Ala
                20                  25                  30

Ser His Met Ala Phe Gln Gln Ala His His Phe His His His His Gln
            35                  40                  45

Gln Gln Gln Gln Gln Leu Gln Met Phe Trp Ala Asn Gln Met Gln
        50                  55                  60

Glu Ile Glu His Thr Thr Asp Phe Lys Asn His Thr Leu Pro Leu Ala
65                  70                  75                  80

Arg Ile Lys Lys Ile Met Lys Ala Asp Glu Asp Val Arg Met Ile Ser
                85                  90                  95

Ala Glu Ala Pro Val Ile Phe Ala Lys Ala Cys Glu Met Phe Ile Leu
            100                 105                 110

Glu Leu Thr Leu Arg Ala Trp Ile His Thr Glu Glu Asn Lys Arg Arg
        115                 120                 125

Thr Leu Gln Lys Asn Asp Ile Ala Ala Ala Ile Ser Arg Thr Asp Val
    130                 135                 140

Phe Asp Phe Leu Val Asp Ile Ile Pro Arg Asp Glu Leu Lys Glu Glu
145                 150                 155                 160

Gly Leu Gly Val Thr Lys Gly Thr Ile Pro Ser Val Val Gly Ser Pro
                165                 170                 175

Pro Tyr Tyr Tyr Leu Gln Gln Gln Gly Met Met Gln His Trp Pro Gln
            180                 185                 190

Glu Gln His Pro Asp Glu Ser
        195
```